(12) United States Patent
Kruegel et al.

(10) Patent No.: US 10,183,919 B2
(45) Date of Patent: Jan. 22, 2019

(54) CLASS OF MU-OPIOID RECEPTOR AGONISTS

(71) Applicants: Andrew C. Kruegel, New York, NY (US); Adam Henke, New York, NY (US); Madalee M. Gassaway, New York, NY (US); Marie-Laure Rives, New York, NY (US); Jonathan A. Javitch, New York, NY (US); Dalibor Sames, New York, NY (US)

(72) Inventors: Andrew C. Kruegel, New York, NY (US); Adam Henke, New York, NY (US); Madalee M. Gassaway, New York, NY (US); Marie-Laure Rives, New York, NY (US); Jonathan A. Javitch, New York, NY (US); Dalibor Sames, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/125,557

(22) PCT Filed: Mar. 12, 2015

(86) PCT No.: PCT/US2015/020273
§ 371 (c)(1),
(2) Date: Sep. 12, 2016

(87) PCT Pub. No.: WO2015/138791
PCT Pub. Date: Sep. 17, 2015

(65) Prior Publication Data
US 2017/0217913 A1    Aug. 3, 2017

Related U.S. Application Data

(60) Provisional application No. 61/951,845, filed on Mar. 12, 2014.

(51) Int. Cl.
| C07D 281/02 | (2006.01) |
| C07D 417/12 | (2006.01) |
| C07D 513/04 | (2006.01) |
| A61K 31/554 | (2006.01) |
| A61K 45/06  | (2006.01) |

(52) U.S. Cl.
CPC .......... C07D 281/02 (2013.01); A61K 31/554 (2013.01); A61K 45/06 (2013.01); C07D 417/12 (2013.01); C07D 513/04 (2013.01)

(58) Field of Classification Search
None
See application file for complete search history.

(56) References Cited

U.S. PATENT DOCUMENTS

| 5,238,936 A | 8/1993 | Regnier et al. |
| 5,849,735 A | 12/1998 | Albright et al. |
| 8,337,941 B2 | 12/2012 | Gubernator et al. |
| 9,075,014 B2 | 7/2015 | Sames et al. |
| 2002/0198191 A1 | 12/2002 | Failli et al. |
| 2005/0227961 A1* | 10/2005 | Kucharik ............. A61K 31/553 514/211.13 |
| 2008/0194522 A1 | 8/2008 | Chen et al. |
| 2010/0035279 A1 | 2/2010 | Gubernator et al. |
| 2013/0171664 A1 | 7/2013 | Sames et al. |
| 2013/0190497 A1 | 7/2013 | Gubernator et al. |
| 2014/0243317 A1 | 8/2014 | Cavalla et al. |
| 2015/0056699 A1 | 2/2015 | Sames et al. |
| 2017/0217913 A1 | 8/2017 | Kruegel et al. |

FOREIGN PATENT DOCUMENTS

| GB | 1269551 A | 4/1972 | |
| WO | WO 2006/023821 A2 | 3/2006 | |
| WO | WO 2006/026368 A2 | 3/2006 | |
| WO | WO 2007/022263 A1 | 2/2007 | |
| WO | WO 2008/006828 A1 | 1/2008 | |
| WO | WO 2008/009416 A1 | 1/2008 | |
| WO | WO 2008/013997 A2 | 1/2008 | |
| WO | WO 2008/027442 A2 | 3/2008 | |
| WO | WO 2009/059047 A2 | 5/2009 | |
| WO | WO 2010/070667   *  | 6/2010 | .......... C07D 281/02 |
| WO | WO 2010/070667 A2 | 6/2010 | |
| WO | WO 2011/094560 A1 | 8/2011 | |
| WO | WO 2012/143703   *  | 10/2012 | .......... C07D 281/14 |
| WO | WO 2012/143703 A1 | 10/2012 | |
| WO | WO 2013/028999 A1 | 2/2013 | |
| WO | WO 2013/029136 A1 | 3/2013 | |
| WO | WO 2013/167906 A1 | 11/2013 | |
| WO | WO 2015/138791 A1 | 9/2015 | |
| WO | WO 2016/086158 A1 | 6/2016 | |
| WO | WO 2007/017768 A2 | 2/2017 | |
| WO | WO 2017/165738 A1 | 9/2017 | |

OTHER PUBLICATIONS

Jamero et al., US Pharm. 2011; 36(5):HS4-HS8.*

(Continued)

*Primary Examiner* — Alicia L Otton
(74) *Attorney, Agent, or Firm* — John P. White; Cooper & Dunham LLP

(57) ABSTRACT

The present invention provides a compound having the structure:

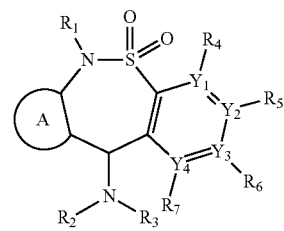

or a pharmaceutically acceptable salt or ester thereof.

37 Claims, 1 Drawing Sheet

(56) References Cited

OTHER PUBLICATIONS

STN Registry database entry for CAS RN 1159977-59-9, Entry Date Jun. 25, 2009, Accessed Mar. 23, 2018.*
STN Registry database entry for CAS RN 887588-50-3, Entry Date Jun. 13, 2006, Accessed Mar. 23, 2018.*
STN Registry database entry for CAS RN 752922-49-9, Entry Date Sep. 27, 2004, Accessed Mar. 23, 2018.*
Ito et al. In Cancer Science 94(1), 3-8 (2003).*
International Search Report dated Jun. 18, 2015 in connection with International Application PCT/US2015/020273.
Notification of Transmittal of the International Search Report and the Written Opinion of the International Searching Authority, or Declaration dated Jun. 18, 2015 in connection with International Application PCT/US2015/020273.
Written Opinion of the International Search Authority dated Jun. 18, 2015 in connection with International Application PCT/US2015/020273.
Extended European Search Report dated Jul. 20, 2017 in connection with European Patent Application EP15762391.9.
Diamond D.M. et al. (2004) "Preclinical research on stress, memory, and the brain in the development of pharmacotherapy for depression" European Neuropsychopharmacol, vol. 14, pp. S491-D495.
Labrid, C. et al. (1988) "Structure-activity relationships of tricyclic antidepressants, with special reference to tianeptine, " Clinical Neuropharmacol, vol. 11, No. suppl. 2, pp. s21-s31.
CAS Registry No. 1369502-93-1, Apr. 17, 2012.

\* cited by examiner

CLASS OF MU-OPIOID RECEPTOR AGONISTS

CROSS-REFERENCE TO RELATED APPLICATIONS

This application is a § 371 national stage of PCT International Application No. PCT/US2015/020273, filed Mar. 12, 2015, which claims the benefit of U.S. Provisional Application No. 61/951,845, filed Mar. 12, 2014, the contents of which are hereby incorporated by reference.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Mu-opioid receptor (MOR) has been the major molecular target for treatment of pain for several decades. However, the vast majority of MOR agonists used clinically today are structurally related to or derived from morphine (and other opioid alkaloids). These compounds suffer from many serious problems, including development of tolerance (increased dosing is required to achieve the same analgesic effects), high addiction liability, and other side effects (e.g., respiratory depression, nausea, and codetipariond (Williams, J. T. et al. 2013). Therefore, there is a continuing interest in the development of new pain medications, including new MOR agonists with improved therapeutic profile (Corbett, A. D. et al. 2006).

There is also both historical and growing interest in the use of MOR agonists as medicaments for depression. Prior to the adoption of tricyclic antidepressants and electroshock therapy as favored treatments for depression, opiates were among the only options available, with the "opium cure" being an accepted treatment modality in the early 20th century (Berrocoso, E. et al. 2009). More recently, studies in both rodents (Besson, A. et al. 1996) and humans (Bodkin, J. A. et al. 1995) have suggested that MOR activation may lead to antidepressant and/or anxiolytic effects. On the molecular level, MORs are extensively expressed in the hippocampus and have been shown to exert a variety of indirect modulatory effects on glutamatergic neurons in this brain region (Xie, C. W. et al. 1997; Svoboda, K. R. et al. 1999). Normalization and modulation of glutamate signaling has been strongly associated with the actions of antidepressants (Paul, I. A. and Skolnick, P. 2003) and indeed, the NMDA antagonist ketamine, shows rapid and efficacious antidepressant activity in human clinical trials (Zarate, C. A. Jr et al. 2006). Further, agonists of the related delta-opioid receptor (DOR) have been demonstrated to show robust antidepressant efficacy (Jutkiewicz, E. M. 2006).

SUMMARY OF THE INVENTION

The present invention provides a compound having the structure:

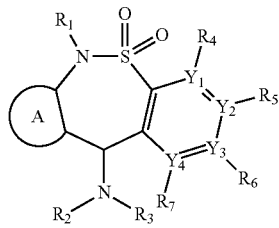

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alklyl)-(1,3-dioxane) or -(alkyl)-(4,5-dihydrooxazole);
$R_3$ is —H or -(alklyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
wherein when A is phenyl, $R_1$ is —$CH_3$, $R_3$, $R_4$, $R_6$, and $R_7$ are each —H, and $R_5$ is Cl, then $R_2$ is other than —$(CH_2)_4C(O)NH_2$, —$(CH_2)_4CO_2H$, —$(CH_2)_5CO_2H$, —$(CH_2)_6CO_2H$, —$(CH_2)_7CO_2H$, —$(CH_2)_{10}CO_2H$, —$(CH_2)_6CO_2CH_2CH_3$, —$(CH_2)_6CH_3$, —$(CH_2)_2OH$, —$(CH_2)_4OH$, —$(CH_2)_7$ OH,
wherein when A is phenyl, $R_1$ is —$CH_3$, $R_3$, $R_4$, $R_5$, $R_6$, and $R_7$ are each —H, then $R_2$ is other than —$(CH_2)$ $CO_2CH_2CH_3$, —$(CH_2)_2CO_2CH_2CH_3$, —$(CH_2)CO_2H$, —$(CH_2)_3CO_2H$, —$(CH_2)_4CO_2H$ or —$(CH_2)_6CO_2H$,
wherein when $R_1$ is —$CH_3$, $R_2$ is —$(CH_2)_5CO_2H$, $R_3$ is —H, $R_4$ and $R_7$ are each H, $R_5$ is —Cl and $R_6$ is —H or $R_5$ and $R_6$ are each —H, then A is other than 2-chlorophenyl or 3-chlorophenyl,
wherein when $R_1$ is —$CH_3$, $R_2$ is $(CH_2)_5CO_2H$, $R_3$ is —H or —$CH_3$, $R_4$ and $R_7$ are each —H, $R_5$ is Cl and $R_6$ is —H or $R_6$ is —Cl and $R_5$ is —H, then A is other than phenyl,
wherein when $R_1$ is —$CH_3$, $R_2$ is —$(CH_2)_3CO_2H$, $R_3$ is —$CH_3$, and $R_4$, $R_5$, $R_6$ and $R_7$ are each —H, then A is other than phenyl, wherein when A is phenyl, $R_1$ is —$CH_3$, $R_3$, $R_4$, $R_6$, and $R_7$ are each —H, and $R_5$ is —$SO_2CH_3$, then $R_2$ is other than —$(CH_2)_3OCH_3$, wherein when A is phenyl, $R_1$ is —$CH_3$, $R_3$, $R_4$, $R_6$, and $R_7$ are each —H, and $R_5$ is —F, then $R_2$ is other than —$(CH_2)_6CO_2H$, or a pharmaceutically acceptable salt or ester thereof.

The present invention also provides a compound having the structure:

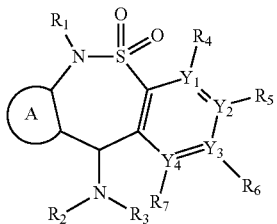

wherein

A is an aryl or heteroaryl, with or without substitution;

$R_1$ is —H or -(alkyl);

$R_2$ is -(alkyl), -(alkenyl), -(alkynyl)-(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, wherein when A is phenyl, $R_1$ is —$CH_3$, $R_3$, $R_4$, $R_6$, and $R_7$ are each —H, and $R_5$ is Cl, then $R_2$ is other than —$(CH_2)_4CO_2H$, —$(CH_2)_6CO_2H$, —$(CH_2)_6CO_2CH_2CH_3$, or —$(CH_2)_6CH_3$, wherein when A is phenyl, $R_1$ is —$CH_3$, $R_3$, $R_4$, $R_6$, and $R_7$ are each —H, and $R_5$ is —$SO_2CH_3$, then $R_2$ is other than —$(CH_2)_3OCH_3$, or a pharmaceutically acceptable salt thereof.

The present invention further provides a compound having the structure:

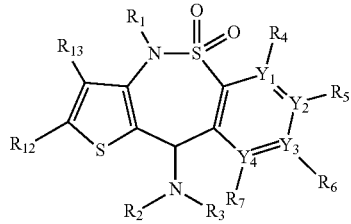

wherein $R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_{12}$ and $R_{13}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present.

The present invention yet further provides a compound having structure:

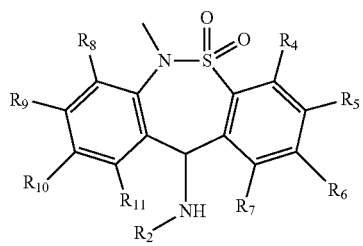

wherein
R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alklyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-O-(alkyl), -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₅ is —Br, or —I;

R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl) or —SO₂-(heteroaryl).

The present invention also provides a compound having the structure:

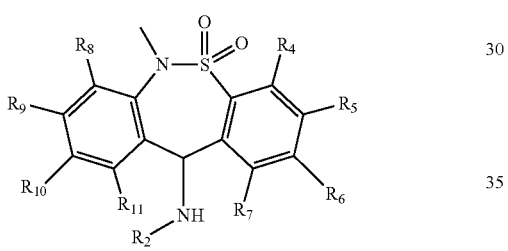

wherein
R₂ is -(alkyl)-O-(alkyl) or (alkyl)-O-(alkyl)-O-(alkyl);
R₅ is —Cl, —Br, —F, or —I;
R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl) or —SO₂-(heteroaryl) ;
R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

The present invention provides a method of activating mu-opioid receptor or delta-opioid receptor comprising contacting the mu-opioid receptor or delta-opioid receptor with a compound having the structure:

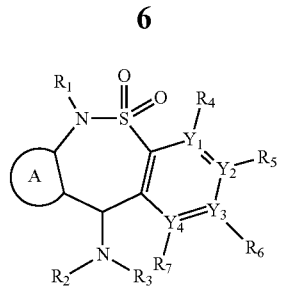

wherein
A is an aryl or heteroaryl, with or without substitution;
R₁ is —H or -(alkyl);
R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alkyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-O-(alkyl), -(alkyl)-(CH)—(O-(alkyl))₂, -(alkyl)-(heteroacyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
R₃ is —H or -(alkyl);
R₄, R₅, R₆ and R₇ are each absent or present, and when present, are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); and
Y₁, Y₂, Y₃ and Y₄ are each independently N or C,
wherein when Y₁ is N, then R₄ is absent, and when Y₁ is C, then R₄ is present; when Y₂ is N, then R₅ is absent, and when Y₂ is C, then R₅ present; when Y₃ is N, then R₆ is absent, and when Y₃ is C, then R₆ is present; when Y₄ is N then R₇ is absent, and when Y₄ is C, then R₇ is present,
or a pharmaceutically acceptable salt or ester thereof, so as to thereby activate the mu-opioid receptor or delta-opioid receptor.

The present invention provides a method of treating a subject afflicted with depression, major depression or pain comprising administering an effective amount of the compound having the structure:

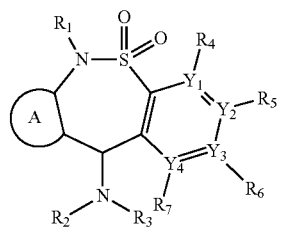

wherein
A is an aryl or heteroaryl, with or without substitution;
R₁ is —H or -(alkyl);

R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alklyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-O-(alkyl), -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₃ is —H or -(alkyl);

R₄, R⁵, R₆ and R₇ are each absent or present, and when present, are each independently —H, —Cl, —Br, —F, —I, —CN, —CF₃, —OCF₃, -(alklyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), SO₂-(aryl), or —SO₂-(heteroaryl); and Y₁, Y₂, Y₃ and Y₄ are each independently N or C,
wherein when Y₁ is N, then R₄ is absent, and when Y₁ is C, then R₄ is present; when Y₂ is N, then R₅ is absent, and when Y₂ is C, then R₅ is present; when Y₃ is N, then R₆ is absent, and when Y₃ is C, then R₆ is present; when Y₄ is N, then R₇ is absent, and when Y₄ is C, then R₇ is present, or a pharmaceutically acceptable salt thereof, to the subject so as to thereby treat the depression, major depression or pain.

The present invention provides a method of treating a subject afflicted with depression or major depression comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of a compound having the structure:

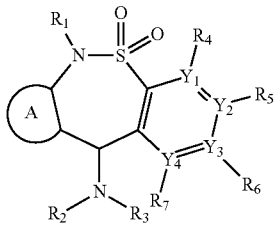

wherein
A is an aryl or heteroaryl, with or without substitution;
R₁ is —H or -(alkyl);
R₂ is -(alkyl), -(alkenyl), (alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alklyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-O-(alkyl), -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₃ is —H or -(alkyl);

R₄, R₅, R₆ and R₇ are each absent or present, and when present, are each independently —H, —Cl, —Br, —F, —I, —CN, —CF₃, —OCF₃, -(alkly), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); and Y₁, Y₂, Y₃ and Y₄ are each independently N or C,
wherein when Y₁ is N, then R₄ is absent, and when Y₁ is C, then R₄ is present; when Y₂ is N, then R₅ is absent, and when Y₂ is C, then R₅ is present; when Y₃ is N, then R₆ is absent, and when Y₃ is C, then R₆ is present; when Y₄ is N, then R₇ is absent, and when Y₄ is C, then R₇ is present, or a pharmaceutically acceptable salt thereof, so as to thereby treat the subject.

The present invention provides a method of treating a subject afflicted with pain comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of a compound having the structure:

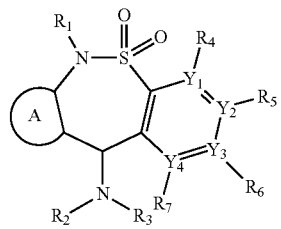

wherein
A is an aryl or heteroaryl, with or without substitution;
R₁ is —H or -(alkyl);
R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alklyl)₂, -(alkyl)-C(O)—N(hydroxyalkyl)₂, -(alkyl)-O-(alkyl), -(alklyl)-S-(alklyl), -(alkyl)-CF₃, -(alkyl)-O-(hydroxyalkyl), -(alklyl)-O-(alklyl)-O-(alklyl), -(alkyl)-(CH)—(O-(alkyl))₂, -(alklyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₃ is —H or -(alkyl);

R₄, R₅, R₆ and R₇ are each absent or present, and when present, are each independently —H, —Cl, —Br, —F, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alklyl), —S(O)-(aryl), —S(O)-(heteroaryl), —SO₂-(alkyl), —SO₂-(aryl), or —SO₂-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject.

The present invention provides a compound having the structure

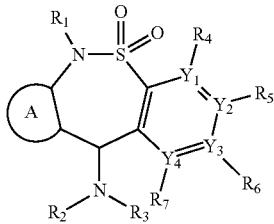

wherein
A is an aryl or heteroaryl, with or without substitution;
$R_1$ is —H or -(alkyl)
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkly), -(alkyl)-$CF_3$, -(alkyl)-O-(hydroxyalkyl), -(alkyl)-O-(alklyl)-O-(alklyl), -(alkyl)-(CH)—(O-(alkyl))$_2$, -(alklyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alklyl), -(alkenyl), -(alkynyl), -(aryl), —$NH_2$, —NH-(alkyl), —NH-(alkenyl), —NH-(alkynyl), —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alklyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a salt or ester thereof, for use as an add-on therapy or in combination with a a NMDA receptor antagonist, an NMDA receptor partial agonist, a neurokinin 1 receptor antagonist, a neurokinin 2 receptor antagonist or a neurokinin 3 receptor antagonist in treating a subject afflicted with depression or major depression.

The present invention provides a compound having the structure

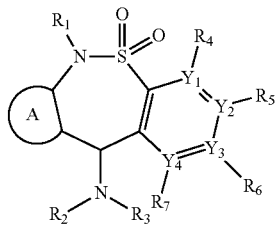

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alklyl), -(alkyl)-$CF_3$, -(alkyl)-O-(hydroxyalkyl), -(alkyl)-O-(alklyl)-O-(alklyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl), —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alklyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ C, then R is present, or a salt or ester thereof, for use as an add-on therapy or in combination with a a NMDA receptor antagonist, an NMDA receptor partial agonist, a neurokinin 1 receptor antagonist, a neurokinin 2 receptor antagonist or a neurokinin 3 receptor antagonist in treating a subject afflicted with pain.

The present invention provides a pharmaceutical composition comprising an amount of a compound having the structure

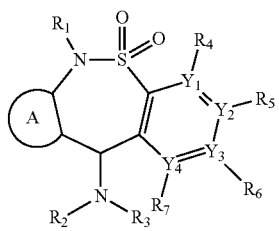

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alklyl)-S-(alkyl), -(alkyl)-$CF_3$, -(alkyl)-O-(hydroxyalkyl), -(alkyl)-O-(alklyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N- methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for us in treating a subject afflicted with depression or major depression.

The present invention provides a pharmaceutical composition comprising an amount of a compound having the structure

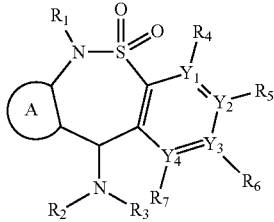

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl) —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for use in treating a subject afflicted with pain.

The present invention provides a compound having the structure:

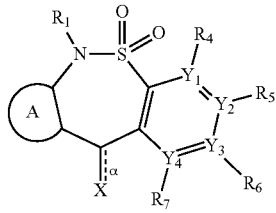

wherein

α is a bond, which may be present or absent;

X is O, OH, OTf, Cl, or Br, wherein when α is present, then X is O, and when α is absent, then X is OH, OTf, Cl, or Br;

A is an aryl or heteroaryl, with or without substitution;

$R_1$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof.

DETAILED DESCRIPTION OF THE INVENTION

Figures 1A, 1B:
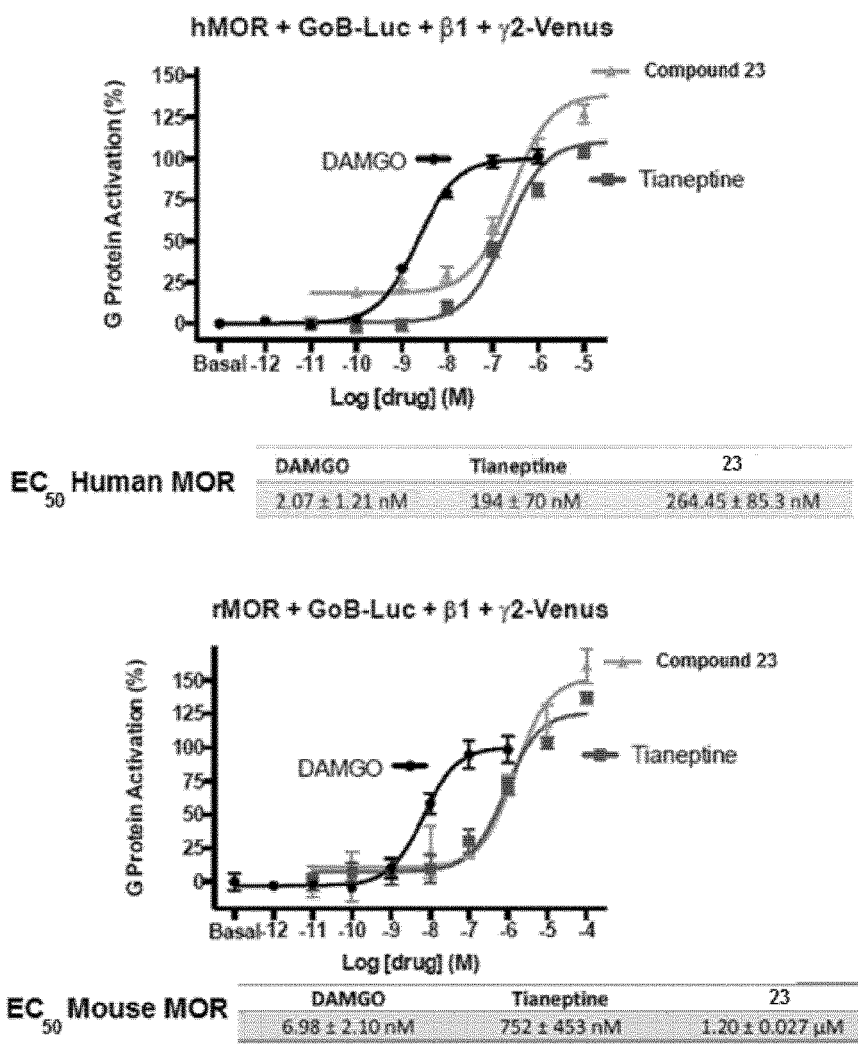
FIG. 1A: $EC_{50}$ (human MOR) of DAMGO, tianeptine and compound 23.
FIG. 1B: EC$_{50}$ (mouse MOR) of DAMGO, tianeptine and compound 23.

The present invention provides a compound having the structure:

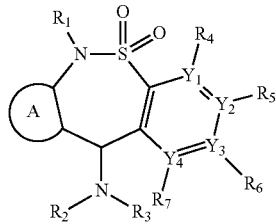

wherein
A is an aryl or heteroaryl, with or without substitution;
R$_1$ is —H or -(alkyl);
R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -alkyl-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
R$_3$ is —H or -(alkyl);
R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and
Y$_1$, Y$_2$, Y$_3$ and Y$_4$ are each independently N or C,
wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present,
wherein when A is phenyl, R$_1$ is —CH$_3$, R$_3$, R$_4$, R$_6$, and R$_7$ are each —H, and R$_5$ is Cl, then R$_2$ is other than —(CH$_2$)$_4$C(O)NH$_2$, —(CH$_2$)$_4$CO$_2$H, —(CH$_2$)$_5$CO$_2$H, —(CH$_2$)$_6$CO$_2$H, —(CH$_2$)$_7$CO$_2$H, —(CH$_2$)$_{10}$CO$_2$H, —(CH$_2$)$_6$CO$_2$CH$_2$CH$_3$, —(CH$_2$)$_6$CH$_3$, —(CH$_2$)$_2$OH, —(CH$_2$)$_4$OH, —(CH$_2$)$_7$ OH,
wherein when A is phenyl, R$_1$ is —CH$_3$, R$_3$, R$_4$, R$_5$, R$_6$, and R$_7$ are each —H, then R$_2$ is other than —(CH$_2$)CO$_2$CH$_2$CH$_3$, —(CH$_2$)$_2$CO$_2$CH$_2$ CH$_3$, —(CH$_2$)CO$_2$H, —(CH$_2$)$_3$CO$_2$H, or —(CH$_2$)$_4$CO$_2$H,
wherein when R$_1$ is —CH$_3$, R$_2$ is —(CH$_2$)$_5$CO$_2$H, R$_3$ is —H, R$_4$ and R$_7$ are each H, R$_5$ is —Cl and R$_6$ is —H or R$_5$ and R$_6$ are each —H, then A is other than 2-chlorophenyl or 3-chlorophenyl,
wherein when R$_1$ is —CH$_3$, R$_2$ is —(CH$_2$)$_3$CO$_2$H, R$_3$ is —CH$_3$, and R$_4$, R$_5$, R$_6$ and R$_7$ are each —H, then A is other than phenyl,
wherein when R$_1$ is —CH$_3$, R$_2$ is —(CH$_2$)$_5$CO$_2$H, R$_3$ is —H or —CH$_3$, R$_4$ and R$_7$ are each —H, R$_5$ is Cl and R$_6$ is —H or R$_6$ is —Cl and R$_5$ is —H, then A is other than phenyl,
wherein when A is phenyl, R$_1$ is —CH$_3$, R$_3$, R$_4$, R$_6$, and R$_7$ are each —H, and R$_5$ is —SO$_2$CH$_3$, then R$_2$ is other than —(CH$_2$)$_3$OCH$_3$,
wherein when A is phenyl, R$_1$ is —CH$_3$, R$_3$, R$_4$, R$_6$, and R$_7$ are each —H, and R$_5$ is —F, then R$_2$ is other than —(CH$_2$)$_6$CO$_2$H,
or a pharmaceutically acceptable salt or ester thereof.

In some embodiments,
R$_2$ is -(alkyl), -(alkenyl), -(alkynyl), -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, (alkyl)-(1,3-dioxane) or -(alkyl)-(4,5-dihydrooxazole).

In some embodiments,
R$_2$ is -(alkyl), -(alkenyl), -(alkynyl), -(alkyl)-OH, -(alkyl)-CO$_2$(alkyl), -(alkyl)-C(O)—NH$_2$, -(alkyl)-C(O)—NH (alkyl), -(alkyl)-C(O)—NH-(hydroxyalkyl), -(alkyl)-C (O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole).

In some embodiments,
R$_2$ is -(alkyl), -(alkenyl), -(alkynyl), -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N (alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-diohydrooxazole).

In some embodiments,
R$_2$ is -(alkyl), -(alkenyl), -(alkynyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-diohydrooxazole).

The present invention also provides a compound having the structure:

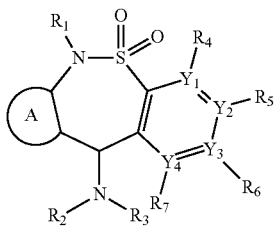

wherein
A is an aryl or heteroaryl, with or without substitution;
R is —H or -(alkyl);
$R_2$ is -(alkyl), -(alkenyl), -(alkynyl) -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
wherein when A is phenyl, $R_1$ is —$CH_3$, $R_3$, $R_4$, $R_6$, and $R_7$ are each —H, and $R_5$ is Cl, then $R_2$ is other than —$(CH_2)_4CO_2H$, —$(CH_2)_6CO_2H$, —$(CH_2)_6CO_2CH_2CH_3$, or —$(CH_2)_6CH_3$,
wherein when A is phenyl, $R_1$ is —$CH_3$, $R_3$, $R_4$, $R_6$, and $R_7$ are each —H, and $R_5$ is —$SO_2CH_3$, then $R_2$ is other than —$(CH_2)_3OCH_3$,
or a pharmaceutically acceptable salt thereof.
In some embodiments, a compound having the structure:

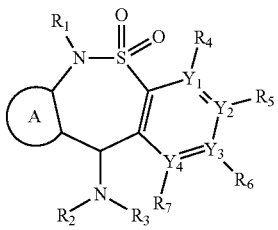

wherein
A is an aryl or heteroaryl, with or without substitution;
$R_1$ is —H or -(alkyl);
$R_2$ is -(alkyl), -(alkenyl), -(alkynyl), -(alkyl)-C(O)—NH (alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
wherein when A is phenyl, $R_1$ is —$CH_3$, $R_3$, $R_4$, $R_6$, and $R_7$ are each —H, and $R_5$ is Cl, then $R_2$ is other than —$(CH_2)_6CH_3$,
wherein when A is phenyl, $R_1$ is —$CH_3$, $R_3$, $R_4$, $R_6$, and $R_7$ are each —H, and $R_5$ is —$SO_2CH_3$, then $R_2$ is other than —$(CH_2)_3OCH_3$,
or a pharmaceutically acceptable salt thereof.
In some embodiments, the compound wherein A is

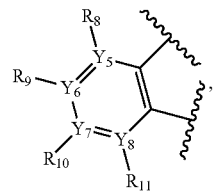

wherein $R_8$, $R_9$, $R_{10}$ and $R_{11}$ are each absent or present, and when present, are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$Y_5$, $Y_6$, $Y_7$ and $Y_8$ are each independently N or C,
wherein when $Y_5$ is N, then $R_8$ is absent, and when $Y_5$ is C, then $R_8$ is present; when $Y_6$ is N, then $R_9$ is absent, and when $Y_6$ is C, then $R_9$ is present; when $Y_7$ is N, then $R_{10}$ is absent, and when $Y_7$ is C, then $R_{10}$ is present; when $Y_8$ is N, then $R_{11}$ is absent, and when $Y_8$ is C, then $R_{11}$ is present.

In some embodiments, the compound wherein
$Y_5$, $Y_6$, $Y_7$ and $Y_8$ are each C; and
$R_8$, $R_9$, $R_{10}$ and $R_{11}$ are each independently —H, —Cl, —Br, —F, —I, —CN, —CF$_3$, —OCF$_3$, —OH, —OAc, -(C$_1$-C$_6$ alkyl), —O-(C$_1$-C$_6$ alkyl), —S-(C$_1$-C$_6$ alkyl), —SO$_2$-(C$_1$-C$_6$ alkyl), —S(O)-(C$_1$-C$_6$ alkyl), —O-(aryl) or —S-(aryl), or -(aryl).

In some embodiments, the compound wherein
$Y_5$, $Y_6$, $Y_7$ and $Y_8$ are each C; and
$R_8$, $R_9$, $R_{10}$ and $R_{11}$ are each independently —H, —CH$_3$, —Cl, —Br, —F, —I, —OCH$_3$, —OH, —OAc, —SCH$_3$, —SO$_2$CH$_3$, —S(O)CH$_3$, -(phenyl), or —O-(phenyl).

In some embodiments, the compound wherein
$Y_5$, $Y_6$, $Y_7$ and $Y_8$ are each C; and
$R_8$, $R_9$, $R_{10}$ and $R_{11}$ are each —H.

In some embodiments, the compound wherein
$Y_5$, $Y_6$, $Y_7$ and $Y_8$ are each C;
$R_7$, $R_8$, and $R_{11}$ are each —H; and $R_{10}$ is —Br.

In some embodiments, the compound wherein
$Y_5$, $Y_6$, $Y_7$ and $Y_8$ are each C
$R_9$, $R_{10}$, and $R_{11}$ are each —H; and $R_8$ is —OCH$_3$.

In some embodiments, the compound wherein
$Y_5$, $Y_6$, $Y_7$ and $Y_8$ are each C
$R_9$, $R_{10}$, and $R_{11}$ are each —H; and $R_8$ is —OH.

In some embodiments, the compound wherein
$Y_5$, $Y_6$, $Y_7$ and $Y_8$ are each C
$R_8$, $R_{10}$, and $R_{11}$ are each —H; and $R_9$ is —F, —Cl, —Br, or —I.

In some embodiments, the compound wherein
$Y_1$, $Y_2$, $Y_3$ and $Y_4$ are each C; and
$R_4$, $R_5$, $R_6$ and $R_7$ are each independently —H, —Cl, —Br, —F, —I, CN, —CF$_3$, —OCF$_3$, —OH, —OAc, —(C$_1$-C$_6$ alkyl), —O—(C$_1$-C$_6$ alkyl), —S—(C$_1$-C$_6$ alkyl), —SO$_2$—(C$_1$-C$_6$ alkyl), —S(O)—(C$_1$-C$_6$ alkyl), —O-(aryl) or —S-(aryl), or -(aryl).

In some embodiments, the compound wherein
$Y_1$, $Y_2$, $Y_3$ and $Y_4$ are each C; and
$R_4$, $R_5$, $R_6$ and $R_7$ are each independently —H, —CH$_3$, —Cl, —Br, —F, —I, —OCH$_3$, —OH, —OAc, —SCH$_3$, —SO$_2$CH$_3$, —S(O)CH$_3$, -(phenyl), or —O-(phenyl).

In some embodiments, the compound wherein
$Y_1$, $Y_2$, $Y_3$ and $Y_4$ are each C; and
$R_4$, $R_5$, $R_6$ and $R_7$ are each —H.

In some embodiments, the compound wherein
$R_4$, $R_6$, and $R_7$ are each —H; and $R_5$ is —CH$_3$, —Cl, —F, —Br, —I, —OCH$_3$, —OH, —OAc, —SCH$_3$, —SO$_2$CH$_3$, —S(O)CH$_3$, -(phenyl), or —O-(phenyl).

In some embodiments, the compound wherein
$R_4$, $R_5$, and $R_7$ are each —H; and $R_6$ is —CH$_3$, —Cl, —F, —I, —OCH$_3$, —OH, —OAc, —SCH$_3$, —SO$_2$CH$_3$, —S(O) CH$_3$, -(phenyl), or —O-(phenyl).

In some embodiments, the compound wherein
$Y_1$, $Y_3$ and $Y_4$ are each C;
$Y_2$ is N and $R_5$ is absent;
$R_4$, $R_6$ and $R_7$ are each are each independently —H, —Cl, —Br, —F, —I, —CN, —CF$_3$, —OCF$_3$, —OH, —OAc, —(C$_1$-C$_6$ alkyl), —O—(C$_1$-C$_6$ alkyl), —S—(C$_1$-C$_6$ alkyl), —SO$_2$—(C$_1$-C$_6$ alkyl), —S(O)—(C$_1$-C$_6$ alkyl), —O-(aryl) or —S-(aryl), or -(aryl).

In some embodiments, the compound wherein
$Y_1$, $Y_3$ and $Y_4$ are each C;
$Y_2$ is N and $R_5$ is absent; and
$R_4$, $R_6$ and $R_7$ are each —H.

In some embodiments, the compound wherein
$R_2$ is —(C$_1$-C$_{12}$ alkyl), —(C$_1$-C$_{12}$ alkenyl), —(C$_1$-C$_{12}$ alkynyl) —(C$_1$-C$_{12}$ alkyl) —OH, —(C$_1$-C$_{12}$ alkyl)-CO$_2$H, —(C$_1$-C$_{12}$ alkyl)-CO$_2$—(C$_1$-C$_6$ alkyl), —(C$_1$-C$_{12}$ alkyl)-C(O)—NH$_2$, —(C$_1$-C$_{12}$ alkyl)-C(O)—NH (C$_1$C$_6$ alkyl), —(C$_1$-C$_{12}$ alkyl)-C(O)—NH—(C$_1$-C$_6$ hydroxyalkyl), —(C$_1$-C$_{12}$ alkyl)-C(O)—N(C$_1$-C$_6$ alkyl)$_2$, —(C$_1$-C$_{12}$ alkyl)-C(O)—N(C$_1$-C$_6$ hydroxyalkyl)$_2$, —(C$_1$-C$_{12}$ alkyl)-O—(C$_1$-C$_6$ alkyl), —(C$_1$-C$_{12}$ alkyl)-S—(C$_1$-C$_6$ alkyl), —(C$_1$-C$_{12}$ alkyl)-CF$_3$, —(C$_1$-C$_{12}$ alkyl)-O—(C$_1$-C$_6$ hydroxyalkyl), —(C$_1$-C$_{12}$ alkyl)-O—(C$_1$-C$_6$ alkyl)-OCH$_3$, —(C$_1$-C$_{12}$ alkyl)-(CH)—(O—(C$_1$-C$_6$ alkyl))$_2$, —(C$_1$-C$_{12}$ alkyl)-(heterocyclyl), —(C$_1$-C$_{12}$ alkyl)-OAc, —(C$_1$-C$_{12}$ alkyl)-tetrahydrofuran, —(C$_1$-C$_{12}$ alkyl)-pyrrolidine, —(C$_1$-C$_{12}$ alkyl)-N-methylpyrrolidine, —(C$_1$-C$_{12}$ alkyl)-(1,3-dioxane) or —(C$_1$-C$_{12}$ alkyl)-(4,5-dihydrooxazole).

In some embodiments, the compound wherein
$R_2$ is —(C$_1$-C$_8$ alkyl), —(C$_1$-C$_6$ alkenyl), —(C$_1$-C$_6$ alkynyl) —(C$_1$-C$_6$ alkyl)-OH, —(C$_1$-C$_6$ alkyl)-CO$_2$H, —(C$_1$-C$_6$ alkyl)-CO$_2$-(C$_1$-C$_2$ alkyl), —(C$_1$-C$_6$ alkyl)-C(O)—NH$_2$, —(C$_1$-C$_6$ alkyl)-C(O)—NH(C$_1$-C$_2$ alkyl), —(C$_1$-C$_6$ alkyl)-C(O)—NH—(C$_1$-C$_2$ hydroxyalkyl), —(C$_1$-C$_6$ alkyl)-C(O)—N(C$_1$-C$_2$ alkyl)$_2$, —(C$_1$-C$_6$ alkyl)-C(O)—N(C$_1$-C$_2$ hydroxyalkyl)$_2$, —(C$_1$-C$_6$ alkyl)-O—(C$_1$-C$_2$ alkyl), —(C$_1$-C$_6$ alkyl)-S—(C$_1$-C$_2$ alkyl), —(C$_1$-C$_3$ alkyl)-CF$_3$, —(C$_1$-C$_3$ alkyl)-O—(C$_1$-C$_2$ hydroxyalkyl), —(C$_1$-C$_3$ alkyl)-O—(C$_1$-C$_2$ alkyl)-OCH$_3$, —(C$_1$-C$_6$alkyl)-(CH)—(O—(C$_1$-C$_2$ alkyl))$_2$, —(C$_1$-C$_6$ alkyl)-(heterocyclyl), —(C$_1$-C$_6$ alkyl)-OAc, —(C$_1$-C$_6$ alkyl)-tetrahydrofuran, —(C$_1$-C$_6$ alkyl)-pyrrolidine, —(C$_1$-C$_6$ alkyl)-N-methylpyrrolidine, —(C$_1$-C$_6$ alkyl)-(1,3-dioxane) or —(C$_1$-C$_6$alkyl)-(4,5-dihydrooxazole).

In some embodiments, the compound wherein
$R_2$ is

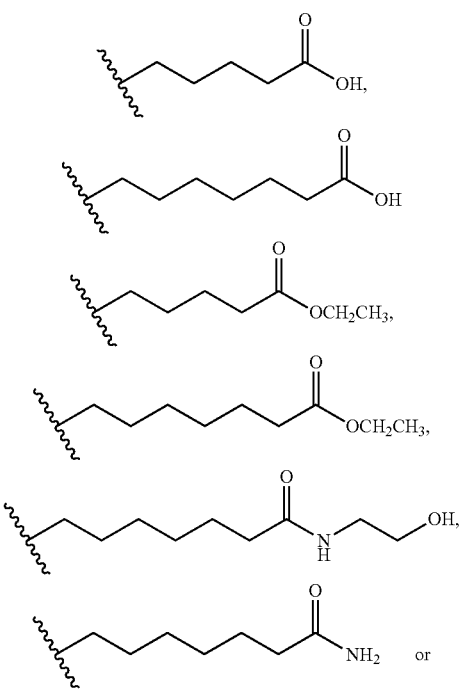

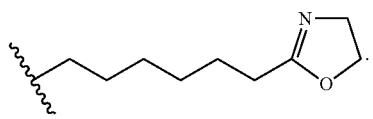
In some embodiments, the compound wherein
$R_2$ is —$CH_3$, —$CH_2CH_3$,
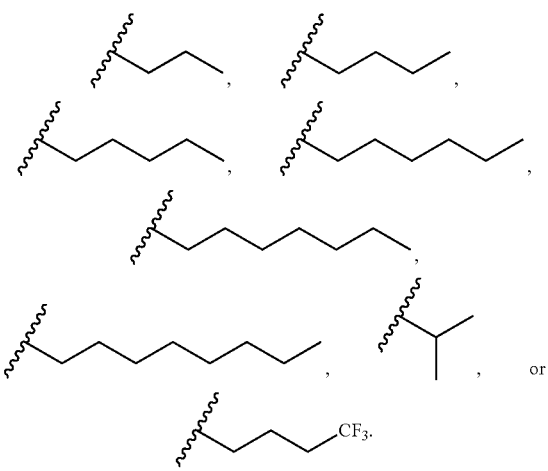
In some embodiments, the compound wherein
$R_2$ is
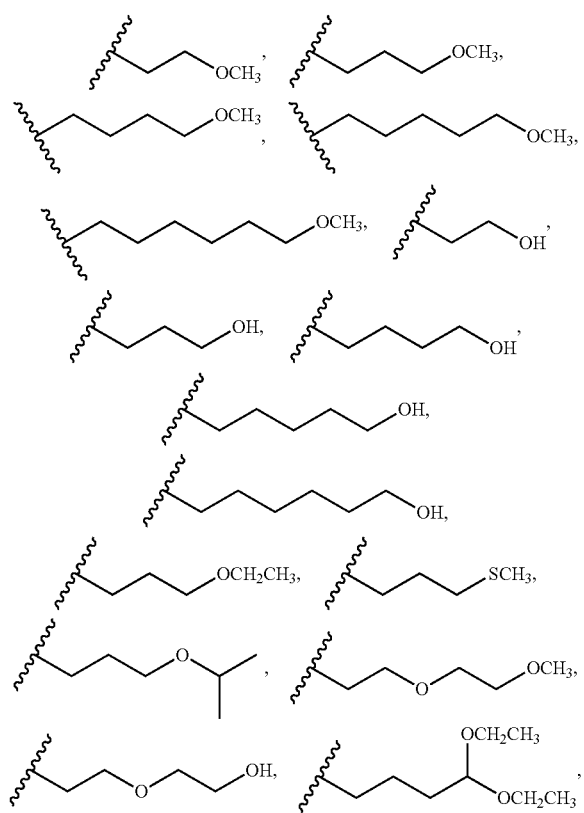
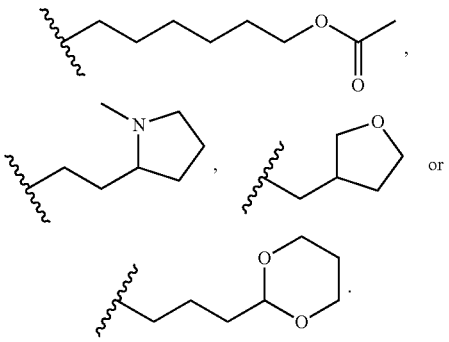
In some embodiment of any of the compounds described herein,
$R_2$ is
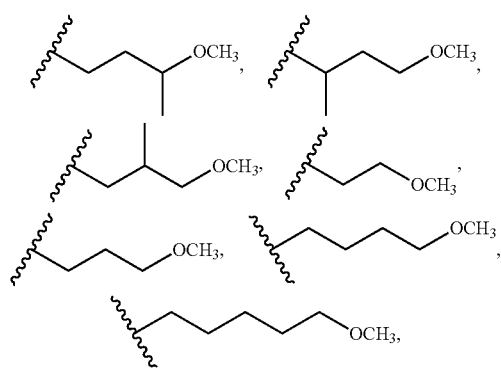
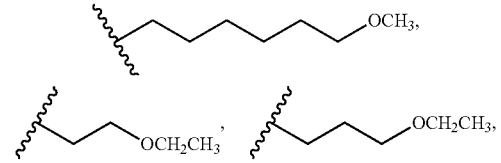
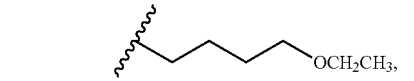
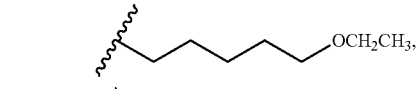
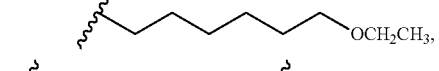
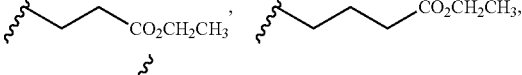
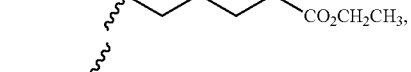
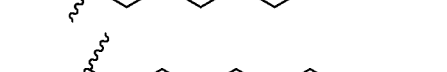
In some embodiments, the compound wherein $R_1$ is —H or —($C_1$-$C_6$ alkyl).

In some embodiments, the compound wherein $R_3$ is —H or —($C_1$-$C_6$ alkyl).

In some embodiments, the compound wherein $R_1$ is —H, —$CH_3$ or —$CH_2CH_3$.

In some embodiments, the compound wherein $R_3$ is —H, —$CH_3$ or —$CH_2CH_3$.

In some embodiments, the compound wherein $R_1$ is —$CH_3$; and $R_3$ is —H.

In some embodiments, the compound wherein $R_1$ is —$CH_3$; and $R_3$ is —$CH_3$.

In some embodiments, the compound wherein $R_1$ is —$CH_2CH_3$; and $R_3$ is H.

In some embodiments, the compound having the structure:

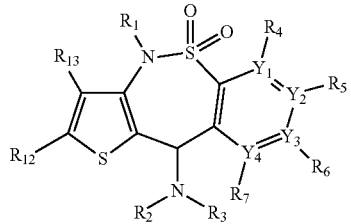

$R_1$ is —H or -(alkyl);
$R_2$ is -(alkyl), -(alkenyl), alkynyl, -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_{12}$ and $R_{13}$ are each independently —H, —Cl, —Br, —F, —I, —CN, —$CF_3$, —$OCF_3$, -(alkyl), -(aryl), -(heteroaryl)-(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present.

In some embodiments, the compound wherein A is

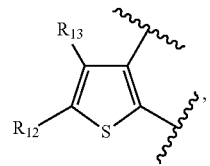

wherein $R_{12}$ and $R_{13}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl) —$SO_2$-(aryl), or —$SO_2$-(heteroaryl).

In some embodiments, the compound wherein $R_{12}$ and $R_{13}$ are each independently —H, —Cl, —Br, —F, —I, —CN, —$CF_3$, —$OCF_3$, —OH, —OAc, —($C_1$-$C_6$ alkyl), —O—($C_1$-$C_6$ alkyl), —S—($C_1$-$C_6$ alkyl), —$SO_2$—($C_1C_6$ alkyl), —S(O)—($C_1$-$C_6$ alkyl), —O-(aryl) or —S-(aryl), or -(aryl).

In some embodiments, the compound wherein $R_{12}$ and $R_{13}$ are each independently —H, —$CH_3$, —Cl, —Br, —F, —I, —$OCH_3$, —OH, —OAc, —$SCH_3$, —$SO_2CH_3$, —S(O)$CH_3$, -(phenyl), or —O-(phenyl).

In some embodiments, the compound wherein $R_{12}$ and $R_{13}$ are each independently —H, —$CH_3$, —Cl, —Br, —F, —$OCH_3$, —$SCH_3$, or —O-(phenyl).

In some embodiments, the compound wherein $R_{12}$ and $R_{13}$ are each —H.

In some embodiments, the compound wherein $R_{12}$ is —H; and $R_{13}$ is —Br.

In some embodiments, the compound wherein $Y_1$, $Y_2$, $Y_3$ and $Y_4$ are each C; and
$R_4$, $R_5$, $R_6$ and $R_7$ are each are each independently —H, —Cl, —Br, —F, —I, —CN, —$CF_3$, —$OCF_3$, —OH, —OAc, —($C_1$-$C_6$ alkyl), —O—($C_1$-$C_6$ alkyl), —S—($C_1$-$C_6$ alkyl), —$SO_2$—$C_1$-$C_6$ alkyl), —S(O)—($C_1$-$C_6$ alkyl), —O-(aryl) or —S-(aryl), or -(aryl).

In some embodiments, the compound wherein $Y_1$, $Y_2$, $Y_3$ and $Y_4$ are each C; and
$R_4$, $R_5$, $R_6$ and $R_7$ are each independently —H, —$CH_3$, —Cl, —Br, —F, —I, —$OCH_3$, —OH, —OAc, —$SCH_3$, —$SO_2CH_3$, —S(O)$CH_3$, -(phenyl), or —O-(phenyl).

In some embodiments, the compound wherein $Y_1$, $Y_2$, $Y_3$ and $Y_4$ are each C; and
$R_4$, $R_5$, $R_6$ and $R_7$ are each —H.

In some embodiments, the compound wherein $Y_1$, $Y_2$, $Y_3$ and $Y_4$ are each C; and
$R_4$, $R_6$, and $R_7$ are each —H; and $R_5$ is —$CH_3$, —Cl, —Br, —F, —I, —$OCH_3$, —OH, —OAc, —$SCH_3$, —$SO_2CH_3$, —S(O)$CH_3$, -(phenyl), or —O-(phenyl).

In some embodiments, the compound wherein $R_4$, $R_5$, and $R_7$ are each —H; and $R_6$ is —$CH_3$, —Cl, —Br, —F, —I, —$OCH_3$, —OH, —OAc, —$SCH_3$, —$SO_2CH_3$, —S(O)$CH_3$, -(phenyl), or —O-(phenyl).

In some embodiments, the compound wherein
$Y_1$, $Y_3$ and $Y_4$ are each C;
$Y_2$ is N and $R_5$ is absent; and
$R_4$, $R_6$ and $R_7$ are each are each independently —H, —Cl, —Br, —F, —I, —CN, —CF$_3$, —OCF$_3$, —OH, —OAc, —(C$_1$-C$_6$ alkyl), —O—(C$_1$C$_6$ alkyl), —S—(C$_1$-C$_6$ alkyl), —SO$_2$—(C$_1$C$_6$ alkyl), —H(O)—(C$_1$C$_6$ alkyl), —O-(aryl), or —S-(aryl), or -(aryl).

In some embodiments, the compound wherein
$Y_1$, $Y_3$ and $Y_4$ are each C;
$Y_2$ is N and $R_5$ is absent; and
$R_4$, $R_6$ and $R_7$ are each —H.

In some embodiments, the compound wherein
$Y_1$, $Y_2$, $Y_3$ and $Y_4$ are each C; and
$R_4$, $R_6$, and $R_7$ are each —H; and $R_5$ is —Br, —Cl or —O-(phenyl).

In some embodiments, the compound wherein
$R_4$, $R_5$, and $R_7$ are each —H; and $R_6$ is —CH$_3$, —Cl, —F, —I, —OCH$_3$, —OH, —OAc, —SCH$_3$, —SO$_2$CH$_3$, —S(O)CH$_3$, -(phenyl), or —O-(phenyl).

In some embodiments, the compound wherein
$Y_1$, $Y_2$, $Y_3$ and $Y_4$ are each C; and
$R_4$, $R_5$, and $R_7$ are each —H; and $R_6$ is —Br, Cl or —O-(phenyl).

In some embodiments, the compound wherein $R_2$ is -(alkyl)-CO$_2$-(alkyl), -(alkyl)-O-(alkyl) or -(alkyl)-O-(alkyl)-O-(alkyl).

In some embodiments, the compound wherein $R_2$ is

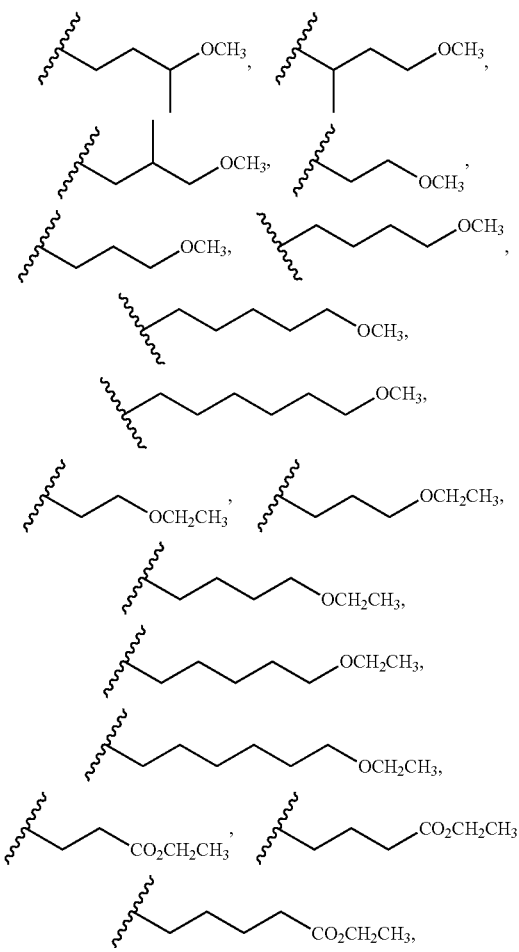

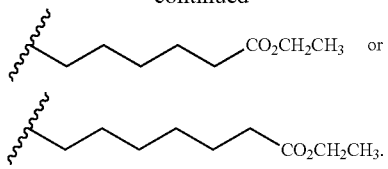

In some embodiments, the compound wherein
$R_2$ is —(C$_1$-C$_{12}$ alkyl), —(C$_1$-C$_{12}$ alkenyl), —(C$_1$-C$_{12}$ alkynyl) —(C$_1$-C$_{12}$ alkyl)-OH, —(C$_1$-C$_{12}$ alkyl)-CO$_2$H, —(C$_1$-C$_{12}$ alkyl)-CO$_2$-(C$_1$-C$_6$ alkyl), —(C$_1$-C$_{12}$ alkyl)-C(O)—NH$_2$, —(C$_1$-C$_{12}$ alkyl)-C(O)—NH(C$_1$-C$_6$ alkyl), —(C$_1$-C$_{12}$ alkyl)-C(O)—NH—(C$_1$-C$_6$ hydroxyalkyl), —(C$_1$-C$_{12}$ alkyl)-C(O)—N(C$_1$-C$_6$ alkyl)$_2$, —(C$_1$-C$_{12}$ alkyl)-C(O)—N(C$_1$-C$_6$ hydroxyalkyl)$_2$, —(C$_1$-C$_{12}$ alkyl)-O—(C$_1$-C$_6$ alkyl), —(C$_1$-C$_{12}$alkyl)-S—(C$_1$-C$_6$ alkyl), —(C$_1$-C$_{12}$ alkyl) —CF$_3$, —(C$_1$-C$_{12}$ alkyl)-O—(C$_1$-C$_6$ hydroxyalkyl), —C$_1$-C$_{12}$ alkyl)-O—(C$_1$-C$_6$ alkyl)-OCH$_3$, —C$_1$-C$_{12}$ alkyl)-(CH)—(O—(C$_1$-C$_6$ alkyl))$_2$, —(C$_6$-C$_{12}$alkyl)-(heterocyclyl), —(C$_1$-C$_{12}$ alkyl)-OAc, —(C$_1$-C$_{12}$ alkyl)-tetrahydrofuran, —(C$_1$-C$_{12}$ alkyl)-pyrrolidine, —(C$_1$-C$_{12}$ alkyl)-N-methylpyrrolidine, —(C$_1$-C$_{12}$ alkyl)-(1,3-dioxane) or —(C$_1$-C$_{12}$ alkyl)-(4,5-dihydrooxazole).

In some embodiments, the compound wherein
$R_2$ is —(C$_1$-C$_8$ alkyl), —(C$_1$-C$_6$ alkenyl), —(C$_1$-C$_6$ alkynyl) —(C$_1$-C$_6$ alkyl)-OH, —(C$_1$-C$_6$ alkyl)-CO$_2$H, —(C$_1$-C$_6$ alkyl)-CO$_2$—(C$_1$-C$_2$ alkyl), —(C$_1$-C$_6$ alkyl)-C(O)—NH$_2$, —(C$_1$-C$_6$ alkyl)-C(O)—NH(C$_1$-C$_2$ alkyl), —(C$_1$-C$_6$ alkyl)-C(O)—NH—(C$_1$-C$_2$ hydroxyalkyl), —(C$_1$-C$_6$ alkyl)-C(O)—N(C$_1$-C$_2$ alkyl)$_2$, —(C$_1$-C$_6$ alkyl)-C(O)—N(C$_1$-C$_2$ hydroxyalkyl)$_2$, —C$_1$-C$_6$ alkyl)-O—(C$_1$-C$_2$ alkyl), —(C$_1$-C$_6$ alkyl)-S—(C$_1$-C$_2$ alkyl), —(C$_1$C$_3$ alkyl)-CF$_3$, —(C$_1$C$_3$ alkyl)-O—(C$_1$-C$_2$ hydroxyalkyl), —(C$_1$-C$_3$ alkyl)-O—(C$_1$-C$_2$ alkyl)-OCH$_3$, —(C$_1$C$_6$ alkyl)-(CH)—(O—(C$_1$-C$_2$ alkyl))$_2$, —(C$_1$-C$_6$ alkyl)-(heterocyclyl), —(C$_1$-C$_6$ alkyl)-OAc, —(C$_1$-C$_6$ alkyl)-tetrahydrofuran, —(C$_1$-C$_6$ alkyl)-pyrrolidine, —(C$_1$-C$_6$ alkyl)-N-methylpyrrolidine, —(C$_1$-C$_6$ alkyl)-(1,3-dioxane) or —(C$_1$-C$_6$ alkyl)-(4,5-dihydrooxazole).

In some embodiments, the compound wherein
$R_2$ is

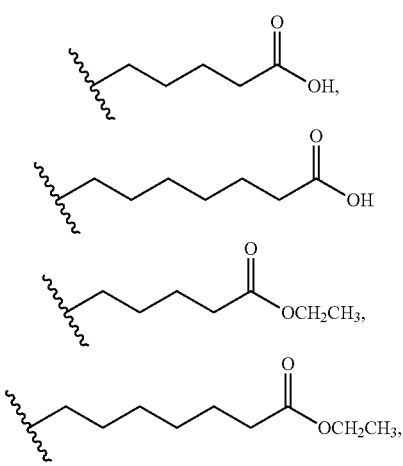

-continued

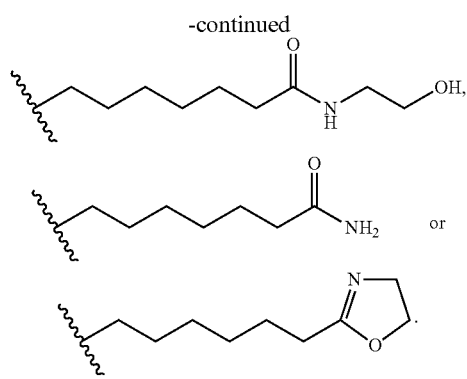

In some embodiments, the compound wherein R₂ is —CH₃, —CH₂CH₃,

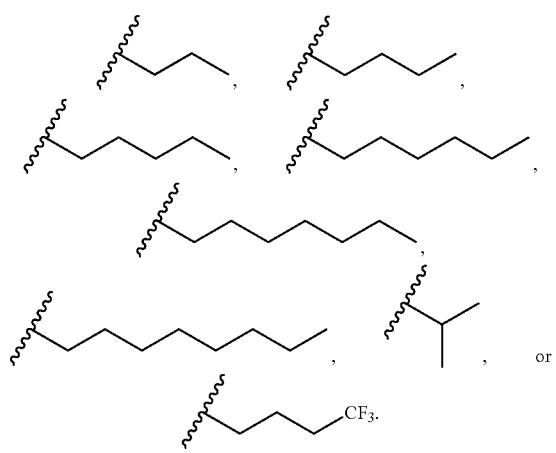

In some embodiments, the compound wherein R₂ is

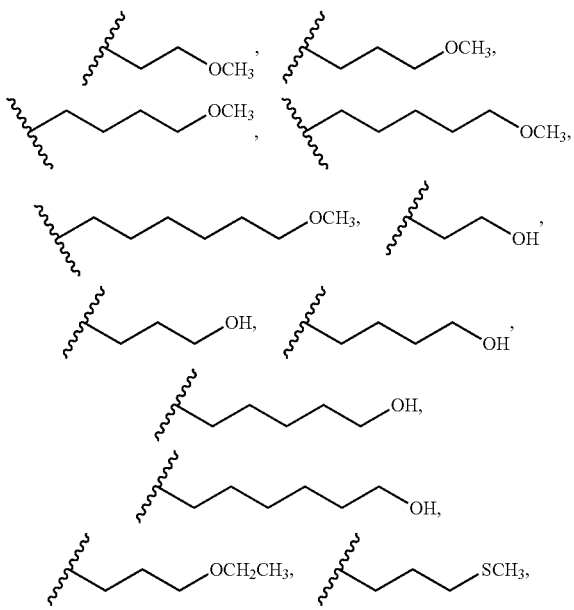

-continued

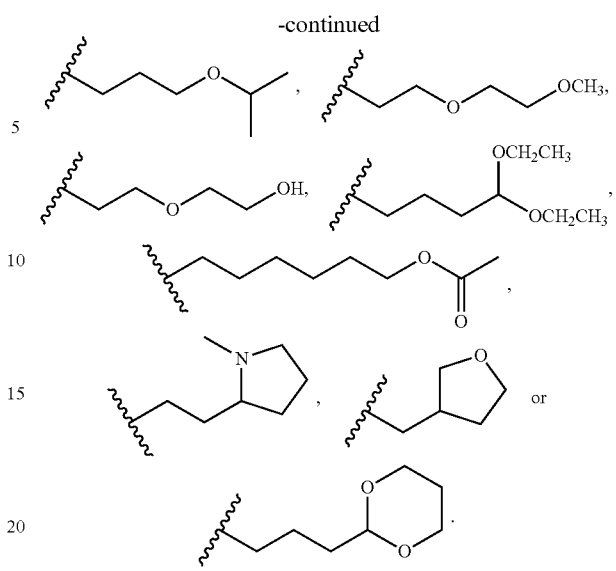

In some embodiments, the compound wherein R₁ is —H or —(C₁-C₆ alkyl).

In some embodiments, the compound wherein R₃ is —H or —(C₁-C₆ alkyl).

In some embodiments, the compound wherein R₁ is —H, —CH₃ or —CH₂CH₃.

In some embodiments, the compound wherein R₃ is —H, —CH₃ or —CH₂CH₃.

In some embodiments, the compound wherein R₁ is —CH₃; and R₃ is —H.

In some embodiments, the compound wherein R₁ is —CH₃; and R₃ is —CH₃.

In some embodiments, the compound wherein R₁ is —CH₂CH₃; and R₃ is H.

The present invention further provides the compound having the structure:

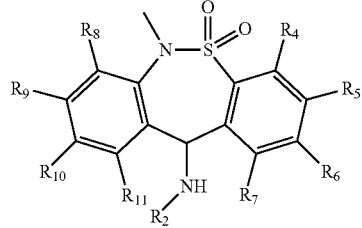

wherein
R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(aikyi)-C(O)—N(alkyl), -(alkyl)-C(O)—N(hydroxyalkyl)₂, -(alkyl)-O-(alkyl), -(alkyl)-S-(alkyl), -(alkyi)—CF₃, -(alkyl)-O-(hydroxyaikyl), -(alkyl)-O-(alkyl)-O-(alkyl), -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₅ is —Cl, —Br, —F, or —I;

R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl).

The present invention provides a compound having the structure:

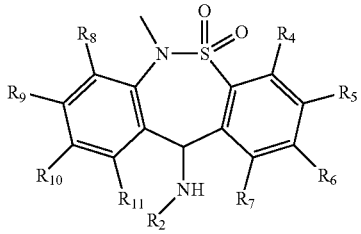

wherein

R$_2$ is -(akyl)-O-(alkyl) or -(alkyl)-O-(alkyl)-O-(alkyl);

R$_5$ is —Cl, —Br, —F, or —I;

R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl);

R$_8$, R$_9$, R$_{10}$ and R$_{11}$ are each independently —H, —Cl, —Br, —F, —I, —CN, —CF$_3$, —OCF$_3$, -(alkyl), -(aryl), -(heteroaryl)-(alkenyl), -(alkynyl), —NH$_2$, —NH-(alkyl), —NH-(alkenyl), —NH-(alkynyl)—NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

The present invention provides a having the structure:

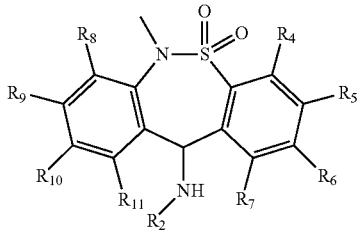

wherein

R$_2$ is -(alkyl), -(alkenyl), -(alkynyl), alkyl)-OH, -alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_5$ is —Br, or —I;

R$_4$, R$_6$ and R$_7$ are each independently —H, —Cl, —Br, —F, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl).

In some embodiments, the compound having the structure:

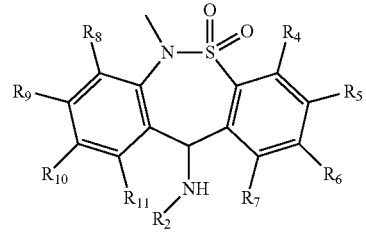

wherein

R$_2$ is -(alkyl)-CO$_2$-(alkyl), -(alkyl)-O-(alkyl) or -(alkyl)-O-(alkyl)-O-(alkyl);

R$_5$ is —Cl, —Br, —F, or —I;

R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl);

R$_8$, R$_9$, R$_{10}$ and R$_{11}$ are each independently —H, —Cl, —Br, —F, —I, —CN, —OCF$_3$, -(alkyl), -(aryl), -(heteroaryl)-(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

In some embodiments, the compound having the structure:

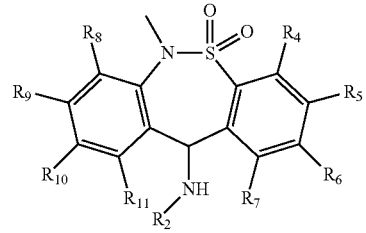

wherein $R_2$ is -(alkyl)-$CO_2$-(alkyl), -(alkyl)-O-(alkyl) or -(alkyl)-O-(alkyl)-O-(alkyl);

$R_5$ is —Cl, —Br, —F, or —I;

$R_4$, $R_6$, $R_7$, $R_8$, $R_9$, $R_{10}$ and $R_{11}$ are each —H.

In some embodiments, the compound having the structure:

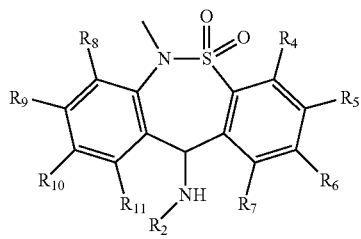

wherein $R_2$ is -(alkyl)-$CO_2$H;

$R_5$ is —Br, —F, or —I;

$R_4$, $R_6$, $R_7$, $R_8$, $R_9$, $R_{10}$ and $R_{11}$ are each —H.

In some embodiments, the compound having the structure:

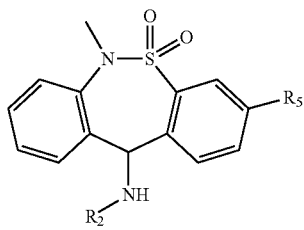

wherein $R_2$ is -(alkyl)-$CO_2$-(alkyl), -(alkyl)-O-(alkyl) or -(alkyl)-O-(alkyl)-O-(alkyl);

$R_5$ is —F.

In some embodiments, the compound having the structure:

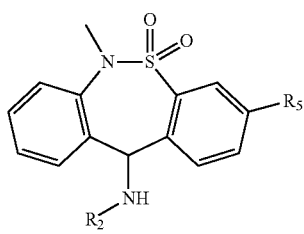

wherein $R_2$ is -(alkyl)-$CO_2$-(alkyl), -(alkyl)-O-(alkyl) or -(alkyl)-O-(alkyl)-O-(alkyl);

$R_5$ is —Cl.

In some embodiments, the compound having the structure:

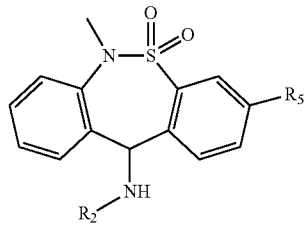

wherein $R_2$ is -(alkyl)-$CO_2$-(alkyl), -(alkyl)-O-(alkyl) or -(alkyl)-O-(alkyl)-O-(alkyl);

$R_5$ is —Br.

In some embodiments, the compound having the structure:

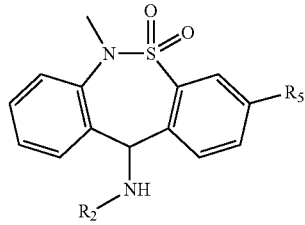

wherein $R_2$ is -(alkyl)-$CO_2$-(alkyl), -(alkyl)-O-(alkyl) or -(alkyl)-O-(alkyl)-O-(alkyl);

$R_5$ is —I.

In some embodiments, the compound wherein $R_2$ is

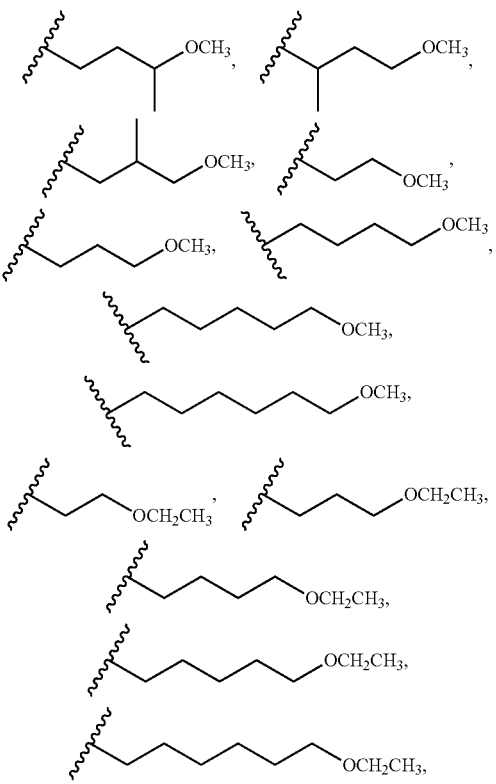

-continued

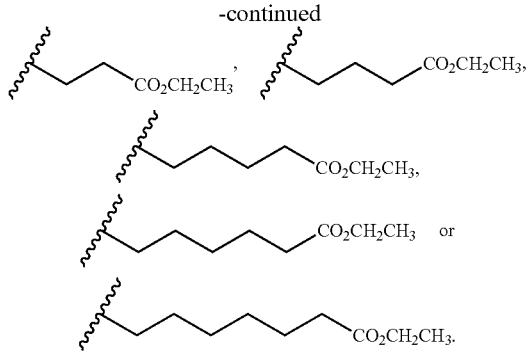

The present invention provides a compound having the structure:

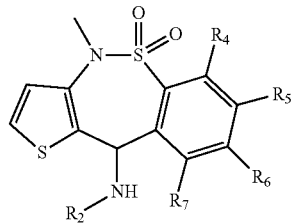

wherein
R$_2$ is -(alkyl), -(alkenyl), -(alkynyl), -(alkyl)-OH, (alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
R$_5$ is —Cl, —Br, —F, or —I;
R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$(aryl) or —SO$_2$-(heteroaryl).

The present invention provides a compound having the structure:

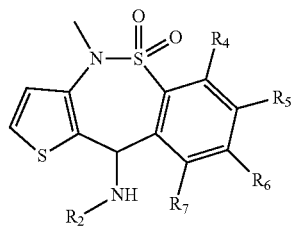

wherein
R$_2$ is -(alkyl)-CO$_2$-(alkyl), -(alkyl)-O-(alkyl) or -(alkyl)-O-(alkyl)-O-(alkyl);
R$_5$ is —Cl, —Br, —F, or —I;
R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-heteroaryl), —SO$_2$-(alkyl), —SO$_2$-(aryl) or —SO$_2$-(heteroaryl).

The present invention provides a compound having the structure:

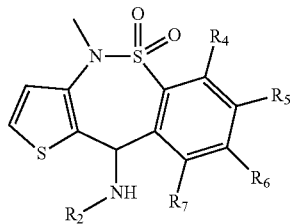

wherein
R$_2$ is -(alkyl), -(alkenyl), -(alkynyl), -(alkyl)-OH, (alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
R$_5$ is —Cl, —Br, —F, or —I;
R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl).

The present invention provides a compound of claim 34 having the structure:

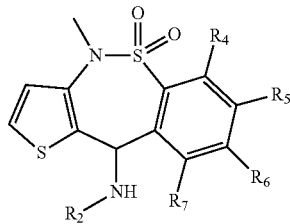

wherein
R$_2$ is -(alkyl)-CO$_2$ (alkyl), -(alkyl)-O-(alkyl) or -(alkyl)-O-(alkyl)-O-(alkyl);

$R_5$ is —Cl, —Br, —F, or —I;

$R_4$, $R_6$ and $R_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl);

$R_8$, $R_9$, $R_{10}$ and $R_{11}$ are each independently —H, —Cl, —Br, —F, —I, —CN, —CF$_3$, —OCF$_3$, -(alkyl), -(aryl), -(heteroaryl)-(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-heteroaryl).

In some embodiments, the compound having the structure:

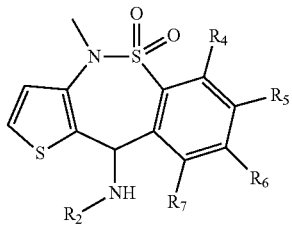

wherein $R_2$ is (alkyl)-CO$_2$H;

$R_5$ is —Cl, —Br, —F, or —I;

$R_4$, $R_6$, and $R_7$ are each —H.

In some embodiments, the compound having the structure:

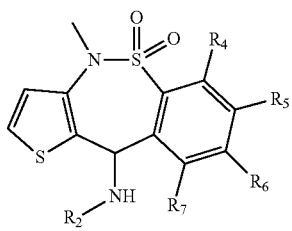

wherein $R_2$ is -(alkyl)-CO$_2$-(alkyl), -(alkyl)-O-(alkyl) or -(alkyl)-O-(alkyl)-O-(alkyl);

$R_5$ is —Cl, —Br, —F, or —I;

$R_4$, $R_6$, and $R_7$ are each —H.

In some embodiments, the compound having the structure:

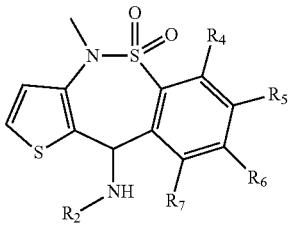

wherein $R_2$ is -(alkyl)-CO$_2$-(alkyl), -(alkyl)-O-(alkyl) or -(alkyl)-O-(alkyl)-O-(alkyl);

$R_5$ is —F.

In some embodiments, the compound having the structure:

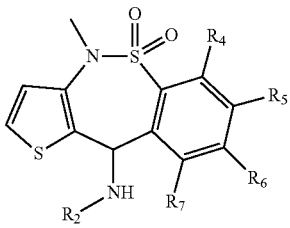

wherein $R_2$ is -(alkyl)-CO$_2$-(alkyl), -(alkyl)-O-(alkyl) or -(alkyl)-O-(alkyl)-O-(alkyl);

$R_5$ is —Cl.

In some embodiments, the compound having the structure:

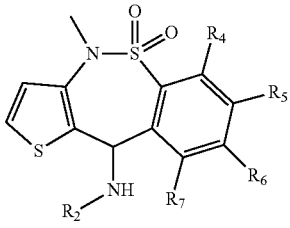

wherein $R_2$ is -(alkyl)-CO$_2$-(alkyl), -(alkyl)-O-(alkyl) or -(alkyl)-O-(alkyl)-O-(alkyl);

$R_5$ is —Br.

In some embodiments, the compound having the structure:

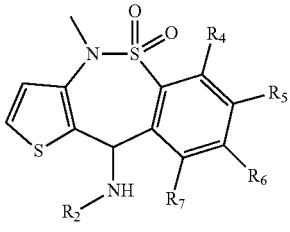

wherein $R_2$ is -(alkyl)-CO$_2$-(alkyl), -(alkyl)-O-(alkyl) or -(alkyl)-O-(alkyl)-O-(alkyl);

$R_5$ is —I.

In some embodiments, the compound wherein R₂ is
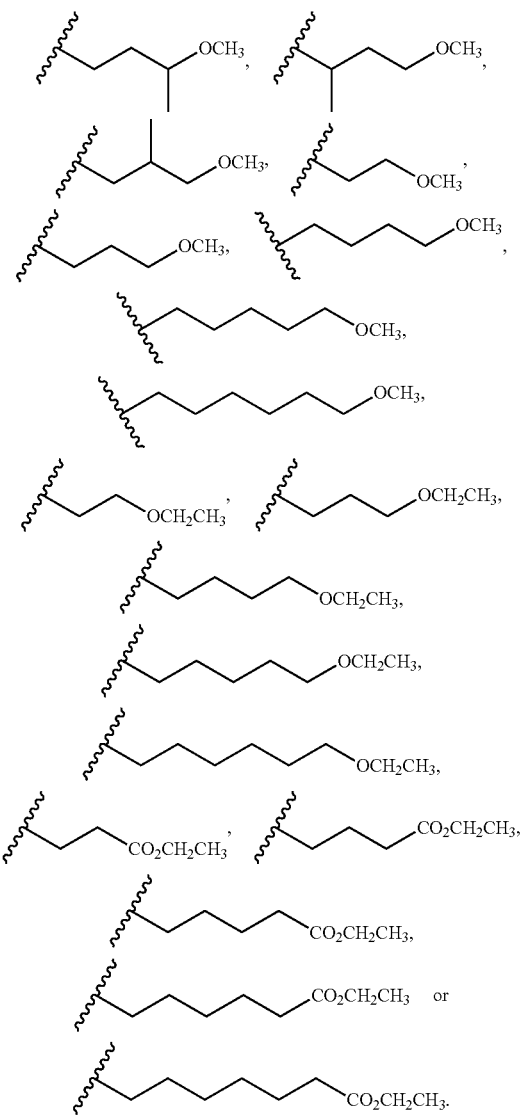
In some embodiments, the compound having the structure:
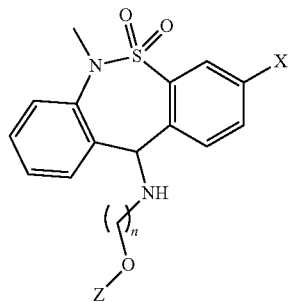
wherein X=F, Cl, Br, I, Me, SMe, OMe or OPh; Z is alkyl; and n=2-10.
In some embodiments, the compound having the structure:
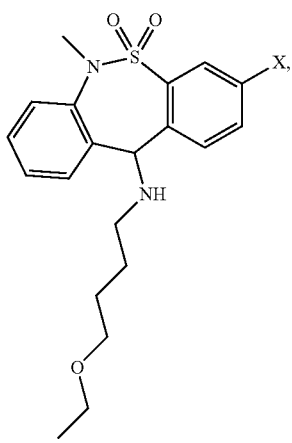
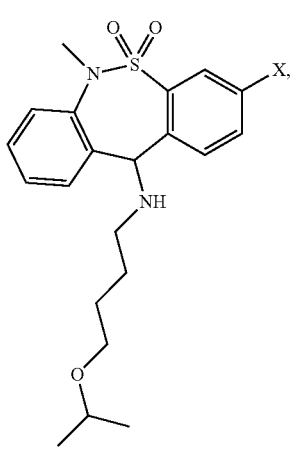
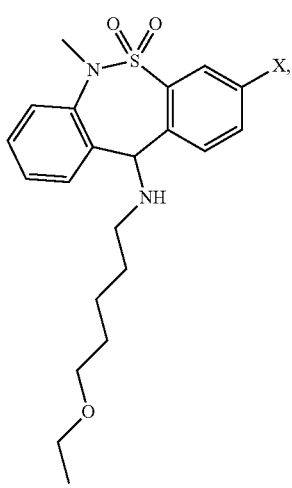

37
-continued
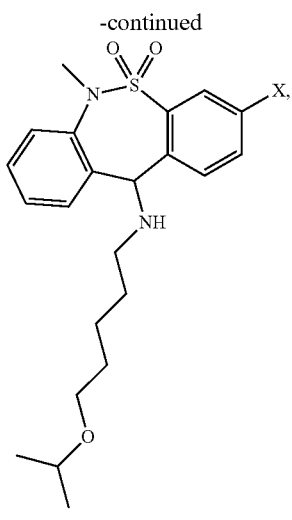
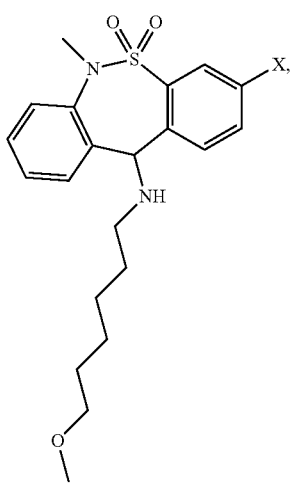
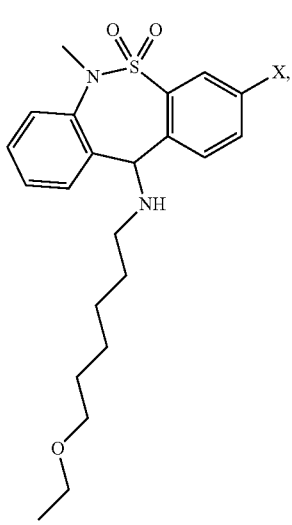
38
-continued
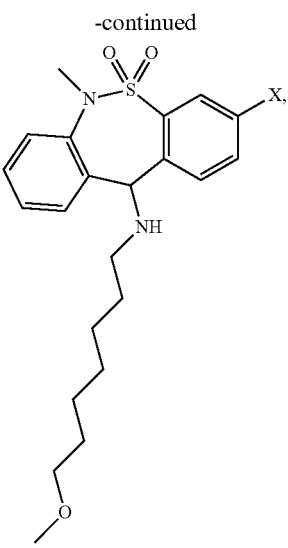
wherein X=X=F, Cl, Br, I, Me, SMe, OMe or OPh.
In some embodiments, the compound is prepared by the following process:
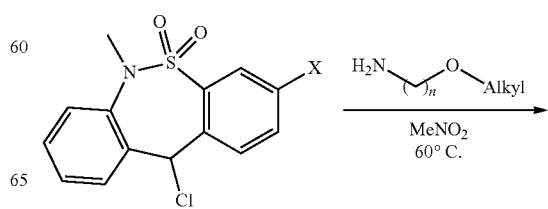

-continued
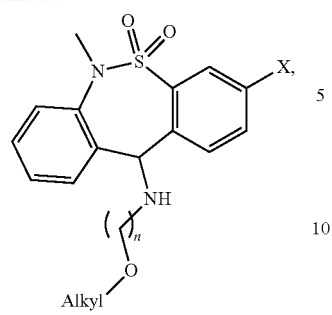
wherein X=F, Cl, Br, I, Me, SMe, OMe or OPh; and n=2-10.
In some embodiments, the compoupd. hoesin the. structure:
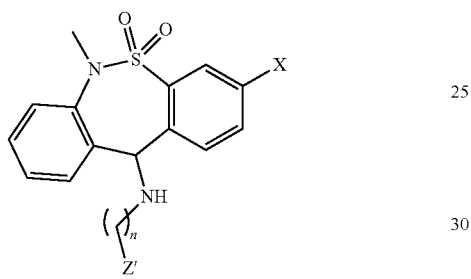
wherein X=F, Cl, Br, I, Me, SMe, OMe or OPh; Z' is heteroaryl; and n=1-10.
In some embodiments, the compound having the structure:
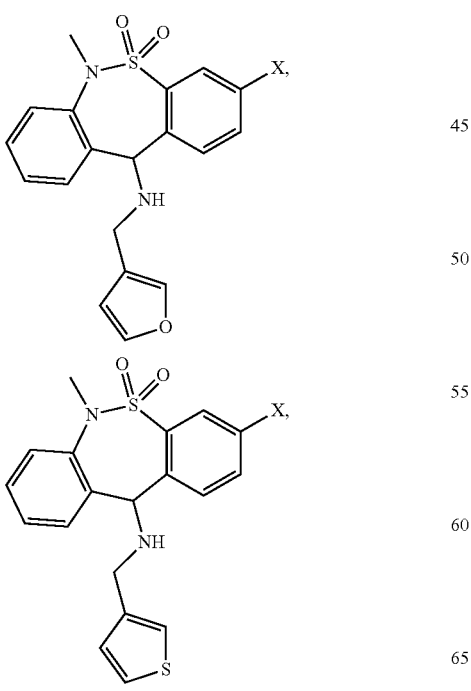
-continued
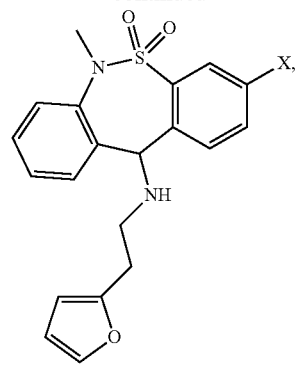
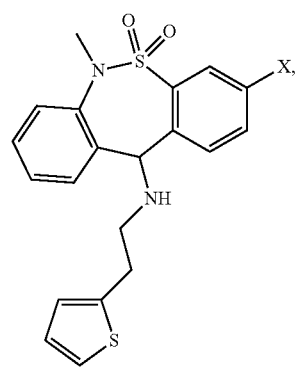
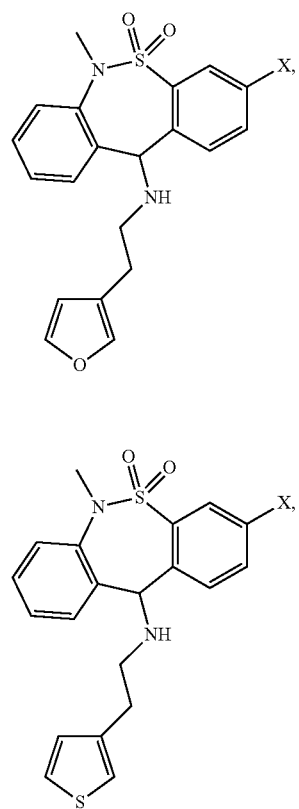

-continued

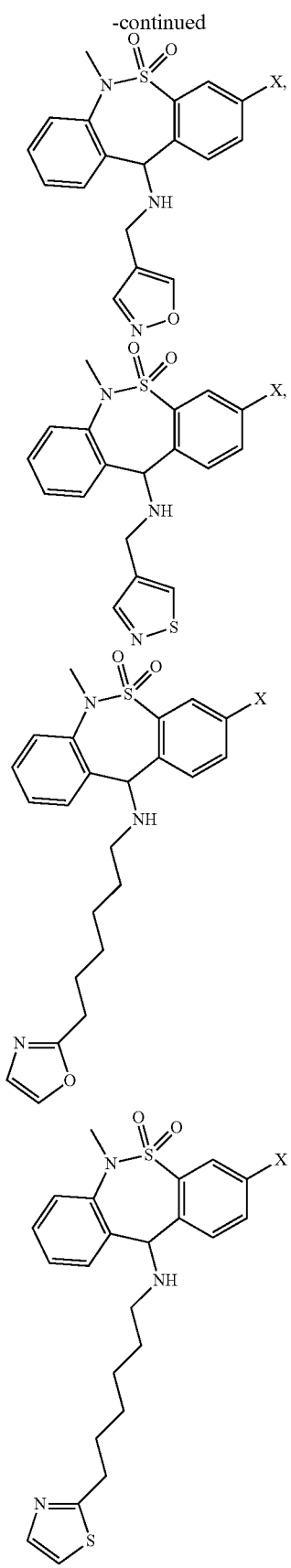

wherein X=F, Cl, Br, I, Me, SMe, OMe or OPh.

In some embodiments, the compound is prepared by the following process:

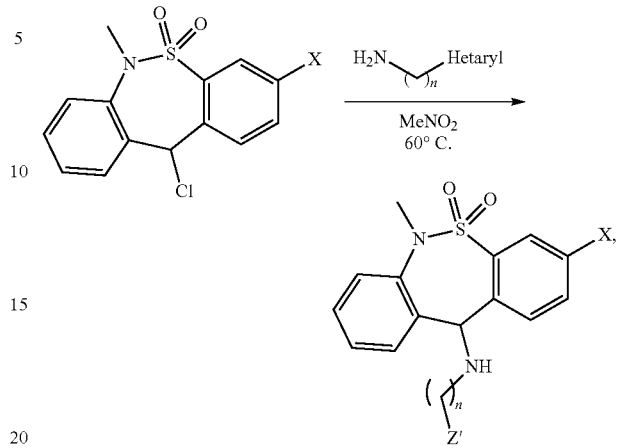

wherein X=F, Cl, Br, I, Me, SMe, OMe or OPh; Z' is hetero aryl; and n=1-10.

In some embodiments, the heteroaryl is furan, thiophene, imidazole, pyrazole, oxazole, thiazole, isoxazole or isothiazole.

In some embodiments, the compound having the structure:

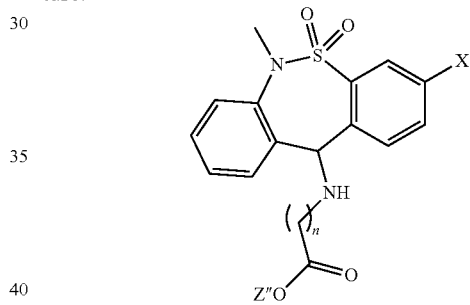

wherein X=F, Cl, Br, I, Me, SMe, OMe or OPh; Z" is Me, Et, Pr, iPR or Phenyl; and n=2-10.

In some embodiments, the compound having the structure:

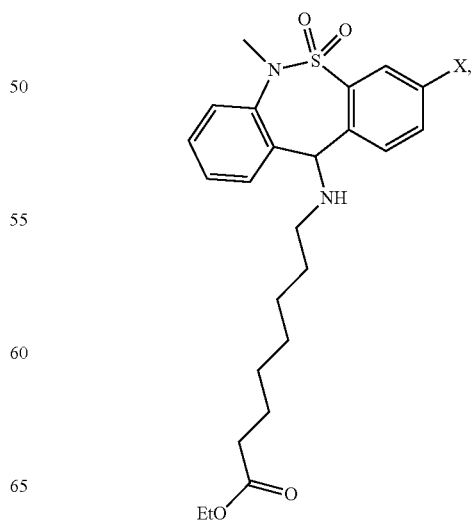

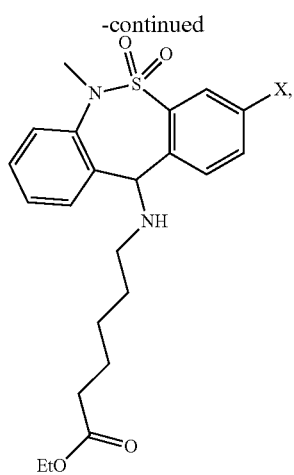
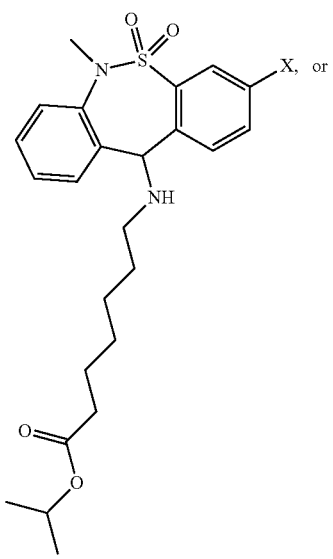
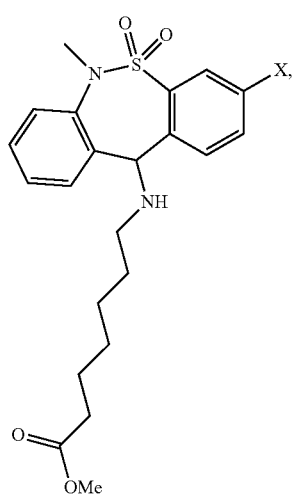
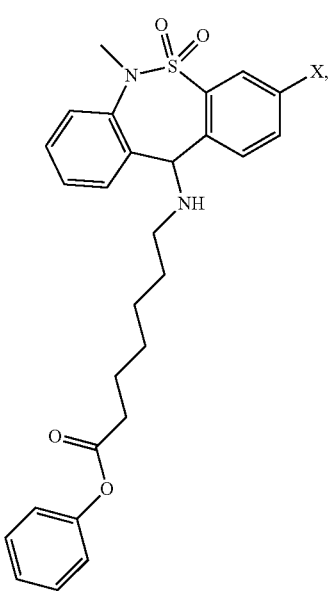
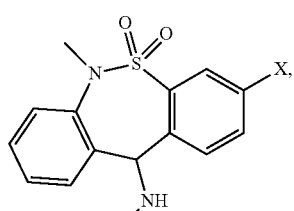
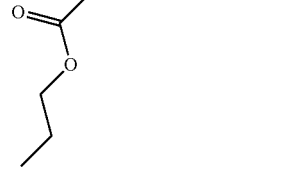
wherein X=F, Cl, Br, I, Me, SMe, OMe or OPh.
In some embodiments, the compound is prepared by the following process:
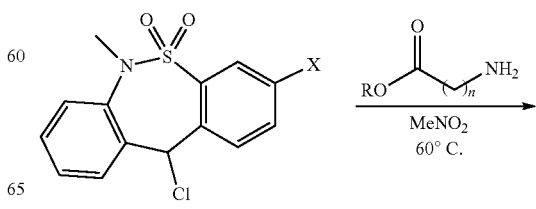

-continued
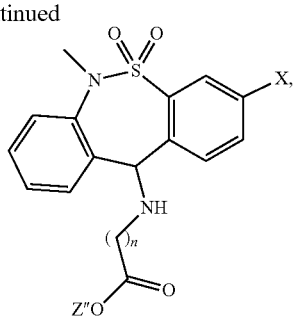
wherein X=F, Cl, Br, I, Me, SMe, OMe or OPh; Z" is Me, Et, Pr, iPR or Phenyl; and n=2-10.
In some embodiments, the compound having the structure:
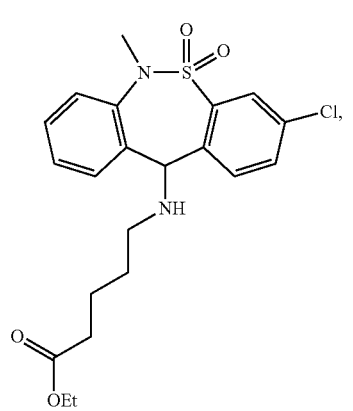
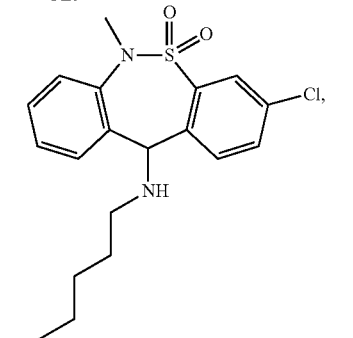
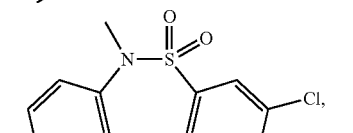
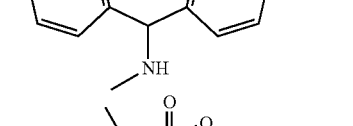
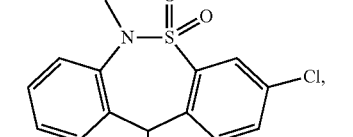
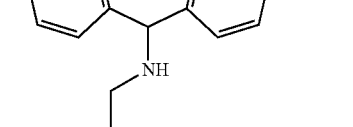
-continued
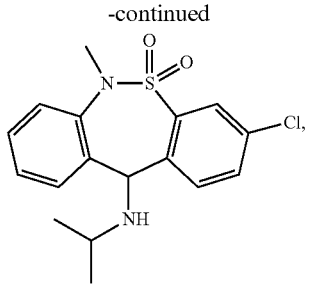
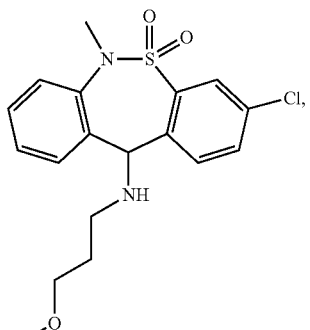
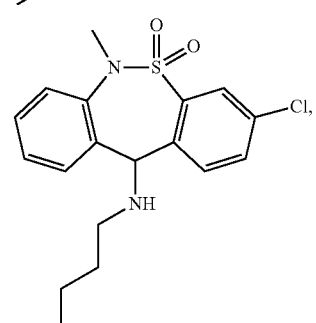
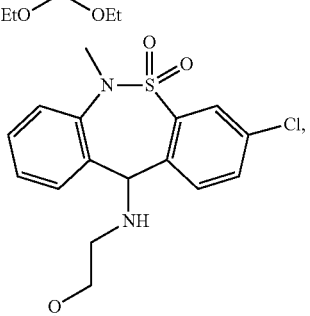
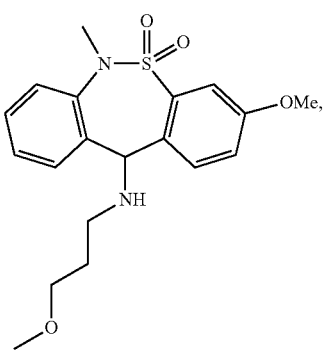

47
-continued
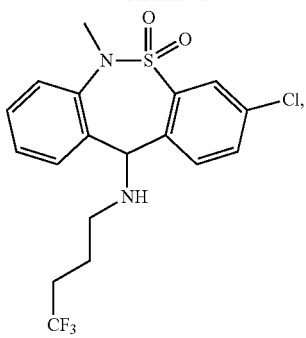
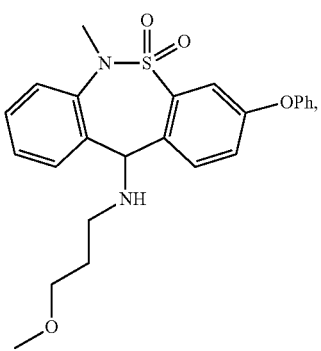
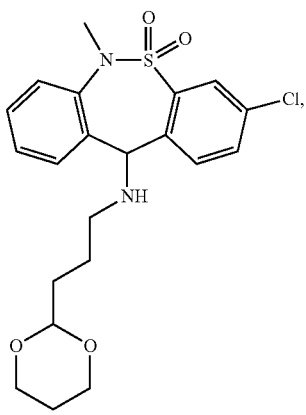
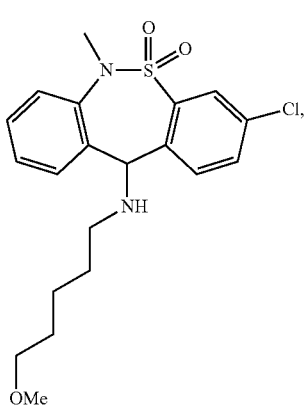
48
-continued
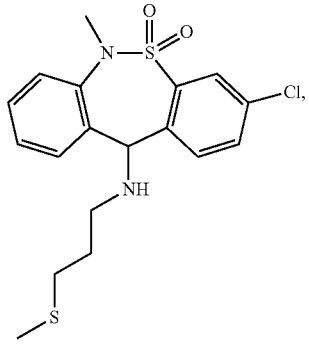
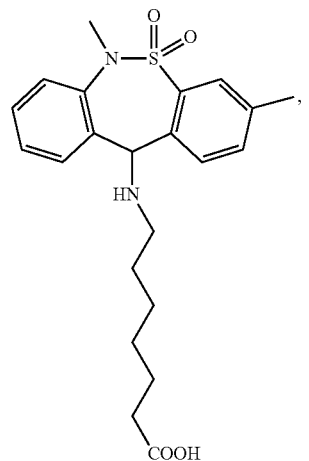
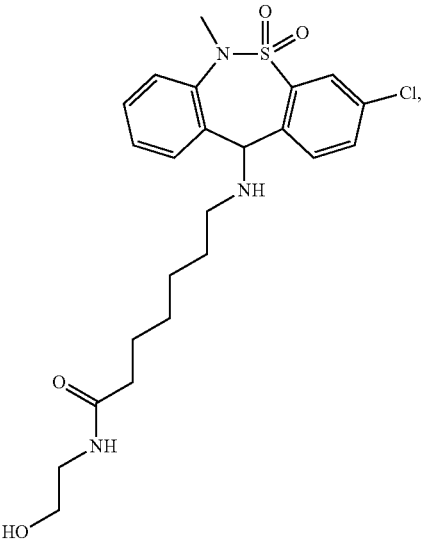

-continued
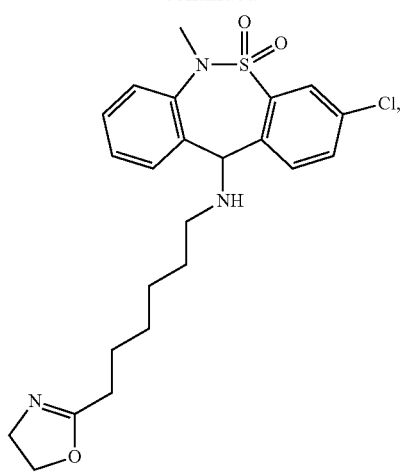
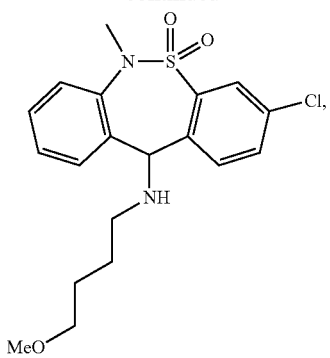
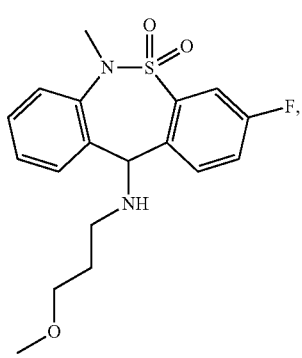
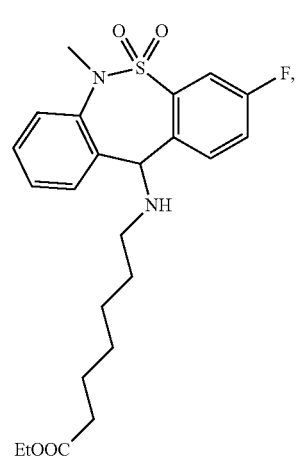
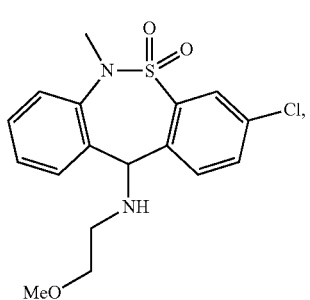

-continued
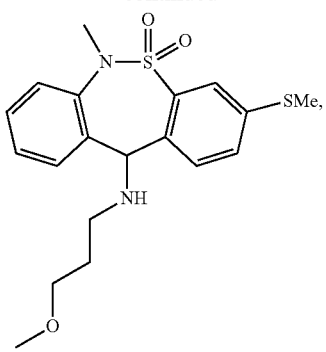
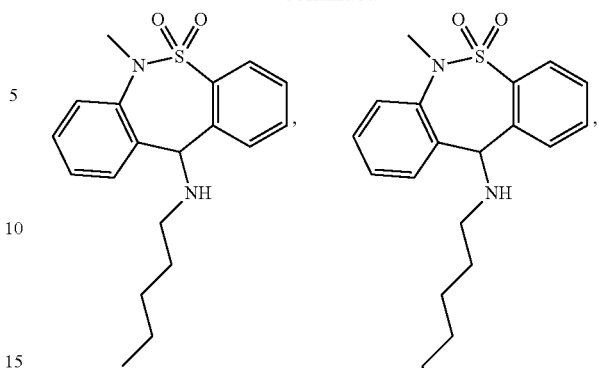
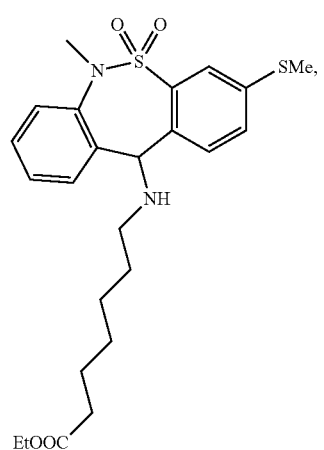
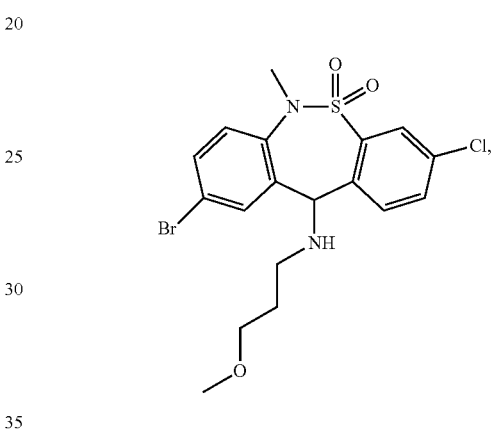
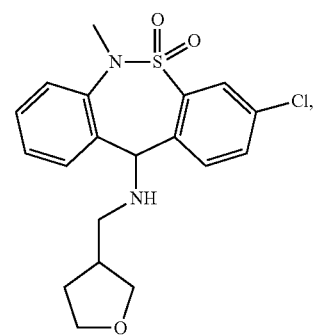
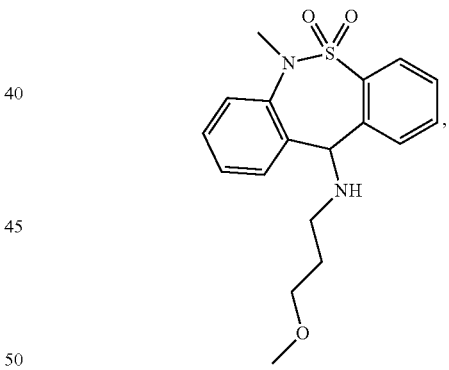
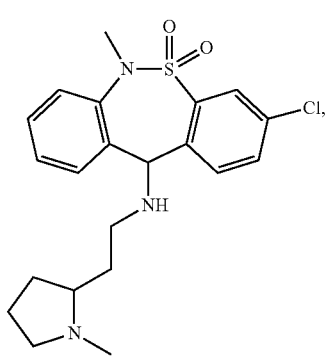
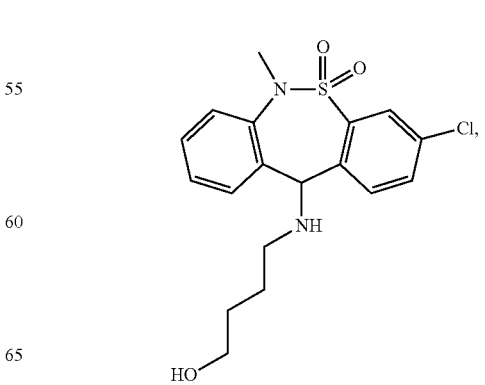

53
-continued
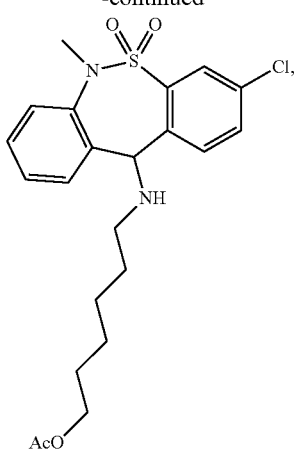
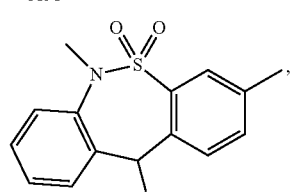
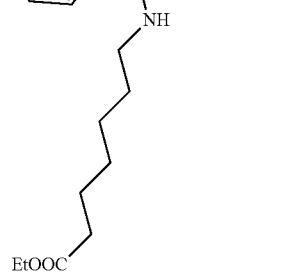
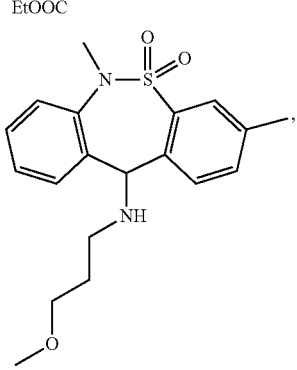
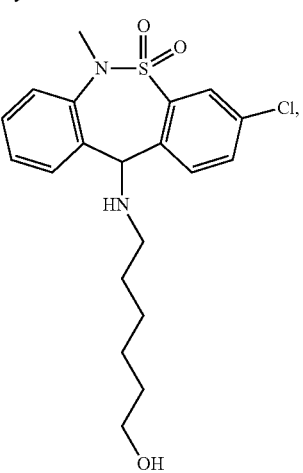
54
-continued
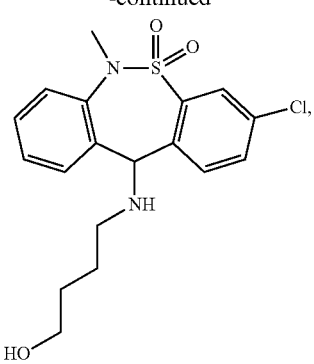
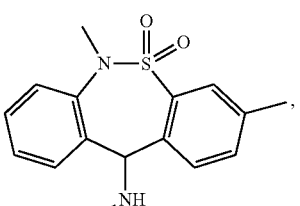
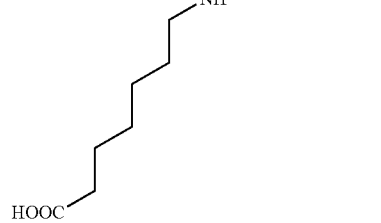
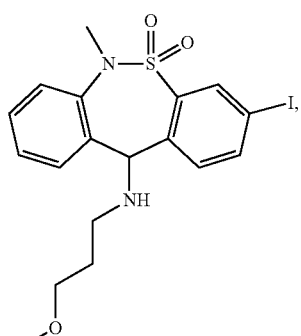
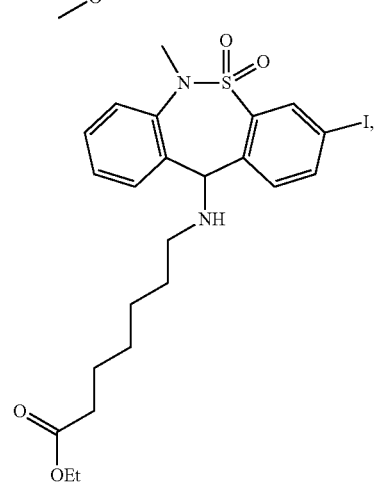

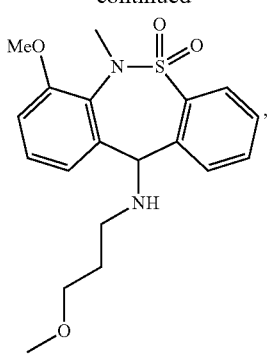
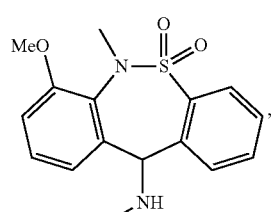
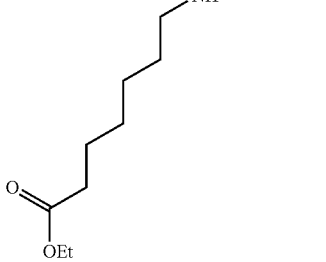
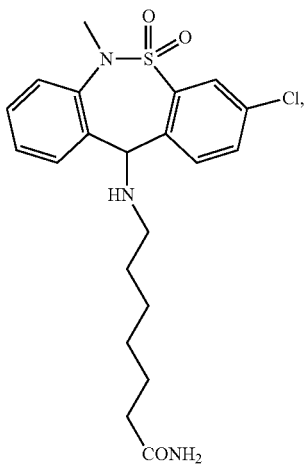
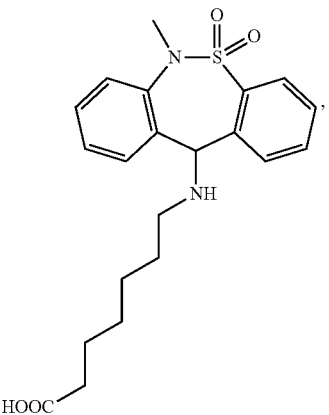
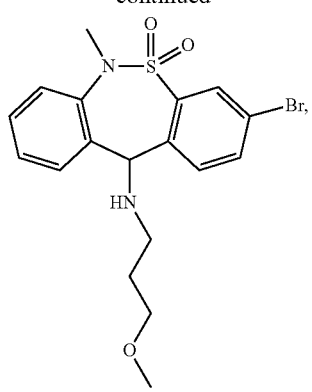
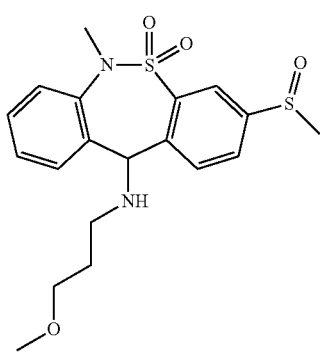
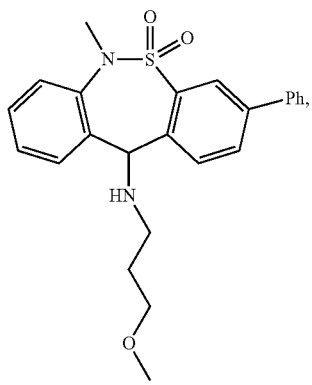 or
or a pharmaceutically acceptable salt thereof.
In some embodiments, the compound having the sturcuture:
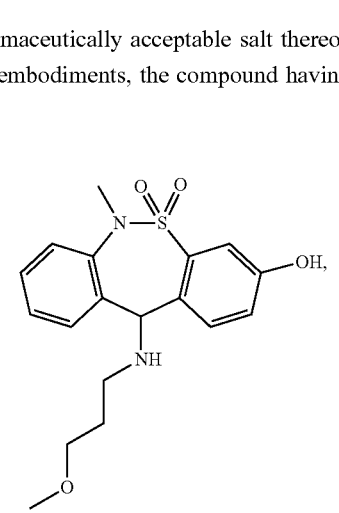

57
-continued
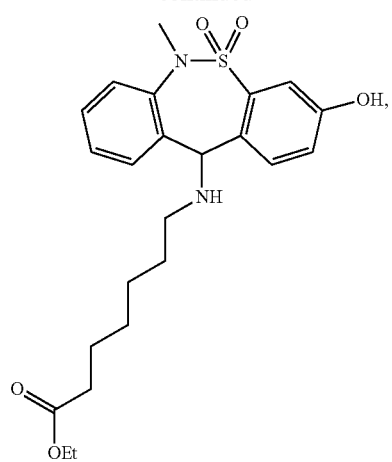
58
-continued
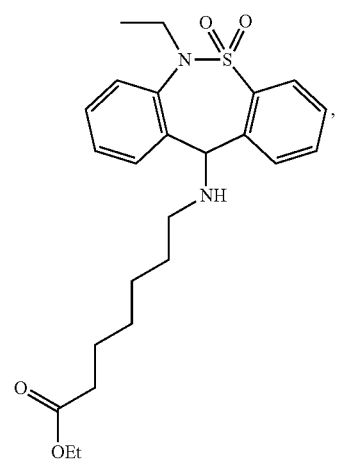
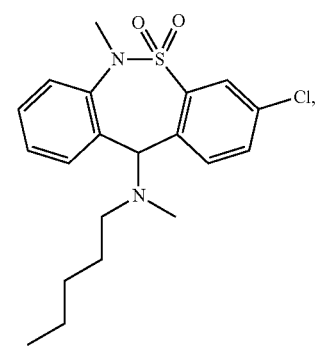
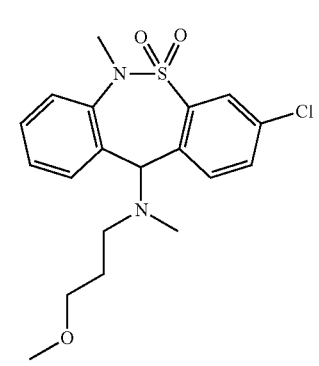
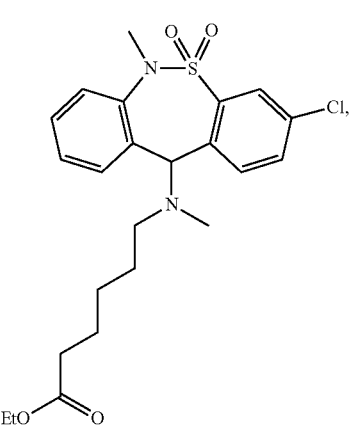

59
-continued
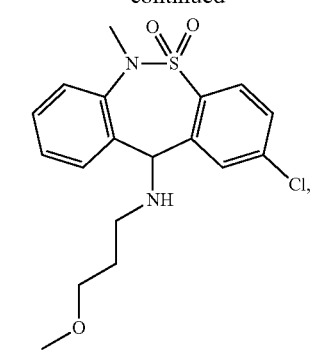
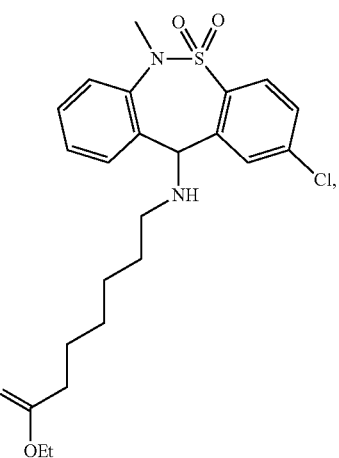
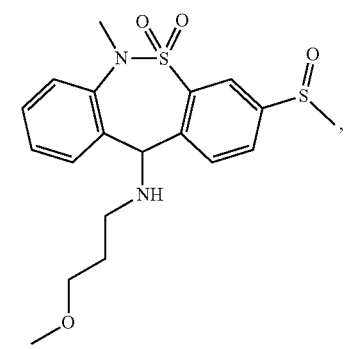
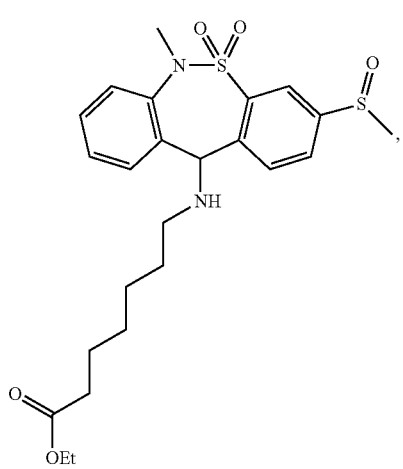
60
-continued
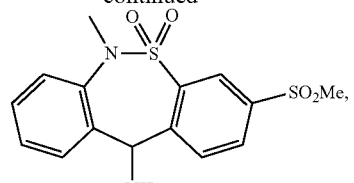
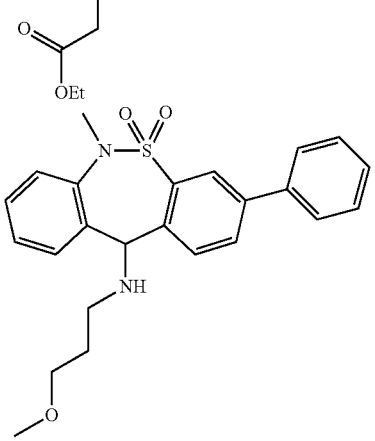
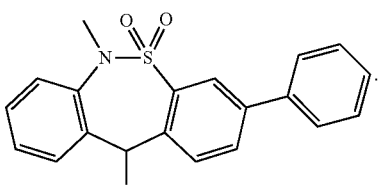
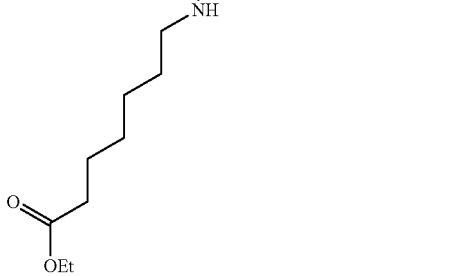
or a pharmaceutically acceptable salt thereof.
In some embodiments, the compound having the structure:
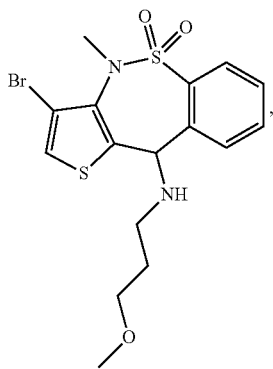

-continued
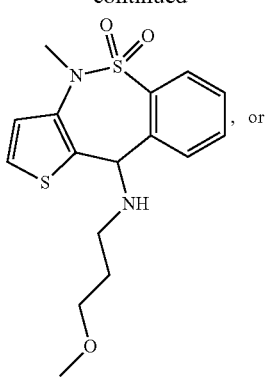, or
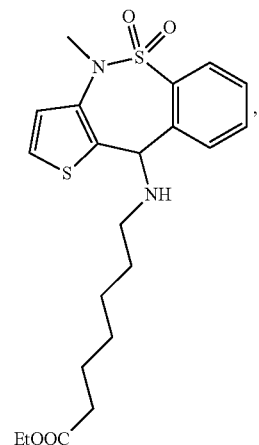
or a pharmaceutically acceptable salt thereof.
In some embodiments, the compound having the structure:
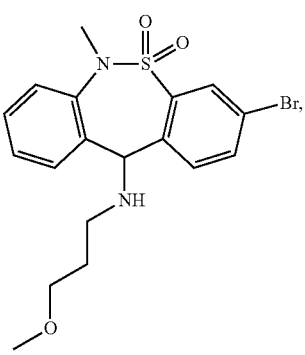
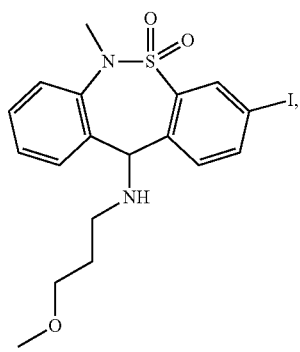
-continued
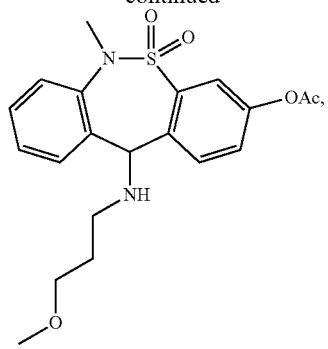
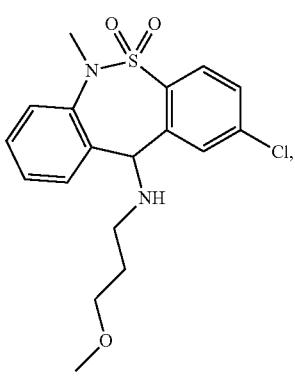
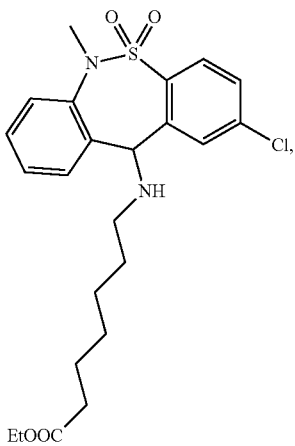
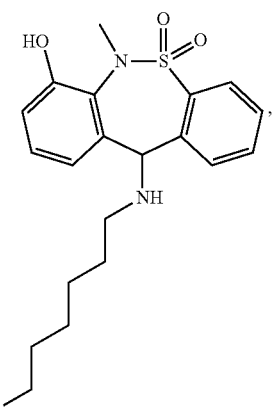

-continued
63
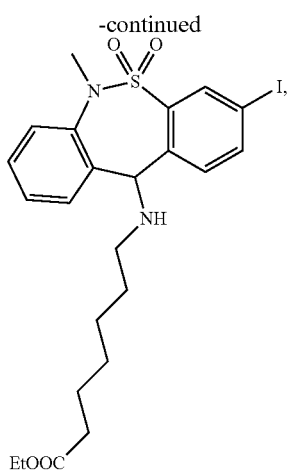
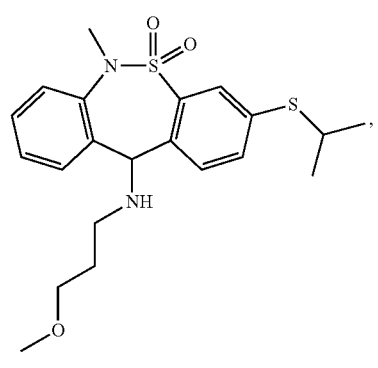
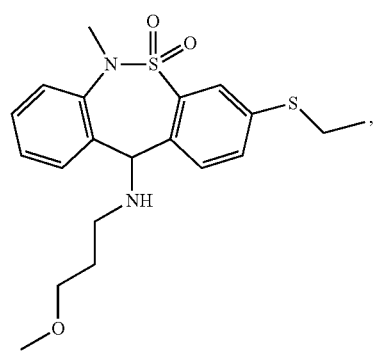
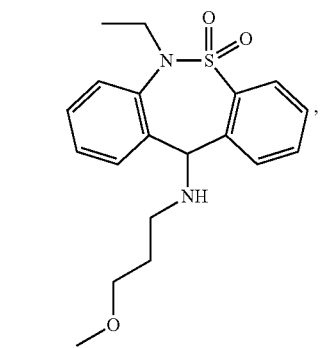
-continued
64
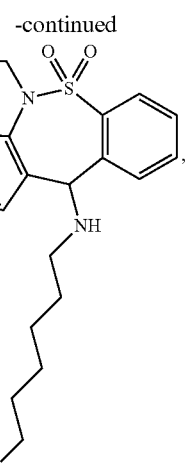
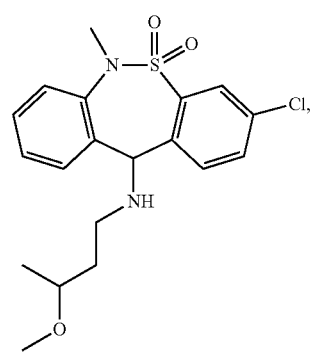
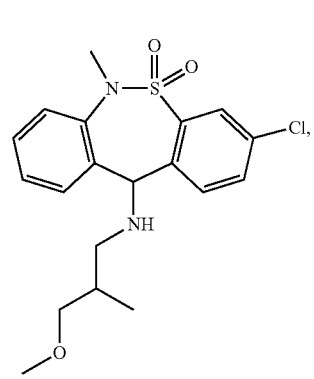
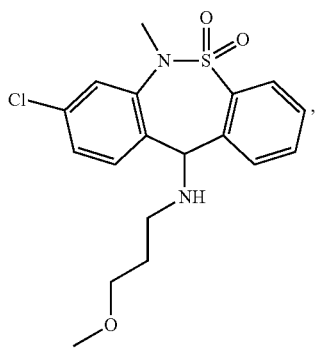

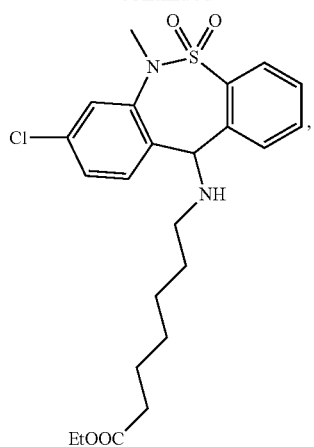
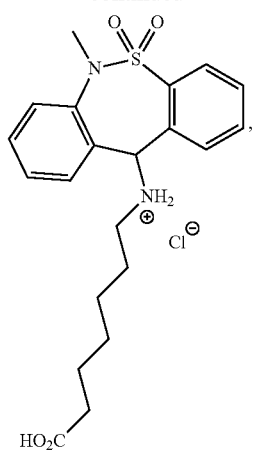

67
-continued
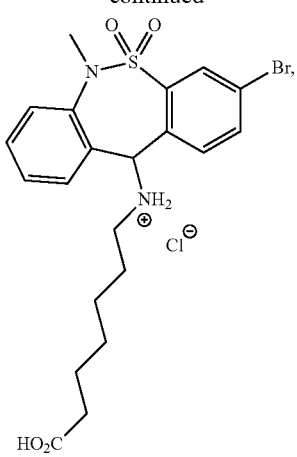
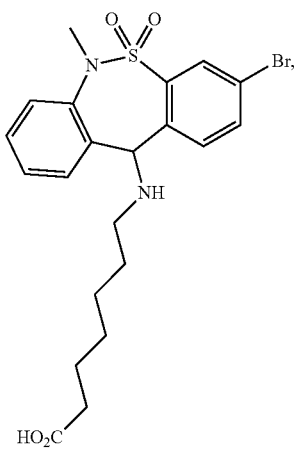
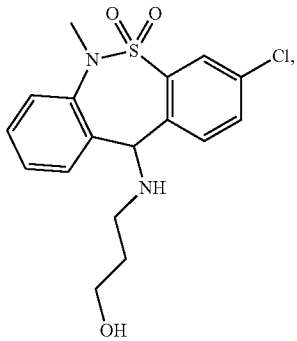
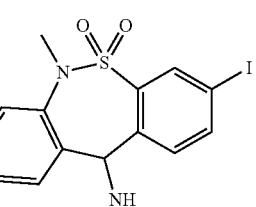 or
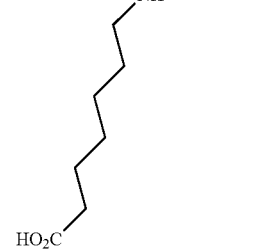
68
-continued
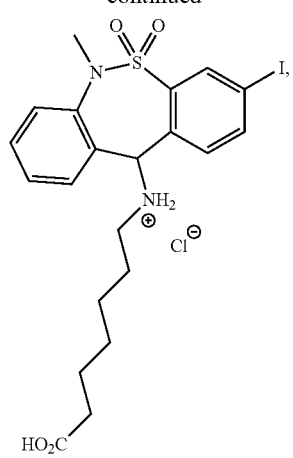
or a pharmaceutically acceptable salt thereof.
In some embodiments, the compound having the structure:
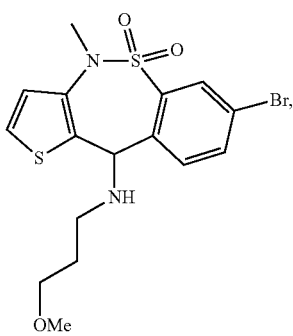
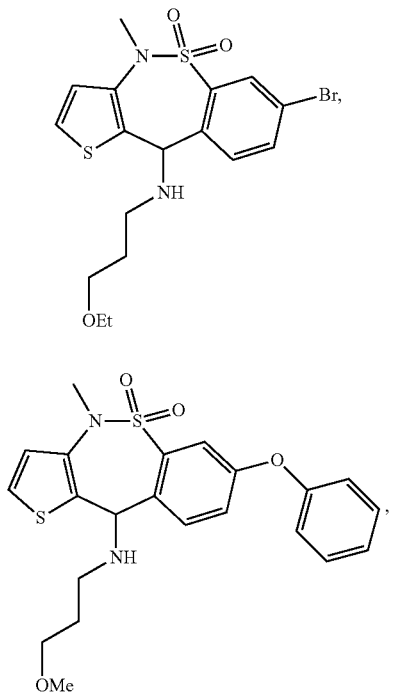

-continued

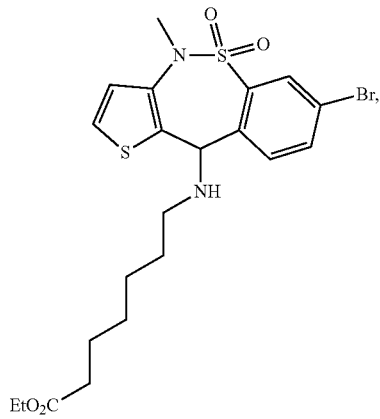

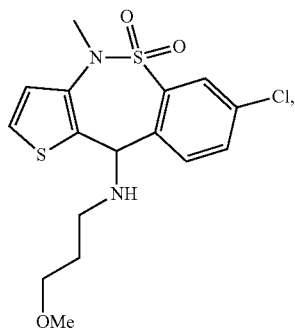

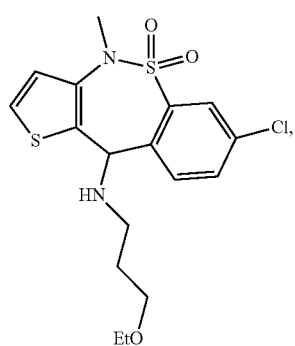

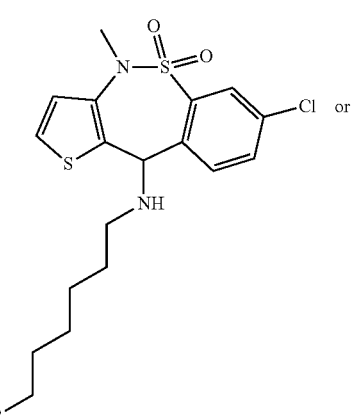

-continued

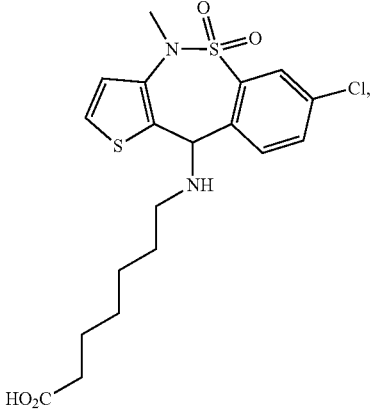

or a pharmaceutically acceptable salt thereof.

In some embodiments, the compound having the structured

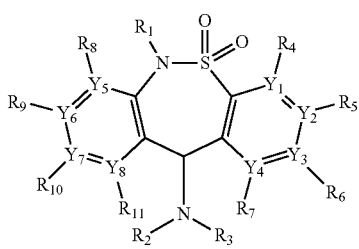

wherein $Y_1$, $Y_2$, $Y_3$, $Y_4$, $Y_5$, $Y_6$, $Y_7$, and $Y_8$ are each C;

$R_1$ is —CH$_3$ or —CH$_2$CH$_3$;

$R_2$ is —(C$_1$-C$_8$ alkyl), —(C$_1$-C$_6$ alkyl)-OH, —(C$_1$-C$_6$ alkyl)-CO$_2$H, —(C$_1$-C$_6$ alkyl)-CO$_2$CH$_2$CH$_3$, —(C$_1$-C$_6$ alkyl)-OCH$_3$, —(C$_1$-C$_6$ alkyl)-C(O)NH$_2$, —(C$_1$-C$_6$ alkyl)CF$_3$, —(C$_1$-C$_6$ alkyl)-SCH$_3$, —(C$_1$-C$_6$ alkyl)—OAc, —(C$_1$-C$_6$ alkyl)-CH(CH$_2$-CH$_3$)$_2$, —(C$_1$-C$_6$ alkyl)-O-(C$_1$-C$_6$ alkyl), —(C$_1$-C$_6$ alkyl)-(1,3-dioxane), —(C$_1$-C$_6$ alkyl)-(1,3-dioxane), —(C$_1$C$_6$ alkyl)-(4,5-dihydrooxazole), —(C$_1$C$_2$ alkyl)-O—(C$_1$-C$_2$ alkyl)-OCH$_3$, —(C$_1$-C$_2$ alkyl)-O—(C$_1$-C$_2$ alkyl)-OH, —(C$_1$-C$_6$ alkyl)-C(O)—NH—(C$_1$C$_2$ hydroxyalkyl), —(C$_1$-C$_2$ alkyl)-tetrahydrofuran, or —(C$_1$-C$_{-2}$ alkyl)-pyrrolidine;

$R_3$ is —H;

$R_8$, $R_9$, $R_{10}$ and $R_{11}$ are each independently —H, —OCH$_3$, or —Br; and $R_4$, $R_5$, $R_6$, and $R_7$ are each independently —H, —Cl, —Br, —F, —I, —CH$_3$, —OCH$_3$, —OH, —OAc, —SCH$_3$, —SCH$_2$CH$_3$, S-iPr, —SO$_2$CH$_3$, —S(O)CH$_3$, -(phenyl), —O—CH$_2$(phenyl) or —O-(phenyl), or a pharmaceutically acceptable salt thereof.

In some embodiments, the compound having the structure:

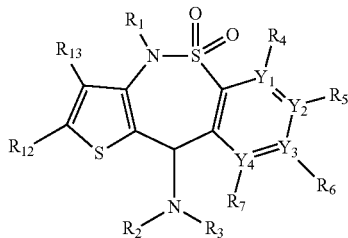

wherein $Y_1$, $Y_2$, $Y_3$, and $Y_4$ are each C;

$R_1$ is —$CH_3$;

$R_2$ is —($C_1$-$C_6$ alkyl)-$OCH_3$, —$C_1$-$C_6$ alkyl)-O—($C_1C_6$ alkyl), —($C_1C_6$ alkyl)-$CO_2CH_2CH_3$ or —($C_1$-$C_6$ alkyl)-$OCH_3$;

$R_3$, $R_4$, $R_5$, $R_6$ and $R_{12}$ are each —H, —Cl, —Br, —F, —I; and $R_{13}$ is —H or —Br, or a pharmaceutically acceptable salt thereof.

In some embodiments, the compound having the structure:

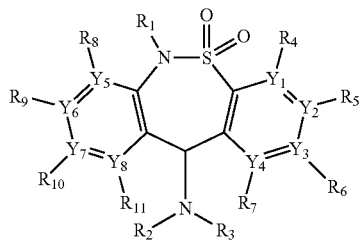

wherein $Y_1$, $Y_2$, $Y_3$, $Y_4$, $Y_5$, $Y_6$, $Y_7$ and $Y_8$ are each C;

$R_1$ is —$CH_3$;

$R_2$ is ($C_1$-$C_8$ alkyl), —($C_1$-$C_6$ alkyl)-OH, —($C_1$-$C_6$ alkyl)-$CO_2H$, —($C_1$-$C_6$ alkyl)-$CO_2CH_2CH_3$, —($C_1$-$C_6$ alkyl)-$OCH_3$, —($C_1$-$C_6$ alkyl)-$C(O)NH_2$, —($C_1$-$C_6$ alkyl)-$CF_3$, —($C_1$-$C_6$ alkyl)-$SCH_3$, —($C_1$-$C_6$ alkyl)-OAc, —$C_1$-$C_6$ alkyl)-$CH(CH_2CH_3)_2$, —($C_1$-$C_6$ alkyl)-O—($C_1$-$C_6$ alkyl), —($C_1$-$C_6$ alkyl)-(1,3-dioxane), —($C_1C_6$ alkyl)-(1,3-dioxane), —($C_1$-$C_6$ alkyl)-(4,5-dihydrooxazole), —($C_1$-$C_2$ alkyl)-O-($C_1$-$C_2$ alkyl)-$OCH_3$, —($C_1$-$C_2$ alkyl)-O—($C_1$-$C_2$ alkyl)-OH, —($C_2$-$C_6$ alkyl)-C(O)—NH—($C_1$-$C_2$ hydroxyalkyl), —($C_1$-$C_2$ alkyl)-tetrahydrofuran, or —($C_1$-$C_2$ alkyl)-pyrrolidine;

$R_3$ is —H;

$R_8$, $R_9$, $R_{10}$ and $R_{11}$ are each independently —H, —$OCH_3$, or —Br; and $R_4$, $R_5$, $R_6$ and $R_7$ are each independently —H, —Cl, —Br, —F, —I, —$CH_3$, —$OCH_3$, —OH, —OAc, —$SCH_3$, —$SO2CH3$, —$S(O)CH_3$, -(phenyl) or —O-(phenyl), or a pharmaceutically acceptable salt thereof.

In some embodiments, the compound having the structure:

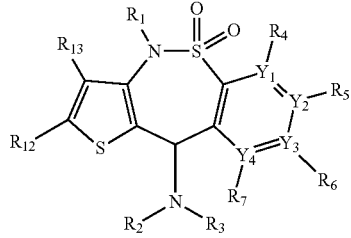

wherein $Y_1$, $Y_2$, $Y_3$, and $Y_4$ are each C;

$R_1$ is —$CH_3$;

$R_2$ is —($C_1$-$C_6$ alkyl)-$CO_2CH_2CH_3$ or —($C_1$-$C_6$ alkyl)-$OCH_3$;

$R_3$, $R_4$, $R_5$, $R_6$ and $R_{12}$ are each —H; and $R_{13}$ is —H or Br, or a pharmaceutically acceptable salt thereof.

In one embodiment of any of the compounds disclosed herein $R_2$ is -(alkyl). In one embodiment of any of the compounds disclosed herein $R_2$ is -(alkenyl). In one embodiment of any of the compounds disclosed herein $R_2$ is -(alkynyl). In one embodiment of any of the compounds disclosed herein $R_2$ is -(alkyl)-$CO_2H$. In one embodiment of any of the compounds disclosed herein $R_2$ is -(alkyl)-$CO_2$-(alkyl). In one embodiment of any of the compounds disclosed herein $R_2$ is -(alkyl)-OH. In one embodiment of any of the compounds disclosed herein $R_2$ is -(alkyl)-C(O)—$NH_2$. In one embodiment of any of the compounds disclosed herein $R_2$ is -(alkyl)-C(O)—NH(alkyl). In one embodiment of any of the compounds disclosed herein $R_2$ is -(alkyl)-C(O)—NH-(hydroxyalkyl). In one embodiment of any of the compounds disclosed herein $R_2$ is -(alkyl)-C(O)—N(alkyl)$_2$. In one embodiment of any of the compounds disclosed herein $R_2$ is -(alkyl)-C(O)—N(hydroxyalkyl)$_2$. In one embodiment of any of the compounds disclosed herein $R_2$ is -(alkyl)-S-(alkyl). In one embodiment of any of the compounds disclosed herein $R_2$ is -(alkyl)-$CF_3$. In one embodiment of any of the compounds disclosed herein $R_2$ is -(alkyl)-O-(hydroxyalkyl), In one embodiment of any of the compounds disclosed herein $R_2$ is -(alkyl)-O-(alkyl)-O-(alkyl). In one embodiment of any of the compounds disclosed herein $R_2$ is -(alkyl)-(CH)—(O-(alkyl)). In one embodiment of any of the compounds disclosed herein $R_2$ is -(alkyl)-(heterocyclyl). In one embodiment of any of the compounds disclosed herein $R_2$ is -(alkyl)-OAc. In one embodiment of any of the compounds disclosed herein $R_2$ is -(alkyl)-tetrahydrofuran. In one embodiment of any of the compounds disclosed herein $R_2$ is -(alkyl)-pyrrolidine. In one embodiment of any of the compounds disclosed herein $R_2$ is -(alkyl)-N-methylpyrrolidine. In one embodiment of any of the compounds disclosed herein $R_2$ is -(alkyl)-(1,3-dioxane). In one embodiment of any of the compounds disclosed herein $R_2$ is -(alkyl)-(4,5-dihydrooxazole).

In one embodiment of any of the compounds disclosed herein $R_2$ is —($C_{1-12}$ alkyl)-$CO_2H$ or any combination of any of —($C_1$ alkyl)-$CO_2H$, —($C_2$ alkyl)-$CO_2H$, —($C_3$ alkyl)-$CO_2H$, —($C_4$ alkyl)-$CO_2H$, —($C_4$ alkyl)-$CO_2H$, —($C_5$ alkyl)-$CO_2H$, —($C_6$ alkyl)-$CO_2H$, —($C_7$ alkyl)-$CO_2H$, —($C_8$ alkyl)-$CO_2H$, —($C_9$ alkyl)-$CO_2H$, —($C_{10}$ alkyl)-$CO_2H$, —($C_{11}$ alkyl)-$CO_2H$ or —($C_{12}$ alkyl)-$CO_2H$.

In one embodiment of any of the compounds disclosed herein $R_2$ is —($C_{1-12}$ alkyl)-$CO_2$-(alkyl) or any combination of any of —($C_1$ alkyl)-$CO_2$-(alkyl), —($C_2$ alkyl)-$CO_2$-(alkyl), —($C_3$ alkyl)-$CO_2$-(alkyl), —($C_4$ alkyl)-$CO_2$-(alkyl), —($C_4$ alkyl)-$CO_2$-(alkyl), —($C_5$ alkyl)-$CO_2$-(alkyl), —($C_6$ alkyl)-$CO_2$-(alkyl), —($C_7$ alkyl)-$CO_2$-(alkyl), —($C_8$alkyl)-$CO_2$-(alkyl), —($C_9$ alkyl)-$CO_2$-(alkyl), —($C_{10}$ alkyl)-$CO_2$-(alkyl), —($C_{11}$ alkyl)-$CO_2$-(alkyl) or —($C_{12}$ alkyl)-$CO_2$-(alkyl).

In one embodiment of any of the compounds disclosed herein $R_2$ is —($C_{1-12}$ alkyl)-O-(alkyl) or any combination of any of —($C_1$ alkyl)-O-(alkyl), —($C_2$ alkyl)-O-(alkyl), —($C_3$ alkyl)-O-(alkyl), —($C_4$ alkyl)-O-(alkyl), —($C_4$ alkyl)-O-(alkyl), —($C_5$ alkyl)-O-(alkyl), —($C_6$ alkyl)-O-(alkyl), —($C_7$ alkyl)-O-(alkyl), —($C_8$ alkyl)-O-(alkyl), —($C_9$ alkyl)-O-(alkyl), —($C_{10}$ alkyl)-O-(alkyl), —($C_{11}$ alkyl) —O-(alkyl) or —($C_{12}$ alkyl)-O-(alkyl).

In one embodiment of any of the compounds disclosed herein $R_5$ is F. In one embodiment of any of the compounds disclosed herein $R_5$ is Cl. In one embodiment of any of the compounds disclosed herein $R_5$ is Br. In one embodiment of any of the compounds disclosed herein $R_5$ is I.

In one embodiment of any of the compounds disclosed herein $R_5$ is other than Cl. In one embodiment of any of the compounds disclosed herein $R_2$ is other than -(alkyl)-$CO_2$H.

In one embodiment of any of the compounds disclosed, A is phenyl.

In one embodiment of any of the compounds disclosed, A is thiophene.

The present invention provides a pharmaceutical composition comprising the compound of the present invention and a pharmaceutically acceptable carrier.

The present invention provides a method of activating mu-opioid receptor comprising contacting the mu-opioid receptor with the compound of the present invention.

The present invention provides a method of activating delta-opioid receptor comprising contacting the delta-opioid receptor with the compound of the present invention.

The present invention provides a method of treating a subject afflicted with depression or major depression comprising administering an effective amount of the compound of the present invention to the subject so as to treat the depression or major depression.

The present invention provides a method of treating a subject afflicted with pain comprising administering an effective amount of the compound of the present invention to the subject so as to treat the pain.

The present invention provides a method of treating a subject afflicted with anxiety comprising administering an effective amount of the compound of the present invention to the subject so as to treat the anxiety.

The present invention provides a method of treating a subject afflicted with a depressive disorder comprising administering an effective amount of the compound of the present invention to the subject so as to treat the depressive disorder,.

The present invention provide-a method of treating a subaect afflicted with a mood disorder comprising administering an effective amount of the compound of the present invention to the subject so as to treat the mood disorder.

The present invention provides a method of activating mu-opioid receptor or delta-opioid receptor comprising contacting the mu-opioid receptor or delta-opioid receptor with a compound having the structure:

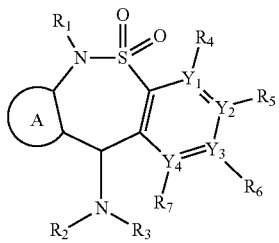

wherein
A is an aryl or heteroaryl, with or without substitution;
$R_1$ is —H or -(alkyl);
$R_2$ is -(alkyl), -(alkenyl), -(alkynyl)-(alkyl)-OH, -(alkyl)-$CO_2$H, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, (alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —OC(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
or a pharmaceutically acceptable salt thereof,
so as to thereby activate the mu-opioid receptor or delta-opioid receptor.

In some embodiments, the mu-opioid receptors or delta-opioid receptors are in a human subject.

The present invention provides a method of treating a subject afflicted with depression, major depression or pain comprising administering an effective amount of the compound having the structure:

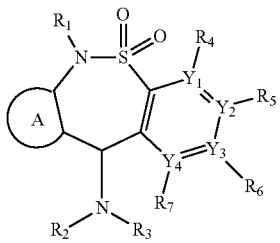

wherein

A is an aryl or heteroaryl, with or without substitution;

$R_1$ is —H or -(alkyl);

$R_2$ is -(alkyl), r(alkenyl), -(alkynyl (alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, to the subject so as to thereby treat the depression, major depression or pain.

The present invention provides a method of treating a subject afflicted with a mood disorder comprising administering an effective amount of the compound having the structure:

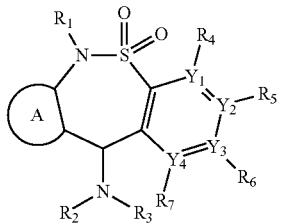

wherein

A is an aryl or heteroaryl, with or without substitution;

$R_1$ is —H or -(alkyl);

$R_2$ is -(alkyl), -(alkenyl), -(alkynyl)-(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$ , -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, -Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, to the subject so as to thereby treat the mood disorder.

The present invention provides a method of treating a subject afflicted with a depressive disorder comprising administering an effective amount of the compound having the structure:

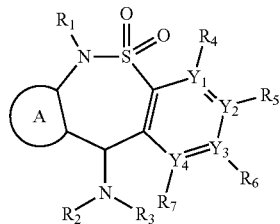

wherein

A is an aryl or heteroaryl, with or without substitution;

$R_1$ is —H or -(alkyl);

$R_2$ is -(alkyl), -(alkenyl), -(alkynyl)-(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_2$ is C, then $R_6$ is present; when $Y_4$ is N, then $R_7$ is absent, and when $Y_4$ is C, then $R_7$ is present, or a pharmaceutically acceptable salt thereof, to the subject so as to thereby treat the depressive disorder.

The present invention also provides a method of treating a subject afflicted with depression or major depression comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of a compound having the structure:

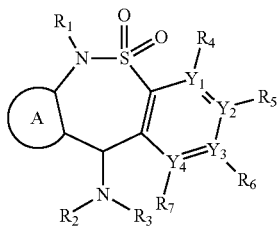

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl) N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH—(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject.

The present invention also provides a method of treating a subject afflicted with pain comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of a compound having the structure:

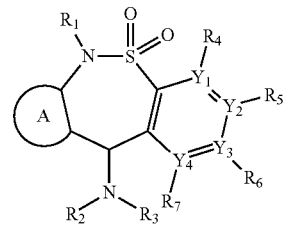

wherein

A is an aryl or heteroaryl, with or without substitution;

$R_1$ —H or -(alkyl);

$R_2$ (alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH—(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject.

In some embodiments of the above method, the compound when A is phenyl, $R_1$ is —$CH_3$, $R_3$, $R_4$, $R_6$, and $R_7$ are each —H, and $R_5$ is Cl, then $R_2$ is other than —$(CH_2)_6$ $CO_2H$.

The present invention also provides a compound having the structure:

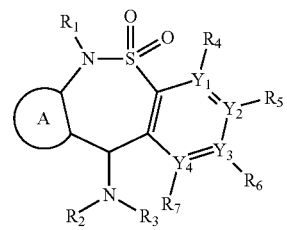

wherein

A is an aryl or heteroaryl, with or without substitution;

$R_1$ is —H or -(alkyl);

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alky-N-methylpyrro dine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C, wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present, or a salt or ester thereof, for use as an add-on a therepy or in combination with an NMDA receptor antagonist, an NMDA receptor partial agonist, neurokinin 1 receptor antagonist, neurokinin 2 receptor antagonist or a neurokinin 3 receptor antagonist in treating a subject afflicted with depression or major depression.

The present invention also provides a compound having the structure:

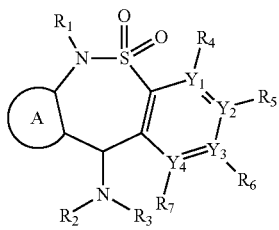

wherein

A is an aryl or heteroaryl, with or without substitution;

R$_1$ is —H or -(alkyl);

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C, wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present, or a salt or ester thereof, for use as an add-on therapy or in combination with an NMDA receptor antagonist, an NMDA receptor partial agonist, a neurokinin 1 receptor antagonist, a neurokinin 2 receptor antagonist or a neurokinin 3 receptor antagonist in treating a subject afflicted with pain.

In some embodiments of the above, the compound wherein when A is phenyl, R$_1$ is —CH$_3$, R$_3$, R$_4$, R$_6$, and R$_7$ are each —H, and R$_5$ is Cl, then R$_2$ is other than —(CH$_2$)$_6$CO$_2$H.

The present invention further provides a pharmaceutical composition comprising an amount of a compound having the structure

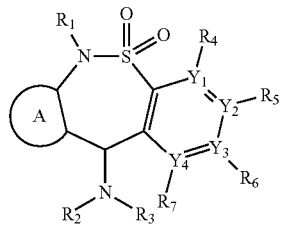

wherein

A is an aryl or heteroaryl, with or without substitution;

R$_1$ is —H or -(alkyl);

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)-O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for use in treating a subject afflicted with depression or major depression.

The present invention further provides a pharmaceutical composition comprising an amount of a compound having the structure

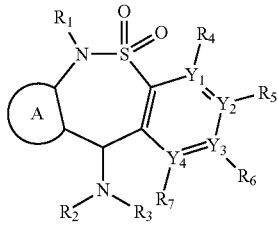

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl.)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for use in treating a subject afflicted with pain.

In some embodiments of the above pharmaceutical composition, the compound wherein when A is phenyl, $R_1$ is —CH$_3$, $R_3$, $R_4$, $R_6$, and $R_7$ are each —H, and $R_5$ is Cl, than $R_2$ is othar than —(CH$_2$)$_6$CO$_2$H.

The present invention also provides a method of treating a subject afflicted with a depressive disorder or mood disorder comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of a compound having the structure:

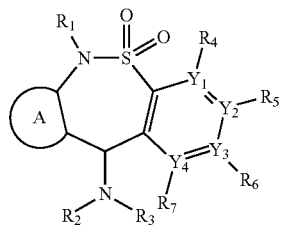

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl); or —SO$_2$(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject.

In some embodiments of the above method, the compound when A is phenyl, $R_1$ is —CH$_3$, $R_3$, $R_4$, $R_6$, and $R_7$ are each —H, and $R_5$ is Cl, then $R_2$ is other than —(CH$_2$)$_6$CO$_2$H.

The present invention also provides a compound having the structure:

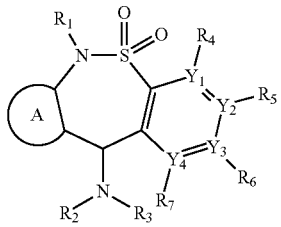

wherein

A is an aryl or heteroaryl, with or without substitution;

R$_1$ is —H or -(alkyl);

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C,
wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present,
or a salt or ester thereof, for use as an add-on therapy or in combination with an NMDA receptor antagonist, an NMDA receptor partial agonist, a neurokinin 1 receptor antagonist, a neurokinin 2 receptor antagonist or a neurokinin 3 receptor antagonist in treating a subject afflicted with a depressive disorder or mood disorder.

In some embodiments of the above, the compound wherein when A is phenyl, R$_1$ is —CH$_3$, R$_3$, R$_4$, R$_6$, and R$_7$ are each —H, and R$_5$ is Cl, then R$_2$ is other than —(CH$_2$)$_6$CO$_2$H.

The present invention further provides a pharmaceutical composition comprising an amount of a compound having the structure

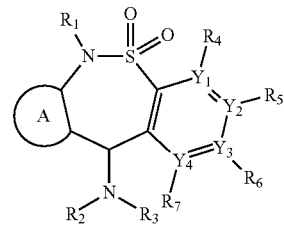

wherein

A is an aryl or heteroaryl, with or without substitution;

R$_1$ is —H or -(alkyl)

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C,
wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present,
or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for use in treating a subject afflicted with a depressive disorder or mood disorder.

In some embodiments of the above pharmaceutical composition, the compound wherein when A is phenyl, R$_1$ is —CH$_3$, R$_3$, R$_4$, R$_6$, and R$_7$ are each —H, and R$_5$ is Cl, then R$_2$ is other than —(CH$_2$)$_6$CO$_2$H.

In some embodiments, a package comprising:
a) a first pharmaceutical composition comprising an amount of a NMDA receptor antagonist, an NMDA receptor partial agonist, a neurokinin 1 receptor antagonist, a neurokinin 2 receptor antagonist or a neurokinin 3 receptor antagonist and a pharmaceutically acceptable carrier;
b) a second pharmaceutical composition comprising an amount of any compound of the present invention, or a salt or ester thereof; and c) instructions for use of the first and second pharmaceutical compositions together to treat a subject afflicted with pain.

In some embodiments, a therapeutic package for dispensing to, or for use in dispensing to, a subject afflicted with pain, which comprises:
a) one or more unit doses, each such unit dose comprising:
 (i) an amount of any compound of the present invention, or a salt or ester thereof; and
 (ii) an amount of a NMDA receptor antagonist, an NMDA receptor partial agonist, a neurokinin 1 receptor antagonist, a neurokinin 2 receptor antagonist or a neurokinin 3 receptor antagonist,
  wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with depression, major depression or pain, which comprises:
(i) an amount of any compound of the present invention , or a salt or ester thereof; and
(ii) an amount of a NMDA receptor antagonist, an NMDA receptor partial agonist, a neurokinin 1 receptor antagonist, a neurokinin 2 receptor antagonist or a neurokinin 3 receptor antagonist,
 wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

In some embodiments, a package comprising:
a) a first pharmaceutical composition comprising an amount of a NMDA receptor antagonist, an NMDA receptor partial agonist, a neurokinin 1 receptor antagonist, a neurokinin 2 receptor antagonist or a neurokinin 3 receptor antagonist and a pharmaceutically acceptable carrier;
b) a second pharmaceutical composition comprising an amount of any compound of the present invention, or a salt or ester thereof; and
c) instructions for use of the first and second pharmaceutical compositions tagethei to treat a subject afflicted with a depressive disorder or mood disorder.

In some embodiments, a therapeutic package for dispensing to, or for use in dispensing to, a subject afflicted with a depressive disorder or mood disorder, which comprises:
a) one or more unit doses, each such unit dose comprising:
 (i) an amount of any compound of the present invention, or a salt or ester thereof; and
 (ii) an amount of a NMDA receptor antagonist, an NMDA receptor partial agonist, a neurokinin 1 receptor antagonist, a neurokinin 2 receptor antagonist or a neurokinin 3 receptor antagonist,
  wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with a depressive disorder or mood disorder, which comprises:
(i) an amount of any compound of the present invention, or a salt or ester thereof; and
(ii) an amount of a NMDA receptor antagonist, an NMDA receptor partial agonist, a neurokinin 1 receptor antagonist, a neutoirigin 2 receptor antagonist or a neurokinin 3 receptor antagonist,
 wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

The present invention also provides a method of treating a subject afflicted with a depressive disorder or mood disorder comprising administering to the subject an effective amount of a NMDA receptor antagonist, an NMDA receptor partial agonist, a neurokinin 1 receptor antagonist, a neurokinin 2 receptor antagonist or a neurokinin 3 receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, an NMDA receptor partial agonist, a neurokinin 1 receptor antagonist, a neurokinin 2 receptor antagonist or a neurokinin 3 receptor antagonist in treating a subject afflicted with a depressive disorder or mood disorder.

The present invention further provides a pharmaceutical composition comprising an amount of any of the compounds of the present invention, or a salt or ester thereof, and an amount of a NMDA receptor antagonist, an NMDA receptor partial agonist, a neurokinin 1 receptor antagonist, a neurokinin 2 receptor antagonist or a neurokinin 3 receptor antagonist for use in treating a subject afflicted with a depressive disorder or mood disorder The present invention also provides a method of treating a subject afflicted with a depressive disorder or mood disorder comprising administering to the subject an effective amount of a NMDA receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, in treating a subject afflicted with a depressive disorder or mood disorder.

The present invention further provides a pharmaceutical composition comprising an amount of any of the compounds of the present invention, or a salt or ester thereof, and an amount of a NMDA receptor antagonist, for use in treating a subject afflicted with a depressive disorder or mood disorder.

The present invention also provides a method of treating a subject afflicted with a depressive disorder or mood disorder comprising administering to the subject an effective amount of an NMDA receptor partial agonist, and an effective amount of any compound of the present invention, or a salt or ester thereof, so as to thereby treat the subject.

The present invention also provides a compound of the present invention or a salt or ester thereof, for use as an add-on therapy or in combination with an NMDA receptor partial agonist in treating a subject afflicted with a depressive disorder or mood disorder.

The present invention further provides a pharmaceutical composition comprising an amount of any of the compounds of the present invention, or a salt or ester thereof, and an amount of an NMDA receptor partial agonist, for, use in treating a subject afflicted with a depressive disorder or mood disorder.

The present invention also provides a method of treating a subject afflicted with a depressive disorder or mood disorder comprising administering to the subject an effective amount of a neurokinin 1 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 1 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 1 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 2 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 2 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 2 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 3 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 3 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 3 receptor antagonist for use in treating a subject afflicted with a depressive disorder or mood disorder.

In some embodiments of the present method, compound, package, use or pharmaceutical composition, the compound has the structure:

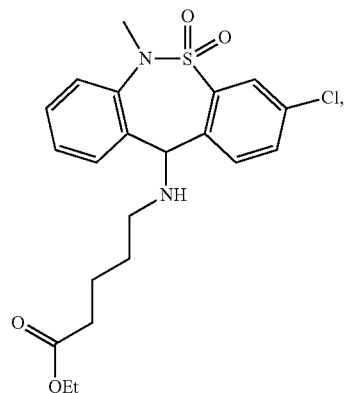

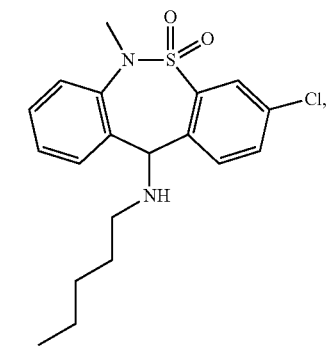

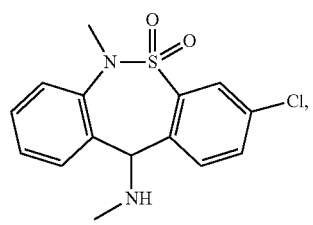

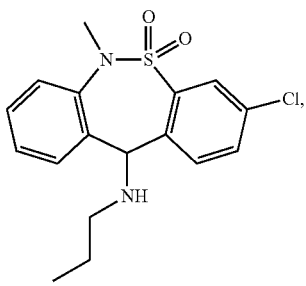
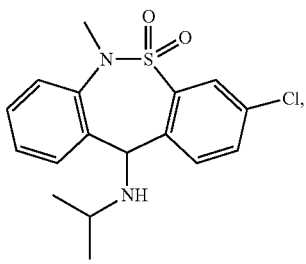
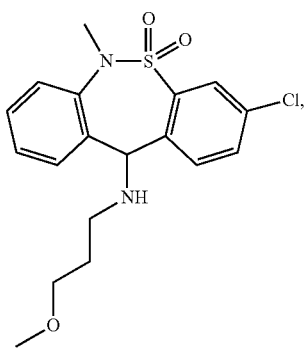
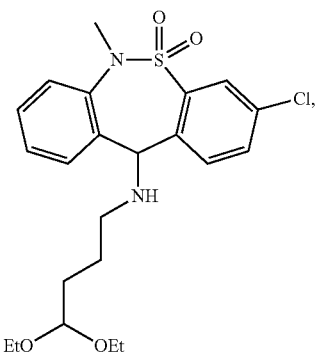
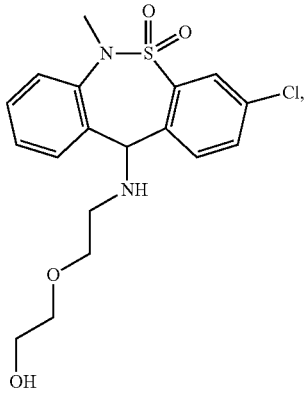
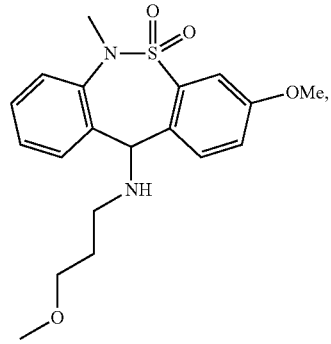
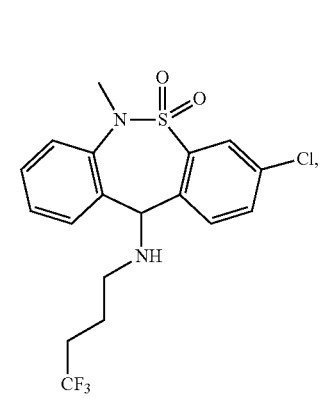
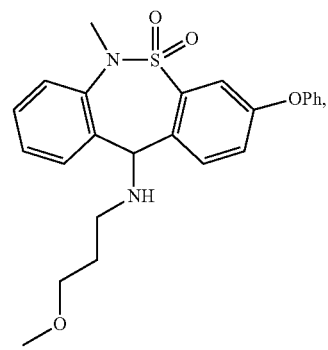
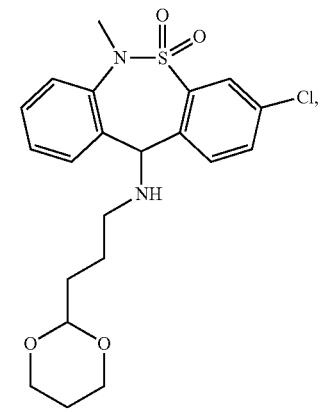

91
-continued
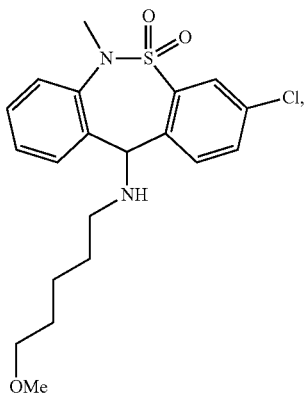
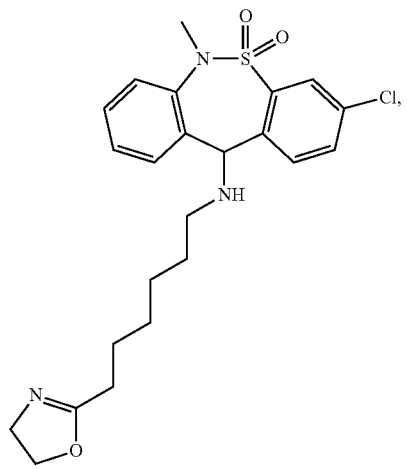
92
-continued
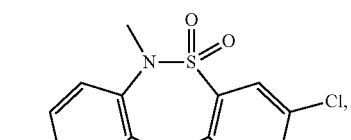
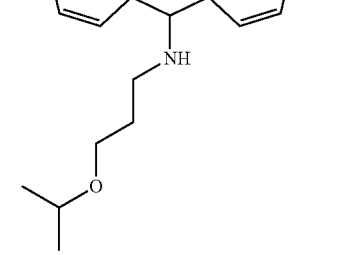
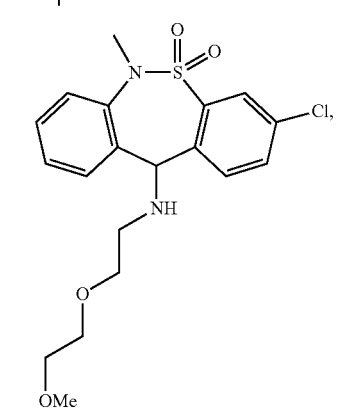
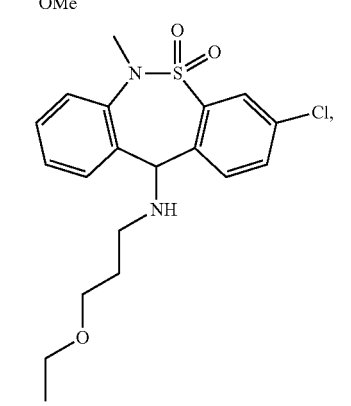

93
-continued
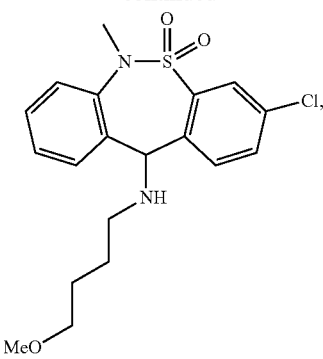
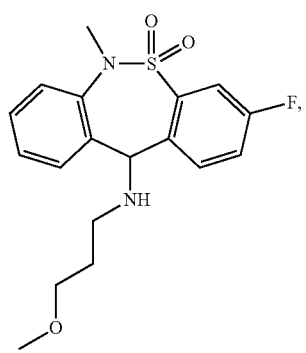
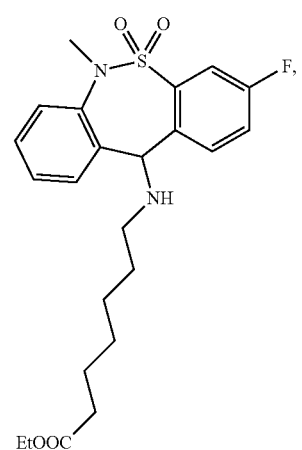
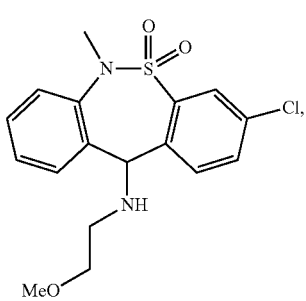
94
-continued
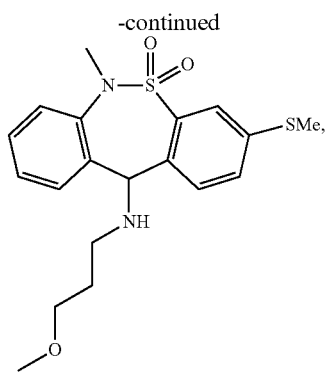
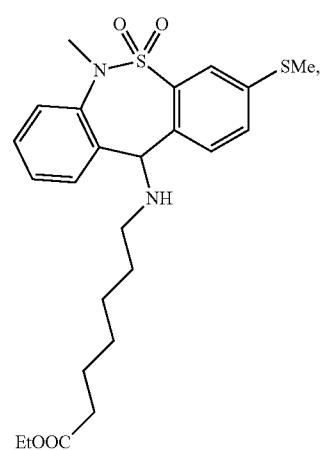
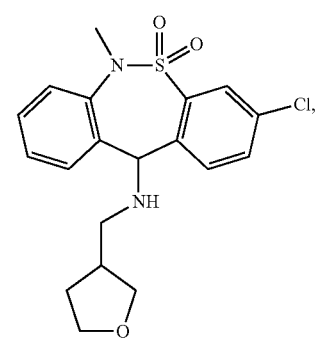
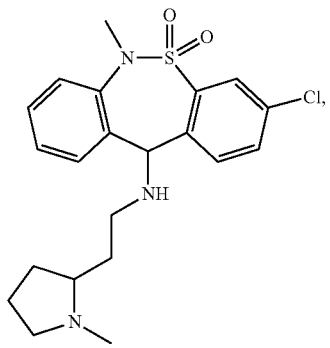

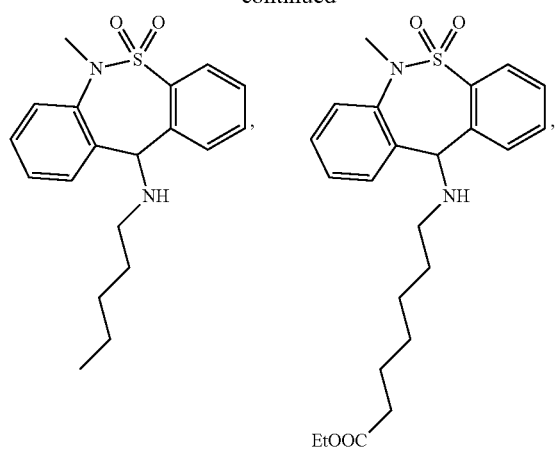
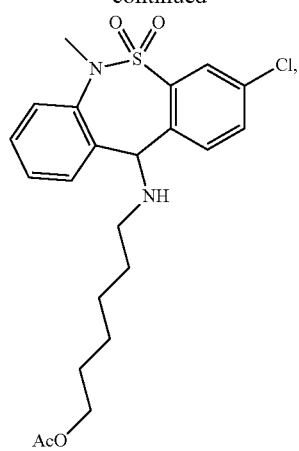
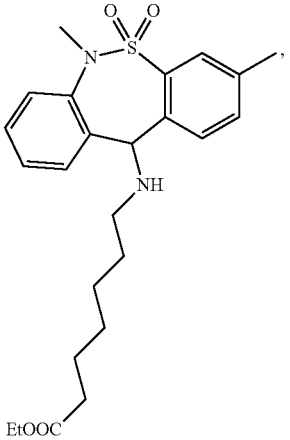
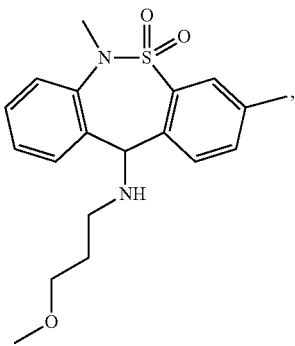
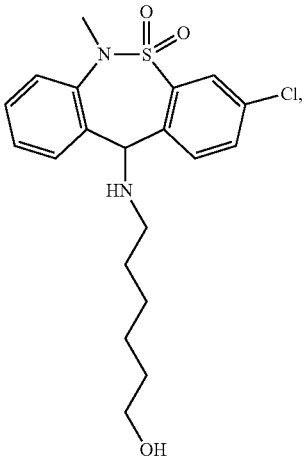

97
-continued
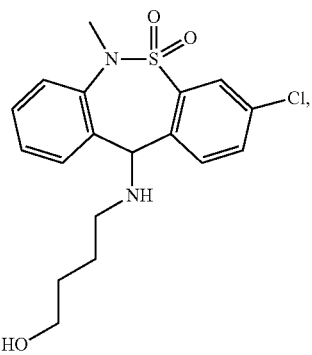
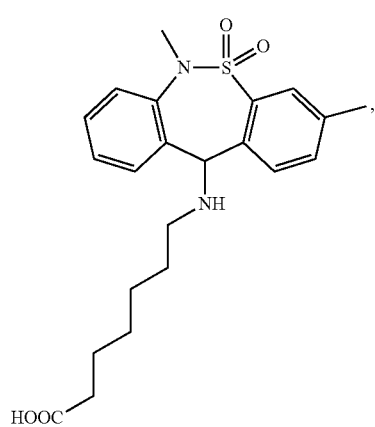
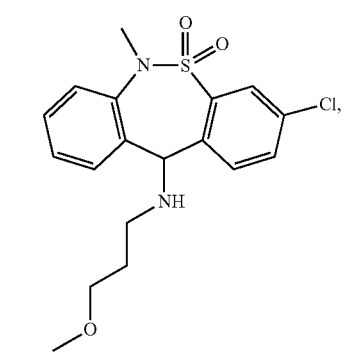
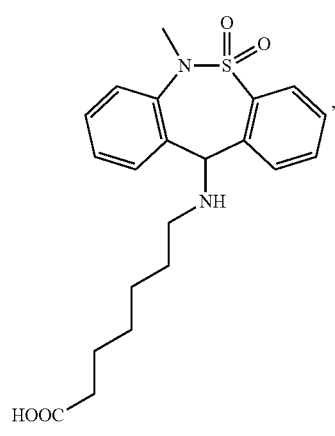
98
-continued
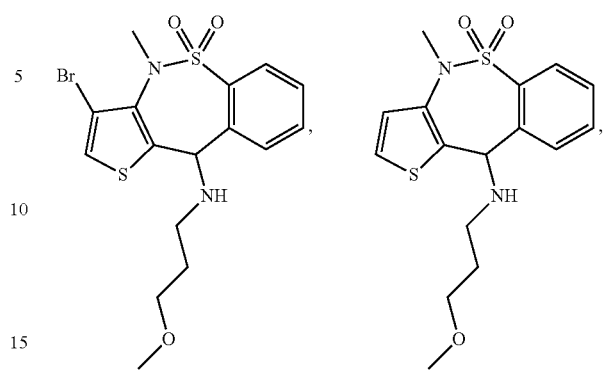
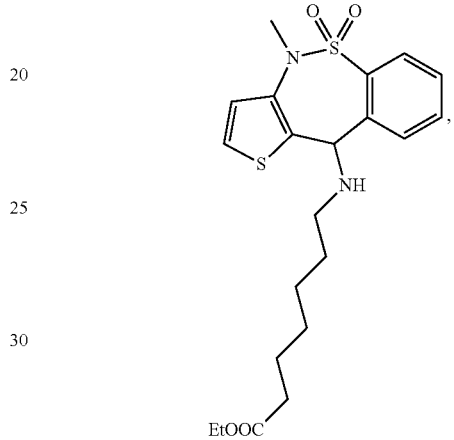
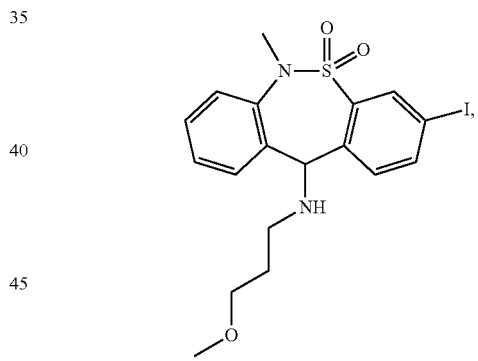
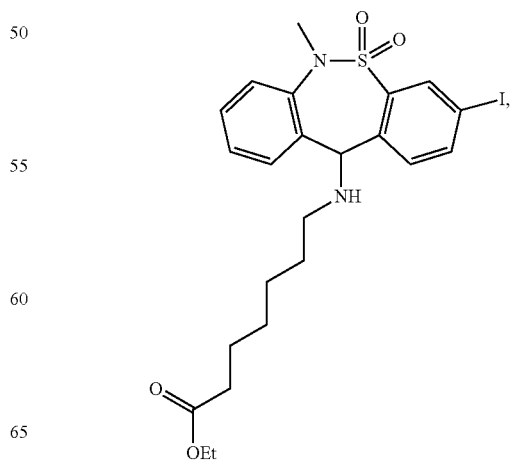

99
-continued
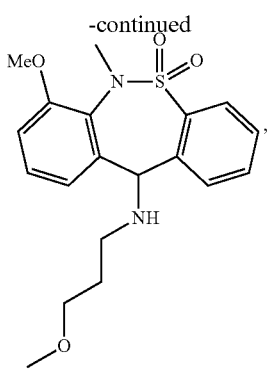
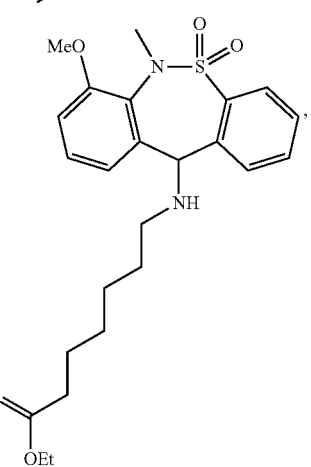
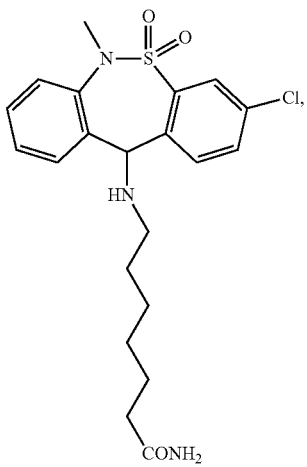
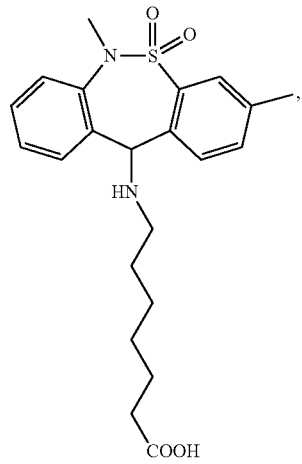
100
-continued
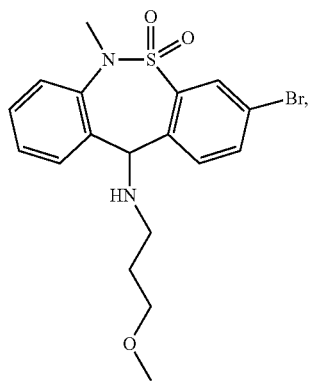
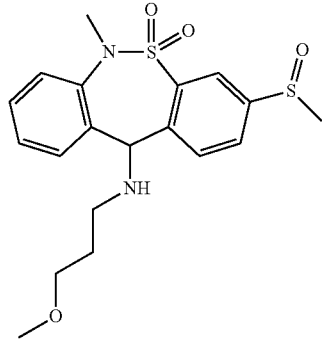
or
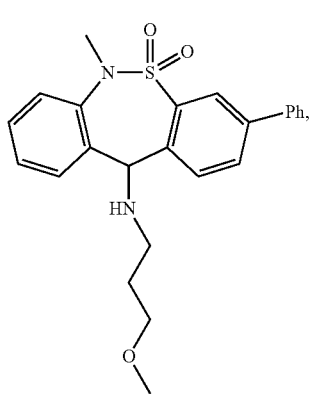
or a pharmaceutically acceptable salt thereof.
In some embodiments of the present method, compound, package, use or pharmaceutical composition, the compound has the structure:
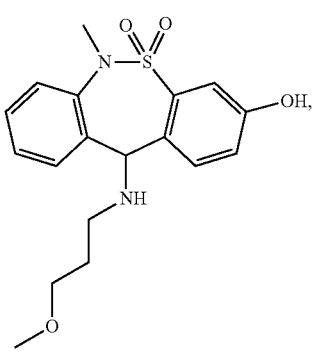

101
-continued
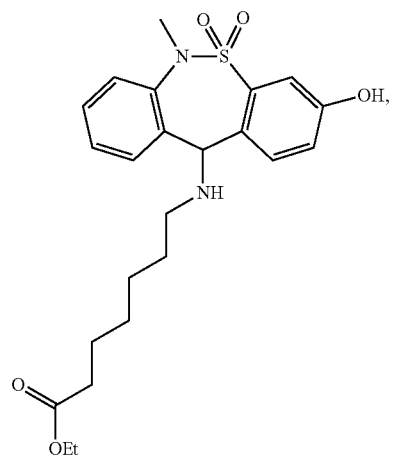
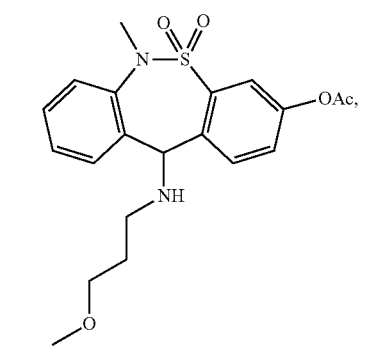
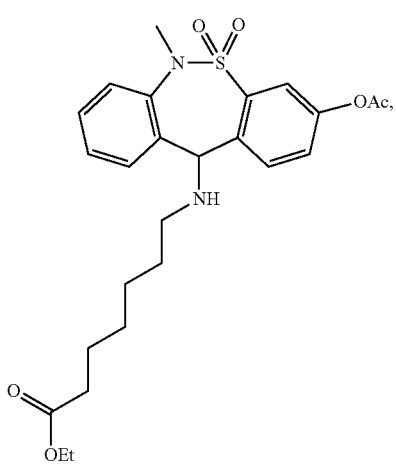
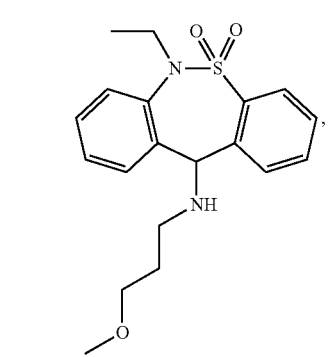
102
-continued
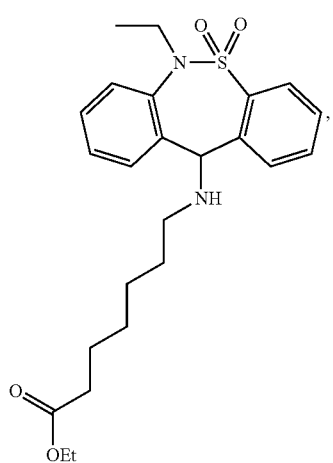
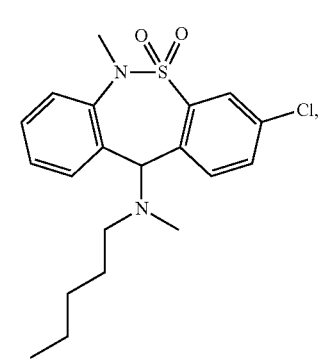
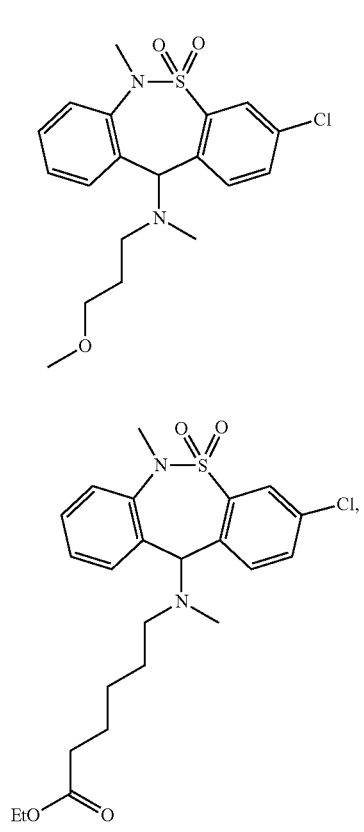

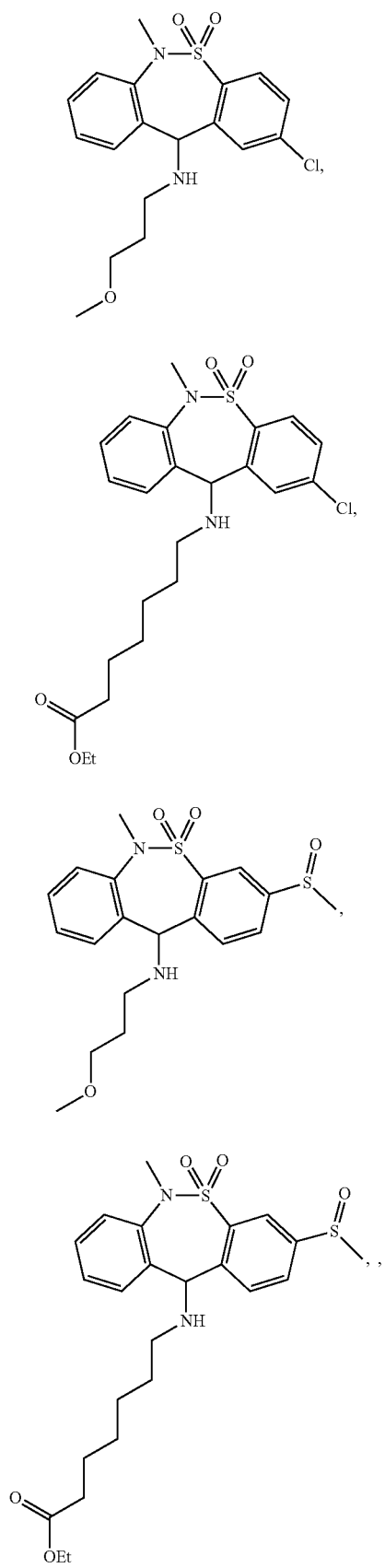
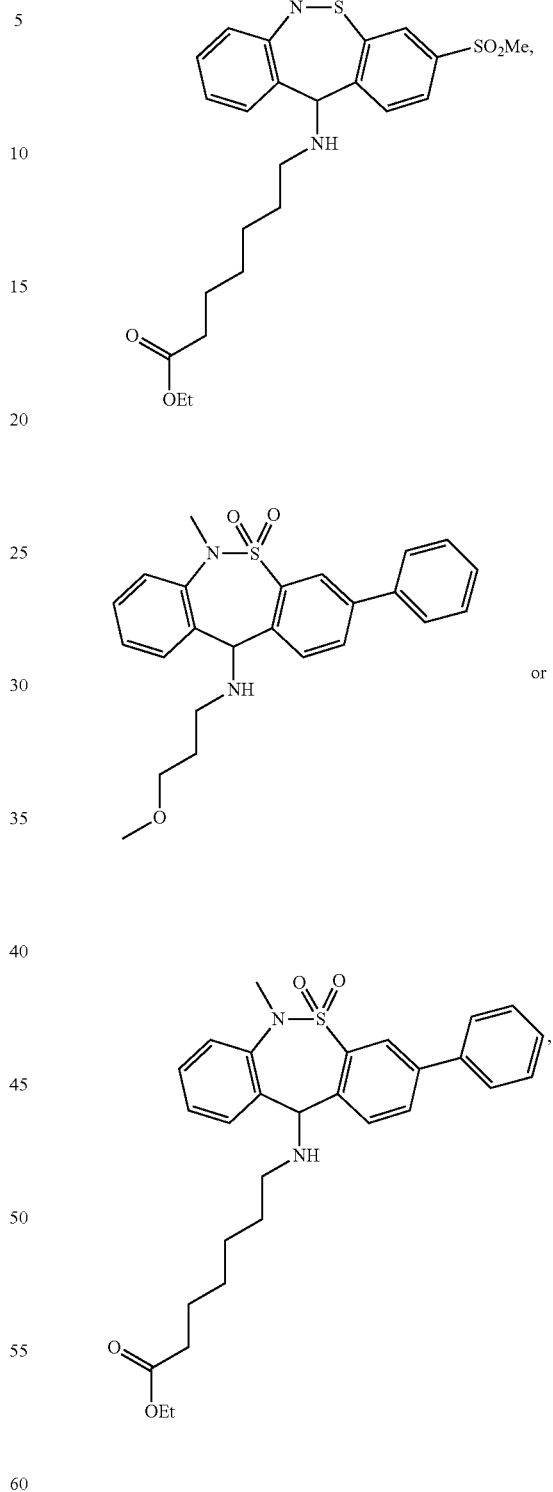
or a pharmaceutically acceptable salt thereof.
In some embodiments of the present method, compound, package, use or pharmaceutical composition, the compound has the structure:

105
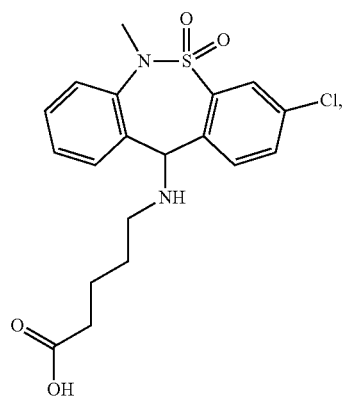
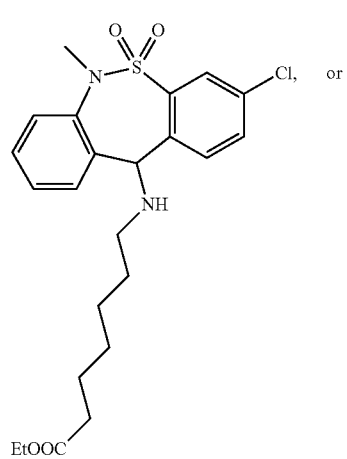 or
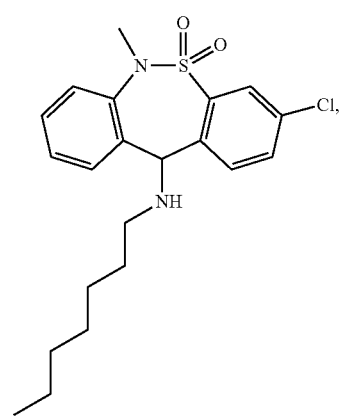
or a pharmaceutically acceptable salt thereof.
In some embodiments of the present method, compound, package, use or pharmaceutical composition, the compound has the structure:
106
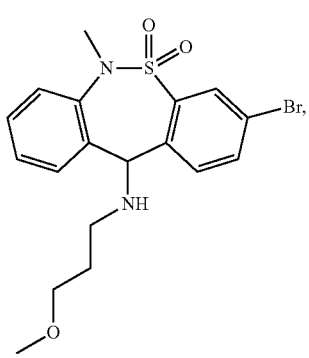
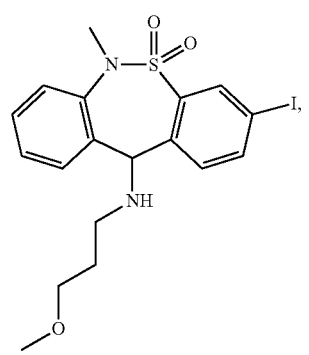
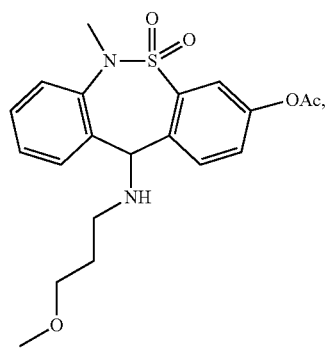
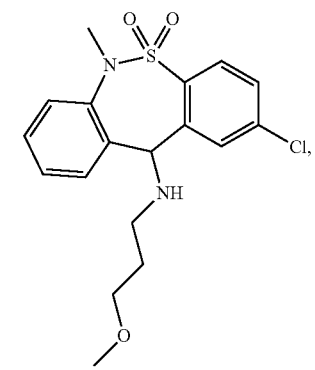

107
-continued
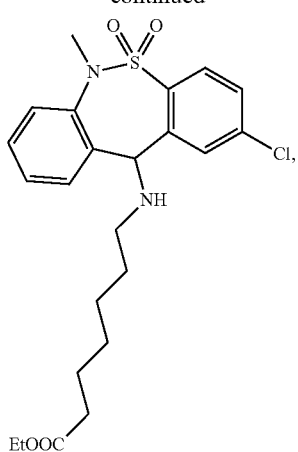
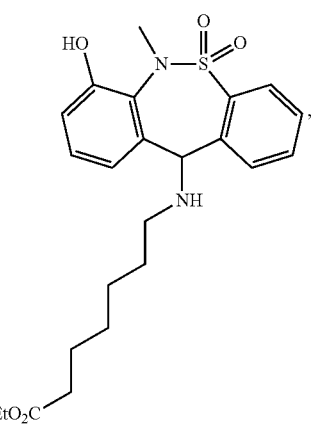
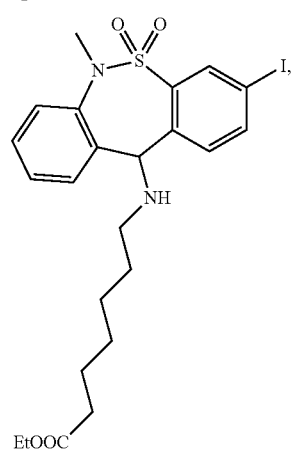
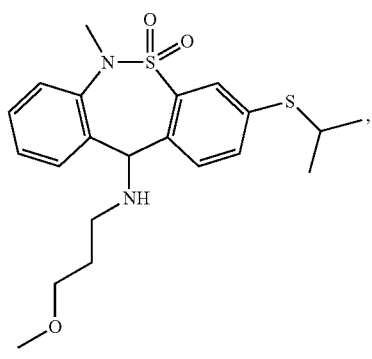
108
-continued
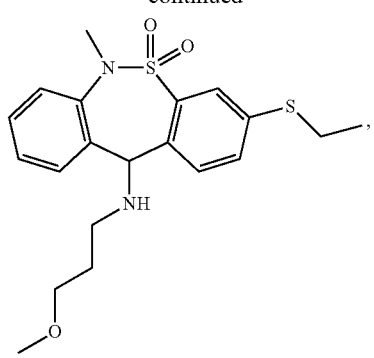
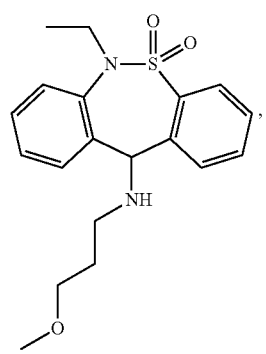
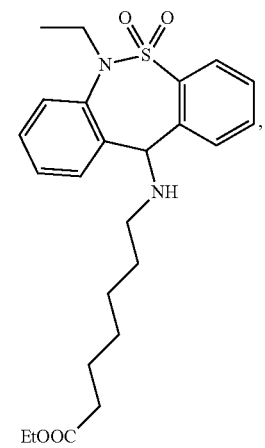
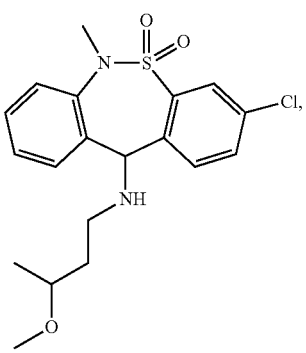

-continued

111
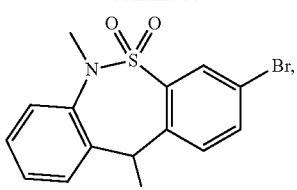
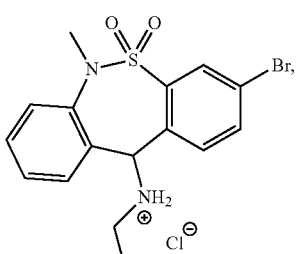
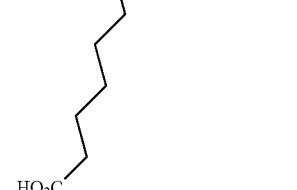
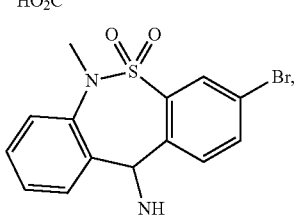
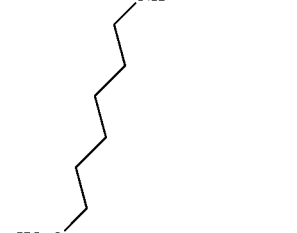
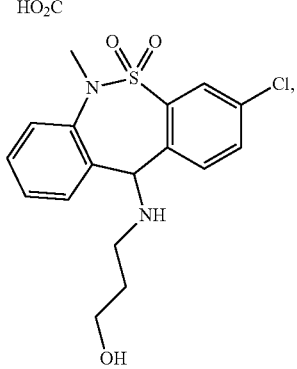
112
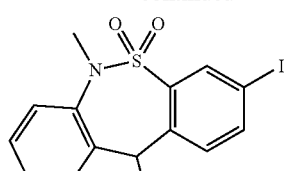
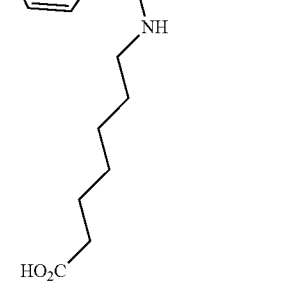
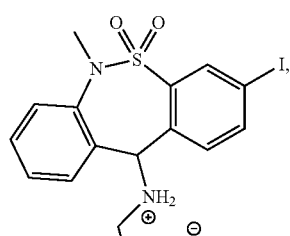
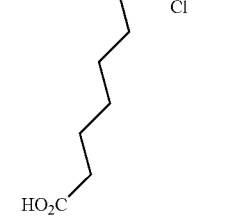
or a pharmaceutically acceptable salt thereof.
In some embodiments of the present method, compound, package, use or pharmaceutical composition, the compound has the structure:
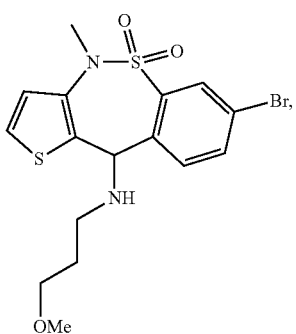

-continued

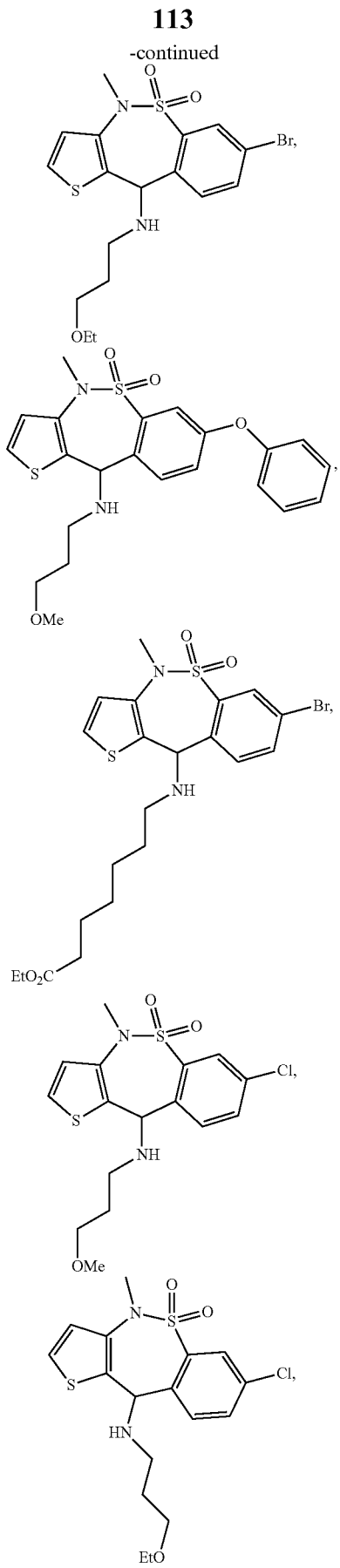

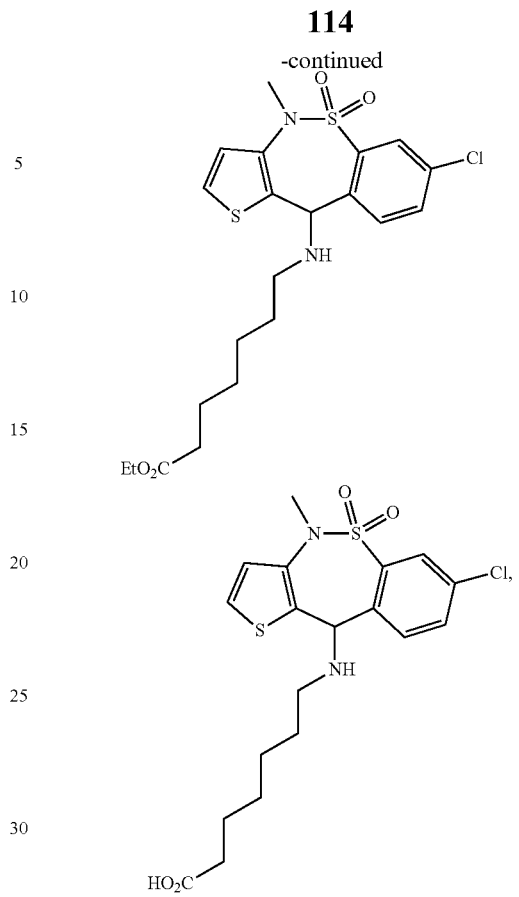

or a pharmaceutically acceptable salt thereof.

The present invention provides a compound having the structure:

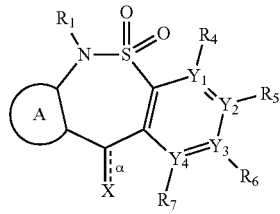

wherein

α is a bond, which may be present or absent;

X is O, OH, OTf, Cl, or Br,
  wherein when α is present, then X is O, and when α is absent, then X is OH, OTf, Cl, or Br;

A is an aryl or heteroaryl, with or without substitution;

$R_1$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof.

In some embodiment of the above compound, the compound has the structure:

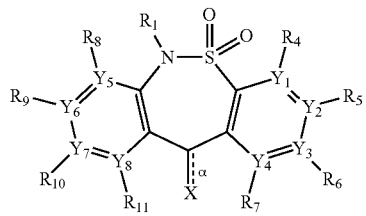

wherein $R_8$, $R_9$, $R_{10}$ and $R_{11}$ are each absent or present, and when present, are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl)—NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

$Y_5$, $Y_6$, $Y_7$ and $Y_8$ are each independently N or C, wherein when $Y_5$ is N, then $R_8$ is absent, and when $Y_5$ is C, then $R_8$ is present; when $Y_6$ is N, then $R_9$ is absent, and when $Y_6$ is C, then $R_9$ is present; when $Y_7$ is N, then $R_{10}$ is absent, and when $Y_7$ is C, then $R_{10}$ is present; when $Y_8$ is N, then $R_{11}$ is absent, and when $Y_8$ is C, then $R_{11}$ is present.

In some embodiment of the above compound, the compound has the structure:

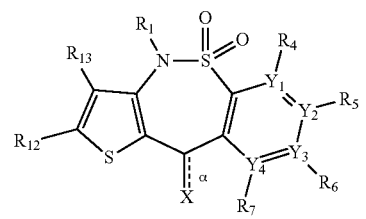

wherein $R_{12}$ and $R_{13}$ are each indeoencdntly —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl)—NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

The present invention provides process for producing the compound of the present invention having the structure:

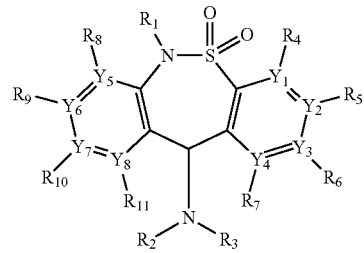

comprising (a) contacting the compound having the structure:

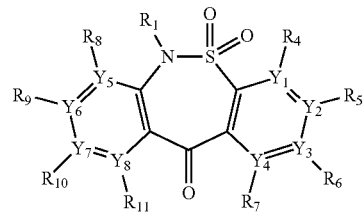

with a reducing agent in a first suitable solvent to produce a compound having the structure:

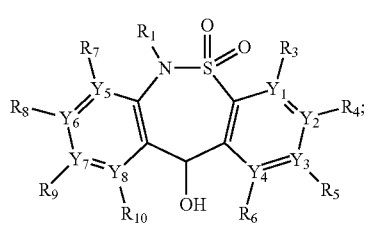

(b) reacting the product of step (a) with a halogenating agent or triflating agent in a second suitable solvent so as to produce a compound having the structure:

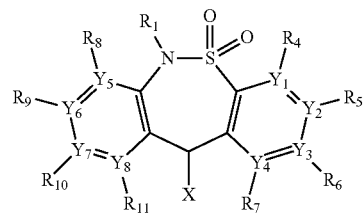

wherein X is OTf, Cl or Br;

(c) reacting the product of step (b) with an amine in the presence of a base in a third suitable solvent so as to produce the compound having the structure:

The present invention provides process for producing the compound of the present invention having the structure:

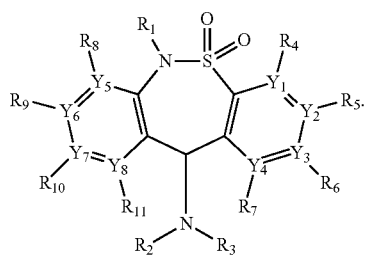

comprising (a) contacting the compound having the structure:

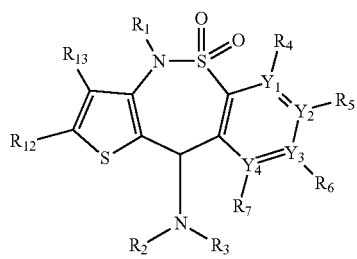

with a reducing agent in a first suitable solvent to produce a compound having the structure:

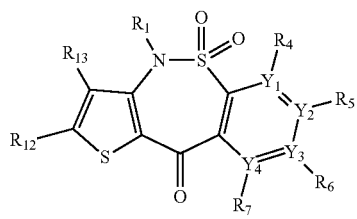

(b) reacting the product of step (a) with a halogenating agent or triflating agent in a second suitable solvent so as to produce a compound having the structure:

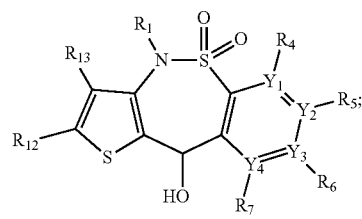

wherein X is OTf, Cl or Br;

(c) reacting the product of step (b) with an amine in the presence of a base in a third suitable solvent so as to produce the compound having the structure:

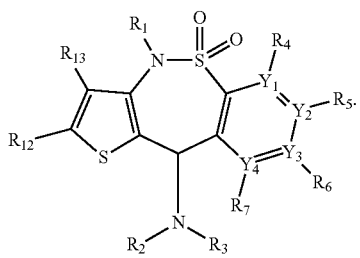

In some embodiments of the process, the reducing agent is Sc borohydride.

In some embodiments of the process, the halogenating agent is sulfonyl chloride or hydrogen chloride.

In some embodiments of the process, the amine is a primary amine or a secondary amine.

In some embodiments of the process, the first suitable solvent is methanol.

In some embodiments of the process, the second suitable solvent is dichloromethane.

In some embodiments of the process, the third suitable solvent nitromethane.

In some embodiments, the aryl or heteroaryl A is subtitited with —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

In some embodiments, the aryl or heteroaryl A is subtitited with Cl, Br, F, I, OH, —OCH$_3$, —CH$_3$.

In some embodiments, the aryl or heteroaryl A is subtitited with —H, —Cl, —Br, —F, —I, —CN, —CF$_3$, —OCF$_3$, —OH, -(alkyl), —O-(alkyl), —S-(alkyl), —O-(aryl) or —S-(aryl).

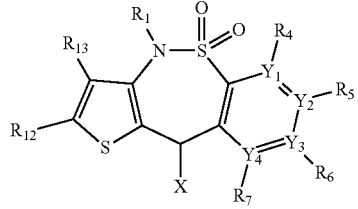

In some embodiments, a compound having the structure

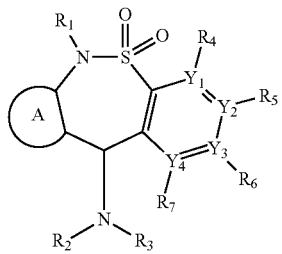

wherein
A is an aryl or heteroaryl, with or without substitution;
$R_1$ is —H or -(alkyl);
$R_2$ is —($C_1$-$C_6$-alkyl), —($C_8$-$C_{12}$-alkyl), —($C_1$-$C_3$ alkyl)-$CO_2$H, —($C_5$ alkyl)-$CO_2$H, —($C_7$-$C_{12}$ alkyl)-$CO_2$H, —($C_1C_5$ alkyl)-$CO_2$—($C_1$-$C_{12}$ alkyl), —($C_7$-$C_{12}$ alkyl)-$CO_2$—($C_1$-$C_{12}$ alkyl), -(alkenyl), -(alkynyl) -(alkyl)-OH, -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O(heteroaryl)-S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ then $R_6$ is present; when $Y_4$ is N, then $R_7$ is absent, when $Y_4$ is C, then $R_7$ is present,
or a pharmaceutically acceptable salt thereof.
In some embodiments, a compound having the structure

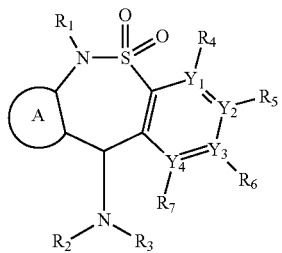

wherein
A is an aryl or heteroaryl, with or without substitution;
$R_1$ is —H or -(alkyl);
$R_2$ is —($C_1C_5$-alkyl), —($C_9$-$C_{12}$-alkyl), —($C_1$-$C_2$ alkyl)-$CO_2$H, —($C_8$-$C_{12}$ alkyl)-$CO_2$H, —($C_1C_4$ alkyl)-$CO_2$—($C_1C_{12}$ alkyl), —($C_8$-$C_{12}$ alkyl)-$CO_2$—($C_1$-$C_{12}$ alkyl), -(alkenyl), -(alkynyl) -(alkyl)-OH, -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl) —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_6$ is C, then $R_7$ is present,
or a pharmaceutically acceptable salt thereof.
In some embodiments, a compound having the structure

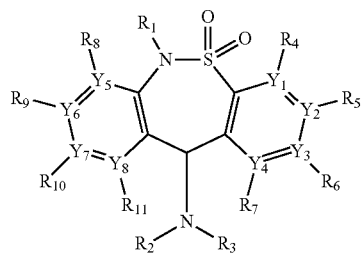

wherein
$R_1$ is —H or -(alkyl);
$R_2$ is -(alkyl), -(alkenyl), -(alkynyl) -(alkyl)-OH, -(alkyl)-$CO_2$H, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, —(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-

(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, $R_8$, $R_9$, $R_{10}$ and $R_{11}$ are each absent or present, and when present, are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —(O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

$Y_5$, $Y_6$, $Y_7$ and $Y_8$ are each independently N or C,
wherein when $Y_5$ is N, then $R_8$ is absent, and when $Y_5$ is C, then $R_8$ is present; when $Y_6$ is N, then $R_9$ is absent, and when $Y_6$ is C, then $R_9$ is present; when $Y_7$ is N, then $R_{10}$ is absent, and when $Y_7$ is C, then $R_{10}$ is present; when $Y_8$ is N, then $R_{11}$ is absent, and when $Y_8$ is C, then $R_{11}$ is present.

wherein when $R_1$ is —CH$_3$; $R_3$, $R_4$, $R_6$, $R_7$, $R_8$, $R_9$, $R_{10}$ and $R_{11}$ are each —H; $Y_1$, $Y_2$, $Y_3$, $Y_4$, $Y_5$, $Y_6$, $Y_7$ and $Y_8$ are each C; and $R_5$ is Cl, then $R_2$ is other than —(CH$_2$)$_4$CO$_2$H, —(CH$_2$)$_6$CO$_2$H, —(CH$_2$)$_6$CO$_2$CH$_2$C$_3$, or —(CH$_2$)$_6$CH$_3$, wherein when $R_1$ is —CH$_3$; $R_3$, $R_4$, $R_6$, $R_7$, $R_8$, $R_9$, $R_{10}$ and $R_{11}$ are each —H; $Y_1$, $Y_2$, $Y_3$, $Y_4$, $Y_5$, $Y_6$, $Y_7$ and $Y_8$ are each C; and $R_5$ is —SO$_2$CH$_3$, the $R_2$ is other than —(CH$_2$)$_3$OCH$_3$, or a pharmaceutically acceptable salt thereof.

In some embodiments of the compound, $R_2$ is —(C$_1$-C$_6$-alkyl), —(C$_8$-C$_{12}$-alkyl), —(C$_1$-C$_3$ alkyl)-CO$_2$H, —(C$_5$ alkyl)-CO$_2$H, —(C$_7$-C$_{12}$ alkyl)-CO$_2$H, —(C$_1$-C$_5$ alkyl)-CO$_2$—(C$_1$-C$_{12}$ alkyl), or —(C$_7$-C$_{12}$ alkyl)-CO$_2$—(C$_1$-C$_{12}$ alkyl).

In some embodiments of the compound, $R_2$ is —(C$_1$-C$_5$-alkyl), —(C$_9$-C$_{12}$-alkyl), —(C$_1$-C$_2$ alkyl)-CO$_2$H, —(C$_8$-C$_{12}$ alkyl)-CO$_2$H, —(C$_1$-C$_4$ alkyl)-CO$_2$—(C$_1$-C$_{12}$ alkyl), —(C$_8$C$_{12}$ alkyl)-CO$_2$—(C$_1$-C$_{12}$ alkyl).

In some embodiments of the compound, $R_5$ is —SO$_2$—(C$_2$-C$_{12}$ alkyl).

In some embodiments of the compound, $R_5$ is —SO$_2$—(C$_3$-C$_{12}$ alkyl)

In some embodiments, a compound having the structure:

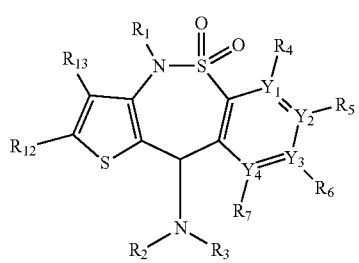

wherein
$R_1$ is —H or -(alkyl);
$R_2$ is -(alkyl), -(alkenyl), -(alkynyl)-(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alklyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present; and
$R_{12}$ and $R_{13}$ are each indeoencdntly —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

or a pharmaceutically acceptable salt thereof.

In some embodiments, a pharmaceutically acceptable salt of any of the above compounds of the present invention.

Various $R_1$-$R_{13}$ groups are added to the 6-methyl-6,11-dihydrodibenzo[1,2]thiazepine 5,5-dioxide core of the compounds disclosed herein. Said compounds act as MOR agonists with similar activity to compounds 6-11, 13-29, 31-53 or 55-84.

Various $R_1$-$R_{13}$ groups are added to the 4methyl-4, 10-dihydrobenzo[f]thieno[3,2-c][1,2]thiazepine 5,5-dioxide core of the compounds disclosed herein. Said compounds act as MOR agonists with similar activity to compounds 6-11, 13-29, 31-53 or 55-84.

Various $R_2$ groups replace the $R_2$ groups found on compounds 6-11, 13-29, 31-37, 29-53 or 55-58. Compounds with such $R_2$ groups act as MOR agonists with similar activity to compounds 6-11, 13-29, 31-53 or 55-84.

Various $R_2$ groups with similar chain lengths replace the $R_2$ groups found on compounds 6-11, 13-29, 31-37, 29-53 or 55-58. Compounds with such $R_2$ groups act as MOR agonists with similar activity to compounds 6-11, 13-29, 31-53 or 55-84.

Various $R_1$ groups replace the $R_1$ groups found on compounds 6-11, 13-29, 31-37, 29-53 or 55-58. Compounds with such $R_1$ groups act as MOR agonists with similar activity to compounds 6-11, 13-29, 31-53 or 55-84.

Various $R_3$ groups replace the $R_3$ groups found on compounds 6-11, 13-29, 31-37, 29-53 or 55-58. Compounds with such $R_1$ groups act as MOR agonists with similar activity to compounds 6-11, 13-29, 31-53 or 55-84.

Embodiments of the compounds dislosed herein include compounds where $R_1$ as H, ethyl, propyl, butyl, pentyl or hexyl. Compounds with $R_1$ as H, ethyl, propyl, butyl, pentyl or hexyl have analogous activity to compounds 6-11, 13-29, 31-53 or 55-84.

Embodiments of the compounds dislosed herein include compounds where $R_3$ as H, methyl, ethyl, propyl, butyl, pentyl or hexyl. Compounds with $R_3$ as H, methyl, ethyl, propyl, butyl, pentyl or hexyl have analogous activity to compounds 6-11, 13-29, 31-53 or 55-84.

Embodiments of the compounds dislosed herein include compounds where one or more of $Y_1$, $Y_2$, $Y_3$ or $Y_4$ is N. Compounds where one or more of $Y_1$, $Y_2$, $Y_3$ or $Y_4$ is N have analogous activity to compounds 6-11, 13-29, 31-53 or 55-584.

Derivatives of the compounds dislosed herein include compounds where one or more of $Y_5$, $Y_6$, $Y_7$ or $Y_8$ is N. Compounds where one or more of $Y_5$, $Y_6$, $Y_7$ or $Y_8$ is N have analogous activity to compounds 6-11, 13-29, 31-53 or 55-58.

In some embodiments, the compound is the structure of any one of compound 59, 60, 61, 62, 63, 64, 65, 66, 67, 68, 69, 70, 71, 72, 73, 74, 75, 76, 77, 78, 79, 80, 81, 82, 83 or 84.

In some embodiments, the compound used in any of the above methods, uses, packages or compositions is any one of compound 59, 60, 61, 62, 63, 64, 65, 66, 67, 68, 69, 70, 71, 72, 73, 74, 75, 76, 77, 78, 79, 80, 81, 82, 83 or 84.

In some embodiments, a salt of the compound of the present invention is used in any of the above methods, uses, packages or compositions.

In some embodiments, a pharmaceutically salt of the compound of the present invention is used in any of the above methods, uses, packages or compositions.

In some embodiments, an ester of the compound of the present invention is used in any of the above methods, uses, packages or compositions.

Any of the above compounds may be used in any of the dislosed methods, uses, packages or pharmaceutical compositions.

Any of the compounds used in the dislosed methods, uses, packages or pharmaceutical compositions may be replaced with any other compound disclosed in the present invention.

Any of the above generic compounds may be used in any of the dislosed methods, uses, packages or compositions, In some embodiments, the methods, uses, packages or pharmaceutical compositions wherein the depressive disorder is depression, major depression, dysthymia, postpartum depression, seasonal affective disorder, atypical depression, psychotic depression, bipolar disorder, premenstrual dysphoric disorder, situational depression or adjustment disorder with depressed mood.

In some embodiments, the methods, uses, packages or pharmaceutical compositions wherein the mood disorder is anxiety, post-traumatic stress disorder (PTSD), acute stress disorder, generalized anxiety disorder (GAD), obsessive-compulsive disorder (OCD), panic disorder, social phobia or social anxiety disorder.

In some embodiments, the NMDA receptor antagonist is an aylcyclohexylamine, dextromorphinan or adamantane.

In some embodiments, the NMDA receptor antagonist is dextromethorphan, dextrorphan, dextrallorphan, memantine, amantadine, rimantadine, nitromemantine (YQW-36), ketamine (and its analogs, e.g. tiletamine), phencyclidine (and its analogs, e.g. tenocyclidine, eticyclidine, rolicyclidine), methoxetamine (and its analogs), gacyclidine (GK-11), neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A) or AP-7.

In some embodiments, the NMDA receptor partial agonist is a NRX-1074 or rapastinel (GLYX-13).

In some embodiments, the neurokinin 1 receptor antagonist is aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ=11974, RP 67580, NKP608, VPD-737, GR 205171, LY686017, AV608, SR140333B, SSR240600C, FK 888 or GR 82334.

In some embodiments, the neurokinin 2 receptor antagonist saredutant, ibodutant, nepadutant, GR-159897 or MEN-10376.

In some embodiments, the neurokinin 3 receptor antagonist is osanetant, talnetant, SB-222200 or SB-218795.

The term "MOR agonist" is intended to mean any compound or substance that activates the mu-opioid receptor (MOR). The agonist may be a partial, full or super agonist.

The term "DOR agonist" is intended to mean any compound or substance that activates the delta-opioid receptor (DOR). The agonist may be a partial, full or super agonist.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers er, diestereomers) are included within the scope of this invention, unless indicated otherwise. Such isomers can be obtained in eadostentiaily pore form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryi and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic marbons carbon-carbon double bonds may be present. Thus, $C_2$-$C_n$ alkenyl is defined to include groups having 1, 2 . . . , n–1 or n methernon For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C^2$-$C_n$ alkynyl. An embodiment can be $C_2$-$C_{12}$ alkynyl or $C_2$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein. a hydrogen contained therein in nelaand he a bond to an —OH group.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic Mansatumatedl heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the cnrrPS pending N-oxides thereof are also encompassed. by this definition.

The term "heterocycle", "heterocyclyl" or "heterocyclic" refers to a mono-or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons.

The term "benzyl" is intended to mean a —$CH_2R_1$ group wherein the $R_1$ is a phenyl group.

The term "thiophene" is intended to mean a heteroaryl having a five-membered ring containing four carbon atoms and one sulfur atom.

The term "tetrahydrofuran" is intended to mean a heterocyclyl having a five-membered ring containing four carbon atoms and one O atom.

The term, "pyrrolidine" is intended to mean a hererocyclyl having a five-membered ring containing four carbon atoms and one nitrogen atom.

The term "1,3 dioxane" is intended to mean a heterocyclyl having a six-membered ring containing four carbon atoms and two oxygen atoms.

The term "4,5-dihydrooxazole" is intended to mean a heterocyclyl having a five-membered ring containing 3 carbon atoms, one oxygen atom and one nitrogen atom.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley—Interscience) $5^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those ordinary skill in he art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Serge et al. (1977) "Pharmaceutical Salts", J. Pharm. Sci. 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Reagents and solvents were obtained from commercial sources and were used without further purification unless otherwise stated. All compounds were prepared in racemic form. All reactions were performed under argon atmosphere unless otherwise stated. All column chromatography was performed on silica gel (40-63 µm). Nuclear magnetic resonance spectra were recorded on Bruker 400 or 500 MHz instruments as indicated. Chemical shifts are reported as δ values in ppm referenced to CDCl$_3$ ($^1$H NMR=7.26 and $^{13}$C NMR=77.16), Acetone-d$_6$ ($^1$H NMR=2.05 and $^{13}$C NMR=29.84), or Methanol-d$_4$ ($^1$H NMR=3.31 and $^{13}$C NMR=49.00). Multiplicity is indicated as follows: s (singlet); d (doublet); t (triplet); q (quartet); p (pentet); h (heptet); dd (doublet of doublets); ddd (doublet of doublet of doublets); dt (doublet of triplets); td (triplet of doublets); m (multiplet); br (broad). For several compounds, spectra are complicated by the presence of conformers, C—F coupling, or the presence of diastereomers. Low-resolution mass spectra were recorded on a JEOL LCmate (ionization mode: APCI+). For compounds 4 and 5 mass spectra are reported for carbocations corresponding to loss of OH or Cl respectiviely, Those having ordinery skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; 6$^{th}$ edition, 2007), the content of which is hereby incorporated by reference.

Preparation of the Amine Side-chain (used in synthesis of 52)

7-Azidoheptanamide

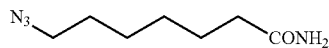

The azide was prepared according the procedure described by Durand, P. et al. 1998. $^1$H NMR (400 MHz, Chloroform-d) δ 5.45 (d, J=28.6 Hz, 2H), 3.26 (t, J=6.8 Hz, 2H), 2.23 (t, J=7.5 Hz, 2H), 1.72-1.54 (m, 4H), 1.47-1.31 (m, 4H).

7Aminoheptanamide

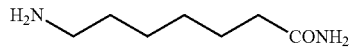

To a solution of the above azide (170 mg, 1.0 mmol) in THF (12 mL) and water (1mL) was added Ph$_3$P (262 mg, 1.0 mmol). The resulting mixture was heated to 60° C. under Ar for 18 h. The solvent was removed and the crude product was used in the next step without further purification.

Preparation of Sulfonyl Chlorides

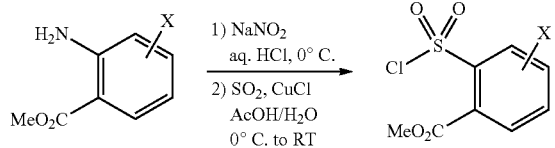

Methyl 4-chloro-2-(chlorosulfonyl)benzoate. A suspension of methyl 2-amino-4-chlorobenzoate (8.35 g, 45.0 mmol) in 20% aqueous HCl (29 mL) was sonicated for several minutes and warmed slightly until all clumps were broken up and the mixture was a uniform suspension of fine particles. This mixture was cooled to 0° C., and a solution af NaNO$_2$ (3.11 g, 45.0 mmol) in water (7.5 mL) was added dropwise, maintaining the internal temperature below 5° C. The resulting mixture was then stirred for 2 h at 0° C. A solution of SO$_2$ (23.1 g, 360 mmol) in AcOH (36.0 mL) and water (3.75 mL) was then prepared by bubbling the gas though the mixed solvents at 0° C. until the mass had increased by the required amount. To this SO$_2$ solution was then added CuCl (1.11 g, 11.25 mmol) followed by the diazonium salt solution portionwise over 30 minutes at 0° C. The resulting mixture was then stirred for 1 h at 0° C. and 1 h at room temperature, poured into ice water (150 mL), and extracted with CH$_2$Cl$_2$ (3×50 mL). The combined organics were poured into saturated aqueous NaHCO$_3$ (75 mL), and solid NaHCO$_3$ was added carefully until effervescence ceased. The organic phase was then separated, washed with brine (50 mL), dried over Na$_2$SO$_4$, and concentrated to provide the crude sulfonyl chloride as a red-brown oil (3.26 g, 81 mass % product by NMR, 22% yield). This material was used in the next step without further purification.

Methyl 4-bromo-2-(chlorosulfonyl)benzoate. Prepared from methyl 2-amino-4-bromobenzoate (10.35 g, 45.0 mmol) according to the procedure described above for methyl 4-chloro-2-(chlorosulfonyl)benzoate. The crude sulfonyl chloride was obtained as a waxy brown solid (5.15 g, 78 mass % product by NMR, 29% yield) and used in the next step without further purification.

Methyl 5-chloro-2-(chlorosulfonyl)benzoate. Prepared from methyl 2-amino-5-chlorobenzoate (5.00 g, 26.9 mmol) according to the procedure described for methyl 4-chloro-2-(chlorosulfonyl)benzoate. The crude sulfonyl chloride was obtained as a yellow oil (3.70 g, 36 mass % product by NMR, 19% yield) and used in the next step without further purification.

Preparation of Substituted 4-Methylbenzo[f]thieno[3,2-c][1,2]thiazepin-10(4H)-one 5,5-dioxides 3a-d

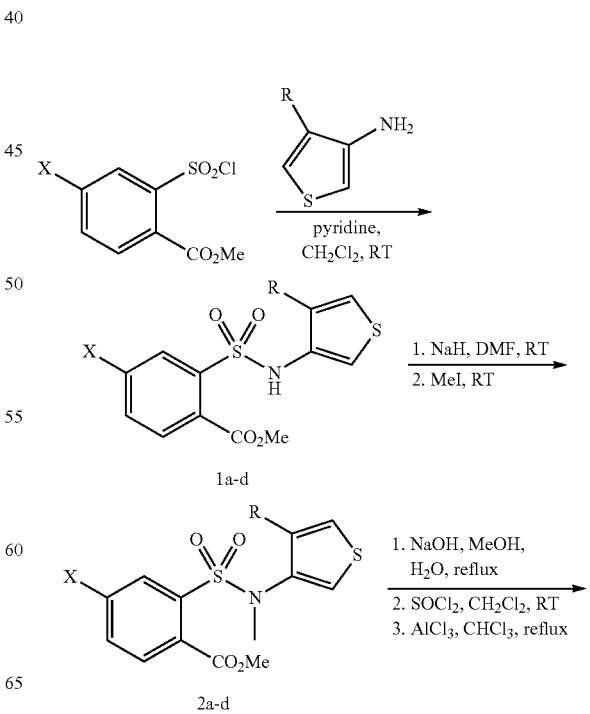

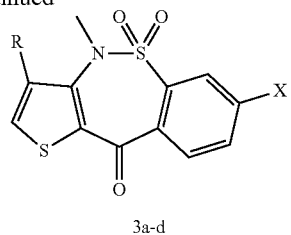

3a-d

Methyl 2-(N-(thiophen-3-yl)sulfamoyl)benzoate (1a)

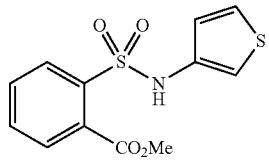

A solution of methyl 2-(chlorosulfonyl)benzoate (1.15 g, 5.00 mmol) in anhydrous $CH_2Cl_2$ (10 mL) was added dropwise to a solution of thiophen-3-amine oxalate (1.04 g, 5.50 mmol) and pyridine (0.55 mL, 6.5 mmol) in dry $CH_2Cl_2$ (15 mL). The resulting mixture was stirred overnight at room temperature. The reaction mixture was then poured on ice and extracted with $CH_2Cl_2$. The combined organic layers were washed with HCl (1.0 M) followed by sat. $NaHCO_3$ and dried over $Na_2SO_4$. The crude product was purified by column chromatography ($CH_2Cl_2$ +2% acetone). The product 1a was obtained as a yellowish oil (1.22 g, 82%). $^1H$ NMR (400 MHz, Acetone-$d_6$) δ $^1H$ NMR (400 MHz, Acetone-$d_6$) δ 7.92-7.84 (m, 1H), 7.81 (dd, J=7.6, 1.4 Hz, 1H), 7.73 (td, J=7.5, 1.3 Hz, 1H), 7.65 (td, J=7.7, 1.4 Hz, 1H), 7.35 (dd, J=5.2, 3.2 Hz, 1H), 7.04 (dd, J=3.2, 1.4 Hz, 1H), 6.96 (dd, J=5.2, 1.4 Hz, 1H), 3.98 (s, 3H); $^{13}C$ NMR (101 MHz, Acetone-$d_6$) δ 168.8, 138.4, 136.0, 133.8, 132.7, 132.0, 131.0, 130.6, 126.4, 124.0, 113.6, 53.7; LR-MS calcd. for $C_{12}H_{12}NO_4S_2$ $[M+H]^+$ 298.02, found 298.55.

Methyl 2-(N-(4-bromothiophen-3-yl)sulfamoyl)benzoate (1b)

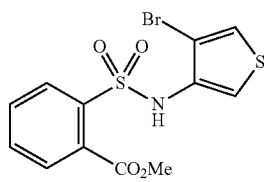

To a solution of 3-amino-4-bromothiophene (prepared according to the procedure described in Uy, R. et al. 2011) (2.01 g, 11.29 mmol) in anhydrous pyridine (8.0 mL) was carefully added methyl 2-(chlorosulfonyl)benzoate (2.52 g, 10.75 mmol) and the resulting solution was left to stir at room temperature for 15 min. The reaction was then diluted with $CH_2Cl_2$ (75 mL) and washed with 7% aq. HCl (2×75 mL), brine (50 mL), saturated aq. $NaHCO_3$ (75 mL), and brine again (50 mL). After drying over $Na_2SO_4$ and concentration the crude product was obtained as a black solid. This material was purified by column chromatography ($CH_2Cl_2$:hexanes-8:2) to yield sulfonamide 1b as a tan, crystalline solid (2.37 g, 59%). $^1H$ NMR (400 MHz, $CDCl_3$) δ 8.34 (s, 1H), 7.95 (dd, J=7.7, 1.3 Hz, 1H), 7.87 (dd, J=7.5, 1.4 Hz, 1H), 7.63 (td, J=7.6, 1.4 Hz, 1H), 7.57 (td, J=7.6, 1.5 Hz, 1H), 7.29 (d, J=3.6 Hz, 1H), 7.13 (d, J=3.6 Hz, 1H), 4.04 (s, 3H); $^{13}C$ NMR (101 MHz, $CDCl_3$) δ 167.6, 138.7, 133.00, 132.97, 131.8, 131.2, 130.7, 130.0, 122.5, 113.4, 106.0, 53.6; LR-MS calcd. for $C_{12}H_{11}BrNO_4S_2$ $[M+H]^+$ 377.93, found 378.38.

Methyl 4-chloro-2-(N-(thiophen-3-yl)sulfamoyl)benzoate (1c)

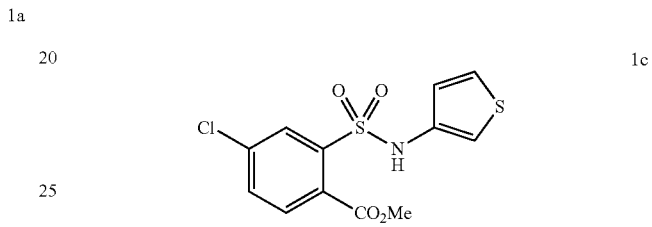

To a suspension of thiophen-3-amine oxalate (2.01 g, 10.63 mmol) in anhydrous $CH_2Cl_2$ (10 mL) at 0° C. under argon was added anhydrous pyridine (7.0 mL) followed by a solution of crude methyl 4-chloro-2-(chlorosulfonyl)benzoate (3.22 g, 81% pure, 9.66 mmol) in anhydrous $CH_2Cl_2$ (10 mL) over ~2 minutes. The resulting dark red-brown solution was then allowed to warm to room temperature and stirred for 1 h. The reaction mixture was then diluted with $CH_2Cl_2$ (100 mL) and washed with 3% aqueous HCl (2×50 mL), brine (50 mL), saturated aqueous $NaHCO_3$ (50 mL), and brine again (50 mL), dried over $Na_2SO_4$, and concentrated to give a dark-red oil (3.33 g). This material was purified by column chromatography (hexanes:EtOAc-8:2) to provide white crystals contaminated with oily brown impurities (2.33 g). These solids were washed 3× with small portions of 8:2 hexanes:EtOAc (removing the supernatant each time by pipette, impurities dissolve) to provide pure sulfonamide 1c as off-white crystals (2.13 g, 66%). $^1H$ NMR (500 MHz, $CDCl_3$) δ 8.21 (s, 1H), 7.89 (d, J=2.1 Hz, 1H), 7.80 (d, J=8.3 Hz, 1H), 7.55 (dd, J=8.3, 2.1 Hz, 1H), 7.18 (dd, J=5.1, 3.2 Hz, 1H), 6.94 (dd, J=.2, 1.3 Hz, 1H), 6.89 (dd, J=5.2, 1.4 Hz, 1H), 4.03 (s, 3H) $^{13}C$ NMR (126 MHz, $CDCl_3$) δ 167.5, 14033, 138.5, 134.2, 132.7, 132.3, 130.8, 128.6, 125.9, 123.6, 114.7, 53.8; LR-MS calcd. for $C_{12}H_{11}ClNO_4S_2$ $[+H]^+$ 331.99, found 332.49.

Methyl 4-bromo-2-(N-(thiophen-3-yl)sulfamoyl)benzoate (1d)

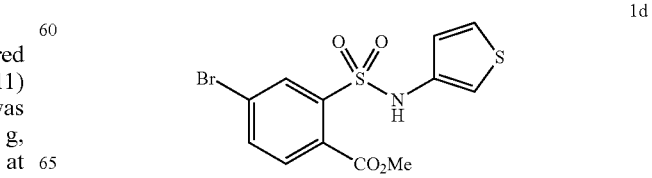

To a solution of crude methyl 4-bromo-2-(chlorosulfonyl)benzoate (5.10 g, 78% pure, 12.72 mmol) in anhydrous pyridine (9.6 mL) was added thiophen-3-amine oxalate (2.65 g, 13.99 mmol) at room temperature, and the resulting dark-red solution was stirred for 1 h. The reaction mixture was then diluted with CH$_2$Cl$_2$ (100 mL) and washed with 7% aqueous HCl (2×50 mL), brine (50 mL), saturated aqueous NaHCO$_3$ (50 mL), and brine again (50 mL), dried over Na$_2$SO$_4$, and concentrated to give a dark-red oil (2.41 g). This material was purified by column chromatography (hexanes:EtOAc-9:1, 2 column volumes→8:2, 2 column volumes→7:3, 2 column volumes) to provide off-white crystals contaminated with oily brown impurities (1.34 g). These solids were washed 2× with small portions of 7:3 hexanes:EtOAc (removing the supernatant each time by pipette, impurities dissolve) to provide pure sulfonamide 1d as tan crystals (1.16 g, 24%). $^1$H NMR (500 MHz, CDCl$_3$) δ 8.19 (s, 1H), 8.04 (s, 1H), 7.75-7.69 (m, 2H), 7.18 (dd, J=5.1, 3.2 Hz, 1H), 6.94 (dd, J=3.2, 1.3 Hz, 1H), 6.89 (dd, J=5.1, 1.3 Hz, 1H), 4.02 (s, 3H); $^{13}$C NMR (126 MHz, CDCl$_3$) δ 167.6, 140.2, 135.8, 134.2, 133.5, 132.3, 129.1, 126.6, 125.9, 123.6, 114.7, 53.9; LR-MS calcd. for C$_{12}$H$_{11}$BrNO$_4$S$_2$ [M+H]$^+$ 375.93, found 376.29.

Methyl 2-(N-methyl-N-(thiophen-3-yl)sulfamoyl)benzoate (2a)

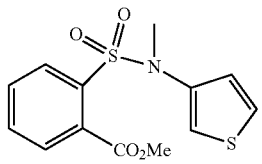

2a

A solution of sulfonamide 1a (1.2 g, 4.04 mmol) in anhydrous DMF (5 mL) was added dropwise to an ice-cold suspension of sodium hydride (60% dispersion in mineral oil, 350 mg, 8.1 mmol) in dry DMF (3 ml). After stirring for 1 h at room temperature, methyl iodide (0.5 mL, 8.1 mmol) was added dropwise, and the mixture was stirred overnight. The reaction mixture was poured on ice and the solid was filtered, washed with water, and dried. The crude product 2a was obtained as a white solid (in sufficient purity) and was used in the next step without further purification.

Methyl 2-(N-(4-bromothiophen-3-yl)-N-methylsulfamoyl)benzoate (2b)

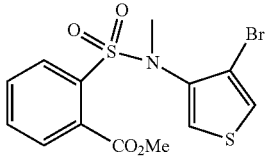

2b

To a suspension of sodium hydride (60% dispersion in mineral oil, 498 mg, 12.44 mmol) in anhydrous DMF (9.0 mL) was added a solution of sulfonamide 1b (2.34 g, 6.22 mmol) in anhydrous DMF (9.0 mL) dropwise over 5 minutes and the resulting mixture was left to stir at room temperature for 1.75 h. Methyl iodide (1.77 g, 0.776 mL, 12.44 mmol) was then added and the mixture stirred for 2 h and then quenched with ice water (125 mL) and extracted with CH$_2$Cl$_2$ (2×50 mL, 25 mL). The combined organics were washed with water (2×50 mL), dried over Na$_2$SO$_4$, and concentrated to yield a dark-brown oil still containing residual DMF. This material was re-dissolved in Et20 (50 mL), washed with water (4×50 mL), dried over Na$_2$SO$_4$, and concentrated to provide a biphasic oil. This crude material was purified by column chromatography (CH$_2$Cl$_2$) to yield sulfonamide 2b as an orange oil, which slowly crystallized into a waxy, orange solid (1.38 g, 57%). $^1$H NMR (400 MHz, CDCl$_3$) δ 7.70 (dd, J=8.3, 0.9 Hz, 1H), 7.60 (td, J=7.6, 1.2 Hz, 1H), 7.53-7.47 (m, 2H), 7.28 (d, J=3.6 Hz, 1H), 7.22 (d, J=3.6 Hz, 1H), 3.86 (s, 3H), 3.33 (s, 3H); $^{13}$C NMR (101 MHz, CDCl$_3$) δ 168.3, 137.5, 136.9, 133.5, 132.7, 130.2, 129.7, 128.5, 125.4, 123.2, 111.8, 53.2, 39.0; LR-MS calcd. for C$_{13}$H$_{13}$BrNO$_4$S$_2$ [M+H]$^+$ 391.94, found 392.42.

Methyl 4-chloro-2-(N-methyl-N-(thiophen-3-yl)sulfamoyl)benzoate (2c)

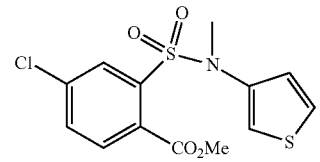

2c

To a suspension of sodium hydride (60% dispersion in mineral oil, 506 mg, 12.66 mmol) in anhydrous DMF (9 mL) was added a solution of sulfonamide 1c (2.1 g, 6.32 mmol) in anhydrous DMF (9 mL) dropwise over 5 minutes, and the resulting mixture was left to stir at room temperature for 1.5 h. Methyl iodide (1.79 g, 0.788 mL, 12.66 mmol) was then added, and the resulting mixture was stirred for 2.5 h and quenched with ice water (125 mL). This aqueous layer was extracted with CH$_2$Cl$_2$ (2×50 mL, 25 mL). The combined organics were washed with water (2×50 mL), dried over MgSO$_4$, and concentrated to yield a dark brown oil. This oil was washed with 3 portions of boiling hexanes (5 mL), cooling and carefully removing the supernatant by pipette each time, and dried in vacuo to yield sulfonamide 2c (1.83 g, 84%). $^1$H NMR (300 MHz, CDCl$_3$) δ 7.53 (dd, J=8.2, 2.0 Hz, 1H), 7.44 (s, 1H), 7.41-7.39 (m, 1H), 7.29-7.25 (m, 1H), 7.05-7.01 (m, 2H), 3.88 (s, 3H), 3.27 (s, 3H); $^{13}$C NMR (75 MHz, CDCl$_3$) δ 167.9, 139.6, 137.1, 136.7, 133.1, 132.3, 130.14, 130.08, 125.9, 125.5, 119.1, 53.8, 39.3. LR-MS cald. for C$_{13}$H$_{13}$ClNO$_4$S$_2$ [M+H]$^+$ 346.00, found 346.89.

Methyl 4-bromo-2-(N-methyl-N-(thiophen-3-yl)sulfamoyl)benzoate (2d)

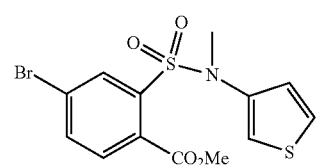

2d

To a suspension of sodium hydride (60% dispersion in mineral oil, 244 mg, 6.12 mmol) in anhydrous DME (4.5 mL) at 0° C. was added a solution of sulfonamide 1d (1.15 g, 3.06 mmol) in anhydrous DMF (4.5 mL) dropwise over 5 minutes, and the resulting mixture was allowed to warm to room temperature and stirred for 1.5 h. Methyl iodide (869 mg, 381 μL, 6.12 mmol) was then added dropwise over 2 minutes and the mixture was stirred for 2 h before quenching with ice water (50 mL) and extracting with Et$_2$O (3×25 mL). The combined organics were washed with water (2×25 mL) and brine (25 mL), dried over Na$_2$SO$_4$, and concentrated to provide a biphasic, pale-brown oil (1.26 g). The material was washed 3× with small portions of boiling hexanes, cooling and carefully removing the supernatant by pipette each time. The residue was then dried in vacuo to provide pure sulfonamide 2d as an orange-brown oil (1095 mg, 92%). $^1$H NMR (500 MHz, CDCl$_3$) δ 7.69 (dd, J=8.2, 1.7 Hz, 1H), 7.52 (d, J=1.6 Hz, 1H), 7.35 (d, J=8.2 Hz, 1H), 7.30-7.27 (m, 1H), 7.04-7.01 (m, 2H), 3.88 (s, 3H), 3.26 (s, 3H); $^{13}$C NMR (126 MHz, CDCl$_3$) δ 167.6, 139.2, 136.4, 135.6, 132.5, 132.3, 129.7, 125.5, 125.1, 124.0, 118.7, 53.5, 38.8; LR-MS calcd. for C$_{13}$H$_{13}$BrNO$_4$S$_2$ [M+H]$^+$ 389.95, found 390.25.

4-Methylbenzo[f]thieno[3,2-c][1,2]thiazepin-10 (4H)-one 5,5-dioxide (3a)

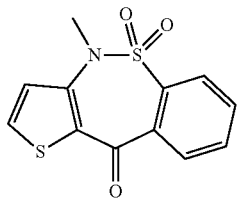

3a

Sodium hydroxide (0.64 g) was added to a solution of crude sulfonamide 2a (1.2 g, 3.85 mmol) in a MeOH/water (2:1) solution (30 mL). After stirring for 2 h at reflux, the reaction mixture was cooled to 0° C. and acidified (pH 1-2) with 10% HCl. The solution was extracted with CH$_2$Cl$_2$ and the combined organic layers were dried over Na$_2$SO$_4$, and concentrated. The carboxylic acid was dissolved in anhydrous CH$_2$Cl$_2$ (20 mL) and thionyl chloride (1.16 mL, 16.0 mmol) was added. After stirring for 16 h at room temperature, the reaction mixture was concentrated and the residue was taken up in CHCl$_3$ (25 mL). Aluminium chloride (1.6 g, 12.0 mmol) was added and the mixture was refluxed for 1 h. The solvent was evaporated and water was added to the ice-cooled residue followed by extraction with CH$_2$Cl$_2$. The combined organic layers were dried over Na$_2$SO$_4$, filtered, and concentrated. The crude product was purified by column chromatography (CH$_2$Cl$_2$:nexanes-2:1). The product 3a was obtained as a yellowish solid (640 mg, 58% over 3 steps). $^1$H NMR (400 MHz, Acetone-d$_6$) δ 8.15-8.03 (m, 3H), 8.00-7.91 (m, 2H), 7.34 (d, J=5.4 Hz, 1H), 3.48 (s, 3H); $^{13}$C NMR (101 MHz, Acetone-d$_6$) δ 183.6, 143.0, 137.5, 136.1, 135.0, 134.8, 134.2, 132.1, 124.5, 124.6, 38.2; LR-MS calcd. for C$_{12}$H$_{10}$NO$_3$S$_2$ [M+H]$^+$ 280.01, found 280.60.

3-Bromo-4-methylbenzo[f]thieno[3,2-c][1,2]thiazepin-10(4H)-one 5,5-dioxide (3b)

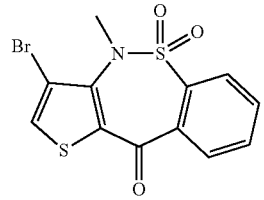

3b

To a solution of sulfonamide 2b (1.22 g, 3.13 mmol) in MeOH (12.5 mL) was added water (6.25 mL) and NaOH (376 mg, 9.39 mmol), and the mixture was refluxed for 1 h. At this time, 10% aq. HCl (5.0 mL) was added and the dense white cake of precipitate which had formed was broken up and washed from the reaction vessel with water. After stirring to break up clumps, the fine, white crystals were collected by vacuum filtration and dried to yield the carboxylic acid (1076 mg), which was used in the next step without further purification. The carboxylic acid (1072 mg, 2.85 mmol) was dissolved in thionyl chloride (12 mL), and the resulting solution left to stir for 13 h at room temperature. The volatiles were then removed to yield the crude acyl chloride as a light-brown solid which was used in the next step without further purification. The acyl chloride was re-dissolved in CHCl$_3$ (13 mL), aluminum chloride (1.22 g, 9.12 mmol) was added, and the resulting mixture was refluxed for 1 h. The reaction was then quenched with ice water (100 mL), stirred until all the brown sludge had broken up into a white suspension, and then extracted with CH$_2$Cl$_2$ (3×50 mL). The combined organics were washed with water (50 mL), dried over Na$_2$SO$_4$, and concentrated to yield a dark-brown solid. This crude material was purified by column chromatography (CH$_2$Cl$_2$:hexanes-6:4) to yield the pure ketone 3b as a tan, crystalline solid (653 mg, 58% over three steps). $^1$H NMR (400 MHz, CDCl$_3$) δ 8.24-8.18 (m, 1H), 8.16-8.09 (m, 1H), 7.86-7.78 (m, 2H), 7.73 (s, 1H), 3.20 (s, 3H); $^{13}$C NMR (126 MHz, CDCl$_3$) 181.2, 140.7, 136.2, 136.0, 134.0, 133.6, 133.2, 132.7, 128.3, 110.2, 38.3; LR-MS calcd. for C$_{12}$H$_9$BrNO$_3$S$_2$ [M+H]$^+$ 359.92, found 360.08.

7-Chloro-4-methylbenzo[f]thieno[3,2-c][1,2]thiazepin-10(4H)-one 5,5-dioxide(3c)

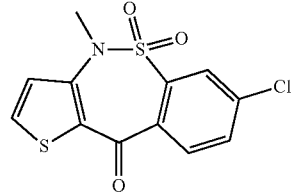

3c

To a solution of sulfonamide 2c (1.83 g, 5.29 mmol) in MeOH (13 mL) and water (6.5 mL) was added sodium hydroxide (396 mg, 15.9 mmol). The resulting mixture was refluxed for 1.5 h after which time the reaction was cooled to room temperature and 10% HCl (10 mL) was added. The reaction was concentrated to remove most of the MeOH, and to this aqueous residue was added water (10 mL), and the mixture was then extracted with $CH_2Cl_2$ (30 mL, 2×20 mL). The combined organics were dried over $Mg_2SO_4$ and concentrated to yield the intermediate carboxylic acid as a tan crystalline solid (1.47 g, 84%) that was used without further purification. The carboxylic acid (1.47 g, 4.44 mmol) was dissolved in $SOCl_2$ (13.8 g, 8.47 mL, 116 mmol) and allowed to stir overnight under argon. After 14 h, the reaction mixture was concentrated to obtain the intermediate acyl chloride, and the resulting dark brown residue was dissolved in $CHCl_3$ (19.4 mL). Aluminum chloride (1.89 g, 14.21 mmol) was added, and the reaction mixture was refluxed for 1 hour after which time the solution was cooled to room temperature and quenched with ice water (100 mL). The resulting aqueous layer was extracted with $CH_2Cl_2$ (3×50 mL), and the combined organics were washed with water (50 mL), dried over $MgSO_4$, and concentrated. The crude product was purified by column chromatography (2:1 $CH_2Cl_2$:hexane→$CH_2Cl_2$) to give a yellow solid (686 mg, 49%). $^1$H NMR (400 MHz, $CDCl_3$) δ 8.12 (d, J=8.4 Hz, 1H), 8.04 (d, J=2.1 Hz, 1H), 7.77-7.71 (m, 2H), 7.04 (d, J=5.4 Hz, 1H), 3.45 (s, 3H); $^{13}$C NMR (101 MHz, $CDCl_3$) δ 181.4, 144.2, 141.3, 139.7, 135.5, 133.7, 133.5, 132.2, 125.9, 122.8, 38.1; LR-MS call. for $C_{12}H_9Cl\ NO_3S_2$ [M+H]$^+$ 313.97, found 314.81.

7-Bromo-4-methylbenzo[f]thieno[3,2-c][1,2]thiazepin-10 (4H)-one 5,5-dioxide (3d)

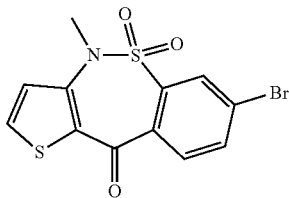

3d

To a solution of sulfonamide 2d (1085 mg, 2.78 mmol) in MeOH (7.0 mL) was added water (3.5 mL) and NaOH (334 mg, 8.34 mmol) and the mixture was refluxed for 1 h. The reaction was then cooled to room temperature, acidified with 10% aqueous HCl (5 mL), and most of the MeOH was removed in vacuo. The remaining aqueous residue was diluted with water (10 mL) and extracted with $CH_2Cl_2$ (20 mL, 2×10 mL). The combined organics were dried over $Na_2SO_4$ and concentrated to provide the carboxylic acid as a tan, crystalline solid (1.00 g), which was used in the next step without further purification. The carboxylic acid (990 mg, 2.63 mmol) was dissolved in thionyl chloride (5.0 mL) and the solution was stirred for 16 h at room temperature. The volatiles were then removed to provide the crude acyl chloride as a brown oil. This material was dissolved in $CHCl_3$ (11.5 mL), aluminum chloride (1.12 g, 8.42 mmol) was added, and the mixture was refluxed for 1 h. The reaction was then cooled to room temperature, quenched with ice water (50 mL), stirred until all the brown sludge had broken up, and then extracted with $CH_2Cl_2$ (3×25 mL). The combined organics were washed with water (25 mL), dried over $Na_2SO_4$, and concentrated to give a brown solid. This material was purified by column chromatography ($CH_2Cl_2$: hexanes-2:1, 5 column volumes→$CH_2Cl_2$, 3 column volumes) to provide pure ketone 3d as a pale-yellow, crystalline solid (579 mg, 59% over three steps). $^1$H NMR (500 MHz, $CDCl_3$) δ 8.20 (d, J=1.9 Hz, 1H), 8.03 (d, J=8.3 Hz, 1H), 7.90 (dd, J=8.3, 2.0 Hz, 1H), 7.75 (d, J=5.4 Hz, 1H), 7.04 (d, J=5.4 Hz, 1H), 3.46 (s, 3H); $^{13}$C NMR (126 MHz, $CDCl_3$) δ 181.6, 141.3, 138.2, 136.8, 135.5, 133.4, 132.6, 131.6, 128.7, 127.8, 122.8, 38.1; LR-MS calcd. for $C_{12}H_9BrNO_3S_2$ [M+H]$^+$ 357.92, found 358.49.

Preparation of Substituted 6-alkyldibenzo[c,f][1,2]thiazepin-11(6H)-one 5,5-dioxides 3f-3ac Ketones 3f-3ac were prepared according to the procedures described below.

3-Chloro-6-methyldibenzo[c,f][1, 2]thiazepin-11 (6H)-one 5,5-dioxide (3f)

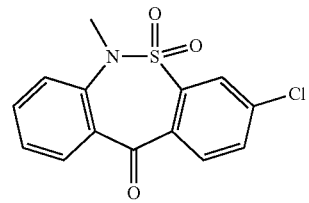

3f

Ketone 3f was purchased from Ark Pharm, Inc. (Libertyville, Ill.) and used without further purification.

3-Fluoro-6-methyldibenzo[c,f][1,2]thiazepin-11 (6H)-one 5,5-dioxide (3g)

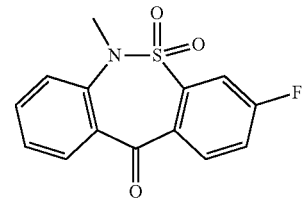

3g

Ketone 3f (462 mg, 1.50 mmol) and cesium fluoride (684 mg, 4.50 mmol) were combined, anhydrous DMSO (3.0 mL) was added, and the mixture was heated to 180° C. for 20 min. After cooling to room temperature, the reaction was diluted with water (60 mL) and extracted with $CH_2Cl_2$ (20 mL, 2×15 mL). The combined organics were washed with water (50 mL), dried over $Na_2SO_4$, and concentrated to give a yellow glass. This was purified by column chromatography ($CH_2Cl_2$:Hexanes-8:2) to yield ketone 3g as a white solid (215 mg, 49%). $^1$H NMR (400 MHz, $CDCl_3$) δ 8.32 (dd, J=8.1, 1.6 Hz, 1H), 8.03 (dd, J=8.6, 5.1 Hz, 1H), 7.71-7.62 (m, 2H), 7.43-7.34 (m, 3H), 3.36 (s, 3H); $^{13}$C NMR (126 MHz, $CDCl_3$) (additional peaks due to C—F coupling) δ 189.4, 165.2, 163.2, 141.3, 139.5, 139.4, 135.1, 134.8, 134.8, 132.5, 132.3, 131.2, 126.4, 124.9, 120.5, 120.3, 113.3, 113.1, 39.2; LR-MS calcd. for $C_{14}H_{11}FNO_3S$ [M+H]$^+$ 292.04, found 292.12.

3-Methoxy-6-methyldibenzo[c,f][1,2]thiazepin-11(6H)-one 5,5-dioxide (3h)

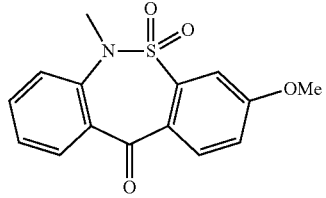

To a solution of sodium metal (115 mg, 5.00 mmol) in anhydrous MeOH (5.0 mL) was added ketone 3f (308 mg, 1.00 mmol) and the mixture was heated to 100° C. for 2 h in a sealed pressure vial. The reaction was then cooled to room temperature, diluted with water (10 mL), and extracted with $CH_2Cl_2$ (3×10 mL). The combined organics were washed with water (2×10 mL), dried over $Na_2SO_4$, and concentrated to yield a yellow crystalline solid. This material was recrystallized from MeOH to yield ketone 3h as white prisms (158 mg, 52%). $^1$H NMR (500 MHz, $CDCl_3$) δ 8.33 (dd, J=8.1, 1.6 Hz, 1H), 8.04 (d, J=8.7 Hz, 1H), 7.63 (ddd, J=8.0, 7.3, 1.7 Hz, 1H), 7.46 (d, J=2.6 Hz, 1H), 7.42-7.34 (m, 2H), 7.18 (dd, J=8.7, 2.6 Hz, 1H), 3.96 (s, 3H), 3.33 (s, 3H); $^{13}$C NMR (126 MHz, $CDCl_3$) δ 189.0, 162.8, 141.2, 139.1, 134.6, 134.5, 132.4, 128.3, 126.6, 125.5, 118.9, 110.8, 56.3, 39.4; LR-MS calcd. for $C_{15}H_{14}NO_4S$ [M+H]$^+$ 304.06, found 303.91

6-Methyl-3-phenoxydibenzo[c,f][1,2]thiazepin-11(6H)-one 5,5-dioxide (3i)

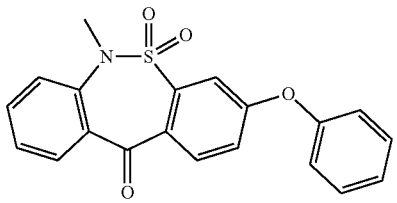

Ketone 3f (308 mg, 1.00 mmol), phenol (2.82 g, 30.0 mmol), and $K_2CO_3$ (691 mg, 5.00 mmol) were combined and heated to 150° C. for 2 h and then to 170° C. for 3.25 h. The hot reaction mixture was then carefully diluted with 10% aq. NaOH and extracted with $Et_2O$ (3×30 mL). The combined organics were washed with water (30 mL) and brine (30 mL), dried over $Na_2SO_4$, and concentrated to yield a yellow foam. This material was purified by column chromatography ($CH_2Cl_2$:Hexanes-1:1, 3 column volumes→6:4, 3 column volumes) to give a pale-yellow foam still contaminated with impurities. This material was re-dissolved in $CH_2Cl_2$ and concentrated again to yield a yellow foam. A small quantity of $Et_2O$ was then added to this material causing complete dissolution followed immediately by crystallization of the product as a cake of fine white crystals. After cooling on ice, the supernatant was removed by pipette and the mass of crystals was washed with small portions of ice-cold $Et_2O$ and hexanes. After drying, the pure ketone 3i was obtained as short pale-yellow needles (288 mg, 79%). $^1$H NMR (400 MHz, $CDCl_3$) δ 8.32 (dd, J=8.1, 1.6 Hz, 1H), 8.00 (d, J=8.6 Hz, 1H), 7.63 (ddd, J=8.0, 7.4, 1.7 Hz, 1H), 7.53 (d, J=2.5 Hz, 1H), 7.47-7.41 (m, 2H), 7.40-7.33 (m, 2H), 7.29-7.24 (m, 1H), 7.22 (dd, J=8.6, 2.5 Hz, 1H), 7.14-7.09 (m, 2H), 3.33 (s, 3H); $^{13}$C NMR (101 MHz, $CDCl_3$) δ 189.3, 161.3, 154.8, 141.2, 139.1, 134.7, 134.4, 132.2, 131.8, 130.5, 129.9, 126.4, 125.6, 125.1, 121.3, 120.4, 114.2, 39.2; LR-MS calcd. for $C_{20}H_{16}NO_4S$ [M+H]$^+$ 366.08, found 365.84.

3,6-Dimethyldibenzo[c,f][1,2]thiazepin-11(6H)-one 5,5-dioxide (3j)

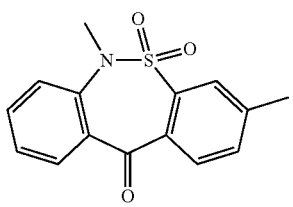

The coupling was conducted according to the procedure of Dreher, S. D. et al. 2009 To a mixture of ketone 3f (308 mg, 1.0 mmol), potassium methyltrifluoroborate (135 mg, 1.1 mmol), $K_2CO_3$ (420 mg, 3.0 mmol), Pd(OAc)$_2$ (5.2 mg, 0.02 mmol), and RuPhos (19.2 mg, 0.04 mmol) was added toluene (4.5 mL) and $H_2O$ (0.5 mL) (both solvents were de-oxygenated prior to use via standard "freeze-pump-thaw" cycle). The sealed reaction vial was heated at 85° C. under Ar for 36 h, and then cooled to room temperature. A saturated aqueous solution of $NH_4Cl$ (10 mL) was added, and the resulting mixture was extracted with $CH_2Cl_2$. The combined organic layers were dried over $Na_2SO_4$ and concentrated. The crude product was purified by column chromatography (hexane: $CH_2Cl_2$–2:3->1:2). The product 3j was obtained as a white solid (280 mg, 97%). $^1$H NMR (400 MHz, Acetone-d$_6$) δ 8.24 (dd, J=8.1, 1.6 Hz, 1H), 7.84 (d, J=7.9 Hz, 1H), 7.78 (s, 1H), 7.74 (ddd, J=8.2, 7.3, 1.7 Hz, 1H), 7.70-7.64 (m, 1H), 7.55 (dd, J=8.1, 0.9 Hz, 1H), 7.43 (td, J=7.7, 7.3, 1.1 Hz, 1H), 3.35 (s, 3H), 2.56 (s, 3H); $^{13}$C NMR (101 MHz, Acetone-d$_6$) δ 191.5, 144.5, 143.0, 137.4, 135.6, 135.0, 134.9, 132.2, 132.0, 131.8, 126.6, 126.3, 125.9, 39.4, 21.4; LR-MS calcd. for $C_{15}H_{14}NO_3S$ [M+H]$^+$ 288.07, found 288.59.

9-Bromo-3-chloro-6-methyldibenzo[c,f][1,2]thiazepin-11(6H)-one 5,5-dioxide (3k)

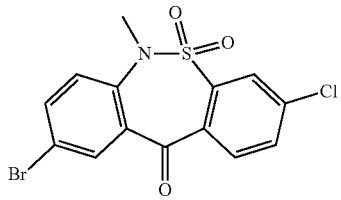

N-bromosuccinimide (187 mg, 1.05 mmol) was added portionwise to a solution of ketone 3f (308 mg, 1.0 mmol) and $FeCl_3$ (324 mg, 2.0 mmol) in $CH_2Cl_2$ (10 mL) and $CH_3CN$ (5 mL), and the reaction mixture was stirred at room temperature for 3 h. Additional N-bromosuccinimide (187 mg, 1.05 mmol) was then added and the reaction mixture was stirred at room temperature for a further 14 h. The reaction mixture was washed with water and brine and dried over NaSO₄. The crude product was purified by column chromatography (CH₂Cl₂: hexane-2:1) followed by crystallization from MeOH. The product 3k was obtained as a white solid (290 mg, 75%). ¹H NMR (400 MHz, Acetone-d₆) δ 8.31 (d, J=2.5 Hz, 1H), 8.00-7.96 (m, 1H), 7.95-7.89 (m, 3H), 7.58 (d, J=8.7 Hz, 1H), 3.44 (s, 3H); ¹³C NMR (101 MHz, Acetone-d₆) δ 189.6, 142.0, 139.1, 139.0, 138.4, 135.3, 134.7, 134.3, 132.8, 127.9, 125.8, 119.4, 39.3; LR-MS calcd. for C₁₄H₁₀BrClNO₃S [M+H]⁺ 387.92, found 388.63.

6-Methyl-3-(methylthio)dibenzo[c,f][1,2]thiazepin-11 (6H)-one 5,5-dioxide (3l)

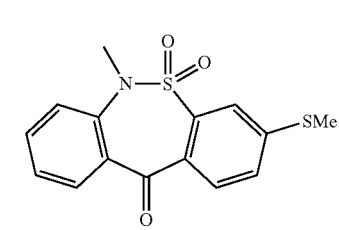

To a solution of sodium thiomethoxide (116 mg, 1.65 mmol) in anhydrous DMF (2.0 mL) was added ketone 3f (462 mg, 1.50 mmol) and the resulting yellow suspension was stirred at room temperature for 1 h. Additional sodium thiomethoxide (26.3 mg, 0.375 mmol) was then added and stirring continued for a further 15 min. The reaction was then quenched with water (10 mL) and extracted with CH₂Cl₂ (10 mL, 2×5 mL). The combined organics were washed with water (20 mL), dried over Na₂SO₄, and concentrated to yield a yellow oil containing residual DMF. This crude was diluted with Et₂O and chilled on ice causing the product to crystallize as pale-yellow needles. These crystals were washed with several small portions of ice-cold Et₂O and dried to give the pure ketone 3l (331 mg, 69%). ¹H NMR (500 MHz, CDCl₃) δ 8.31 (dd, J=8.1, 1.6 Hz, (1H), 7.92 (d, J=8.3 Hz, 1H), 7.73 (d, J=2.0 Hz, 1H), 7.62 (ddd, J=8.0, 7.4, 1.7 Hz, 1H), 7.48 (dd, J=8.3, 2.0 Hz, 1H), 7.40-7.33 (m, 2H), 3.33 (s, 3H), 2.59 (s, 3H); ¹³C NMR (126 MHz, CDCl₃) δ 189.5, 146.5, 141.4, 137.7, 134.7, 132.4, 132.2, 131.8, 131.7, 129.2, 126.4, 125.2, 121.4, 39.3, 15.0. LR-MS calcd. for C₁₅H₁₄NO₃S₂ [M+H]⁺ 320.04, found 320.75.

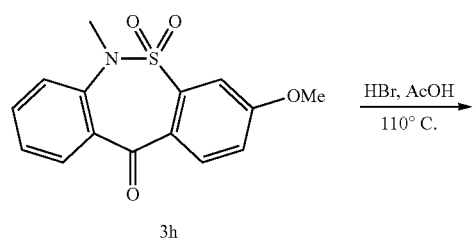

3-Hydroxy-6-methyldibenzo[c,f][1,2]thiazepin-11 (6H)-one 5,5-dioxide (3m)

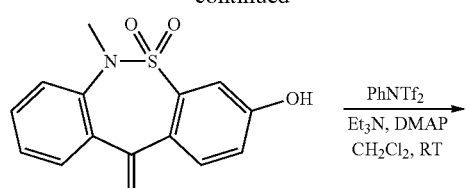

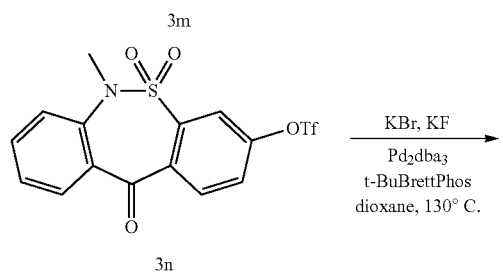

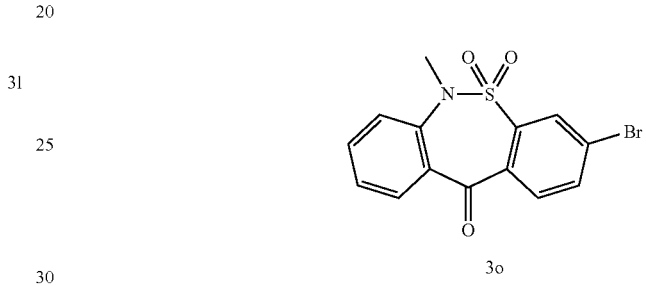

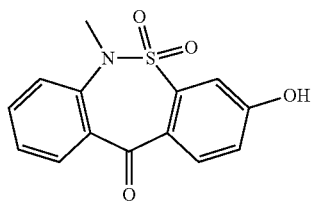

A solution of ketone 3f (330 mg, 1.09 mmol) in acetic acid (3 mL) and concentrated aqueous HBr (3 mL) was heated to 115° C. for 40 h. The reaction mixture was then poured into an ice-water mixture, and the precipitate was filtered and dissolved in CH₂Cl₂. The organic layer was dried over Na₂SO₄ and concentrated. The crude product was purified by column chromatography (CH₂Cl₂+3% acetone). The ketone 3m was obtained as a colorless oil (240 mg, 76%). ¹H NMR (400 MHz, Acetone-d₆) δ 9.82 (s, 1H), 8.28 (dd, J=8.1, 1.6 Hz, 1H), 7.91 (d, J=8.5 Hz, 1H), 7.72 (ddd, J=8.2, 7.2, 1.7 Hz, 1H), 7.55 (dd, J=8.1, 1.0 Hz, 1H), 7.43 (ddd, J=8.2, 7.2, 1.2 Hz, 1H), 7.40 (d, J=2.5 Hz, 1H), 7.25 (dd, J=8.5, 2.5 Hz, 1H), 3.36 (s, 3H); ¹³C NMR (101 MHz, Acetone-d₆) δ 189.9, 161.8, 142.6, 139.6, 135.4, 135.2, 132.5, 132.2, 128.5, 126.8, 126.4, 120.8, 112.8, 39.5. LR-MS calcd. for C₁₄H₁₂NO₄S [M+H]⁺ 290.05, found 289.99.

6-Methyl-5,5-dioxido-11-oxo-6,11-dihydrodibenzo[c,f][1,2]thiazepin-3-yl trifluoromeanesulfonate (3n)

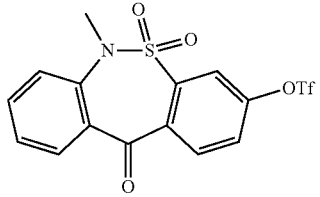

3n

To an ice-cold solution of ketone 3m (110 mg, 0.38 mmol), Et$_3$N (0.11 mL), and 4-dimethyl-aminopyridine (10 mg) in dry CH$_2$Cl$_2$ (10 mL) was added solid N-phenyl-bis(trifluoromethanesulfonimide) (170 mg, 0.49 mmol). The resulting reaction mixture was stirred at room temperature for 2.5 h. The mixture was concentrated and the crude product was purified by column chromatography (hexanes:EtOAc-3:1). The ketone 3n was obtained as a white solid (130 mg, 81%). $^1$H NMR (400 MHz, Acetone-d$_6$) δ 8.24 (dd, J=8.1, 1.6 Hz, 1H), 8.16 (d, J=8.5 Hz, 1H), 8.03 (d, J=2.4 Hz, 1H), 8.00 (dd, J=8.5, 2.5 Hz, 1H), 7.84-7.76 (m, 1H), 7.62 (d, J=8.0 Hz, 1H), 7.53-7.45 (m, 1H), 3.43 (s, 3H); $^{13}$C NMR (101 MHz, Acetone-d$_6$) δ 190.7, 151.80, 142.7, 139.6, 137.6, 136.2, 135.3, 132.2, 131.2, 127.6, 127.0, 125.9, 119.4, 39.4; LR-MS calcd. for Cl$_{15}$H$_{11}$F$_3$NO$_6$S$_2$ [M+H]$^+$ 422.00, found 421.93.

3-Bromo-6-methyldibenzo[c,f][1,2]thiazepin-11(6H)-one 5,5-dioxide (3o)

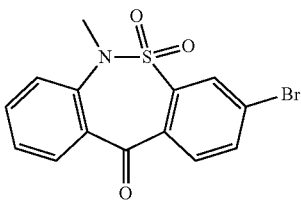

3o

The halide exchange was conducted using the procedure of Pan, J. et al. 2011. In a glove-box, triflate 3n (230 mg, 0.55 mmol), KBr (130 mg, 1.1 mmol), and KF (16 mg, 0.27 mmol) were added to a reaction vial and sealed with a screw-cap equipped with a teflon septum. To another reaction vial were added Pd$_2$(dba)$_3$ (10.2 mg, 2.0 mol %) and t-BuBrettPhos (15.9 mg, 6.0 mol %). The vial was sealed with a screw-cap equipped with a teflon septum. 1,4-Dioxane (0.7 mL) (de-oxygenated before use by standard "freeze-pump-thaw" technique) was added via syringe to the vial with the Pd-catalyst and phosphine, and the mixture was stirred at 120° C. in a preheated oil bath for 5 min. The catalyst solution was allowed to cool to room temperature and added to the reaction vial containing triflate 3n, KBr, and KF via syringe, followed by addition of dioxane (2 mL, de-oxygenated). The resulting mixture was stirred at 130° C. in a preheated oil bath for 8 h. The reaction mixture was poured on ice and extracted with CH$_2$Cl$_2$. The combined organic layers were washed with brine, dried over Na$_2$SO$_4$ and concentrated. The crude product was purified by column chromatography (CH$_2$Cl$_2$:hexane-2:1). The ketone 3o was obtained as a white solid (70 mg, 36%). $^1$H NMR (400 MHz, Acetone-d$_6$) δ 8.23 (ddd, J=8.1, 1.7, 0.3 Hz, 1H), 8.10-8.04 (m, 2H), 7.88 (dt, J=8.4, 0.8 Hz, 1H), 7.77 (ddd, J=8.2, 7.2, 1.7 Hz, 1H), 7.59 (dd, J=8.2, 1.0 Hz, 1H), 7.46 (ddd, J=8.3, 7.2, 1.2 Hz, 1H), 3.42 (s, 3H); $^{13}$C NMR (101 MHz, Acetone) δ 190.1, 141.9, 138.1, 136.6, 135.5, 135.0, 133.2, 131.2, 130.5, 127.6, 125.9, 125.0, 38.5. LR-MS calcd. for C$_{14}$H$_{11}$BrNO$_3$S [M+H] 351.96, found 351.83.

6-Methyl-3-(trimethylsilyl)dibenzo[c,f][1,2]hiazepin-6H)-one 5,5-dioxide (3p)

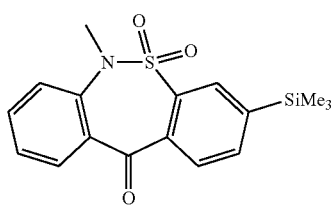

3p

Ketone 3p was prepared from the aryl chloride utilizing the trimethylsilylation procedure of of McNiell, E. et al. 2007. Ketone 3f (462 mg, 1.50 mmol), Pd$_2$dba$_3$ (20.6 mg, 0.0225 mmol), t-BuDavePhos (2'-(Di-tert-butylphosphino)-N,N-dimethylbiphenyl-2-amine, 46.1 mg, 0.135 mmol), and LiOAc (495 mg, 7.50 mmol) were combined under argon. Anhydrous DMF (4.5 mL), water (54 pL, 3.00 mmol), and hexamethyldisilane (369 µL, 1.80 mmol) were then added, and the resulting orange-brown mixture was heated to 100° C. for 33 h. After cooling to room temperature, the reaction mixture was diluted with water (20 mL) and extracted with Et$_2$O (3×10 mL). The combined organics were washed with water (10 mL), dried over Na$_2$SO$_4$, and concentrated to yield a yellow crystalline solid. This crude was recrystallized from MeOH to obtain pure ketone 3p as fine yellow needles (301 mg, 58%). $^1$H NMR (500 MHz, CDCl$_3$) δ 8.30 (dd, J=8.1, 1.6 Hz, 1H), 8.04 (d, J=0.8 Hz, 1H), 7.91 (d, J=7.5 Hz, 1H), 7.85(dd, J=7.6, 1.1 Hz, 1H), 7.63 (ddd, J=8.1, 7.3, 1.7 Hz, 1H), 7.41-7.29 (m, 2H), 3.35 (s, 3H), 0.36 (s, 9H); $^{13}$C NMR (126 MHz, CDCl$_3$) δ 191.2, 147.4, 141.9, 138.3, 136.6, 136.0, 134.8, 132.1, 131.2, 130.5, 129.7, 126.0, 124.6, 39.1,-1.2; LR-MS calcd. for C$_{17}$H$_{20}$NO$_3$SSi [M+H]$^+$ 346.09, found 345.86.

3-Iodo-6-methyldibenzo[c,f][1,2]thiazepin-11(6H)-one 5,5-dioxide (3q)

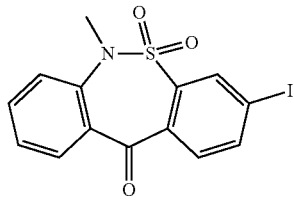

3q

To a solution of ketone 3p (108 mg, 0.313 mmol) in anhydrous CH$_2$Cl$_2$ (0.94 mL) at 0° C. was added a solution of iodine monochloride (173 mg, 1.06 mmol) in anhydrous CH$_2$Cl$_2$ (0.63 mL) dropwise over 3 min. The resulting dark-brown solution was allowed to warm to room temperature, stirred for 35 min (extended reaction times produce polyiodinated byproducts), and quenched with saturated aqueous Na$_2$S$_2$O (3 mL). The resulting mixture was diluted with water (15 mL) and extracted with CH$_2$Cl$_2$ (2×15 mL). The combined organics were washed with water (15 mL), dried over Na$_2$SO$_4$, and concentrated to yield a yellow solid. This material was purified by column chromatography (CH$_2$Cl$_2$:Hexanes-1:1) to yield impure product. This crude product was recrystallized from MeOH and the resulting fine-white needles were dissolved in CH$_2$Cl$_2$ and concentrated, causing a second crystallization to occur once most of the solvent had been removed. The powdery white crystals thus obtained were washed with ice-cold MeOH and dried to yield the pure ketone 3q (68.4 mg, 55%). $^1$H NMR (400 MHz, CDCl$_3$) δ 8.32-8.27 (m, 2H), 8.06 (dd, J=8.1, 1.7 Hz, 1H), 7.69-7.62 (m, 2H), 7.38 (ddd, J=8.2, 7.3, 1.1 Hz, 1H), 7.34 (dd, J=8.1, 0.9 Hz, 1H), 3.35 (s, 3H); $^{13}$C NMR (101 MHz, CDCl$_3$) δ 190.1, 142.4, 141.5, 138.1, 135.6, 135.1, 133.9, 133.1, 132.2, 131.0, 126.3, 124.7, 98.7, 39.2; LR-MS calcd. for C$_{14}$H$_{11}$INO$_3$S [M+H]$^+$ 399.95, found 399.78.

dropwise to a solution of N-methylaniline (0.17 mL, 1.52 mmol) and pyridine (0.15 mL, 1.65 mmol) in dry CH$_2$Cl$_2$ (10 mL). The resulting mixture was stirred overnight at room temperature. The reaction mixture was then poured on ice and extracted with CH$_2$Cl$_2$. The combined organic layers were dried over Na$_2$SO$_4$. The crude product was purified by column chromatography (CH$_2$Cl$_2$ ->CH$_2$Cl$_2$+2% acetone). The product 2s was obtained as a colorless oil (330 mg, 81%). $^1$H NMR (400 MHz, Acetone-d$_6$) δ 8.87 (d, J=5.0 Hz, 1H), 8.47 (s, 1H), 7.61 (d, J=5.0 Hz, 1H), 7.44-7.32 (m, 3H), 7.31-7.24 (m, 2H), 4.36 (q, J=7.1 Hz, 2H), 3.34 (s, 3H), 1.33 (t, J=7.1 Hz, 3H); $^{13}$C NMR (101 MHz, Acetone-d$_6$) δ 166.4, 154.6, 150.7, 142.0, 141.8, 131.2, 130.1, 128.7, 128.0, 122.8, 63.3, 39.1, 14.2; LR-MS calcd. for C$_{15}$H$_{17}$N$_2$O$_4$S [M+H]$^+$ 321.09, found 321.15.

11-Methylbenzo[f]pyrido[3,4-c][1,2]thiazepin-5(11H)-one 10,10-dioxide(3s)

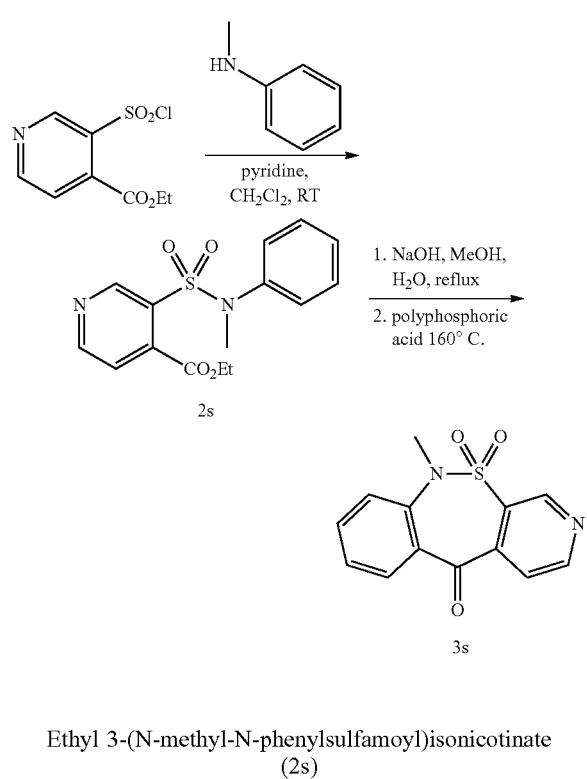

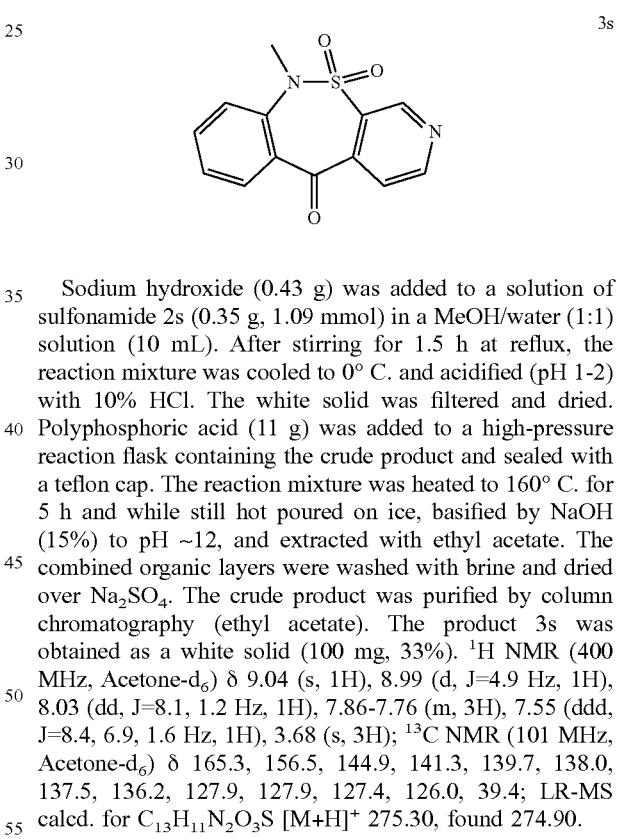

Ethyl 3-(N-methyl-N-phenylsulfamoyl)isonicotinate (2s)

Sodium hydroxide (0.43 g) was added to a solution of sulfonamide 2s (0.35 g, 1.09 mmol) in a MeOH/water (1:1) solution (10 mL). After stirring for 1.5 h at reflux, the reaction mixture was cooled to 0° C. and acidified (pH 1-2) with 10% HCl. The white solid was filtered and dried. Polyphosphoric acid (11 g) was added to a high-pressure reaction flask containing the crude product and sealed with a teflon cap. The reaction mixture was heated to 160° C. for 5 h and while still hot poured on ice, basified by NaOH (15%) to pH ~12, and extracted with ethyl acetate. The combined organic layers were washed with brine and dried over Na$_2$SO$_4$. The crude product was purified by column chromatography (ethyl acetate). The product 3s was obtained as a white solid (100 mg, 33%). $^1$H NMR (400 MHz, Acetone-d$_6$) δ 9.04 (s, 1H), 8.99 (d, J=4.9 Hz, 1H), 8.03 (dd, J=8.1, 1.2 Hz, 1H), 7.86-7.76 (m, 3H), 7.55 (ddd, J=8.4, 6.9, 1.6 Hz, 1H), 3.68 (s, 3H); $^{13}$C NMR (101 MHz, Acetone-d$_6$) δ 165.3, 156.5, 144.9, 141.3, 139.7, 138.0, 137.5, 136.2, 127.9, 127.9, 127.4, 126.0, 39.4; LR-MS calcd. for C$_{13}$H$_{11}$N$_2$O$_3$S [M+H]$^+$ 275.30, found 274.90.

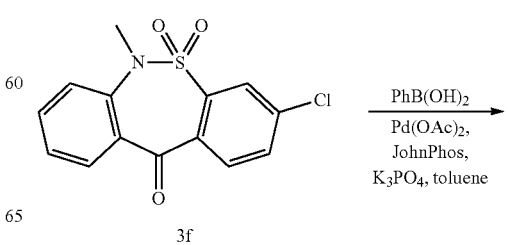

A solution of ethyl 3-(chlorosulfonyl)isonicotinate (300 mg, 1.27 mmol) in anhydrous CH$_2$Cl$_2$ (8 mL) was added

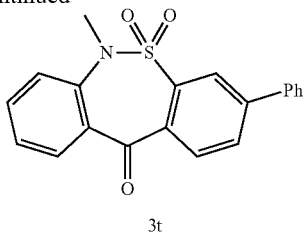

3t

6-Methyl-3-phenyldibenzo[c,f][1,2]thiazepin-11(6H)-one 5,5-dioxide (3t)

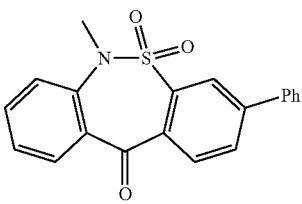

3t

The coupling was conducted according to the procedure of Buchwald et al. 2004. Ketone 3f (308 mg, 1.0 mmol), phenylboronic acid (228 mg, 1.5 mmol), K$_3$PO$_4$ (425 mg, 2.0 mmol), Pd(OAc)$_2$ (2.2 mg, 1 mol %) and 2-(di-tert-butylphosphino)biphenyl (JohnPhos) (6.0 mg, 2 mol %) were added to a reaction vial and sealed with a screw-cap equipped with a teflon septum. The vial was evacuated and backfilled with argon (3×), and toluene (3 mL, de-oxygenated before use by standard "freeze-pump-thaw" technique) was added via syringe, and the reaction mixture was stirred at 100° C. for 18 h. The reaction mixture was diluted with CH$_2$Cl$_2$, washed with water, dried over Na$_2$SO$_4$ and concentrated. The crude product was crystallized from MeOH/ethyl acetate (~5:1). The ketone 3t was obtained as orange crystals (315 mg, 90%). $^1$H NMR (400 MHz, Acetone-d$_6$) δ 8.27 (dd, J=8.1, 1.7 Hz, 1H), 8.18 (dd, J=1.9, 0.3 Hz, 1H), 8.15 (dd, J=8.0, 1.9 Hz, 1H), 8.04 (dd, =8.0, 0.4 Hz, 1H), 7.89-7.83 (m, 2H), 7.76 (ddd, J=8.2, 7.2, 1.7 Hz, 1H), 7.61-7.54 (m, 3H), 7.51 (dd, J=7.3, 1.3 Hz, 1H), 7.45 (ddd, J=8.2, 7.2, 1.2 Hz, 1H), 3.42 (s, 3H); $^{13}$C NMR (101 MHz, Acetone-d$_6$) δ 191.5, 145.8, 143.1, 139.0, 138.2, 136.0, 135.7, 133.0, 132.4, 132.1, 131.7, 130.2, 129.9, 128.2, 126.6, 125.9, 124.0, 39.4; LR-MS calcd. for C$_{20}$H$_{16}$NO$_3$S [M+H]$^+$ 350.08, found 350.14.

6-Methyl-3-(methylsulfonyl)dibenzo[c,f][1,2]thiazepin-11(6H)-one 5,5-dioxide (3u)

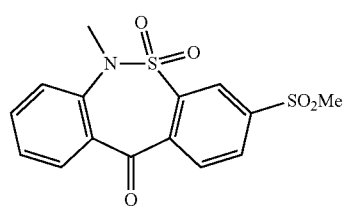

3u

To a suspension of ketone 3l (222 mg, 0.695 mmol) in MeOH (3.0 mL) at 0° C. was added a solution of Oxone (855 mg, 1.39 mmol) in water (3.0 mL), and the resulting white suspension was allowed to warm to room temperature and stirred for 18.5 h. The reaction mixture was then diluted with water (10 mL) and extracted with CH$_2$Cl$_2$ (3×10 mL). The combined organics were washed with water (10 mL), dried over Na$_2$SO$_4$, and concentrated to yield a white solid. This crude material was purified by column chromatography (CH$_2$Cl$_2$:Et$_2$O-20:1) to provide the pure ketone 3u as a white crystalline solid (220 mg, 90%). $^1$H NMR (400 MHz, CDCl$_3$) δ 8.49 (d, J=1.7 Hz, 1H), 8.31-8.24 (m, 2H), 8.11 (d, J=8.0 Hz, 1H), 7.69 (ddd, J=8.1, 7.3, 1.7 Hz, 1H), 7.44-7.38 (m, 1H), 7.36 (dd, J=8.2, 0.8 Hz, 1H), 3.40 (s, 3H), 3.16 (s, 3H); $^{13}$C NMR (101 MHz, CDCl$_3$) δ 190.1, 144.0, 141.6, 140.9, 138.6, 135.5, 133.0, 132.2, 132.0, 130.1, 126.3, 124.4, 124.1, 44.5, 39.0; LR-MS calcd. for C$_{15}$H$_{14}$NO$_5$S$_2$ [M+H]$^+$ 352.03, found 352.31.

6-Methyl-3-(methylsulfinyl)dibenzo[c,f][1,2]thiazepin-11(6H)-one 5,5-dioxide (3v)

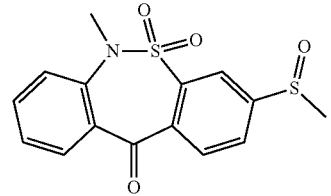

3v

To a suspension of ketone 3l (216 mg, 0.676 mmol) in MeOH (3.0 mL) at 0° C. was added a solution of Oxone (229 mg, 0.372 mmol) in water (3.0 mL), and the resulting pale-yellow suspension was allowed to warm to room temperature and stirred for 2.5 h. The reaction mixture was then diluted with water (10 mL) and extracted with CH$_2$Cl$_2$ (3×10 mL). The combined organics were washed with water (10 mL), dried over Na$_2$SO$_4$, and concentrated to yield an off-white foam. This crude material was purified by column chromatography (CH$_2$Cl$_2$:Et$_2$O-8:2) to provide the pure ketone 3v as an off-white crystalline solid (157 mg, 69%). $^1$H NMR (400 MHz, Acetone-d$_6$) δ 8.26 (d, J=1.5 Hz, 1H), 8.23 (dd, J=8.1, 1.6 Hz, 1H), 8.14 (dd, J=8.0, 1.6 Hz, 1H), 8.09 (d, J=8.0 Hz, 1H), 7.78 (ddd, J=8.8, 7.3, 1.7 Hz, 1H), 7.59 (dd, J=8.2, 0.8 Hz, 1H), 7.49-7.43 (m, 1H), 3.42 (s, 3H), 2.90 (s, 3H); $^{13}$C NMR (101 MHz, Acetone-d$_6$) δ 191.6, 153.4, 143.0, 139.2, 138.4, 136.0, 133.0, 132.1, 131.2, 129.5, 126.7, 125.7, 121.1, 44.1, 39.4; calcd. for C$_{15}$H$_{14}$NO$_4$S$_2$ [M+H]$^+$ 336.04, found 336.23.

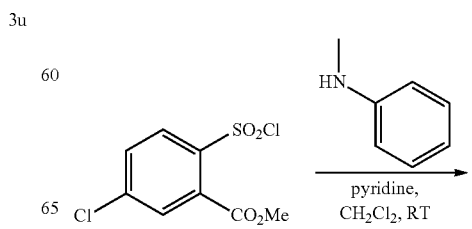

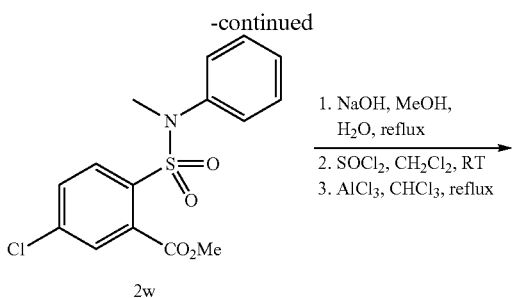

2w

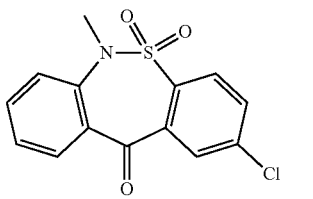

3w

2-Chloro-6-methyldibenzo[c,f][1,2]thiazepin-11(6H)-one 5,5-dioxide (3w)

To a solution of N-methylaniline (0.65 mL, 6.0 mmol) and anhydrous pyridine (0.55 mL, 6.5 mmol) in anhydrous CH$_2$Cl$_2$ (20 mL) was added a solution of methyl 5-chloro-2-(chlorosulfonyl)benzoate (3.70 g of crude material, 36 mass % pure =1.35 g, 5.0 mmol) in anhydrous CH$_2$Cl$_2$ (10 mL), and the mixture was allowed to stir at room temperature overnight. The reaction was then diluted with water and extracted with CH$_2$Cl$_2$ (3×30 ml). The combined organics were washed with 1M aqueous HCl (30 mL) and saturated aqueous NaHCO3 (30 mL), dried over Na$_2$SO$_4$, and concentrated to provide the crude product. This material was purified by column chromatography (hexanes:EtOAc-3:1) to provide sulfonamide 2w as an orange oil still containing slight impurities (1.30 g), which was used in the next step without further purification. To a solution of sulfonamide 2w (1.30 g) in MeOH (20 mL) was added water (10 mL) and NaOH (0.66 g, 13.5 mmol), and the resulting mixture was refluxed for 1.5 h. After cooling to room temperature, the mixture was made strongly acidic with 10% aqueous HCl and extracted with CH$_2$Cl$_2$. The combined organics were dried over Na$_2$SO$_4$ and concentrated. The crude carboxylic acid thus obtained was dissolved in anhydrous CH$_2$Cl$_2$ (20 mL), thionyl chloride (2.0 mL, 27.4 mmol) was added, and the solution was stirred for 6 h at room temperature before concentrating in vacuo. The crude acyl chloride thus obtained was dissolved in CHCl$_3$ (20 mL), aluminum chloride (1.50 g, 11.2 mmol) was added, and the resulting mixture was refluxed for 1.5 h. The volatiles were then removed in vacuo and the residue was quenched with cold water and extracted with CH$_2$Cl$_2$. The combined organics were dried over Na$_2$SO$_4$ and concentrated to provide the crude product. This material was purified by column chromatography (1:1 CH$_2$Cl$_2$:hexanes-1:1) followed by recrystallization from methanol to provide the pure ketone 3w as a pinkish solid (450 mg, 29% from sulfonyl chloride). $^1$H NMR (400 MHz, Acetone) δ 8.21 (dd, J=8.1, 1.6 Hz, 1H), 8.00-7.95 (m, 1H), 7.93-7.88 (m, 2H), 7.77 (ddd, J=8.3, 7.3, 1.7 Hz, 1H), 7.58 (dd, J=8.2, 0.9 Hz, 1H), 7.48-7.42 (m, 1H), 3.40 (s, 3H); $^{13}$C NMR (101 MHz, Acetone) δ 190.8, 143.0, 140.0, 139.2, 136.2, 136.0, 133.0, 132.2, 131.8, 131.2, 128.0, 126.7, 125.8, 39.4; LR-MS calcd. for C$_{14}$H$_{11}$ClNO$_3$S [M+H]$^+$ 308.01, found 308.37.

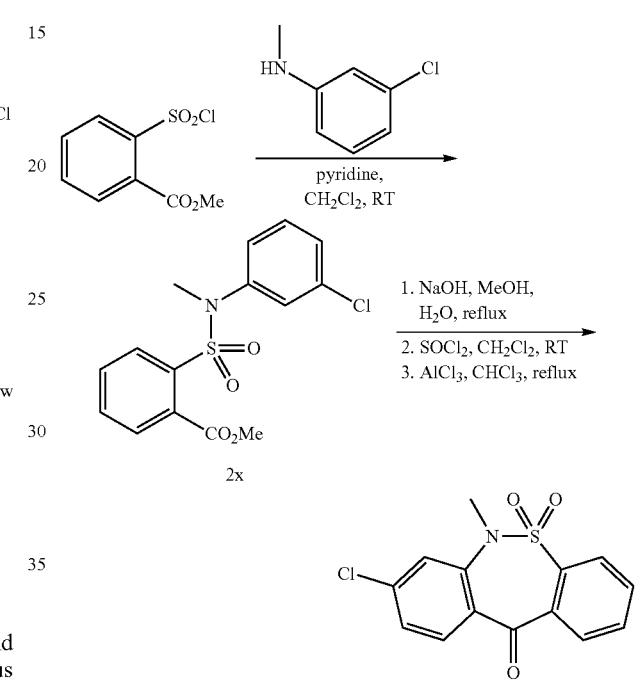

8-Chloro-6-methyldibenzo[c,f][1,2]thiazepin-11(6H)-one 5,5-dioxide (3x)

To a solution of N-methyl-3-chloroaniline (643 µL, 5.25 mmol) in anhydrous pyridine (3.8 mL) was added methyl 2-(chlorosulfonyl)benzoate (1.17 g, 5.00 mmol), and the resulting mixture was stirred for 3 h at room temperature. The reaction mixture was then diluted with CH$_2$Cl$_2$ (35 mL), washed with 7% aqueous HCl (2×35 mL), brine (35 mL), saturated aqueous NaHCO$_3$ (35 mL), and brine again (35 mL), dried over Na$_2$SO$_4$, and concentrated to provide pure sulfonamide 2x as a viscous yellow oil (1.14 g, 67%). To a solution of sulfonamide 2x (1.09 g, 3.21 mmol) in MeOH (8.2 mL) was added water (4.1 mL) and NaOH (385 mg, 3.21 mmol), and the resulting mixture was refluxed for 45 minutes. The solution was diluted with water (50 mL), washed with Et$_2$O (30 mL), made strongly acidic with 10% aqueous HCl, and extracted with CH$_2$Cl$_2$ (30 mL, 2×20 mL). The combined organics were washed with water (20 mL), dried over Na$_2$SO$_4$, and concentrated to provide the pure carboxylic acid intermediate as a yellow solid (1.04 g, 99%). The carboxylic acid (1.00 g, 3.07 mmol) was dissolved in thionyl chloride (6.6 mL), and the resulting solution was stirred for 2 h and then concentrated in vacuo to provide the intermediate acyl chloride as a tan solid. This material was dissolved in CHCl₂ (13 mL), aluminum chloride (1.31 g, 9.82 mmol) was added, and the resulting mixture was refluxed for 1 h. The reaction was then quenched with ice water (100 mL) and extracted with CH$_2$Cl$_2$ (50 mL, 2×25 mL). The combined organics were washed with water (50 mL), dried over Na$_2$SO$_4$, and concentrated to give the crude product as a viscous brown oil. When a small quantity of MeOH was added to this oil, tan crystals formed. These were crushed up and the supernatant was removed by pipet. The crystals were washed with an additional small portion of ice-cold MeOH and then recrystallized from MeOH to provide pure ketone 3x as glistening tan needles (400 mg, 42%). $^1$H NMR (500 MHz, CDCl$_3$) δ 8.27 (d, J=8.6 Hz, 1H), 7.97-7.91 (m, 2H), 7.76-7.70 (m, 2H), 7.35-7.30 (m, 2H), 3.35 (s, 3H); $^{13}$C NMR (126 MHz, CDCl$_3$) δ 189.9, 142.8, 140.8, 136.8, 136.3, 133.6, 133.5, 132.3, 131.7, 129.2, 126.2, 125.3, 124.1, 38.8; LR-MS calcd. for C$_{14}$H$_{11}$ClNO$_3$S [M+H]$^+$ 308.01, found 308.47.

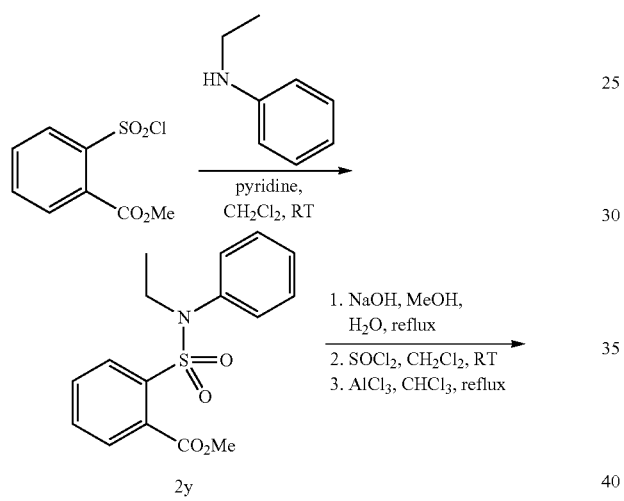

6-Ethyldibenzo[c,f][1,2]thiazepin-11 (6H)-one 5,5-dioxide (3y)

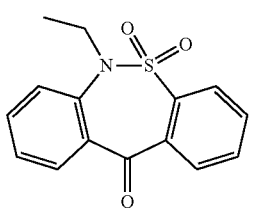

Sulfonamide 2y was synthesized from 2-(chlorosulfonyl)benzoate (1.17 g, 5.00 mmol) and N-ethylaniline (663 μL, 5.25 mmol) according to the procedure described for 2x and obtained as a viscous, yellow-orange oil (1.20 g, 75%). Sulfonamide 2y (1.14 g, 3.58 mmol) was converted to the corresponding carboxylic acid according to the procedure described under the synthesis of ketone 3x, and obtained as a viscous brown oil (1.09 g, 99%). This carboxylic acid (1.06 g, 3.47 mmol) was dissolved in thionyl chloride (7.5 mL), stirred for 2 h at room temperature, and then concentrated in vacuo to provide the acyl chloride intermediate as a viscous yellow oil. This material was dissolved in CHCl$_3$ (15 mL), aluminum chloride (1.48 g, 11.1 mmol) was added, and the resulting mixture was refluxed for 1.5 h. The reaction was then quenched with ice water (100 mL) and extracted with CH$_2$Cl$_2$ (50 mL, 2×25 mL). The combined organics were washed with water (50 mL), dried over Na$_2$SO$_4$, and concentrated to give the crude product as a dark-green glass. This material was purified by column chromatography (CH$_2$Cl$_2$:hexanes-8:2) to provide a tan solid (297 mg) still containing some impurities. This was then recrystallized from MeOH to provide pure ketone 3y as off-white crystals (231 mg, 23%). $^1$H NMR (400 MHz, CDCl$_3$) δ 8.31-8.27 (m, 1H), 8.02-7.96 (m, 2H), 7.74-7.68 (m, 2H), 7.66-7.60 (m, 1H), 7.42-7.36 (m, 2H), 3.84 (q, J=7.2 Hz, 2H), 0.98 (t, J=7.2 Hz, 3H); $^{13}$C NMR (101 MHz, CDCl$_3$) δ 191.0, 140.1, 139.1, 136.1, 134.7, 133.2, 132.9, 132.4, 132.2, 131.8, 126.5, 125.5, 125.4, 47.5, 14.1; LR-MS calcd. for C$_{15}$H$_{14}$NO$_3$S [M+H]$^+$ 288.07, found 288.08.

3-(Ethylthio)-6-methyldibenzo[c,f][1,2]thiazepin-11 (6H)-one 5,5-dioxide (3z)

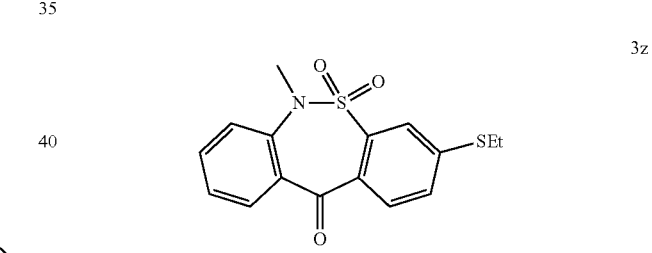

To a suspension of NaH (60% dispersion in mineral oil, 28.0 mg, 0.700 mmol) in anhydrous DMF (0.67 mL) was added ethanethiol (50 μL, 0.675 mmol), and the resulting mixture was stirred at room temperature for 15 minutes. Ketone 3f (154 mg, 0.500 mmol) was then added, and the mixture was stirred for 1.75 h at room temperature. The reaction was quenched with water (10 mL) and extracted with CH$_2$Cl$_2$ (10 mL, 2×5 mL). The combined organics were washed with water (20 mL), dried over Na$_2$SO$_4$ and concentrated to give a yellow oil still containing residual DMF (mostly removed by heating under high vacuum). When a small quatity of Et$_2$O (~3 mL) was added to this oil, fine white needles crystallized from the mixture. After cooling on ice, the supernatant was removed by pipette and the crystals were washed with several small portions of ice-cold Et$_2$O and then dried in vacuo to provide pure ketone 3z as fine white needles (108 mg, 65%). $^1$H NMR (400 MHz, CDCl$_3$) δ 8.30 (dd, J=8.0, 1.1 Hz, 1H), 7.89 (d, J=8.2 Hz, 1H), 7.75 (d, J=1.6 Hz, 1H), 7.64-7.58 (m, 1H), 7.49 (dd, J=8.2, 1.7 Hz, 1H), 7.40-7.31 (m, 2H), 3.32 (s, 3H), 3.09 (q, J=7.4 Hz, 2H), 1.40 (t, J=7.4 Hz, 3H); $^{13}$C NMR (101 MHz, CDCl$_3$) δ 189.6, 145.3, 141.4, 137.5, 134.7, 132.3, 132.2,

3-(Isopropylthio)-6-methyldibenzo[c,f][1,2]thiazepin-11(6H)-one 5,5-dioxide (3aa)

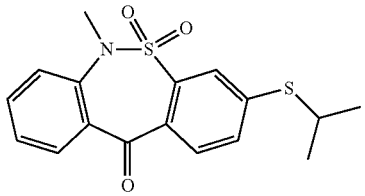

3aa

Ketone 3aa was prepared from ketone 3f (308 mg, 1.00 mmol) and 2-propanethiol according to the procedure described for ketone 3z and obtained as powdery yellow crystals (264 mg, 76%). $^1$H NMR (400 MHz, CDCl$_3$) δ 8.30 (dd, J=8.1, 1.6 Hz, 1H), 7.89 (d, J=8.2 Hz, 1H), 7.80 (d, J=1.9 Hz, 1H), 7.64-7.59 (m, 1H), 7.54 (dd, J=8.2, 1.9 Hz, 1H), 7.39-7.31 (m, 2H), 3.65 (hept, J=6.7 Hz, 1H), 3.32 (s, 3H), 1.40 (d, J=6.7 Hz, 6H); $^{13}$C NMR (101 MHz, CDCl$_3$) δ 189.7, 144.5, 141.4, 137.4, 134.8, 132.5, 132.3, 132.2, 132.1, 131.5, 126.3, 125.0, 124.5, 39.2, 37.0, 22.9; LR-MS calcd. for C$_{17}$H$_{18}$NO$_3$S$_2$ [M+H]$^+$ 348.07, found 348.08.

3-(Benzyloxy)-6-methyldibenzo[c,f][1,2]thiazepin-11(6H)-one 5,5-dioxide (3ab)

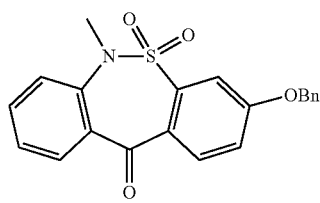

3ab

To a mixture of ketone 3m (145 mg, 0.500 mmol) and K$_2$CO$_3$ (138 mg, 1.00 mmol) in anhydrous acetone (1.0 mL) was added benzyl bromide (89.2 µL, 0.750 mmol), and the mixture was refluxed for 3 h. The mixture was then cooled to room temperature, diluted with acetone (10 mL), and filtered, washing the filter cake with additional acetone. The combined filtrates were concentrated to provide a yellow-orange oil. This material was recrystallized from MeOH to provide pure ketone 3ab as off-white crystals (125 mg, 66%). $^1$H NMR (500 MHz, CDCl$_3$) δ 8.33 (dd, J=8.1, 1.4 Hz, 1H), 8.02 (d, J=8.7 Hz, 1H), 7.63 (td, J=8.0, 1.6 Hz, 1H), 7.55 (d, J=2.6 Hz, 1H), 7.47-7.34 (m, 7H), 7.24 (dd, J=8.7, 2.6 Hz, 1H), 5.22 (s, 2H), 3.31 (s, 3H); $^{13}$C NMR (126 MHz, CDCl$_3$) δ 189.1, 161.8, 141.2, 139.0, 135.5, 134.7, 134.5, 132.4, 132.3, 129.0, 128.7, 128.5, 127.8, 126.6, 125.5, 119.6, 111.7, 71.0, 39.3; LR-MS calcd. for C$_{21}$H$_{18}$NO$_4$S [M+H]$^+$ 380.10, found 380.39.

132.0, 131.63, 130.3, 126.3, 125.1, 122.5, 39.2, 26.3, 13.8; LR-MS calcd. for C$_{16}$H$_{16}$NO$_3$S$_2$ [M+H]$^+$ 334.06, found 334.24.

6-Methyl-5,5-dioxido-11-oxo-6,11-dihydrodibenzo[c,f][1,2]thiazepin-3yl acetate (3ac)

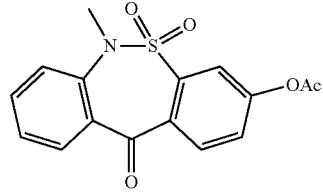

3ac

To a solution of ketone 3m (230 mg, 0.795 mmol) and pyridine (0.30 mL) in anhydrous CH$_2$Cl$_2$ (10 mL) was added acetyl chloride (0.50 mL) at 0° C. The mixture was then allowed to warm to room temperature and stirred for 1 h. The reaction was then quenched with ice water and extracted with CH$_2$Cl$_2$. The combined organics were dried over Na$_2$SC$_4$ and concentrated to provide the crude product. This material was purified by cold crystallization from MeOH to give the pure ketone 3ac as a white solid (210 mg, 80%). $^1$H NMR (400 MHz, Acetone-d$_6$) δ 8.25 (dd, J=8.1, 1.6 Hz, 1H ), 8.01 (d, J=8.4 Hz, 1H), 7.79-7.73 (m, 2H), 7.63 (dd, J=8.4, 2.3 Hz, 1H), 7.58 (dd, J=8.2, 1.0 Hz, 1H), 7.45 (ddd, J=8.2, 7.2, 1.2 Hz, 1H), 3.39 (s, 3H), 2.37 (s, 3H); $^{13}$C NMR (101 MHz, Acetone-d$_6$) δ 190.92, 169.23, 154.35, 142.82, 138.73, 135.81, 134.59, 134.05, 132.16, 131.62, 127.81, 126.78, 125.97, 119.67, 39.44, 21.01; LR-MS calcd. for C$_{16}$H$_{14}$NO$_5$S [M+H]$^+$ 332.06, found 331.72.

Preparation of N-substituted 11-amino-6-alkyl-6,11-dihydrodiaryl [c,f][1,2]thiazepine 5,5-dioxides

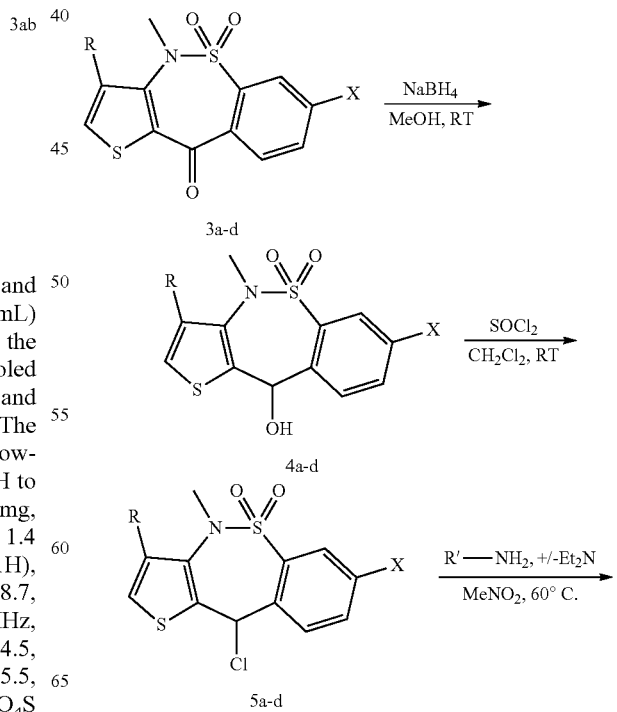

-continued

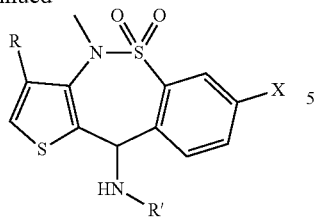

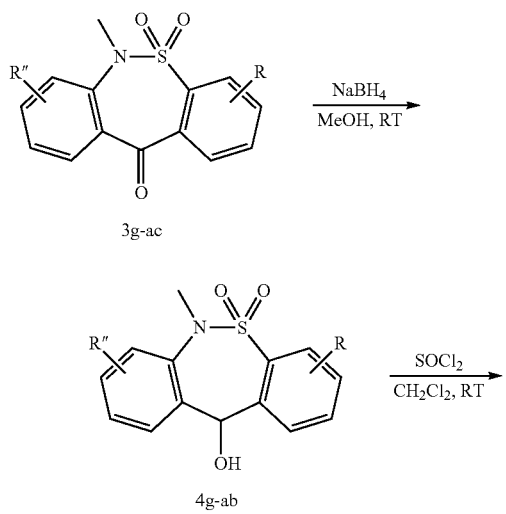

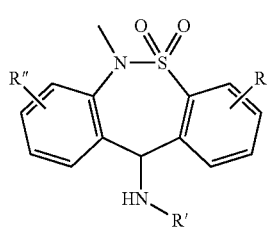

General Procedure for Preparation of Alcohols 4a-4ab.

Sodium borohydride (2.0 mmol) was added to an ice-cooled solution (or suspension) of ketone 3 (1.0 mmol) in MeOH (7 mL). After stirring for 2-3 h at room temperature, the reaction was quenched by adding saturated aqueous ammonium chloride (5 mL) and saturated aqueous NaHCO$_3$ (5 mL). MeOH was evaporated and the precipitate was filtered, washed with water, and dried (alternatively, the residue was extracted with EtOAc and the combined organic layers were washed with water, dried over Na$_2$SO$_4$, filtered, and concentrated). The crude product was crystallized from MeOH/water or used in the next step without further purification.

10-Hydroxy-4-methyl-4,10-dihydrobenzo[f]thieno[3,2-c][1,2]thiazepine 5,5-dioxide (4a)

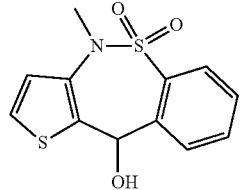

The product 4a was obtained as a white solid (270 mg, 89%). $^1$H NMR (400 MHz, Acetone-d$_6$) δ 8.03 (d, J=7.8 Hz, 1H), 7.87 (d, J=7.7 Hz, 1H), 7.85-7.77 (m, 1H), 7.59 (t, J=7.6 Hz, 1H), 7.37 (d, J=5.5 Hz, 1H), 7.00 (d, J=5.5 Hz, 1H), 6.65 (d, J=6.8 Hz, 1H), 6.15 (d, J=7.1 Hz, 1H), 3.02 (s, 3H); $^{13}$C NMR (101 MHz, Acetone-d$_6$) δ 139.2, 135.8, 135.0, 134.0, 131.0, 128.7, 128.0, 126.9, 125.6, 124.1, 69.2, 39.8; LR-MS calcd. for C$_{12}$H$_{10}$NO$_2$S$_2$ [M−OH]$^+$ 264.01, found 264.68.

3-Bromo-10-hydroxy-4-methyl-4,10-dihydrobenzo[f]thieno[3,2-c][1,2]thiazepine 5,5-dioxide (4b)

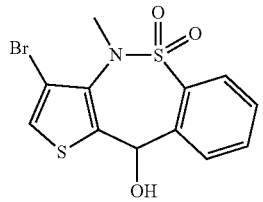

The product 4b was obtained as a pale-yellow glass (176 mg, 98%). $^1$H NMR (500 MHz, CDCl$_3$) δ 7.97 (d, J=7.7 Hz, 1H), 7.75-7.66 (m, $^2$H), 7.55 (t, J=7.5 Hz, 1H), 7.30 (s, 1H), 6.05 (d, J=10.1 Hz, 1H), 4.67 (dd, J=9.8, 5.4 Hz, 1H), 2.86 (s, 3H); $^{13}$C NMR (126 MHz, CDCl$_3$) 136.0, 134.9, 134.6, 133.9, 132.6, 129.7, 129.4, 128.9, 123.2, 108.9, 71.5, 39.2; LR-MS calcd. for C$_{12}$H$_9$BrNO$_2$S$_2$ [M−OH]$^+$ 343.92, found 344.69.

7-Chloro-10-hydroxy-4-methyl-4,10-dihydrobenzo[f]thieno[3,2-c][1,2]thiazepine 5,5-dioxide (4c)

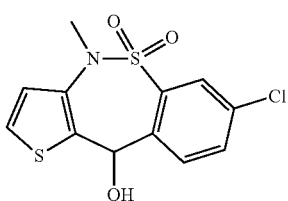

The product 4c was obtained as a tan solid (335.7 mg, 98%). $^1$H NMR (400 MHz, CDCl$_3$) δ 7.94 (d, J=2.0 Hz, 1H), 7.68-7.60 (m, 2H), 7.29 (d, J=5.4 Hz, 1H) 6.84 (d, J=5.5 Hz, 1H), 6.10 (d, J=10.0 Hz, 1H), 4.61 (d, J=10.1 Hz, 1H), 3.10

(s, 3H); $^{13}$C NMR (101 MHz, CDCl$_3$) δ 136.1, 135.8, 135.0, 135.0, 134.2, 131.1, 127.9, 127.8, 125.2, 124.1, 71.0, 39.3; LR-MS cald. for C$_{12}$H$_9$ClNO$_2$S$_2$ [M−OH]$^+$ 297.98, found 298.00.

7-Bromo-10-hydroxy-4-methyl-4,10-dihydrobenzo[f]thieno[3,2-c][1,2]thiazepine 5,5-dioxide (4d)

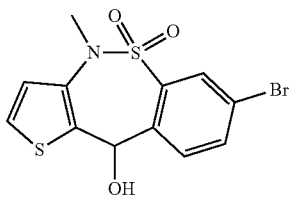

The product 4d was obtained as a yellowish-tan solid (579 mg, 100%). $^1$H NMR (500 MHz, CDCl$_3$) δ 8.10 (d, J=2.0 Hz, 1H), 7.80 (dd, J=8.1, 2.0 Hz, 1H), 7.57 (d, J=8.2 Hz, 1H), 7.31 (d, J=5.4 Hz, 1H), 6.85 (d, J=5.5 Hz, 1H), 6.05 (d, J=10.6 Hz, 1H), 4.49 (d, J=10.6 Hz, 1H), 3.11 (s, 3H); $^{13}$C NMR (126 MHz, CDCl$_3$) δ 137.2, 136.4, 136.0, 135.3, 131.5, 130.6, 127.5, 125.4, 124.1, 122.8, 71.3, 39.3; LR-MS cald. for C$_{12}$H$_9$BrNO$_2$S$_2$ [M−OH]$^+$ 341.93, found 342.47.

3-Fluoro-11-hydroxy-6-methyl-6,11-dihydrodibenzo[c,f][1,2]thiazepine 5,5-dioxide (4g)

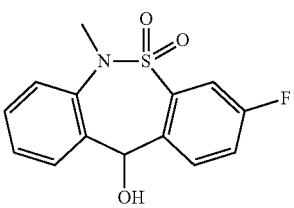

The product 4g was obtained as a white crystalline solid (215 mg, 100%). $^1$H NMR (400 MHz, CDCl$_3$) δ 7.69 (dt, J=8.7, 4.3 Hz, 2H), 7.61 (dd, J=7.6, 1.6 Hz, 1H), 7.41 (td, J=7.6, 1.7 Hz, 1H), 7.37-7.26 (m, 3H), 5.93 (d, J=9.7 Hz, 1H), 4.25 (d, J=9.8 Hz, 1H), 3.19 (s, 3H); $^{13}$C NMR (101 MHz, CDCl$_3$) (additional peaks due to C—F coupling) δ 163.3, 160.8, 138.9, 135.3, 134.0, 133.9, 132.6, 132.6, 131.8, 130.1, 127.9, 127.1, 120.3, 120.1, 115.9, 115.7, 39.5; LR-MS calcd. for C$_{14}$H$_{11}$FNO$_2$ [M−OH]$^+$ 276.05, found 276.12.

11-Hydroxy-3-methoxy-6-methyl-6,11-dihydrodibenzo[c,f][1,2]thiazepine 5,5-dioxide (4h)

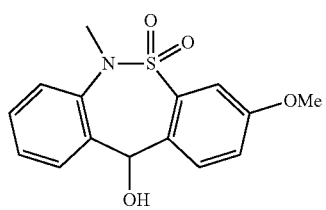

The product 4h was obtained as a white crystalline solid (153 mg, 100%). $^1$H NMR (500 MHz, CDCl$_3$) δ 7.60 (dd, J=7.7, 1.5 Hz, 1H), 7.56 (d, J=8.5 Hz, 1H), 7.49 (d, J=2.7 Hz, 1H), 7.38 (td, J=7.6, 1.6 Hz, 1H), 7.32 (td, J=7.5, 1.4 Hz, 1H), 7.28 (dd, J=7.9, 1.3 Hz, 1H), 7.09 (dd, J=8.4, 2.7 Hz, 1H), 5.81 (d, J=10.3 Hz, 1H), 4.43 (d, J=10.3 Hz, 1H), 3.88 (s, 3H), 3.14 (s, 3H); $^{13}$C NMR (126 MHz, CDCl$_3$) δ 159.7, 139.4, 138.0, 135.1, 132.6, 132.5, 129.9, 129.6, 127.6, 127.1, 119.0, 113.5, 56.0, 39.8; LR-MS calcd. for C$_{15}$H$_{14}$NO$_3$S [M−OH]$^+$ 288.07, found 287.93.

11-Hydroxy-6-methyl-3-phenoxy-6,11-dihydrodibenzo[c,f][1,2]thiazepine 5,5-dioxide (4i)

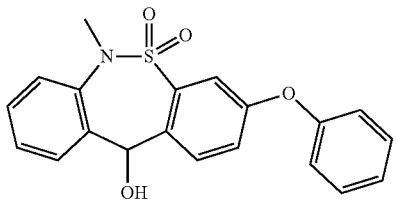

The product 4i was obtained as a pale-yellow glass (291 mg, 100%). $^1$H NMR (400 MHz, CDCl$_3$) δ 7.63-7.58 (m, 3H), 7.42-7.36 (m, 3H), 7.32 (ddd, J=15.8, 7.8, 1.5 Hz, 2H), 7.19 (ddd, J=11.0, 5.2, 1.8 Hz, 2H), 7.08-7.03 (m, 2H), 5.89 (d, J=9.5 Hz, 1H), 4.41 (d, J=9.8 Hz, 1H), 3.17 (s, 3H); $^{13}$C NMR (101 MHz, CDCl$_3$) δ 157.9, 155.8, 139.1, 138.4, 135.4, 132.4, 132.0, 131.9, 130.3, 129.9, 127.7, 127.1, 124.8, 122.3, 119.8, 117.8, 76.7, 39.5; LR-MS calcd. for C$_{20}$H$_{16}$NO$_3$S [M−OH]$^+$ 350.09, found 350.01.

11-Hydroxy-3,6-dimethyl-6,11-dihydrodibenzo[c,f][1,2]thiazepine 5,5-dioxide (4j)

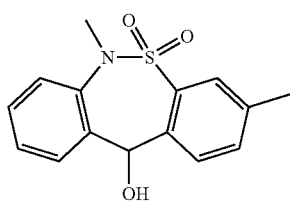

The product 4j was obtained as a white solid (220 mg, 91%). $^1$H NMR (400 Acetone-d$_6$) δ 7.82 (d, -8.0 Hz, 1H), 7.68 (dd, J=7.4, 1.6 Hz, 1H), 7.64 (s, 1H), 7.50-7.41 (m, 2H), 7.41-7.30 (m, 2H), 6.40 (d, J=5,6 Hz, 1H), 5.41 (d, J=5.7 Hz, 1H), 3.36 (s, 3H), 2.39 (s, 3H); $^{13}$C NMR (101 MHz, Acetone-d$_6$) δ 143.1, 139.0, 139.0, 138.6, 138.2, 133.8, 129.5, 128.6, 128.5, 128.3, 127.4, 127.3, 70.8, 37.8, 20.7; LR-MS calcd. for C$_{15}$H$_{14}$NO$_2$S [M−OH]$^+$ 272.07, found 272.75.

9-Bromo-3-chloro-11-hydroxy-6-methyl-6,11-dihydrodibenzo[c,f][1,2]thiazepine 5,5-dioxide (4k)

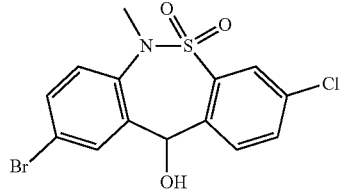

The crude product was crystallized from MeOH/H₂O. The product 4k was obtained as a white solid (280 mg, 96%). ¹H NMR NMR (400 MHz, Acetone-$d_6$) δ 8.01 (dd, J=8.5, 0.7 Hz, 1H), 7.89 (dd, J=2.4, 0.6 Hz, 1H), 7.79 (d, J=2.2 Hz, 1H), 7.70 (dd, J=8.5, 2.2 Hz, 1H), 7.59 (ddd, J=8.5, 2.4, 0.4 Hz, 1H), 7.46 (d, J=8.5 Hz, 1H), 6.50 (d, J=5.4 Hz, 1H), 5.83 (d, J=5.6 Hz, 1H), 3.39 (s, 3H); ¹³C NMR (101 MHz, Acetone-$d_6$) δ 144.4, 140.6, 139.1, 137.7, 134.4, 133.3, 132.8, 130.6, 130.1, 129.2, 127.7, 122.2, 69.2, 38.2; LR-MS calcd. for $C_{14}H_{10}BrClNO_2S$ [M–OH]⁺ 371.93, found 372.86.

11-Hydroxy-6-methyl-3-(methylthio)-6,11-dihydrodibenzo [c,f][1,2]thiazepine 5,5-dioxide (4l)

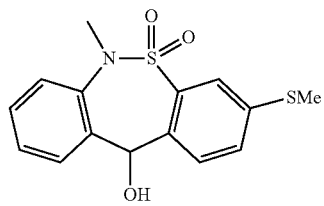

The product 4l was obtained as a pale-yellow crystalline solid (323 mg, 100%). ¹H NMR (500 MHz, CDCl₃) δ 7.75 (d, J=2.0 Hz, 1H), 7.57 (dd, J=7.6, 1.3 Hz, 1H), 7.54 (d, J=8.2 Hz, 1H), 7.37 (ddd, J=9.2, 7.9, 1.9 Hz, 2H), 7.32-7.27 (m, 2H), 5.89 (d, J=9.4 Hz, ¹H), 4.44 (d, J=9.4 Hz, 1H), 3.16 (s, 3H), 2.51 (s, 3H); ¹³C NMR (126 MHz, CDCl₃) δ 140.8, 138.8, 137.4, 136.0, 134.0, 131.2, 130.4, 130.3, 129.7, 127.7, 127.0, 124.8, 75.9, 39.2, 15.4; LR-MS calcd. for $C_{15}H_{14}NO_2S_2$[M–OH]⁺ 304.05, found 304.71.

3,11-Dihydroxy-6-methyl-6,11-dihydrodibenzo[c,f][1,2]thiazepine 5,5-dioxide (4m)

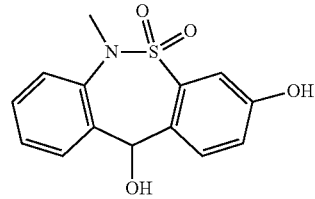

To an ice-cold suspension of ketone 3ac (95 mg, 0.287 mmol) in MeOH (5 mL) was added NaBH₄ (210 mg), and the effervescent mixture was allowed to immediately warm to room temperature and stirred for 1.5 h. The reaction was then cooled back to 0° C., additional NaBH₄ (100 mg) was added, and the mixture was again allowed to warm to room temperature and stirred for a further 1.5 h. The reaction mixture was then poured into saturated aqueous NH₄Cl (20 mL), and the pH was adjusted to ~3 with 1M aqueous HCl. The mixture was then extracted with CH₂Cl₂ and the combined organics were dried over Na₂SO₄ and concenrtated to give the crude product. This material was purified by column chromatography (CH₂Cl₂ +2% MeOH) to provide pure alcohol 4m as an off-white solid (72 mg, 86%). ¹H NMR (400 MHz, Acetone-$d_6$) δ 8.91 (s, 1H), 7.75 (d, J=8.6 Hz, 1H), 7.67 (dd, J=7.5, 1.7 Hz, 1H), 7.45 (dd, J=7.7, 1.5 Hz, 1H), 7.41-7.30 (m, 3H), 7.07 (dd, J=8.6, 2.6 Hz, 1H), 6.26 (d, J=5.7 Hz, 1H), 5.29 (d, J=6.0 Hz, 1H), 3.34 (s, 3H); ¹³C NMR (101 MHz, Acetone-$d_6$) (spectrum complicated by conformers) δ 157.8, 142.6, 140.2, 138.9, 131.6, 129.8, 129.6, 128.63, 128.57, 128.1, 120.0, 119.9, 114.73, 114.65, 71.8, 71.6, 38.4; LR-MS calcd. for $C_{14}H_{12}NO_3S$ [M–OH]⁺ 274.05, found 274.45.

3-Bromo-11-hydroxy-6-methyl-6,11-dihydrodibenzo[c,f][1,2]thiazepine 5,5-dioxide (4o)

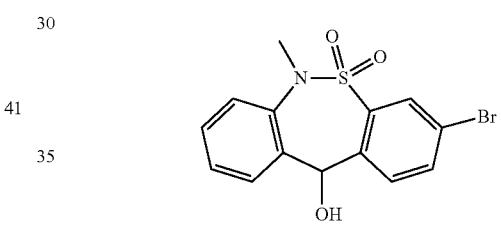

The product 4o was obtained as a white solid (70 mg, 88%). ¹H NMR (400 MHz, Acetone-$d_6$) δ 7.95-7.90 (m, 2H), 7.81 (dd, J=8.5, 2.1 Hz, 1 H), 7.73-7.69 (m, 1H), 7.50 (dd, J=7.6, 1.6 Hz, 1H), 7.41 (dd, J=7.2, 5.2 Hz, 1H), 7.38 (dd, J=7.1, 1.7 Hz, 1H), 6.44 (d, J=5.4 Hz, 1H), 5.62 (d, J=5.4 Hz, 1H ), 3.41 (s, 3H); ¹³C NMR (101 MHz, Acetone-$d_6$) δ 142.8, 141.4, 140.4, 138.1, 136.0, 130.6, 129.9, 129.5, 129.1, 128.7, 127.2, 121.8, 70.1, 38.1; LR-MS calcd. for $C_{14}H_{11}BrNO_2S$ [M–OH]⁺ 335.97, found 335.93.

11-Hydroxy-3-iodo-6-methyl-6,11-dihydrodibenzo[c,f][1,2]thiazepine 5,5-dioxide (4q)

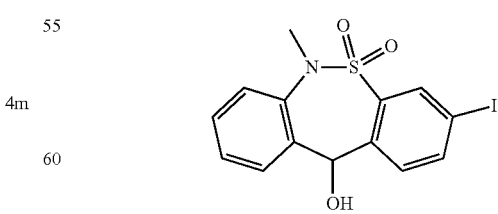

The product 4q was obtained as a white solid (74.8 mg, 95%). ¹H NMR (500 MHz, CDCl₃) (observed as a ~4:1 ratio of 2 conformers resulting in partial integrals) δ 8.27 (d, J=1.8 Hz, 1H), 7.99 (dd, J=7.7, 1.1 Hz, 0.2H), 7.93 (dd, J=8.1, 1.8 Hz, 0.8H), 7.68 (d, J=7.2 Hz, 0.2H), 7.65-7.58 (m, 1H), 7.53 (td, J=7.6, 1.3 Hz, 0.2H), 7.44-7.37 (m, 1.8H), 7.37-7.29 (m, 1.8H), 5.92 (s, 1H), 4.40 (d, J=9.6 Hz, 0.2H), 4.15 (d, J=7.5 Hz, 0.8H), 3.20 (s, 2.4H), 3.14 (s, 0.6H); $^{13}$C NMR (126 MHz, CDCl$_3$) (additional peaks due to conformers) δ 142.4, 138.8, 138.7, 137.5, 136.5, 135.4, 133.6, 132.1, 131.7, 131.4, 130.6, 130.1, 130.0, 128.9, 128.4, 127.9, 127.6, 127.0, 126.9, 93.6, 76.2, 39.3; LR-MS calcd. for C$_{14}$H$_{11}$INO$_2$S [M—OH]$^+$ 383.96, found 383.71.

11-Hydroxy-7-methoxy-6-methyl-6,11-dihydrodibenzo[c,f][1,2]thiazepine 5,5-dioxide (4r)

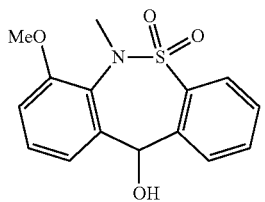

4r

Alcohol 4r was synthesized according to the following scheme via the procedures described below.

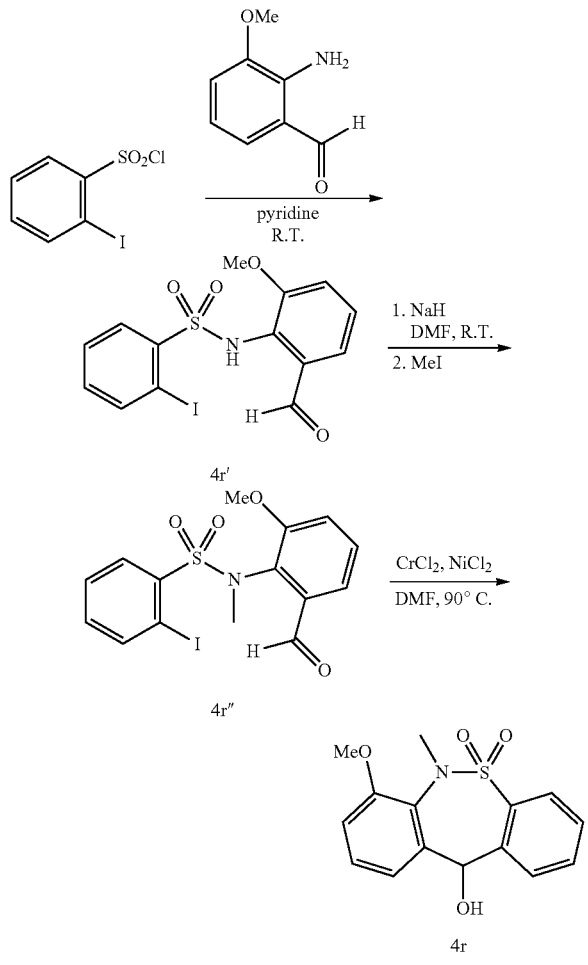

To a solution of 2-amino-3-methoxybenzaldehyde (800 mg, 5.29 mmol) anhydrous pyridine (3.75 mL) was added 2-iodobenzenesulfonyi chloride (1.52 g, 5.04 mmol), and the orange-brown solution was stirred at room temperature for 1 h. The reaction mixture was then diluted with CH$_2$Cl$_2$ (50 mL), washed with 7% aqueous HCl (2×50 mL), brine (50 mL), saturated aqueous NaHCO$_3$ (50 mL), and brine again (50 mL), dried over Na$_2$SO$_4$, and concentrated to yield an orange-brown oil. This crude material was purified by repeated column chromatography (column 1: CH$_2$Cl$_2$, 4 column volumes→CH$_2$Cl$_2$:Et$_2$O-1:1, 2 column volumes/column 2: hexanes:EtOAc-7:3, 2 column volumes 1:1, until finished) to obtain pure sulfonamide 4r' as a tan crystalline solid (668 mg, 32%). $^1$H NMR (400 MHz, CDCl$_3$) δ 10.32 (s, 1H), 8.19 (s, 1H), 8.10 (dd, J=7.8, 0.9 Hz, 1H), 7.76 (dd, J=7.9, 1.5 Hz, 1H), 7.48 (d, J=7.8 Hz, 1H), 7.31 (dd, J=11.1, 4.2 Hz, 1H), 7.27 (t, J=8.0 Hz, 1H), 7.17 (dd, J=7.7, 1.6 Hz, 1H), 6.91 (dd, J=8.2, 1.1 Hz, 1H), 3.42 (s, 3H); $^{13}$C NMR (101 MHz, CDCl$_3$) δ 191.1, 153.1, 142.5, 142.2, 133.5, 132.7, 131.0, 127.9, 127.7, 127.0, 121.8, 116.1, 93.1, 55.3; LR-MS calcd. for C$_{14}$H$_{13}$INO$_4$S [M+H]$^+$ 417.96, found 418.52.

To a suspension of sodium hydride (60% dispersion in mineral oil, 120 mg, 3.00 mmol) in anhydrous DMF (2.2 mL) was added a solution of sulfonamide 4r' (626 mg, 1.50 mmol) in anhydrous DMF (2.2 mL) dropwise over 4 minutes, and the resulting lemon-yellow solution was stirred for 30 minutes at room temperature. Methyl iodide (187 μL, 3.00 mmol) was then added, and the mixture was stirred for 1 h and then quenched with ice water (30 mL). The resulting white precipitate was collected, washed with hexanes and Et$_2$O, and dried to yield the first crop of pure sulfonamide 4r" as an off-white crystalline solid (231 mg). The filtrate was then washed with hexanes and extracted with 4:1 Et2O:CH$_2$Cl$_2$ (2×25 mL), adding the CH$_2$Cl$_2$ first to ensure dissolution and then diluting with Et$_2$O. The combined organics were washed with water (2×50 mL), dried over Na$_2$SO$_4$, and concentrated to yield a pale-yellow oily solid. Upon addition of a small quantity of Et$_2$O to this material abundant crystals formed. After removal of the supernatant these crystals were washed with three small portions of ice-cold Et$_2$O and dried to obtain a second crop of pure sulfonamide 4r" (281 mg). Total yield of 4r" was 512 mg (79%). $^1$H NMR (400 MHz, CDCl$_3$) δ 10.36 (d, J=0.8 Hz, 1H), 8.11 (dd, J=7.8, 1.2 Hz, 1H), 7.79 (dd, J=8.0, 1.6 Hz, 1H), 7.56 (dd, J=7.8, 1.4 Hz, 1H), 7.43-7.38 (m, 1H), 7.38-7.34 (m, 1H), 7.14 (td, J=7.7, 1.7 Hz, 1H), 6.99 (dd, J=8.2, 1.3 Hz, 1H), 3.53 (s, 3H), 3.39 (s, 3H); $^{13}$C NMR (101 MHz, CDCl$_3$) 190.3, 157.3, 143.1, 143.0, 136.8, 133.1, 131.9, 130.9, 130.1, 128.0, 119.9, 116.7, 91.9, 55.4, 40.0; LR-MS calcd. for C$_{15}$H$_{15}$INO$_4$S [M+H]$^+$ 431.98, found 432.66.

To a dark-green suspension of CrCl$_2$ (474 mg, 3.86 mmol) and NiCl$_2$ (50.0 mg, 0.386 mmol) in anhydrous DMF (4.8 mL) was added a solution of sulfonamide 4r" (416 mg, 0.965 mmol) in anhydrous DMF (4.8 mL) dropwise over 4 minutes. The resulting nearly black mixture was heated to 90° C. for 1.5 h then quenched with water (50 mL) and extracted with Et$_2$O (50 mL, 2×25 mL). The combined organics were washed with brine (50 mL), dried over Na$_2$SO$_4$, and concentrated to yield a yellow oil.

This crude was purified by column chromatography (CH$_2$Cl$_2$, 2 column volumes→CH$_2$Cl$_2$:Et$_2$O-80:1, 2 column volumes→40:1, 2 column volumes→20:1, 2 column volumes) to obtain impure product as a white foam. On addition of a small quantity of Et$_2$O, crystallization occurred. After washing the crystals, this crystallization procedure (concentration from CH$_2$Cl$_2$ solution followed by addition of Et$_2$O) was repeated to yield the pure alcohol 4r as fine white crystals (132 mg, 45%). $^1$H NMR (500 MHz, CDCl$_3$) (significant broadening of some peaks was observed due to conformers) δ 7.99 (d, J=7.8 Hz, 1H), 7.70 (br s, 1H), 7.58 (t, J=6.9 Hz, 1H), 7.49 (t, J=7.7 Hz, 1H), 7.32 (t, J=8.0 Hz, 1H), 7.21 (br s, 1H), 6.95 (d, J=7.7 Hz, 1H), 6.01 (br s, 1H), 4.10 (br s, 1H), 3.93 (s, 3H), 3.05 (br s, 3H); $^{13}$C NMR (126 MHz, CDCl$_3$) δ 156.0, 139.5, 138.4, 137.5, 133.1, 129.1, 128.8, 128.6, 126.7, 121.5, 112.1, 74.9, 56.3, 37.1; LR-MS calcd. for C$_{15}$H$_{14}$NO$_3$S [M–OH]$^+$ 288.07, found 288.72.

11-Hydroxy-6-methyl-3-phenyl-6,11-dihydrodibenzo[c,f][1,2]thiazepine 5,5dioxide (4t)

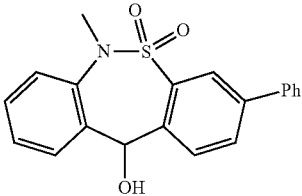

The product 4t was obtained as a white solid (235 mg, 94%). $^1$H NMR (400 MHz, Acetone-d$_6$) δ 8.08-8.03 (m, 2H), 7.91 (dd, J=8.2, 1.9 Hz, 1H), 7.74 (dd, J=7.3, 1.7 Hz, 1H), 7.72-7.66 (m, 2H), 7.54-7.46 (m, 3H), 7.45-7.34 (m, 3H), 6.51 (d, J=5.5 Hz, 1H), 5.55 (d, J=5.7 Hz, 1H), 3.41 (s, 3H); $^{13}$C NMR (101 MHz, Acetone-d$_6$) δ 142.8, 141.8, 140.0, 139.9, 139.7, 138.6, 131.4, 130.0, 129.7, 129.0, 128.8, 128.4, 128.0, 127.8, 127.4, 126.4, 70.6, 38.0; LR-MS calcd. for C$_{20}$H$_{16}$NO$_2$S [M–OH]$^+$ 334.09, found 334.15.

11-Hydroxy-6-methyl-3-(methylsulfonyl)-6,11-dihydrodibenzo[c,f][1,2]thiazepine 5,5-dioxide (4u)

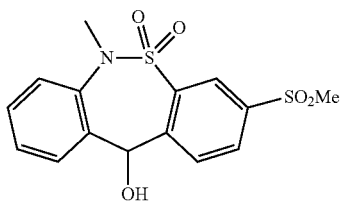

The product 4u was obtained as a white solid (217 mg, 99%). $^1$H NMR (400 MHz, Acetone-d$_6$) δ 8.32 (d, J=1.8 Hz, 1H), 8.28 (d, J=8.3 Hz, 1H), 8.18 (dd, J=8.3, 1.8 Hz, 1H), 7.75 (dd, J=7.2, 1.8 Hz, 1H), 7.56-7.52 (m, 1H), 7.41 (pd, J=7.3, 1.6 Hz, 2H), 6.62 (d, J=5.3 Hz, 1H), 5.81 (d, J=5.3 Hz, 1H), 3.45 (s, 3H), 3.22 (s, 3H); $^{13}$C NMR (101 MHz, Acetone-d$_6$) δ 146.5, 142.6, 142.2, 140.6, 137.7, 131.6, 130.0, 129.3, 128.6, 128.2, 127.2, 126.9, 69.7, 44.1, 37.9; LR-MS calcd. for C$_{15}$H$_{14}$NO$_4$S [M–OH]$^+$ 336.04, found 336.19.

11-Hydroxy-6-methyl-3-(methylsulfinyl)-6,11-dihydrodibenzo[c,f][1,2]thiazepine 5,5-dioxide (4v)

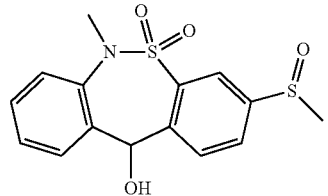

The product 4v was obtained as a white foam (152 mg, 98%, 1:1 mixture of diastereomers). $^1$H NMR (400 MHz, CDCl$_3$) (partial integrals due to mixture of diastereomers) δ 8.15 (d, J=1.5 Hz, 0.5H), 8.03 (d, J=1.5 Hz, 0.5H), 7.98-7.85 (m, 1.5H), 7.76 (dd, J=8.1, 1.6 Hz, 0.5H), 7.63 (d, J=3.4 Hz, 1H), 7.41-7.29 (m, 3H), 6.21 (s, 1H), 4.58 (br s, 1H), 3.29 (s, 1.5H), 3.29 (s, 1.5H), 2.73 (s, 1.5H), 2.73 (s, 1.5H); $^{13}$C NMR (101 z, CDCl$_3$) (additional peaks due to mixture of diastereomers) δ 146.4, 142.2, 142.1, 139.2, 138.8, 138.3, 138.1, 137.5, 129.8, 129.7, 129.3, 129.1, 128.8, 128.3, 127.9, 127.6, 127.2, 123.5, 123.3, 73.0, 72.8, 43.8, 38.5, 38.4; LR-MS calcd. for C$_{15}$H$_{14}$NO$_3$S$_2$ [M–OH]$^+$ 320.04, found 320.20.

2-Chloro-11-hydroxy-6-methyl-6,11-dihydrodibenzo[c,f][1,2]thiazepine 5,5-dioxide (4w)

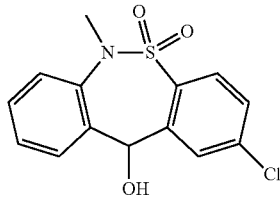

The product 4w was obtained as a white solid (195 mg, 95%). $^1$H NMR (400 MHz, Acetone-d$_6$) δ 8.00 (d, J=1.5 Hz, 1H), 7.86 (d, J=8.5 Hz, 1H), 7.74 (dd, J=7.1, 1.8 Hz, 1H), 7.58-7.49 (m, 2H), 7.46-7.36 (m, 2H), 6.53 (d, J=5.3 Hz, 1H), 5.74 (d, J=5.4 Hz, 1H), 3.42 (s, 3H); $^{13}$C NMR (101 MHz, Acetone-d$_6$) δ 143.6, 142.8, 138.7, 138.2, 138.1, 130.3, 129.8, 129.0, 128.9, 128.4, 126.8, 126.6, 69.4, 37.7; LR-MS calcd. for C$_{14}$H$_{11}$ClNO$_2$ [M–OH]$^+$ 292.02, found 292.38.

8-Chloro-11-hydroxy-6-methyl-6,11-dihydrodibenzo[c,f][1,2]thiazepine 5,5-dioxide (4x)

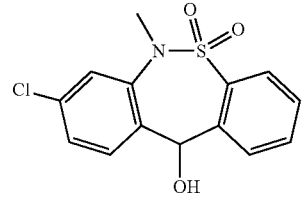

The product 4x was obtained as an off-white foam (384 mg, 100%). $^1$H NMR (500 MHz, CDCl$_3$) δ 7.96 (dd, J=7.8, 1.1 Hz, 1H), 7.68 (d, J=7.5 Hz, 1H), 7.62 (td, J=7.5, 1.3 Hz, 1H), 7.58-7.55 (m, 1H), 7.52 (td, J=7.6, 1.2 Hz, 1H), 7.30-7.26 (m, 2H), 5.94 (d, J=9.0 Hz, 1H), 4.50 (d, J=9.5 Hz, 1H), 3.14 (s, 3H); $^{13}$C NMR (126 MHz, CDCl$_3$) δ 140.2, 137.6, 136.6, 135.0, 134.0, 133.8, 132.8, 130.1, 128.9, 128.1, 127.7, 126.6, 75.9, 39.1; LR-MS calcd. for C$_{14}$H$_{11}$ClNO$_2$S [M–OH]$^+$ 292.02, found 292.51.

6-Ethyl-11-hydroxy-6,11-dihydrodibenzo[c,f][1,2]thiazepine 5,5-dioxide (4y)

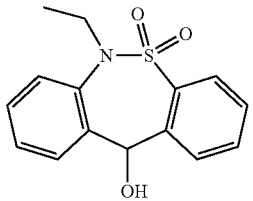

4y

The product 4y was obtained as a pale-yellow glass (226 mg, 100%). $^1$H NMR (500 MHz, CDCl$_3$) δ 7.98 (dd, J=7.8, 1.1 Hz, 1H), 7.68 (d, J=7.5 Hz, 1H), 7.65-7.57 (m, 2H), 7.50 (td, J=7.6, 1.2 Hz, 1H), 7.41-7.32 (m, 3H), 5.99 (s, 1H), 4.22 (d, J=6.6 Hz, 1H), 3.77-3.68 (m, 2H), 0.90 (t, J=7.2 Hz, 3H); $^{13}$NMR (126 MHz, CDCl$_3$) δ 139.0, 138.1, 137.2, 137.0, 133.3, 131.9, 129.9, 129.8, 128.9, 127.9, 127.8, 127.4, 76.6, 47.0, 13.9; LR-MS calcd. for C$_{15}$H$_{14}$NO$_2$S [M–OH]$^+$ 272.07, found 271.97.

3-(Ethylthio)-11-hydroxy-6-methyl-6,11-dihydrodibenzo[c,f][1,2]thiazepine 5,5-dioxide (4z)

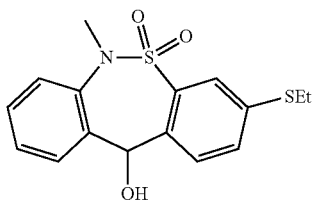

4z

The product 4z was obtained as a yellow glass (106 mg, 98%). $^1$H NMR (400 MHz, CDCl$_3$) δ 7.84 (s, 1H), 7.63-7.53 (m, 2H), 7.46 (d, J=7.6 Hz, 1H), 7.42-7.26 (m, 3H), 5.92 (d, J 9.0 Hz, 1H), 4.47 (d, J=9.2 Hz, 1H), 3.18 (s, 3H), 3.02 (dd, J=14.2, 7.0 Hz, 2H), 1.36 (t, J=7.2 Hz, 3H); $^{13}$C NMR (101 MHz, CDCl$_3$) δ 139.3, 138.8, 137.4, 135.9, 134.6, 132.1, 131.2, 130.4, 129.8, 127.7, 127.0, 126.6, 75.8, 39.2, 27.0, 14.0; LR-MS calcd. for C$_{16}$H$_{16}$NO$_2$S$_2$ [M–OH]$^+$ 318.06, found 318.29.

11-Hydroxy-3-(isopropylthio)-6-methyl-6,11-dihydrodibenzo[c,f][1,2]thiazepine 5,5-dioxide (4aa)

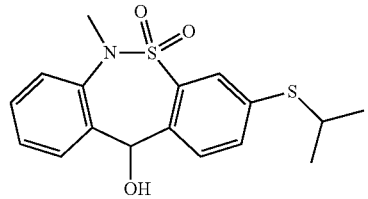

4aa

The product 4aa was obtained as a yellow glass (264 mg, 100%). $^1$H NMR (500 MHz, CDCl$_3$) δ 7.88 (s, 1H), 7.60-7.54 (m, 2H), 7.49 (dd, J=8.0, 0.8 Hz, 1H), 7.36-7.25 (m, 2H), 5.94 (d, J=8.5 Hz, 1H), 4.47 (d, J=8.8 Hz, 1H), 3.52-3.40 (m, 1H), 3.16 (s, 3H), 1.31 (dd, J=6.7, 3.0 Hz, 6H); $^{13}$C NMR (126 MHz, CDCl$_3$) δ 138.5, 138.0, 137.4, 136.5, 135.6, 134.6, 130.6, 129.9, 129.6, 129.0, 127.7, 127.0, 75.0, 39.0, 37.8, 22.9; LR-MS calcd. for C$_{17}$H$_{18}$NO$_2$S$_2$ [M–OH]$^+$ 332.08, found 332.32.

3-(Benzyloxy)-11-hydroxy-6-methyl-6,11-dihydrodibenzo[c,f][1,2]thiazepine 5,5-dioxide (4ab)

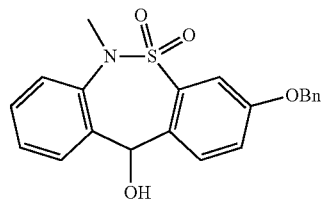

4ab

The product 4ab was obtained as a powdery white solid (115 mg, 97%). $^1$H NMR (500 MHz, CDCl$_3$) δ 7.62-7.58 (m, 2H), 7.56 (d, J=8.4 Hz, 1H), 7.46-7.30 (m, 7H), 7.28 (dd, J=7.9, 1.1 Hz, 1H), 7.17 (dd, J=8.4, 2.7 Hz, 1H), 5.80 (d, J=10.6 Hz, 1H), 5.15 (s, 2H), 4.41 (d, J=10.6 Hz, 1H), 3.12 (s, 3H); $^{13}$C NMR (126 MHz, CDCl$_3$) δ 158.8, 139.6, 138.0, 136.0, 134.8, 132.9, 132.8, 129.9, 129.8, 128.9, 128.5, 127.8, 127.6, 127.1, 119.8, 114.5, 70.8, 39.9; LR-MS calcd. for C$_{21}$H$_{18}$NO$_3$S [M–OH]$^+$ 364.10, found 364.41.

General Procedure for Preparation of Chlorides 5a-5ab

Thionyl chloride (4.0-6.0 mmol) was added dropwise to a solution of alcohol 4 (1.0 mmol) in anhydrous CH$_2$Cl$_2$ (7 mL) (in some cases neat thionyl chloride was used). The reaction mixture was stirred for 2-18 h at room temperature and then concentrated to give the chloride 5 as a white or off-white solid, which was used directly in the following reaction without further purification.

10-Chloro-4-methyl-4,10-dihydrobenzo[f]thieno[3,2-c][1,2]thiazepine 5,5dioxide (5a)

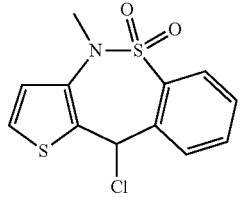

Full conversion was not achieved despite use of an excess of thionyl chloride and a prolonged reaction time. The crude product was obtained as a brown solid (170 mg, mixture of 4a and 5a-1:2 determined by $^1$H NMR) and was used in the next step without further purification. $^1$H NMR (400 MHz Acetone-$d_6$) δ 8.03 (d, J=7.8 Hz, 1H), 7.93 (d, J=7.6 Hz, 1H ), 7.82 (dd, J=7.5, 1.4 Hz, 1H), 7.74 (td, J=7.6, 1.3 Hz, 1H), 7.64 (d, J=5.5 Hz, 1H), 7.13 (s, 1H), 7.03 (d, J=5.5 Hz, 1H), 3.08 (s, 3H).

3-Bromo-10-chloro-4-methyl-4,10-dihydrobenzo[f]thieno[3,2-c][1,2]thiazepine 5,5-dioxide (5b)

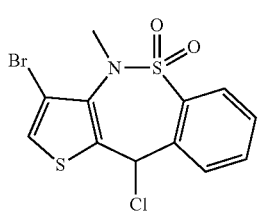

The product 5b was obtained as a pale-tan solid (168 mg, 94%). $^1$H NMR (400 MHz, CDCl$_3$) δ 8.08 (dd, J=7.7, 1.2 Hz, 1H), 7.78 (d, J=7.6 Hz, 1H), 7.70 (td, J=7.6, 1.3 Hz, 1H), 7.61 (td, J=7.6, 1.2 Hz, 1H), 7.36 (s, 1H), 6.74 (s, 1H), 2.97 (s, 3H); $^{13}$C NMR (101 MHz, CDCl$_3$) 136.6, 136.0, 134.2, 132.6, 131.5, 131.0, 129.9, 129.8, 123.8, 110.0, 58.1, 39.2; LR-MS calcd. for $C_{12}H_9BrNO_2S_2$ [M−Cl]$^+$ 343.92, found 344.71

7,10-Dichloro-4-methyl-4,10-dihydrobenzo[f]thieno[3,2-c][1,2]thiazepine 5,5-dioxide (5c)

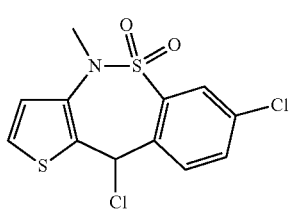

The product 5c was obtained as a dark brown foam in quantitative yield. $^1$H NMR (400 MHz, CDCl$_3$) δ 7.99 (d, J=2.1 Hz, 1H), 7.74 (d, J=8.3 Hz, 1H), 7.64 (dd, J=8.2, 2.2 Hz, 1H), 7.32 (d, J=5.3 Hz, 1H), 6.85 (d, J=4.7 Hz, 2H), 3.13 (s, 3H); $^{13}$C NMR (101 MHz, CDCl$_3$) δ 137.28, 137.05, 135.80, 133.93, 131.73, 131.36, 129.10, 126.22, 125.84, 124.62, 57.62, 39.39. LR-MS cald. for $C_{12}H_9ClNO_2S_2$ [M−Cl]$^+$ 297.98, found 298.00.

7-Bromo-10-chloro-4-methyl-4,10-dihydrobenzo[f]thieno[3,2-c][1,2]thiazepine 5,5-dioxide (5d)

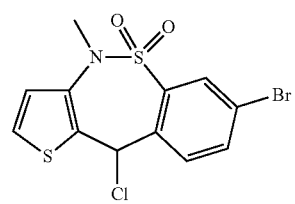

The product 5d was obtained as a brown solid containing 6% starting material by NMR (577 mg, 92% corrected for starting material impurity). $^1$H NMR (500 MHz, CDCl$_3$) δ 8.14 (d, J=2.0 Hz, 1H), 7.80 (dd, J=8.3, 2.0 Hz, 1H), 7.67 (d, J=8.3 Hz, 1H), 7.32 (d, J=5.5 Hz, 1H), 6.85 (d, J=6.8 Hz, 1H), 6.84 (s, 1H), 3.13 (s, 3H); $^{13}$C NMR (126 MHz, CDCl$_3$) δ 137.3, 137.04, 137.00, 131.9, 131.8, 130.9, 126.1, 125.8, 124.6, 123.6, 57.7, 39.4; LR-MS cald. for $C_{12}H_9BrNO_2S_2$ [M−Cl]$^+$ 341.93, found 342.47.

11-Chloro-6-methyl-6,11-dihydrodibenzo[c,f][1,2]thiazepine 5,5-dioxide (5e)

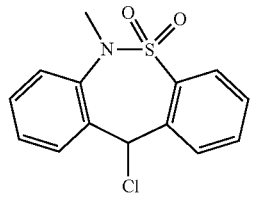

The chloride 5e was prepared according the procedure described in Gilleron et al. 2007. NMR (500 MHz, Acetone-$d_6$) δ 7.97 (dd, J=7.3, 1.8 Hz, 1H), 7.83-7.78 (m, 1H), 7.74-7.63 (m, 4H), 7.59 (t, J=7.6 Hz, 1H), 7.43 (t, J=7.5 Hz, 1H), 6.65 (s, 1H), 3.56 (s, 3H).

3,11-Dichloro-6-methyl-6,11-dihydrodibenzo[c,f][1,2]thiazepine 5,5-dioxide (5f)

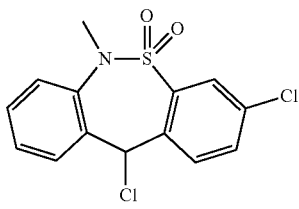

Chloride 5f was purchased from Ark Pharm, Inc. (Libertyville, Ill.) and used without further purification.

11-Chloro-3-fluoro-6-methyl-6,11-dihydrodibenzo[c,f][1,2]thiazepine 5,5-dioxide (5g)

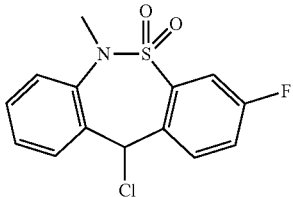

5g

The product 5g was obtained as a white solid (219 mg, 99%). $^1$H NMR (500 MHz, CDCl$_3$) δ 7.71 (dd, J=8.1, 2.7 Hz, 1H), 7.58-7.49 (m, 3H), 7.43 (d, J=7.5 Hz, 1H), 7.39-7.34 (m, 1H), 7.26-7.21 (m, 1H), 6.14 (s, 1H), 3.59 (s, 3H); $^{13}$C NMR (126 MHz, CDCl$_3$) (additional peaks due to C—F coupling) δ 163.9, 161.8, 142.5 139.3 137.8 133.8, 133.8, 131.7, 131.3, 130.1, 129.5, 129.0, 119.8, 119.7, 115.5, 115.3, 63.7, 39.3; LR-MS calcd. for C$_{14}$H$_{11}$FNO$_2$S [M–Cl]$^+$ 276.05, found 275.78.

11-Chloro-3-methoxy-6-methyl-6,11-dihydrodibenzo[c,f][1, 2]thiazepine 5,5-dioxide (5h)

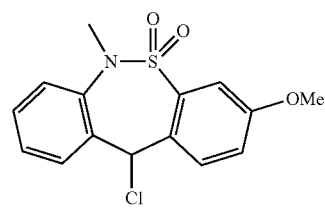

5h

The product 5h was obtained as an off-white solid (158 mg, 99%). $^1$H NMR (500 MHz, CDCl$_3$) δ 7.57-7.39 (m, 5H), 7.34 (t, J=7.4 Hz, 1H), 7.05 (dd, J=8.6, 2.6 Hz, 1H), 6.14 (s, 1H), 3.88 (s, 3H), 3.58 (s, 3H); $^{13}$C NMR (126 MHz, CDCl$_3$) δ 160.7, 141.6, 139.5, 138.3, 133.4, 131.4, 130.0, 129.5, 128.8, 127.1, 119.3, 112.0, 64.7, 56.0, 39.3; LR-MS calcd. for C$_{15}$H$_{14}$NO$_3$S [M–Cl]$^+$ 288.07, found 287.94.

11-Chloro-6-methyl-3-phenoxy-6,11-dihydrodibenzo[c,f][1,2]thiazepine 5,5-dioxide (5i)

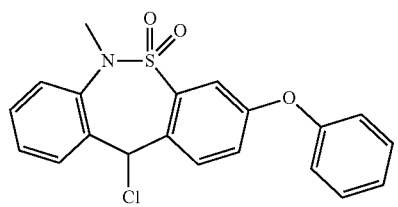

5i

The product 5i was obtained as an off-white solid (283 mg, 97%). $^1$H NMR (500 MHz, CDCl$_3$) δ 7.57 (d, J=2.6 Hz, 1H), 7.55-7.47 (m, 3H), 7.45-7.33 (m, 4H), 7.21 (t, J=7.4 Hz, 1H), 7.11 (dd, J=8.6, 2.6 Hz, 1H), 7.09-7.03 (m, 2H), 6.14 (s, 1H), 3.58 (s, 3H); $^{13}$C NMR (126 MHz, CDCl$_3$) δ 159.3, 155.3, 142.0, 139.4, 138.1, 133.5, 131.5, 130.4, 130.0, 129.5, 129.0, 128.9, 125.1, 121.5, 120.2, 116.7, 64.4, 39.3; LR-MS calcd. for C$_{20}$H$_{16}$NO$_3$S [M–Cl]$^+$ 350.09, found 349.75.

11-Chloro-3,6-dimethyl-6,11-dihydrodibenzo[c,f][1, 2]thiazepine 5,5-dioxide (5j)

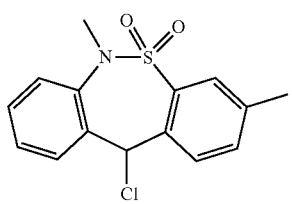

5j

The product 5j was obtained as an off-white solid (220 mg, 94%). $^1$H NMR (500 MHz, CDCl$_3$) δ 7.83 (s, 1H), 7.56-7.47 (m, 2H), 7.46-7.40 (m, 2H), 7.37-7.31 (m, 2H), 6.13 (s, 1H), 3.58 (s, 3H), 2.42 (s, 3H); $^{13}$C NMR (126 MHz, CDCl$_3$) δ 141.0, 140.2, 139.5, 138.2, 133.3, 132.3, 131.5, 131.4, 130.0, 129.4, 128.8, 128.4, 64.4, 39.1, 21.2; LR-MS calcd. for C$_{15}$H$_{14}$NO$_2$S [M–Cl]$^+$ 272.07, found 272.75.

9-Bromo-3, 1-dichloro-6-methyl-6,11-dihydrodibenzo[c,f][1,2]thiazepine 5,5-dioxide (5k)

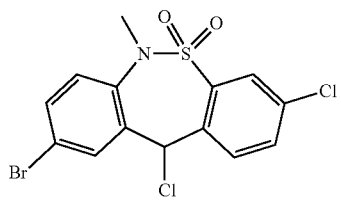

5k

The product 5k was obtained as an off-white solid (270 mg, 99%). $^1$H NMR (400 MHz, Acetone-d$_6$) δ 7.91 (s, 1H), 7.90 (s, 1H), 7.82 (d, J=8.4 Hz, 1H ), 7.79-7.73 (m, 2H), 7.64 (d, J=8.5 Hz, 1H), 6.47 (s, 1H), 3.54 (s, 3H); $^{13}$C NMR (101. MHz, Acetone-d$_6$) δ 143.0, 140.4, 139.9, 136.6, 135.2, 135.0, 134,4, 134.0, 1336, 132.1, 127.9, 122.1, 62.6, 39.4; LR-MS calcd. for C$_{14}$H$_{10}$BrClNO$_2$S [M–Cl]$^+$ 371.93, found 372.84.

11-Chloro-6-methyl-3-(methylthio)-6,11-dihydrodibenzo[c,f][1,2]thiazepine 5,5-dioxide (5l)

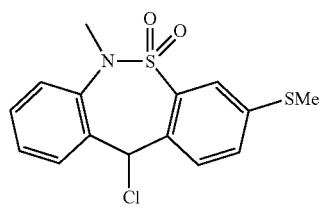

5l

The product 5l was obtained as an off-white solid (329 mg, 98%) $^1$H NMR (400 MHz, CDCl$_3$) δ 7.78 (s, 1H), 7.56-7.47 (m, 2H), 7.45-7.40 (m, 2H), 7.38-7.32 (m, 2H), 6.12 (s, 1H), 3.58 (s, 3H), 2.53 (s, 3H). $^{13}$C NMR (101 MHz, CDCl$_3$) δ 142.9, 140.9, 139.4, 137.9, 131.9, 131.5, 130.9, 130.1, 129.6, 129.5, 128.9, 124.1, 64.5, 39.3, 15.3; LR-MS calcd. for C$_{15}$H$_{14}$NO$_2$S$_2$ [M−Cl]$^+$ 304.05, found 304.74.

3-Bromo-11-chloro-6-methyl-6,11-dihydrodibenzo[c,f][1,2]thiazepine 5,5dioxide (5o)

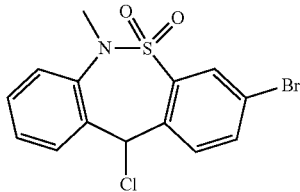

The product 5o was obtained as a white solid (60 mg, 95%). $^1$H NMR (400 MHz, CDCl$_3$) δ 8.14 (d, J=2.0 Hz, 1H), 7.66 (dd, J=8.3, 2.1 Hz, 1H), 7.54-7.50 (m, 2H), 7.45-7.40 (m, 2H), 7.38-7.33 (m, 1H), 6.10 (s, 1H), 3.58 (s, 3H); $^{13}$C NMR (101 MHz, CDCl$_3$) δ 142.0, 139.2, 137.5, 135.6, 134.1, 133.0, 131.7, 131.0, 130.2, 129.5, 129.0, 124.3, 63.7, 39.3; LR-MS calcd. for C$_{14}$H$_{11}$BrNO$_2$S [M−Cl]$^+$ 335.97, found 336.01.

11-Chloro-3-iodo-6-methyl-6,11-dihydrodibenzo[c,f][1,2]thiazepine 5,5dioxide (5q)

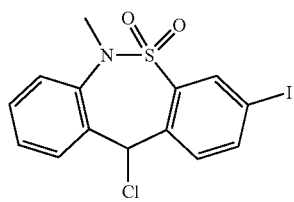

The product 5q was obtained as a gray solid (73.4 mg, 96%). $^1$H (400 MHz, CDCl$_3$) δ 8.32 (d, J=1.8 Hz, 1H), 7.87 (dd, J=8.2, 1.8 Hz, 1H), 7.57-7.48 (m, 2H), 7.43 (d, J=7.1 Hz, 1H), 7.39-7.33 (m, 1H), 7.27 (d, J=7.1 Hz, 1H), 6.08 (s, 1H), 3.57 (s, 3H); $^{13}$C NMR (101 MHz, CDCl$_3$) δ 141.8, 141.5, 139.3, 137.6, 136.7, 134.7, 132.9, 131.7, 130.1, 129.5, 129.0, 95.4, 63.8, 39.3; LR-MS calcd. for C$_{14}$H$_{11}$INO$_2$S [M−Cl]$^+$ 383.96, found 383.70.

11-Chloro-7-methoxy-6-methyl-6,11-dihydrodibenzo[c,f][1,2]thiazepine 5,5-dioxide (5r)

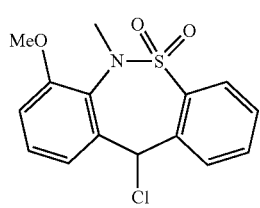

The product 5r was obtained as a white solid (70.4 mg, quantitative). $^1$H NMR (400 MHz, CDCl$_3$) δ 8.04-7.97 (m, 1H), 7.56-7.47 (m, 3H), 7.31 (t, J=8.0 Hz, 1H), 7.05 (d, J=8.4 Hz, 1H), 6.99 (d, J=7.7 Hz, 1H), 6.03 (s, 1H), 3.97 (s, 3H), 3.54 (s, 3H); $^{13}$C NMR (101 MHz, CDCl$_3$) δ 158.4, 141.2, 140.1, 135.1, 132.2, 131.7, 130.4, 130.0, 128.1, 127.4, 121.3, 114.1, 64.7, 56.4, 38.1; LR-MS calcd. for C$_{15}$H$_{14}$NO$_3$S [M−Cl]$^+$ 288.07, found 288.07.

11-Chloro-6-methyl-3-phenyl-6,11-dihydrodibenzo[c,f][1,2]thiazepine 5,5-dioxide (5t)

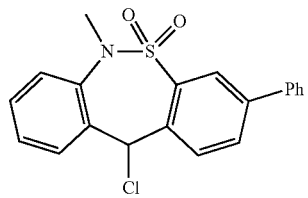

The product 5t was obtained as a white solid (235 mg, 99 1). $^1$H NMR (400 MHz, CDCl$_3$) δ 8.23 (d, J=1.9 Hz, 1H), 7.76 (dd, J=8.1, 2.0 Hz, 1H), 7.65-7.59 (m, 3H), 7.56 (dd, J=7.9, 1.4 Hz, 1H), 7.52 (td, J=7.9, 7.5, 1.5 Hz, 1H), 7.49-7.44 (m, 3H), 7.44-7.38 (m, 1H), 7.36 (td, J=7.6, 1.5 Hz, 1H), 6.21 (s, 1H), 3.61 (s, 3H); $^1$C NMR (101 MHz, CDCl$_3$) δ 143.5, 140.9, 139.5, 138.6, 138.0, 133.7, 132.1, 131.5, 130.9, 130.1, 129.5, 129.2, 128.8, 128.7, 127.3, 126.6, 64.3, 39.2; LR-MS calcd. for C$_{20}$H$_{16}$NO$_2$S [M−Cl]$^+$ 334.09, found 334.15.

11-Chloro-6-methyl-3-(methylsulfonyl)-6,11-dihydrodibenzo[c,f][1,2]thiazepine 5,5-dioxide (5u)

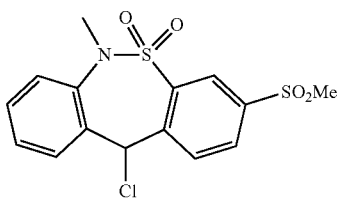

Neat thionyl chloride was used. The product 5u was obtained as an off-white solid (210 mg, 94%). $^1$H NMR (400 MHz, CDCl$_3$) δ 8.57 (d, J=1.8 Hz, 1H), 8.10 (dd, J=8.1, 1.9 Hz, 1H), 7.79 (d, J=8.2 Hz, 1H), 7.58-7.51 (m, 2H), 7.47 (d, J=7.5 Hz, 1H), 7.43-7.35 (m, 1H), 6.21 (s, 1H), 3.60 (s, 3H), 3.10 (s, 3H); $^{13}$C NMR (101 MHz, CDCl$_3$) δ 142.5, 142.0, 140.4, 139.0, 136.9, 132.6, 132.1, 130.9, 130.3, 129.5, 129.2, 127.7, 63.0, 44.5, 39.2; LR-MS calcd. for C$_{15}$H$_{14}$NO$_4$S$_2$ [M−Cl]$^+$ 336.04, found 336.18.

11-Chloro-6-methyl-3-(methylsulfinyl)-6,11-dihydrodibenzo[c,f][1,2]thiazepine 5,5-dioxide (5v)

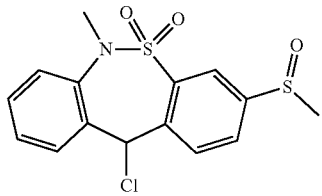

Chloride 5v was prepared by an alternative procedure described as follows. To a solution of alcohol 4v (74.9 mg, 0.222 mmol) in anhydrous $CH_2Cl_2$ (3.4 mL) was added a 2.0 M solution of HCl in anhydrous $Et_2O$ (0.67 mL, 1.33 mmol) and the resulting solution was stirred at room temperature for 1.25 h. It was then concentrated directly in vacuo to yield the pure chloride 5v as an off-white solid (76.0 mg, 96%, 1:1 mixture of diastereomers). $^1$H NMR (400 MHz, $CDCl_3$) (partial integrals due to mixture of diastereomers) δ 8.13 (s, 1H), 7.95 (dt, J=8.1, 2.1 Hz, 1H), 7.77 (d, J=7.7 Hz, 1H), 7.58-7.50 (m, 2H), 7.47 (d, J=7.1 Hz, 1H), 7.41-7.35 (m, 1H), 6.20 (s, 0.5H), 6.19 (s, 0.5H), 3.61 (s, 1.5H), 3.60 (s, 1.5H), 2.80 (s, 1.5H), 2.77 (s, 1.5H); $^{13}$C NMR (101 MHz, $CDCl_3$) (additional peaks due to mixture of diastereomers) δ 148.8, 141.6, 139.1, 137.7, 137.4, 132.8, 132.7, 131.9, 130.3, 130.2, 129.5, 129.5, 129.1, 127.3, 123.7, 123.5, 63.5, 63.5, 44.0, 39.2; LR-MS calcd. for $C_{15}H_{14}NO_3S_2$ [M−Cl]$^+$ 320.04, found 320.20.

2,11-Dichloro-6-methyl-6,11-dihydrodibenzo[c,f][1,2]thiazepine 5,5-dioxide (5w)

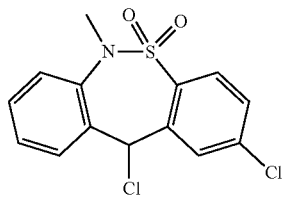

The product 5w was obtained as a white solid (195 mg, 99%). $^1$H NMR (400 MHz, $CDCl_3$) δ 7.97 (d, J=8.5 Hz, 1H), 7.60-7.50 (m, 4H), 7.46 (d, J=7.4 Hz, 1H), 7.41-7.35 (m, 1H), 6.11 (s, 1H), 3.60 (s, 3H); $^{13}$C NMR (101 MHz, $CDCl_3$) δ 139.1, 138.7, 138.3, 137.3, 136.9, 131.6, 130.9, 130.1, 129.9, 129.6, 129.2, 128.8, 63.1, 38.9; LR-MS calcd. for $C_{14}H_{11}ClNO_2S$ [M−Cl]$^+$ 292.02, found 292.38.

8,11-Dichloro-6-methyl-6,11-dihydrodibenzo[c,f][1,2]thiazepine 5,5-dioxide (5x)

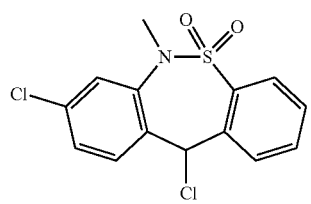

The product 5x was obtained as an off-white solid (390 mg, 100%). $^1$H NMR (500 MHz, $CDCl_3$) δ 8.04-7.99 (m, 1H), 7.59-7.51 (m, 4H), 7.39 (d, J=8.3 Hz, 1H), 7.32 (dd, J=8.3, 2.0 Hz, 1H), 6.14 (s, 1H), 3.55 (s, 3H); $^{13}$C NMR (126 MHz, $CDCl_3$) δ 140.7, 140.2, 136.9, 136.4, 134.8, 132.8, 131.5, 131.1, 130.4, 129.5, 129.0, 128.1, 63.6, 39.0; LR-MS calcd. for $C_{14}H_{11}NO_2S$ [M−Cl]$^+$ 292.02, found 292.56.

11-Chloro-6-ethyl-6,11-dihydrodibenzo[c,f][1,2]thiazepine 5,5-dioxide (5y)

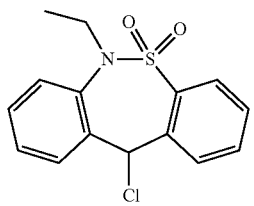

The product 5y was obtained as a white solid (230 mg, 98%) $^1$H NMR (500 MHz, $CDCl_3$) δ 8.04-8.00 (m, 1H), 7.59-7.45 (m, 6H), 7.37 (td, J=7.6, 1.3 Hz, 1H), 6.22 (s, 1H), 4.12 (dq, J=14.4, 7.2 Hz, 1H), 3.83 (dq, J=14.2, 7.1 Hz, 1H), 1.45 (t, J=7.2 Hz, 3H); $^{13}$C NMR (126 MHz, $CDCl_3$) δ 140.7, 138.4, 138.1, 135.1, 132.5, 131.4, 131.2, 130.8, 130.4, 130.2, 129.0, 128.3, 64.1, 48.0, 16.3; LR-MS calcd. for $C_{15}H_{14}NO_2S$ [M−Cl]$^+$ 272.07, found 271.97.

11-Chloro-3-(ethylthio)-6-methyl-6,11-dihydrodibenzo[c,f][1,2]thiazepine 5,5-dioxide (5z)

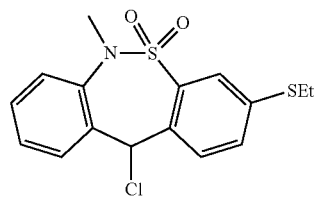

The product 5z was obtained as a pale-pinkish solid (109 mg, 100%). $^1$H NMR (500 MHz, $CDCl_3$) δ 7.83 (d, J=1.5 Hz, 1H), 7.55-7.47 (m, 2H), 7.44-7.37 (m, 3H), 7.37-7.32 (m, 1H), 6.11 (s, 1H), 3.58 (s, 3H), 3.03 (q, J=7.4 Hz, 2H), 1.36 (t, J=7.4 Hz, 3H); $^{13}$C NMR (126 MHz, $CDCl_3$) δ 141.6, 140.9, 139.4, 137.9, 131.9, 131.5, 131.4, 131.0, 130.1, 129.5, 128.9, 125.7, 64.4, 39.3, 26.8, 14.0; LR-MS calcd. for $C_{16}H_{16}NO_2S_2$ [M−Cl]$^+$ 318.06, found 318.11.

11-Chloro-3-(isopropylthio)-6-methyl-6,11-dihydrodibenzo[c,f][1,2]thiazepine 5,5-dioxide (5aa)

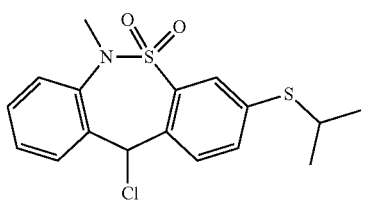

The product 5aa was obtained as a pale-orange solid (265 mg, 98%). $^1$H NMR (500 MHz, CDCl$_3$) δ 7.91 (s, 1H), 7.56-7.47 (m, 2H), 7.47-7.41 (m, 3H), 7.35 (td, J=7.6, 1.5 Hz, 1H), 6.12 (s, 1H), 3.58 (s, 3H), 3.57-3.49 (m, 1H), 1.35 (t, J=6.2 Hz, 6H); $^{13}$C NMR (126 MHz, CDCl$_3$) 140.8, 140.7, 139.4, 137.9, 133.2, 132.1, 131.9, 131.5, 130.1, 129.5, 128.9, 128.1, 64.3, 39.2, 37.5, 23.1; LR-MS calcd. for C$_{17}$H$_{18}$NO$_2$S$_2$ [M–Cl]$^+$ 332.08, found 337.30.

3-(Benzyloxy)-11-chloro-6-methyl-6,11-dihydrodibenzo[c,f][1,2]thiazepine 5,5-dioxide (5ab)

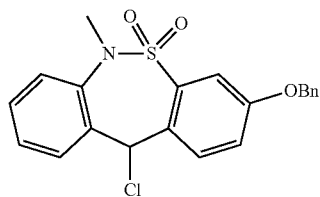

5ab

The product 5ab was obtained as an off-white solid (113 mg, 99%). $^1$H NMR (500 MHz, CDCl$_3$) δ 7.60 (d, J=2.7 Hz, 1H), 7.53 (dd, J=7.8, 1.3 Hz, 1H), 7.49 (td, J=7.5, 1.4 Hz, 1H), 7.46 (d, J=8.7 Hz, 1H), 7.44-7.38 (m, 5H), 7.37-7.32 (m, 2H), 7.11 (dd, J=8.6, 2.7 Hz, 1H), 6.14 (s, 1H), 5.12 (s, 2H), 3.58 (s, 3H); $^{13}$C NMR (126 MHz, CDCl$_3$) δ 159.86, 141.66, 139.48, 138.21, 135.86, 133.39, 131.41, 130.03, 129.50, 128.88, 128.81, 128.54, 127.78, 127.30, 119.70, 113.13, 70.75, 64.67, 39.30; LR-MS calcd. for C$_{21}$H$_{18}$NO$_3$S [M–Cl]$^+$ 364.10, found 364.44.

General Procedures for Preparation of N-substituted 11-amino-6-alkyl-6, 11-dihydrodiaryl [c,f][1, 2]thiazepine 5, 5-dioxides N-substituted 11-amino-6-alkyl-6,11-dihydrodiaryl[c,f][1,2]thiazepine 5,5-dioxides were prepared via amination of the corresponding chlorides 5 with amines according to general methods A, B, or C.

Method A:
An amine (0.26 mmol) and Et$_3$N (0.40 mmol) were added to a solution of the chloride 5 (0.2 mmol) in nitromethane (1 mL). The reaction vial was sealed under Ar and heated to 60° C. for 20 min. The reaction mixture was concentrated, and the crude product was purified by column chromatography.

Method B:
To a suspension of chloride 5 (0.500 mmol) in nitromethane (1.0 mL) was added an amine (1.00 mmol), and the mixture was warmed to 60° C. and left to stir until TLC indicated that the reaction was complete (typically <30 min.). The reaction mixture was concentrated, and the residue partitioned between Et$_2$O (10 mL) and water (10 mL). The ethereal layer was separated and the aqueous extracted again with Et$_2$O (10 mL). The combined organics were washed with H$_2$O (10 mL) and 10% NH$_4$OH (10 mL), dried over Na$_2$SO$_4$, and concentrated to yield the product. If necessary, the product was further purified by column chromatography. Alternatively, in some cases no extraction was performed and the concentrated reaction was purified directly by column chromatography.

Method C:
To a suspension of chloride 5 (0.500 mmol) in nitromethane (1.0 mL) was added an amine hydrochloride (0.600 mmol) and Et$_3$N (1.20 mmol) and the mixture was warmed to 60° C. and left to stir until TLC indicated that the reaction was complete (typically <30 min.). The reaction mixture was concentrated and the residue partitioned between Et$_2$O (10 mL) and water (10 mL). The ethereal layer was separated and the aqueous extracted again with Et$_2$O (10 mL). The combined organics were washed with H$_2$O (10 mL) and 10% NH$_4$OH (10 mL), dried over Na$_2$SO$_4$, and concentrated to yield the product. If necessary, the product was further purified by column chromatography. Alternatively, in some cases no extraction was performed and the concentrated reaction was purified directly by column chromatography.

Ethyl 7-((4-methyl-5,5-dioxido-4,10-dihydrobenzo[f]thieno[3,2-c][1,2]thiazepin-10-yl)amino) heptanoate (6)

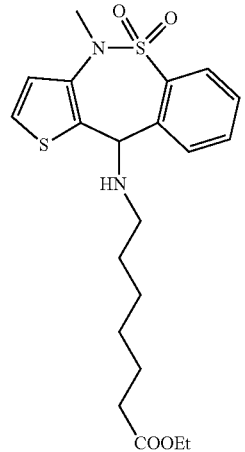 [SMILES: CCOC(=O)CCCCCCNC1c2ccccc2S(=O)(=O)N(C)c2ccsc21]

Method A. The crude product was purified by column chromatography (hexanes: ethyl acetate-2:1). The product 6 was obtained as a viscous yellow oil (96 mg, 56% after two steps). A second round of column chromatography was performed (hexanes: ethyl acetate-1:1) to remove the intense yellow color (54 mg of a yellowish solid was obtained after the second purification). $^1$H NMR (400 MHz, Acetone-d$_6$) δ 7.98-7.92 (m, 1H), 7.80 (td, J=7.6, 1.2 Hz, 1H), 7.74 (d, J=7.2 Hz, 1H), 7.61 (td, J=7.6, 1.2 Hz, 1H), 7.33 (d, J=5.5 Hz, 1H), 6.96 (d, J=5.5 Hz, 1H), 5.55 (d, J=9.4 Hz, 1H), 4.07 (q, J=7.1 Hz, 2H), 2.96 (s, 3H), 2.78 (t, J=8.2 Hz, 2H, partially overlaps with the residual acetone peak), 2.69-2.58 (m, 1H) 2.27 (t, J=7.4 Hz, 2H), 1.67-1.51 (m, 4H), 1.48-1.31 (m, 4H), 1.20 (t, J=7.1 Hz, 3H); $^{13}$C NMR (101 MHz, Acetone-d$_6$) δ 173.6, 137.2, 136.2, 136.2, 134.8, 132.0, 129.2, 129.0, 128.7, 125.7, 124.6, 60.9, 60.4, 48.3, 39.8, 34.6, 30.7, 27.6, 25.7; LR-MS calcd. for C$_{21}$H$_{29}$N$_2$O$_4$S$_2$ [M+H]$^+$ 437.16, found 438.13.

10-((3-Methoxypropyl)amino)-4-methyl-4,10-dihydrobenzo[f]thieno[3,2-c][1,2]thiazepine 5,5-dioxide (7)

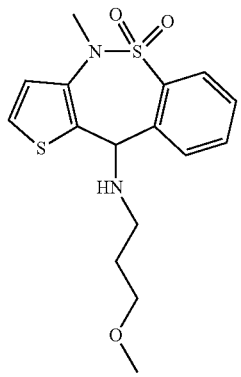 [SMILES: COCCCNC1c2ccccc2S(=O)(=O)N(C)c2ccsc21]

Method A. The crude product was purified by column chromatography (hexanes: ethyl acetate-1:2). The product 7 was obtained as a viscous blue oil (43 mg, 54% after two steps). A second round of column chromatography was performed (hexane: ethyl acetate-1:1) to remove the intense blue color (23 mg of a yellowish solid was obtained after the second purification). $^1$H NMR (400 MHz, Acetone-d$_6$) δ 7.95 (dd, J=7.7, 1.0 Hz, 1H), 7.80 (td, J=7.6, 1.2 Hz, 1H), 7.74 (d, J=7.3 Hz, 1H), 7.61 (td, J=7.6, 1.2 Hz, 1H), 7.33 (d, J=5.5 Hz, 1H), 6.97 (d, J=5.5 Hz, 1H), 5.55 (br d, 1H), 3.50 (t, J=6.2 Hz, 2H), 3.28 (s, 3H), 3.19-3.06 (m, J=1H ), 2.96 (H, 3H), 2.91 2.68 (m, 2H, partially overlaps with the residual acetone peak), 1.78 (p, J=6.4 Hz, 2H); $^{13}$C NMR (101 z, Acetone-d$_6$) δ 137.2, 136.2, 136.1, 134.8, 131.9, 129.0, 128.9, 128.7, 125.8, 124.5, 71.4, 60.9, 58.6, 45.7, 39.8, 31.0; LR-MS calcd. for C$_{16}$H$_{21}$N$_2$O$_3$S$_2$ [M+H]$^+$ 353.10, found 353.86.

6-Methyl-11(pentylamino)-6,11-dihydrodibenzo[c,f][1,2]thiazepine 5,5-dioxide (8)

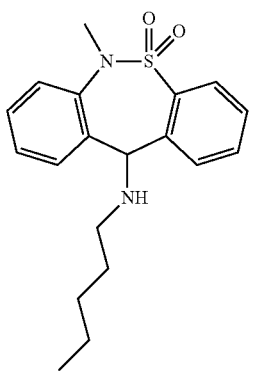 [SMILES: CCCCCNC1c2ccccc2N(C)S(=O)(=O)c2ccccc21]

Method A. The crude product was purified by column chromatography (hexanes: ethyl acetate-2:1). The product 8 was obtained as a viscous colorless oil (65 mg, 94%). $^1$H NMR (400 MHz, Methanol-d$_4$) δ 7.93 (d, J=7.7 Hz, 1H), 7.63-7.59 (m, 2H), 7.56-7.46 (m, 2H), 7.45-7.37 (m, 2H), 7.32 (td, J=7.3, 1.8 Hz, 1H), 5.08 (s, 1H ), 3.27 (s, 30), 2.53-2.36 (m, 2H), 1.57-1.40 (m, 2H), 1.31-1.16 (m, 4H), 0.86 (t, J=6.9 Hz, 3H); $^{13}$C NMR (101 MHz, Methanol-d$_4$) δ 140.6, 139.9, 139.3, 139.2, 133.8, 132.0, 132.0, 130.4, 129.6, 129.4, 128.9, 128.7, 67.9, 38.9, 30.5, 30.2, 23.5, 14.3; LR-MS calcd. for C$_{19}$H$_{25}$N$_2$O$_2$ [M+H]$^+$ 345.16, found 345.91.

Ethyl 7-((6-methyl-5,5-dioxido-6,11-dihydrodibenzo[c,f][1,2]thiazepin-11-yl)amino)heptanoate (9)

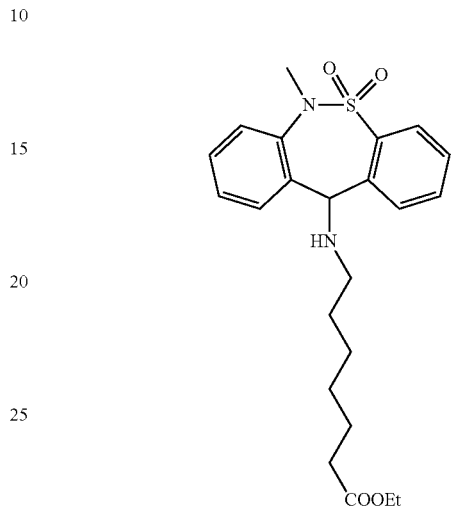

Method A. The crude product was purified by column chromatography (hexanes: ethyl acetate-2:1). The product 9 was obtained as a viscous colorless oil (68 mg, 79%). $^1$H NMR (400 MHz, Methanol-d$_4$) δ 7.93 (d, J=7.7 Hz, 1H), 7.65-2.58 (m, 2H), 7.56-7.46 (m, 2H), 7.46-7.36 (m, 2H), 7.33 (dd, J=7.4, 1.7 Hz, 1H), 5.09 (s, 1H), 4.09 (q, J=7.1 Hz, 2H), 3.28 (s, 3H), 2.54-2.36 (m, 2H), 2.26 (t, J=7.4 Hz, 2H), 1.61-1.42 (m, 4H), 1.31-1.18 (m, 7H); $^{13}$C NMR (101 MHz, Methanol-d$_4$) δ 175.5, 140.6, 139.9, 139.4, 139.2, 133.8, 132.0, 132.0, 130.4, 129.6, 129.4, 128.9, 128.8, 67.9, 61.4, 48.5, 38.9, 35.0, 30.3, 29.8, 27.9, 25.9, 14.5; LR-MS calcd. for C$_{23}$H$_{31}$N$_2$O$_4$S [M+H]$^+$ 431.20, found 432.32.

11-((3-Methoxypropyl)amino)-6-methyl-6,11-dihydrodibenzo[c,f][1,2]thiazepine 5,5-dioxide (10)

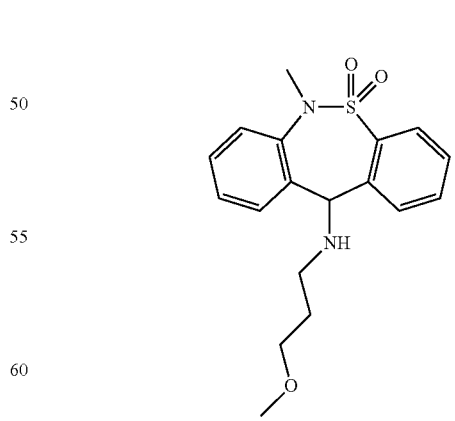

Method A. The crude product was purified by column chromatography (hexanes: ethyl acetate-1:2). The product 10 was obtained as a viscous colorless oil (59 mg, 85%). $^1$H NMR (400 MHz, Acetone-d$_6$) δ 7.89 (dd, J=7.8, 1.2 Hz, 1H), 7.68 (d, J=7.7 Hz, 1H), 7.60 (td, J=7.5, 1.3 Hz, 1H), 7.52 (dt, J=7.6, 2.0 Hz, 2H), 7.46 (dd, J=7.8, 1.2 Hz, 1H), 7.38 (td, J=7.6, 1.6 Hz, 1H), 7.32 (td, J=7.5, 1.4 Hz, 1H), 5.20 (s, 1H), 3.44-3.35 (m, 5H), 3.22 (s, 3H), 2.58 (t, J=6.7 Hz, 2H), 1.73 (p, J=6.6 Hz, 2H); $^{13}$C NMR (101 MHz, Acetone-d$_6$) δ 141.0, 140.1, 140.1, 139.9, 133.0, 130.7, 130.6, 129.7, 128.9, 128.8, 128.5, 71.6, 66.7, 58.5, 46.1, 38.6, 30.8; LR-MS calcd. for C$_{18}$H$_{23}$N$_2$O$_3$S [M+H]$^+$ 347.14, found 347.90.

9-Bromo-3-chloro-1 (3-methoxypropyl)amino)-6-thyl-6,11-dihydrodibenzo[c,f][1,2] thiazepine 5,5-dioxide (11)

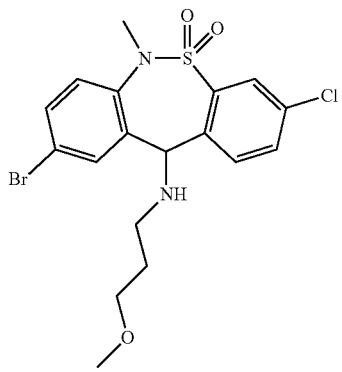 [SMILES: COCCCNC1c2cc(Br)ccc2N(C)S(=O)(=O)c2cc(Cl)ccc21]

Method A. The crude product was purified by column chrcmadograppy (hexanes: ethyl acetate-2:1). The product 11 was obtained as a white solid (75 mg, 82%). $^1$H NMR (400 MHz, Acetone-d$_6$) δ 7.83 (d, J=2.2 Hz, 1H), 7.74-7.70 (m, 2H), 7.66 (dd, J=8.3, 2.2 Hz, 1H), 7.58 (dd, J=8.5, 2.4 Hz, 1H), 7.44 (d, J=8.5 Hz, 1H), 5.23 (s, 1H), 3.42-3.38 (m, 5H), 3.23 (s, 3H), 2.80 (br s, 1H), 2.60 (td, J=6.8, 2.1 Hz, 2H), 1.79-1.69 (m, 2H); $^{13}$C NMR (101 MHz, Methanol-d$_4$) δ 141.8, 141.7, 139.6, 137.5, 135.4, 134.6, 133.6, 133.5, 130.9, 128.9, 122.4, 101.4, 72.2, 66.5, 58.9, 46.3, 39.0, 30.5; LR-MS calcd. for C$_{18}$H$_{21}$BrClN$_2$O$_3$S [M+H]$^+$ 461.01, found 462.07.

3-Chloro-11-((6-hydroxyhexyl)amino)-6-methyl-6,11-dihydrodibenzo[c,f][1,2]thiazepine 5,5-dioxide (12)

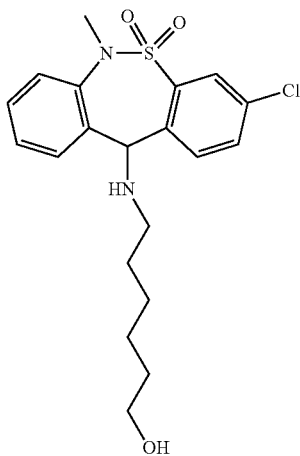 [SMILES: CN1c2ccccc2C(NCCCCCCO)c2ccc(Cl)cc2S1(=O)=O]

Method B. The product 12 was obtained as a viscous colorless oil (230 mg, 92%). $^1$H NMR (400 MHz, Methanol-d$_4$) δ 7.88 (t, J=1.2 Hz, 1H), 7.62 (s, 1H), 7.62 (s, 1H), 7.47 (td, J=7.2, 1.5 Hz, 1H), 7.44-7.38 (m, 2H), 7.37-7.31 (m, 1H), 5.08 (s, 1H), 3.50 (t, J=6.6 Hz, 2H), 3.33 (s, 3H), 2.53-2.38 (m, 2H), 1.57-1.43 (m, 4H), 1.35-1.23 (m, 4H); $^{13}$C NMR (101 MHz, Acetone-d$_6$) δ 142.4, 140.6, 139.8, 138.6, 134.2, 133.0, 132.8, 131.0, 130.0, 129.4, 128.8, 128.2, 66.5, 62.4, 48.7, 39.2, 33.7, 30.8, 27.9, 26.6; LR-MS calcd. for C$_{20}$H$_{26}$ClN$_2$O$_3$S [M+H]$^+$ 409.13, found 410.05.

6-((3-Chloro-6-methyl-5,5-dioxido-6,11-dihydrodibenzo[c,f][1,2]thiazepin-11-yl)amino)hexyl acetate (13)

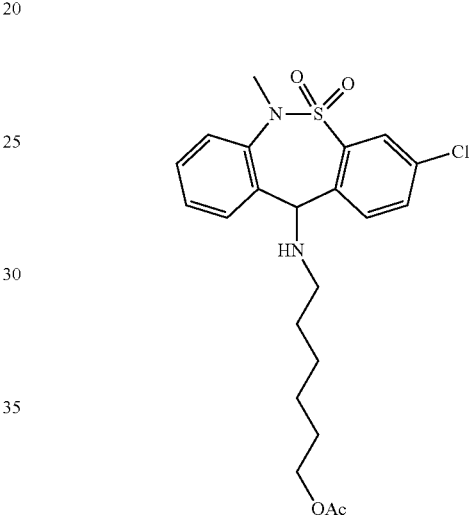

Ester 13 was prepared by O-acetylation of alcohol 12 according to the following procedure. Compound 12 (200 mg, 0.49 mmol) was dissolved in Et$_2$O (3 mL) and a solution of HCl in Et$_2$O (1 mL, 2.0 M) was added (to form an HCl salt of 12). Et$_2$O and the excess of HCl were evaporated. The residue was dissolved in AcOH (3 mL), and acetyl chloride (0.5 mL) was added. The reaction mixture was stirred at room temperature for 14 h, concentrated, diluted with ice-cold water, and basified with NaOH (1.0 M) to pH ~10. The mixture was then extracted with CH$_2$Cl$_2$ and the combined organic layers were dried over Na$_2$SO$_4$. After removing the solvent, the product 13 was obtained as a colorless viscous oil (190 mg, 86%). $^1$H NMR (400 MHz, Methanol-d$_4$) δ 7.88 (t, J=0.9 Hz, 1H), 7.62 (s, 1H), 7.61 (s, 1H), 7.50-7.37 (m, 3H), 7.37-7.30 (m, 1H), 5.08 (s, 1H), 4.01 (t, J=6.6 Hz, 2H), 3.32 (s, 3H), 2.54-2.37 (m, 2H), 2.00 (s, 3H), 1.63-1.53 (m, 2H), 1.53-1.43 (m, 2H), 1.34-1.21 (m, 4H); $^{13}$C NMR (101 MHz, Methanol-d$_4$) δ 153.8, 122.7, 121.1, 119.8, 118.7, 116.1, 114.6, 114.3, 112.9, 111.4, 110.0, 109.7, 48.1, 46.4, 29.4, 20.1, 11.2, 10.4, 8.7, 7.6, 1.7; LR-MS calcd. for C$_{22}$H$_{28}$ClN$_2$O$_4$S [M+H]$^+$ 451.15, found 452.16.

Ethyl 7-((3,6-dimethyl-5,5-dioxido-6,11-dihydrodibenzo[c,f][1,2]thiazepin-11-yl)amino) heptanoate (14)

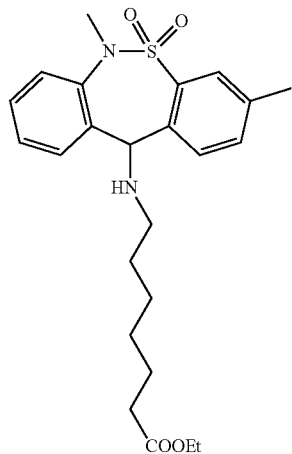 [SMILES: CCOC(=O)CCCCCCNC1c2ccccc2N(C)S(=O)(=O)c2cc(C)ccc21]

Method A. The crude product was purified by column chromatography (hexanes: ethyl acetate-2:1). The product 14 was obtained as a viscous. colorless oil (59 mg, 66%). $^1$H NMR (400 MHz, Acetone-$d_6$) δ 7.69 (s, 1H), 7.54 (d, J=7.9 Hz, 1H), 7.50 (dd, J=7.6, 1.6 Hz,) 1H), 7.45 (dd, J=7.8, 1.3 Hz, 1H). 7.42-7.33 (m, 2H), 7.30 (td, J=7.4, 1.4 Hz, 1H), 5.13 (s, 1H), 4.06 (q, J=7.1 Hz, 2H), 3.35 (s, 3H), 2.49 (t, J=7.0 Hz, 2H), 2.40 (s, 3H), 2.37 (br s, 1H), 2.24 (t, J=7.4 Hz, 2H), 1.63-1.43 (m, 4H), 1.38-1.23 (m, 4H), 1.19 (t, J=7.1 Hz, 3H); $^{13}$C NMR (101 MHz, Acetone-$d_6$) δ 173.6, 141.1, 140.2, 140.1, 139.1, 136.9, 133.6, 131.0, 131.1, 129.6, 129.0, 129.0, 128.4, 66.8, 60.4, 48.6, 38.8, 34.6, 30.6, 27.7, 25.6, 20.8, 14.6; LR-MS calcd. for $C_{24}H_{33}N_2O_4S$ $[M+H]^+$ 445.22, found 446.22.

11-((3-Methoxypropyl)amino)-3,6-dimethyl-6,11-dihydrodibenzo[c,f][1,2]thiazepine 5,5-dioxide (15)

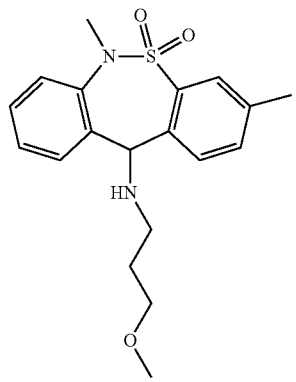 [SMILES: COCCCNC1c2ccccc2N(C)S(=O)(=O)c2cc(C)ccc21]

Method A. The crude product was purified by column chromatography (hexanes: ethyl acetate-2:1->1:1). The product 15 was obtained as a viscous colorless oil (47 mg, 65 1). $^1$H NMR (400 MHz, Acetone-$d_6$) δ 7.68 (s, 1H), 7.53 (d, J=7.9 Hz, 1H), 7.49 (dd, J=7.6, 1.6 Hz, 1H), 7.45 (dd, J=7.8, 1.3 Hz, 1H), 7.42-7.33 (m, 2H), 7.30 (td, J=7.4, 1.4 Hz, 1H), 5.13 (s, 1H), 3.39 (t, J=6.2 Hz, 2H), 3.36 (s, 3H), 3.22 (s, 3H), 2.57 (t, J=6.8 Hz, 2H), 2.46 (br s, 1H), 2.39 (s, 3H), 1.72 (p, J=6.6 Hz, 2H); $^{13}$C NMR (101 MHz, Acetone-$d_6$) δ 141.1, 140.2, 139.1, 136.9, 133.6, 130.8, 129.6, 129.0, 128.4, 71.6, 66.7, 58.5, 46.1, 38.7, 30.9, 20.8; LR-MS calcd. for $C_{19}H_{25}N_2O_3S$ $[M+H]^+$ 361.16, found 361.96.

7-((3,6-Dimethyl-5,5-dioxido-6,11-dihydrodibenzo[c,f][1,2]thiazepin-11-yl)amino)heptanoic acid hydrochloride salt (16a)

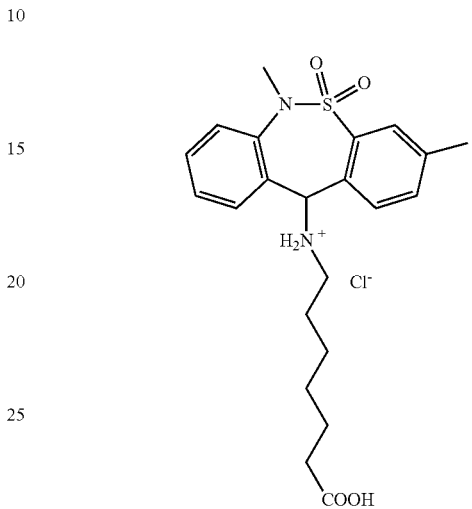

Compound 14 (25 mg, 0.056 mmol) was heated in HCl (0.5 M, 2 mL) to 70° C. for 2 h. The reaction mixture was then concentrated and dried. The product 16a was obtained as a viscous yellowish oil (25 mg, quant. yield). $^1$H NMR (400 MHz, Methanol-$d_4$) δ 7.93 (s, 1H), 7.80 (d, J=7.8 Hz, 1H), 7.76 (d, J=7.7 Hz, 1H), 7.67 (d, J=7.7 Hz, 1H), 7.63 (t, J=7.6 Hz, 1H), 7.55 (d, J=7.9 Hz, 1H), 7.47 (t, J=7.5 Hz, 1H), 5.95 (s, 1H), 3.18 (s, 3H), 3.02-2.67 (m, 2H), 2.53 (s, 3H), 2.26 (t, J=7.3 Hz, 2H), 1.76-1.49 (m, 4H), 1.37-1.25 (m, 4H); $^{13}$C NMR (101 MHz, Methanol-$d_4$) δ 177.4, 144.1, 142.9, 139.7, 135.8, 135.5, 134.8, 133.3, 130.1, 128.9, 128.6, 126.1, 68.0, 47.9, 39.8, 34.6, 29.4, 27.1, 26.7, 25.6, 21.2. LR-MS calcd. for $C_{22}H_{29}N_2O_4S$ $[M]^+$ 417.18, found 418.20.

7-((3,6-Dimethyl-5,5-dioxido-6,11-dihydrodibenzo[c,f][1,2]thiazepin-11-yl)amino)heptanoic acid (16b)

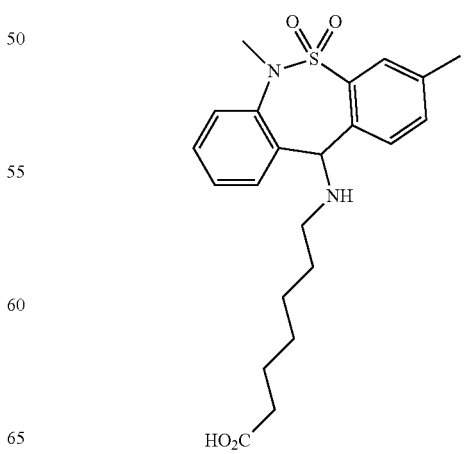

The free base compound 16b is synthesized according to the procedure used to prepare compound 18.

Ethyl 5-((3-chloro-6-methyl-5,5-dioxido-6,11-dihydrodibenzo[c,f][1,2]thiazepin-11-yl)amino)pentanoate (17)

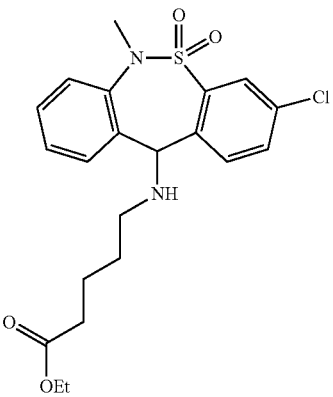

Method C. The product 17 was purified by column chromatography (CH$_2$Cl$_2$:Et$_2$O-40:1) and obtained as a viscous pale-yellow oil (130 mg, 60%). $^1$H NMR (500 MHz, CDCl$_3$) δ 7.96 (d, J=2.1 Hz, 1H), 7.50-7.34 (m, 5H), 7.30 (dd, J=7.2, 1.8 Hz, 1H), 5.00 (s, 1H), 4.11 (q, J=7.1 Hz, 2H), 3.36 (s, 3H), 2.48 (t, J=7.0 Hz, 2H), 2.27 (t, J=7.4 Hz, 2H), 1.70-1.58 (m, 2H), 1.52 (ddd, J=11.9, 7.0, 3.7 Hz, 2H), 1.24 (t, J=7.1 Hz, 3H); $^{13}$C NMR (126 MHz, CDCl$_3$) δ 173.6, 140.4, 138.7, 136.8, 134.5, 132.4, 131.4, 130.3, 129.5, 128.6, 128.2, 128.1, 66.3, 60.4, 47.8, 38.9, 34.2, 29.6, 22.8, 14.4; LR-MS calcd. for C$_{21}$H$_{26}$ClN$_2$O$_4$S [M+H]$^+$ 437.13, found 437.51.

5-((3-Chloro-6-methyl-5,5-dioxido-6,11-dihydrodibenzo[c,f][1,2]thiazepin-11-yl)amino)pentanoic acid (18)

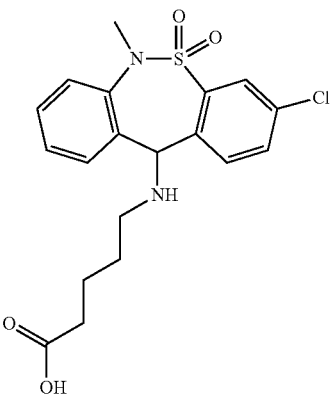 [SMILES: CN1c2ccccc2C(NCCCCC(=O)O)c2ccc(Cl)cc2S1(=O)=O]

Acid 18 was prepared by hydrolysis of ester 17 according to the following procedure. To a solution of 17 (120 mg, 0.275 mmol) in ethanol (0.75 mL) and H$_2$O (0.25 mL) was added NaOH (11.8 mg, 0.296 mmol), and the resulting solution was refluxed for 1 h. Most of the ethanol was removed in vacuo and the mixture was diluted with water (5 mL) and washed with Et$_2$O (2×5 mL). It was then carefully acidified to pH 4-5 with 10% aq. HCl, saturated with (NH$_4$)$_2$SO$_4$, and extracted with CHCl$_3$ (2×5 mL). The combined organics were washed with H$_2$O (3 mL), dried over Na$_2$SO$_4$, and concentrated to yield the product 18 as a foamy off-white solid (105 mg, 94%). $^1$H NMR (500 MHz, CDCl$_3$) δ 7.97 (d, J=1.9 Hz, 1H), 7.51 (ddd, J=8.4, 7.4, 5.7 Hz, 3H), 7.44-7.38 (m, 1H), 7.36 (dd, J=8.0, 1.3 Hz, 1H), 7.30 (td, J=7.6, 1.4 Hz, 1H), 5.27 (s, 1H), 4.42 (br s, 2H), 3.27 (s, 3H), 2.55 (dd, J=11.0, 8.2 Hz, 1H), 2.42 (dd, J=9.9, 6.9 Hz, 1H), 2.25 (dd, J=10.9, 5.0 Hz, 2H), 1.71-1.45 (m, 4H); $^{13}$C NMR (126 MHz, CDCl$_3$) δ 177.3, 140.2, 139.5, 135.3, 134.0, 133.2, 132.9, 132.0, 130.3, 128.6, 128.1, 127.6, 66.3, 46.9, 39.2, 34.2, 28.4, 22.6; LR-MS calcd. for C$_{19}$H$_{22}$ClN$_2$O$_4$S [M+H]$^+$ 409.10, found 408.69.

3-Chloro-6-methyl-11-(pentylamino)-6,11-dihydrodibenzo[c,f][1,2]thiazepine 5,5-dioxide (19)

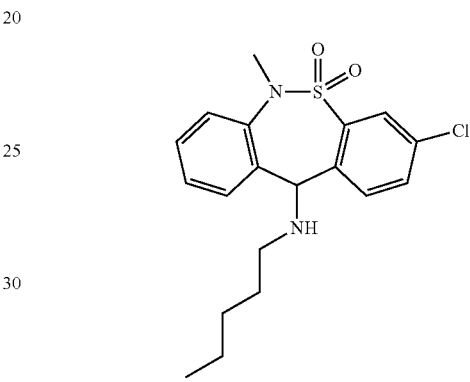

Method B. The product 19 was purified by column chromatography (CH$_2$Cl$_2$:hexanes-8:2, 4 column volumes→CH$_2$Cl$_2$, 3 column volumes) and obtained as a viscous colorless oil (52.9 mg, 28%). $^1$H NMR (400 MHz, CDCl$_3$) δ 7.96 (d, J=1.7 Hz, 1H), 7.48-7.42 (m, 2H), 7.41-7.32 (m, 3H), 7.32-7.27 (m, 1H), 5.01 (s, 1H), 3.38 (s, 3H), 2.46 (t, J=7.2 Hz, 2H), 2.01 (br s, 1H), 1.57-1.37 (m, 2H), 1.35-1.20 (m, 4H), 0.86 (t, J=7.0 Hz, 3H); $^{13}$C NMR (101 MHz, CDCl$_3$) δ 140.5, 139.0, 138.6, 137.1, 134.3, 132.3, 131.2, 130.1, 129.4, 128.5, 128.3, 128.1, 66.2, 48.3, 38.8, 29.9, 29.6, 22.7, 14.1; LR-MS calcd. for C$_{19}$H$_{24}$ClN$_2$O$_2$S [M+H]$^+$ 379.12, found 378.75.

3-Chloro-6-methyl-11-(methylamino)-6,11-dihydrodibenzo[c,f][1,2]thiazepine 5,5-dioxide (20)

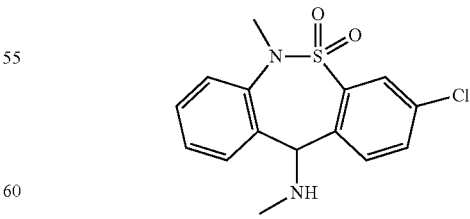

Compound 20 was prepared according to a modified Method C using 10 equivalents of methylamine HCl and 20 equivalents of Et$_3$N. The product 20 was purified by column chromatography (EtOAc:Hexanes-6:4, 5 column volumes→EtOAc, 2 column volumes) and obtained as a pale-yellow glass (134 mg, 83%). $^1$H NMR (400 MHz, CDCl$_3$) δ 7.97 (d, J=2.1 Hz, 1H), 7.50-7.27 (m, 6H), 4.88 (s, 1H), 3.34 3H), 2.34 (s, 3H), 2.10 (br s, 1H); $^{13}$C NMR (101 MHz, CDCl$_3$) δ 140.4, 138.8, 138.1, 136.5, 134.5, 132.3, 131.6, 130.6, 129.5, 128.6, 128.2, 128.1, 68.4, 38.9, 35.0; LR-MS calcd. for C$_{15}$H$_{16}$ClN$_2$O$_2$S [M+H]$^+$ 323.06, found 323.53.

3-Chloro-6-methyl-11-(propylamino)-6,11-dihydrodibenzo [c,f][1,2]thiazepine 5,5-dioxide (21)

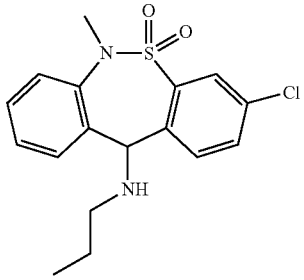 [SMILES: CCCNC1c2ccccc2N(C)S(=O)(=O)c2cc(Cl)ccc21]

Compound 21 was prepared according to a modified Method B using 10 equivalents of n-propylamine. The product 21 was obtained as a viscous pale-yellow oil (169 mg, 96%). $^1$H NMR (400 MHz, CDCl$_3$) δ 7.98-7.93 (m, 1H), 7.48-7.26 (m, 6H), 5.01 (s, 1H), 3.38 (s, 3H), 2.44 (t, J=7.1 Hz, 2H), 2.02 (br s, 1H), 1.57-1.44 (m, 2H), 0.89 (t, J=7.4 Hz, 3H); $^{13}$C NMR (101 MHz, CDCl$_3$) (δ 140.6, 139.1, 138.6, 137.1, 134.3, 132.2, 131.3, 130.1, 129.4, 128.5, 128.3, 128.2, 66.2, 50.1, 38.8, 23.3, 11.9; LR-MS calcd. for C$_{17}$H$_{20}$ClN$_2$O$_2$S [M+H]$^+$ 351.09, found 351.51.

3-Chloro-11-(isopropylamino)-6-methyl-6,11-dihydrodibenzo [c,f][1,2]thiazepine 5,5-dioxide (22)

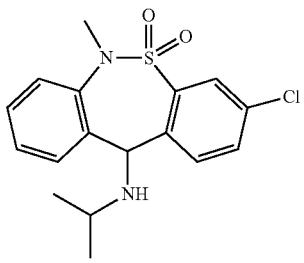 [SMILES: CC(C)NC1c2ccccc2N(C)S(=O)(=O)c2cc(Cl)ccc21]

Compound 22 was prepared according to a modified Method B using 10 equivalents of isopropylamine. The product 22 was obtained as a yellow glass (173 mg, 99%). $^1$H NMR (500 MHz, CDCl$_3$) δ 7.95 (d, J=2.1 Hz, 1H), 7.47-7.40 (m, 2H), 7.39-7.32 (m, 3H), 7.28 (td, J=7.3, 1.6 Hz, 1H), 5.09 (s, 1H), 3.37 (s, 3H), 2.57 (hept, J=6.2 Hz, 1H), 2.15 (br s, 1H), 1.08 (d, J=6.2 Hz, 3H), 1.04 (d, J=6.2 Hz, 3H); $^{13}$C NMR (126 MHz, CDCl$_3$) δ 140.5, 138.8, 138.6, 137.2, 134.2, 132.2, 131.6, 130.4, 129.3, 129.4, 129,1, I 28.0, 63.2, 45.4, 38.7, 22.92, 22.86; LR-MS calcd. for C$_{17}$H$_{20}$ClN$_2$O$_2$S [M+H]$^+$ 351.09, found 351.81.

3-Chloro-11-((3-methoxypropyl)amino)-6-methyl-6,11-dihydrodibenzo [c,f][1,2]thiazepine 5,5-dioxide (23)

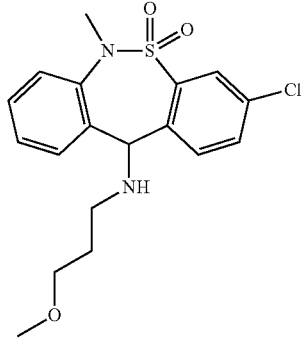

Method B. The product 23 was obtained as a viscous pale-yellow oil (188 mg, 99%). $^1$H NMR (500 MHz, CDCl$_3$) δ 7.94 (t, J=1.2 Hz, 1H), 7.44 (d, J=1.3 Hz, 2H), 7.41-7.37 (m, 2H), 7.37-7.33 (m, 1H), 7.28 (td, J=7.3, 1.6 Hz, 1H), 5.02 (s, 1H), 3.45-3.39 (m, 2H), 3.37 (s, 3H), 3.29 (s, 3H), 2.64-2.52 (m, 2H), 2.18 (br s, 1H), 1.82-1.68 (m, 2H); $^{13}$C NMR (126 MHz, CDCl$_3$) δ 140.5, 139.0, 138.6, 137.1, 134.3, 132.3, 131.1, 130.0, 129.4, 128.5, 128.3, 128.1, 71.3, 66.0, 58.8, 45,8, 38.6, 30.0; LR-MS calcd. for C$_{18}$H$_{22}$ClN$_2$O$_3$S [M+H]$^+$ 381.10, found 380.79.

3-Chloro-11-((4,4-diethoxybutyl)amino)-6-methyl-6,11-dihydrodibenzo[c,f][1,2]thiazepine 5,5-dioxide (24)

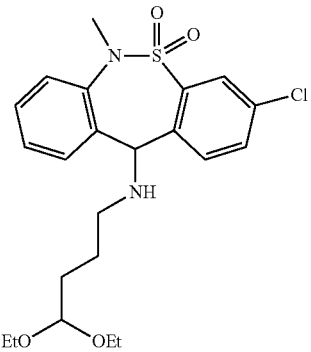 [SMILES: CCOC(CCCNC1c2ccccc2N(C)S(=O)(=O)c2cc(Cl)ccc21)OCC]

Method B. The product 24 was purified by column chromatography (CH$_2$Cl$_2$:Et$_2$O-20:1, 4 column volumes to 8:2, 2 column volumes) and obtained as a viscous pale-yellow oil (204 mg, 90%). $^1$H NMR (500 MHz, CDCl$_3$) δ 7.94 (d, J=1.5 Hz, 1H), 7.46-7.41 (m, 2H), 7.35 (tdd, J=15.0, 7.1, 2.3 Hz, 3H), 7.27 (td, J=7.3, 1.8 Hz, 1H), 5.00 (s, 1H), 4.43 (t, J=5.5 Hz, 1H), 3.64-3.56 (m, 2H), 3.49-3.40 (m, 2H), 3.36 (s, 3H), 2.49 (t, J=6.9 Hz, 2H), 2.04 (br s, 1H), 1.65-1.58 (m, 2H), 1.58-1.50 (m, 2H), 1.16 (td, J=7.0, 2.7 Hz, 6H); $^{13}$C NMR (126 MHz, CDCl$_3$) δ 140.5, 138.9, 138.6, 137.0, 134.3, 132.2, 131.2, 130.1, 129.4, 12854, 128.2, 128.1, 102.8, 66.0, 65,9, 61.3, 61.2, 47.9, 38.7, 31.5, 25.3, 15.4; LR-MS calcd. for C$_{22}$H$_{30}$ClN$_2$O$_4$S [M+H]$^+$ 453.16, found 452.98.

3-Chloro-11-((2-(2-hydroxyethoxy)ethyl)amino)-6-methyl-6,11-dihydrodibenzo[c,f][1,2]thiazepine 5,5-dioxide (25)

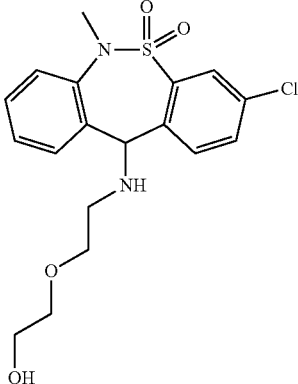

Method B. In this case, $CH_2Cl_2$ was used as the extraction solvent. The product 25 was purified by column chromatography ($CH_2Cl_2$:$Et_2O$-1:1 for 4 column volumes, then 2% $Et_3N$ added to eluent) and obtained as a viscous colorless oil (158 mg, 80%). $^1$H NMR (500 MHz, $CDCl_3$) δ 7.95 (t, J=1.0 Hz, 1H), 7.45 (d, J=1.2 Hz, 2H), 7.42-7.33 (m, 3H), 7.31-7.26 (m, 1H), 5.03 (s, 1H), 3.67-3.63 (m, 2H), 3.61-3.53 (m, 2H), 3.50 (dd, J=5.8, 3.4 Hz, 2H), 3.36 (s, 3H), 2.68-2.63 (m, 2H), 2.60 (br s, 2H); $^{13}$C NMR (126 MHz, $CDCl_3$) δ 140.5, 138.6, 138.4, 136.7, 134.5, 132.4, 131.5, 130.3, 129.6, 128.5, 128.3, 128.0, 72.3, 70.4, 66.2, 61.8, 47.5, 38.7; LR-MS calcd. for $C_{18}H_{22}ClN_2O_4S$ [M+H]$^+$ 397.10, found 396.93.

3-Chloro-11-(heptylamino)-6-methyl-6,11-dihydrodibenzo [c,f][1,2]thiazepine 5,5-dioxide (26)

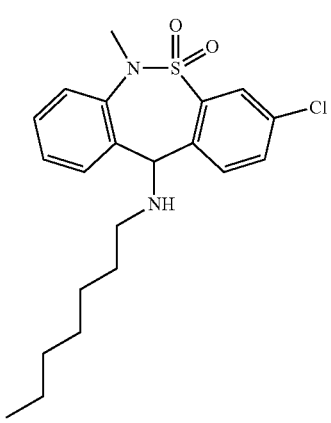

Method B. The product 26 was purified by column chromatography (hexanes:EtOAc-9:1+2% $Et_3N$) and obtained as viscous colorless oil (161 mg, 79%). $^1$H NMR (500 MHz, $CDCl_3$) δ 7.96 (d, J=1.9 Hz, 1H), 7.47-7.42 (m, 2H), 7.41-7.33 (m, 3H), 7.29 (td, J=7.3, 1.5 Hz, 1H), 5.01 (s, 1H), 3.38 (s, 3H), 2.46 (t, J=3.1 Hz, 2H), 1.99 (s, 1H), 1.54-1.41 (m, 2H), 1.32-1.17 (m, 8H), 0.86 (t, J=7.0 Hz, 3H); $^1$C NMR (126 MHz, $CDCl_3$) δ 140.6, 139.1, 138.6, 137.2, 134.3, 132.3, 131.2, 130.1, 129.4, 128.5, 128.3, 128.1, 66.2, 48.3, 38.7, 31.9, 30.2, 29.3, 27.4, 22.7, 14.2; LR-MS calcd. for $C_{21}H_{28}ClN_2O_2S$ [M+H]$^+$ 407.16, found 406.94.

3-Methoxy-11-((3-methoxypropyl)amino)-6-methyl-6,11-dihydrodibenzo [c,f][1,2]thiazepine 5,5-dioxide (27)

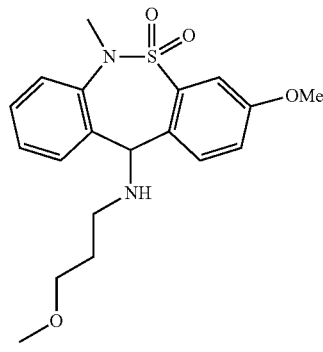 [SMILES: COCCCNC1c2ccccc2N(C)S(=O)(=O)c2cc(OC)ccc21]

Method B. The product 27 was purified by column chromatography ($CH_2Cl_2$:$Et_2O$-8:2, 2 column volumes→1:1, 3 column volumes) and obtained as a viscous colorless oil. (32.1 mg, 85%). $^1$H NMR (500 MHz, $CDCl_3$) δ 7.47 (d, J=2.7 Hz, 1H), 7.42-7.36 (m, 3H), 7.34 (td, J=7.5, 1.6 Hz, 1H), 7.27 (dt, J=7.5, 1.6 Hz, 1H), 7.01 (dd, J=8.5, 2.7 Hz, 1H), 4.92 (s, 1H), 3.84 (s, 3H), 3.40 (pd, J=9.4, 6.3 Hz, 2H), 3.35 (s, 3H), 3.29 (s, 3H), 2.55 (t, J=6.8 Hz, 2H), 2.17 (br s, 1H), 1.80-1.67 (m, 2H); $^{13}$C NMR (126 MHz, $CDCl_3$) δ 159.3, 139.9, 139.2, 139.1, 131.8, 130.7, 130.4, 129.2, 128.1, 128.0, 118.7, 112.9, 71.3, 67.0, 58.8, 55.9, 45.6, 38.9, 30.1; LR-MS calcd. for $C_{19}H_{25}N_2O_4S$ [M+H]$^+$ 377.15, found 376.95.

3-Chloro-6-methyl-11-((4,4,4-trifluorobutyl)amino)-6,11-dihydrodibenzo [c,f][1,2]thiazepine 5,5-dioxide (28)

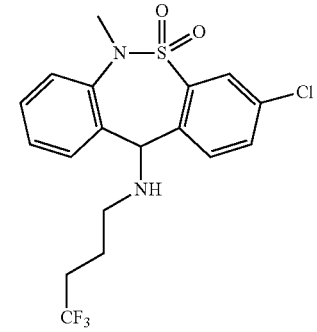 [SMILES: CN1c2ccccc2C(NCCCC(F)(F)F)c2ccc(Cl)cc2S1(=O)=O]

Method B. The product 28 was purified by column chromatography (hexanes:EtOAc-8:2+2% $Et_3N$) and obtained as a viscous pale-yellow oil (168 mg, 80%). $^1$H NMR (500 MHz, $CDCl_3$) δ 7.97 (d, J=2,2 Hz, 1H), 7.48 (dd, -8.2, 2.2 Hz, 1H), 7.42-7.34 (m, 4H), 7.33-7.28 (m, 1H), 4.97 (s, 1H), 3.30 (s, 3H), 2.58-2.46 (m, 2H), 2.26 (br s, 1H), 2.21-2.08 (m, 2H), 1.71 (dq, J=13.9, 6.9 Hz, 2H); $^{13}$C NMR (126 MHz, $CDCl_3$) (additional peaks due to C—F coupling) δ 140.1, 139.0, 137.4, 136.4, 134.5, 132.4, 131.8, 131.0, 129.6, 128.7, 128.4, 128.1, 127.9, 126.2, 66.7, 46.6, 39.0, 31.6 (q, 1C), 22.6; LR-MS calcd. for $C_{18}H_{19}ClF_3N_2O_2S$ [M+H]$^+$ 419.08, found 418.88.

11-((3-Methoxypropyl)amino)-6-methyl-3-phenoxy-6,11-dihydrodibenzo [c,f][1,2]thiazepine 5,5-dioxide (29)

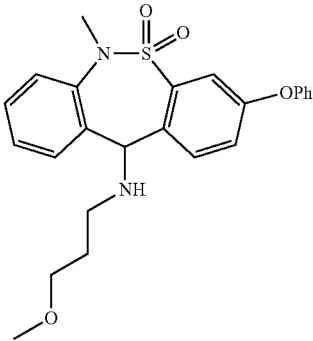 [SMILES: COCCCNC1c2ccccc2N(C)S(=O)(=O)c2cc(Oc3ccccc3)ccc21]

Method B. The product 29 was purified by column chromatography (CH$_2$Cl$_2$:Et$_2$O-9:1, 2 column volumes to 8:2, 2 column volumes) and obtained as a viscous pale-yellow oil (37.4 mg, 85%). $^1$H NMR (500 MHz, CDCl$_3$) δ 7.59 (d, J=2.2 Hz, 1H), 7.47-7.33 (m, 6H), 7.29 (t, J=7.3 Hz, 1H), 7.16 (t, J=7.1 Hz, 1H), 7.09 (dd, J=8.4, 2.3 Hz, 1H), 7.02 (d, J=8.3 Hz, 2H), 4.98 (s, 1H), 3.47-3.40 (m, 2H), 3.38 (s, 3H), 3.30 (s, 3H), 2.59 (t, J=6.7 Hz, 2H), 2.07 (br s, 1H), 1.84-1.71 (m, 2H); $^{13}$C NMR (126 MHz, CDCl$_3$) δ 157.5, 156.0, 140.5, 139.3, 138.9, 132.7, 131.7, 130.3, 130.2, 129.3, 128.1, 124.5, 121.7, 119.7, 117.9, 71.3, 66.6, 58.8, 45.8, 38.7, 30.1; LR-MS calcd. for C$_{24}$H$_{27}$N$_2$O$_4$S [M+H]$^+$ 439.17, found 438.88.

3-Chloro-11-((5-hydroxypentyl)amino)-6-methyl-6,11-dihydrodibenzo [c,f][1,2]thiazepine 5,5-dioxide (30)

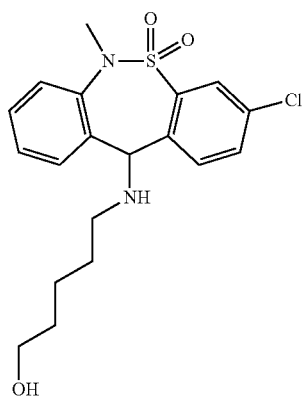

Method B. The product 30 was purified by column chromatography (CH$_2$Cl$_2$: Et$_2$O-6:4) and obtained as a viscous pale-yellow oil (317 mg, 80%). $^1$H NMR (500 MHz, CDCl$_3$) δ 7.96 (s, 1H), 7.51-7.26 (m, 6H), 5.00 (s, 1H), 3.63-3.54 (m, 2H), 3.36 (d, J=2.1 Hz, 3H), 2.55-2.43 (m, 2H), 1.97 (br s, 2H), 1.58-1.46 (m, 4H), 1.43-1.31 (m, 2H); $^{13}$C NMR (126 MHz, CDCl$_3$) δ 140.4, 138.7, 138.5, 136.9, 134.3, 132.3, 131.5, 130.3, 129.5, 128.5, 128.2, 128.0, 66.4, 62.6, 48.0, 38.8, 32.5, 29.8, 23.5; LR-MS calcd. for C$_{19}$H$_{24}$ClN$_2$O$_3$S [M+H]$^+$ 395.12, found 394.85.

11-((3-(1,3-Dioxan-2-yl)propyl)amino)-3-chloro-6-methyl-6,11-dihydrodibenzo[c,f][1,2]thiazepine 5,5-dioxide (31)

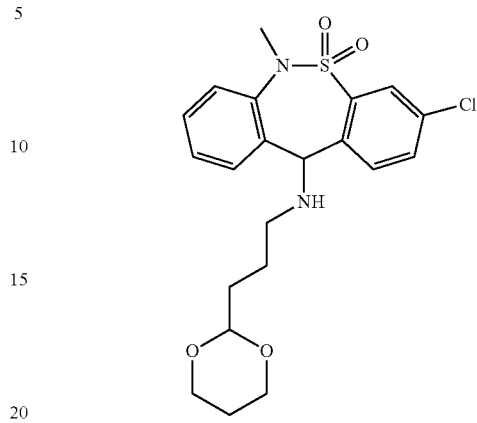

Acetal 31 was prepared by transacetalization of compound 24 according to the following procedure. Diethyl acetal 24 (22.6 mg, 0.0500 mmol) was dissolved in 1,3-propanediol (0.50 mL), p-toluenesulfonic acid monohydrate (14.3 mg, 0.0750 mmol) was added, and the solution was stirred for 3 days at room temperature. The mixture was then diluted with water (5 mL), basified with saturated NH$_4$OH, and extracted with Et$_2$O (3×5 mL). The combined organics were washed with water (5 mL), dried over Na$_2$SO$_4$, and concentrated to yield a pale-yellow glass. This was purified by repeated (2x) column chromatography (hexanes:EtOAc-1:1, 5 column volumes→EtOAc, 2 column volumes) to yield the pure product 31 as a viscous pale-yellow oil (8.6 mg, 39%). $^1$H NMR (500 MHz, CDCl$_3$) δ 7.95 (t, J=1.1 Hz, 1H ), 7.49-7.42 (m, 2H), 7.42-7.33 (m, 3H), 7.29 (td, J=7.4, 1.5 Hz, 1H), 5.04 (s, 1H), 4.49 (t, J=4.5 Hz, 1H), 4.07 (ddd, J=8.5, 4.3, 1.2 Hz, 2H), 3.76-3.67 (m, 2H), 3.39 (s, 3H), 2.54-2.45 (m, 2H), 2.1-1.95 (m, 1H), 1.73 (br s, 1H), 1.66-1.55 (m, 4H), 1.35-1.29 (m, 1H); $^{13}$C NMR (126 MHz, CDCl$_3$) δ 140.6, 138.6, 137.2, 134.6, 134.4, 132,3, 131.1, 129.9, 129.5, 128.5, 128.3, 128.1, 102.1, 67.0, 65.6, 47.9, 38.7, 33.0, 25.9, 24.4; LR-MS calcd. for C$_{21}$H$_{26}$ClN$_2$O$_4$S [M+H]$^+$ 437.13, found 436.99.

3-Chloro-11-((5-methoxypentyl)amino)-6-methyl-6,11-dihydrodibenzo [c,f][1,2]thiazepine 5,5-dioxide (32)

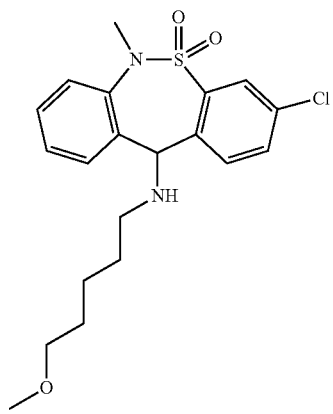 [SMILES: COCCCCCNC1c2ccccc2N(C)S(=O)(=O)c2cc(Cl)ccc21]

Compound 32 was prepared by O-methylation of alcohol 30 according to the following procedure. To a mixture of 30 (118 mg, 0.300 mmol) and NaH (12.0 mg of 60% dispersion in mineral oil, 0.300 mmol) was added anhydrous THF (0.38 mL, freshly distilled from Na benzophenone), and the yellow-orange mixture was stirred for 1 h at room temperature. Dimethyl sulfate (28.6 µL, 0.300 mmol) was then added to the red-orange mixture and the reaction was stirred for 1 h at room temperature. The reaction was then quenched with water (10 mL) and extracted with $Et_2O$ (3×5 mL). The combined organics were washed with 10% $NH_4OH$ (5 mL), dried over $Na_2SO_4$, and concentrated to yield a thick yellow oil. This crude was purified by column chromatography (hexanes:EtOAc-6:4) to yield the pure product 32 as a viscous pale-yellow oil (29.4 mg, 24%). $^1H$ NMR (500 MHz, $CDCl_3$) δ 7.95 (d, J=2.0 Hz, 1H), 7.48-7.33 (m, 5H), 7.31-7.27 (m, 1H), 5.00 (s, 1H), 3.37 (s, 3H), 3.33 (t, J=6.5 Hz, 2H), 3.30 (s, 3H), 2.47 (t, J=7.1 Hz, 2H), 1.95 (br s, 1H), 1.58-1.46 (m, 4H), 1.39-1.30 (m, 2H); $^{13}C$ NMR (126 MHz, $CDCl_3$) δ 140.5, 138.8, 138.7, 137.0, 134.4, 132.3, 131.3, 130.2, 129.5, 128.6, 128.3, 128.1, 72.8, 66.3, 58.7, 48.2, 38.8, 30.0, 29.6, 24.0; LR-MS calcd. for $C_{20}H_{26}ClN_2O_3S$ $[M+H]^+$ 409.14, found 409.03.

3-Chloro-6-methyl-11-((3-(methylthio)propyl)amino)-6,11-dihydrodibenzo[c,f][1,2]thiazepine 5,5-dioxide (33)

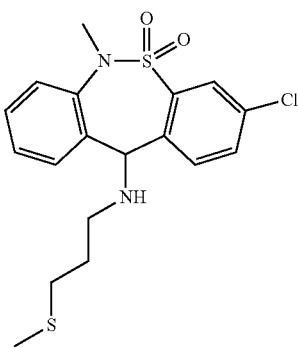

Method B. The product 33 was obtained as a viscous pale-yellow oil (194 mg, 98%). $^1H$ NMR (400 MHz, $CDCl_3$) δ 7.96 (d, J=2.1 Hz, 1H), 7.50-7.27 (m, 6H), 5.00 (s, 1H), 3.34 (s, 3H), 2.65-2.46 (m, 4H), 2.07 (br s, 1H) 2.06 (s, 3H), 1.77 (p, J=7.0 Hz, 2H); $^{13}C$ NMR (101 MHz, $CDCl_3$) δ 140.3, 138.8, 138.3, 136.8, 134.4, 132.4, 131.5, 130.5, 129.5, 128.6, 128.2, 128.0, 66.4, 46.9, 38.9, 32.1, 29.4, 15.7; LR-MS calcd. for $C_{18}H_{22}ClN_2O_2S_2$ $[M+H]^+$ 397.08, found 396.84.

Ethyl 7-((3-chloro-6-methyl-5,5-dioxido-6,11-dihydrodibenzo[c,f][1,2]thiazepin-11-yl)amino)heptanoate (34)

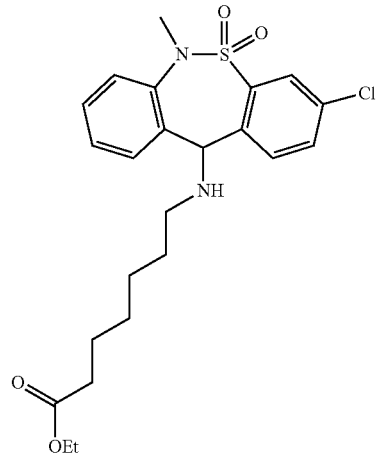 [SMILES: CCOC(=O)CCCCCCNC1c2ccccc2N(C)S(=O)(=O)c2cc(Cl)ccc21]

Method C. The product 34 was purified by column chromatography ($CH_2Cl_2$:$Et_2O$, 40:1, 6 column volumes→1:1, 2 column volumes) and obtained as a viscous pale-yellow oil (91 mg, 78%). $^1H$ NMR (400 MHz, $CDCl_3$) δ 7.95 (d, J=2.0 Hz, 1H), 7.48-7.26 (m, 6H), 5.00 (s, 1H), 4.10 (q, J=7.1 Hz, 2H), 3.36 (s, 3H), 2.45 (t, J=7.1 Hz, 2H), 2.26 (t, J=7.5 Hz, 2H), 2.03 (br s, 1H), 1.65-1.53 (m, 2H), 1.53-1.41 (m, 2H), 1.35-1.26 (m, 4H), 1.23 (t, J=7.1 Hz, 3H); $^{13}C$ NMR (101 MHz, $CDCl_3$) δ 173.8, 140.5, 138.9, 138.6, 137.0, 134.3, 132.3, 131.3, 130.1, 129.4, 128.5, 128.2, 128.1, 66.2, 60.3, 48.2, 38.8, 34.3, 30.0, 29.1, 27.0, 24.9, 14.4; LR-MS calcd. for $C_{23}H_{30}ClN_2O_4S$ $[M+H]^+$ 465.16, found 465.13.

3-Chloro-11-((3-isopropoxypropyl)amino)-6-methyl-6,11-dihydrodibenzo[c,f][1,2]azepine 5,5-dioxide (35)

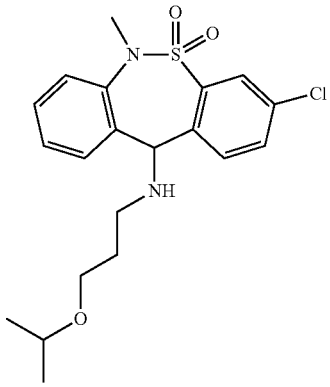 [SMILES: CC(C)OCCCNC1c2ccccc2N(C)S(=O)(=O)c2cc(Cl)ccc21]

Method B. The product 35 was obtained as a viscous pale-yellow oil (197 mg, 96%). $^1H$ NMR (500 MHz, $CDCl_3$) δ 7.94 (d, J=1.9 Hz, 1H), 7.51-7.26 (m, 6H), 5.06 (s, 1H), 3.57-3.43 (m, 3H), 3.39 (s, 3H), 2.59 (t, J=6.5 Hz, 2H), 2.26 (s, 1H), 1.83-1.68 (m, 2H), 1.10 (t, J=6.5 Hz, 6H); $^{13}C$ NMR (126 MHz, $CDCl_3$) δ 140.5, 139.4, 138.5, 137.3, 134.2, 132.2, 130.8, 129.6, 129.3, 128.5, 128.7, 128.1, 71.6, 66.6, 65.5, 46.0, 38.6, 30.4, 22.2; LR-MS calcd. for C$_{20}$H$_{26}$ClN$_2$O$_3$S [M+H]$^+$ 409.14, found 409.24.

3-Chloro-11-((2-(2-methoxyethoxy)ethyl)amino)-6-methyl-6,11-dihydrodibenzo[c,f][1,2]thiazepine 5,5-dioxide (36)

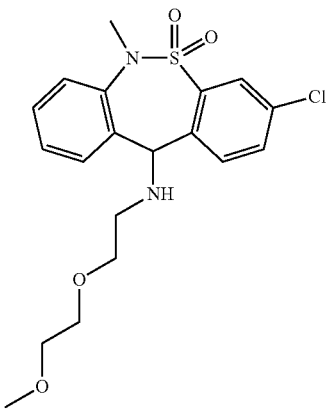 [SMILES: COCCOCCNC1c2ccccc2N(C)S(=O)(=O)c2cc(Cl)ccc21]

Compound 36 was prepared by O-methylation of alcohol 25 according to the procedure described for compound 32. The product 36 was purified by column chromatography (EtOAc) and obtained as a viscous pale-yellow oil (21.6 mg, 26%). $^1$H NMR (400 MHz, CDCl$_3$) δ 7.94 (d, J=2.1 Hz, 1H), 7.52-7.26 (m, 6H), 5.08 (s, 1H), 3.66-3.48 (m, 6H), 3.44 (s, 3H), 3.34 (s, 3H), 2.75-2.62 (m, 2H), 2.34 (br s, 1H); $^{13}$C NMR (101 MHz, CDCl$_3$) δ 141.0, 139.6, 138.5, 137.1, 134.5, 132.3, 131.1, 129.7, 129.6, 128.4, 128.3, 72.0, 70.7, 70.5, 65.6, 59.1, 47.6, 38.5; LR-MS calcd. for C$_{19}$H$_{24}$ClN$_2$O$_4$S [M+H]$^+$ 411.11, found 411.35.

3-Chloro-11-((3-ethoxypropyl)amino)-6-methyl-6,11-dihydrodibenzo [c,f][1,2]thiazepine 5,5-dioxide (37)

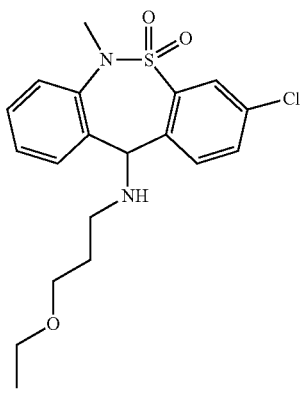 [SMILES: CCOCCCNC1c2ccccc2N(C)S(=O)(=O)c2cc(Cl)ccc21]

Method B. The product 37 was purified by column chromatography (hexanes:EtOAc-1:1, 4 column volumes→EtOAc, 2 column volumes) and obtained as a viscous pale-yellow oil (176 mg, 89%). $^1$H NMR (500 MHz, CDCl$_3$) δ 7.93 (s, 1H), 7.51-7.23 (m, 6H), 5.05 (s, 1H), 3.53-3.40 (m, 4H), 3.37 (s, 3H), 2.59 (t, J=6.4 Hz, 2H), 2.35 (br s, 1H), 1.83-1.70 (m, 2H), 1.14 (t, J=6.9 Hz, 3H); $^{13}$C NMR (126 MHz, CDCl$_3$) δ 140.5, 139.1, 138.5, 137.1, 134.2, 132.2, 131.0, 129.8, 129.3, 128.4, 128.2, 128.1, 69.1, 66.3, 65.6, .45.9, 38.6, 30.0, 15.2; LR-MS calcd. for C$_{19}$H$_{24}$ClN$_2$O$_3$S [M+H]$^+$ 395.12, found 394.49.

3-Chloro-11-((4-hydroxybutyl)amino)-6-methyl-6,11-dihydrodibenzo[c,f][1,2]thiazepine 5,5-dioxide (38)

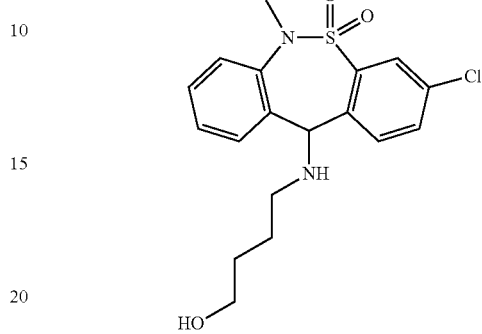

Method B. The product 38 was purified by column chromatography (CH$_2$Cl$_2$:Et$_2$O-6:4, 4 column volumes→CH$_2$Cl$_2$:Et$_2$O:MeOH-12:8:1, 2 column volumes) and obtained as a viscous colorless oil (148 mg, 78%). $^1$H NMR (400 MHz, CDCl$_3$) δ 7.96 (d, J=2.2 Hz, 1H), 7.49 (dd, J=8.2, 2.2 Hz, 1H), 7.44-7.39 (m, 2H), 7.39-7.27 (m, 3H), 4.97 (s, 1H), 3.61-3.47 (m, 2H), 3.28 (br s, 2H), 3.24 (s, 3H), 2.44 (t, J=5.7 Hz, 2H), 1.70-1.53 (m, 3H), 1.53-1.42 (m, 1H); $^{13}$C NMR (101 MHz, CDCl$_3$) δ 139.9, 139.2, 135.7, 135.5, 134.6, 132.6, 131.6, 129.7, 128.6, 128.0, 127.7, 67.3, 62.6, 47.9, 39.3, 31.7, 27.8; LR-MS calcd. for C$_{18}$H$_{22}$ClN$_2$O$_3$S [M+H]$^+$ 381.10, found 380.97.

3-Chloro-11-((4-methoxybutyl)amino)-6-methyl-6,11-dihydrodibenzo [c,f][1,2]thiazepine 5,5-dioxide (39)

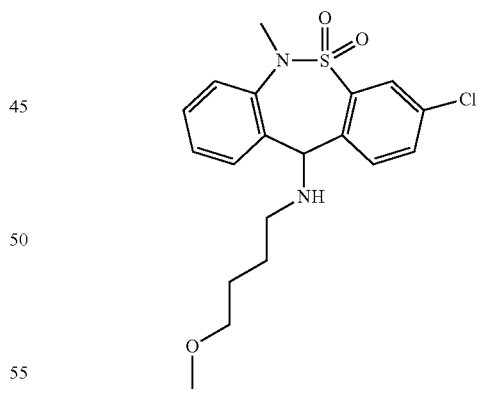

Compound 39 was prepared by O-methylation of alcohol 38 according to the procedure described for compound 32. The product was purified by repeated column chromatography (column 1: hexanes:EtOAc-1:1/column 2: hexanes:EtOAc-1:1+2% Et$_3$N, 6 column volumes→EtOAc+2% Et$_3$N, 2 column volumes) and obtained as a viscous pale-yellow oil (3.4 mg, 4.3%). The N-methylation byproduct was also obtained (4.6 mg, 5.8%). $^1$H NMR (400 MHz, CDCl$_3$) δ 7.96 (d, J=1.9 Hz, 1H ), 7.50-7.27 (m, 6H), 5.02 (s, 1H), 3.38 (s, 3H), 3.34 (t, J=6.0 Hz, 2H), 3.30 (s, 3H), 2.50 (t, J=6.7 Hz, 2H), 2.07 (br s, 1H), 1.67-1.46 (m, 4H); LR-MS calcd. for C₁₉H₂₄ClN₂O₃S [M+H]⁺ 395.12, found 394.97.

3-Fluoro-11-((3-methoxypropyl)amino)-6-methyl-6,11-dihydrodibenzo[c,f][1,2]thiazepine 5,5-dioxide (40)

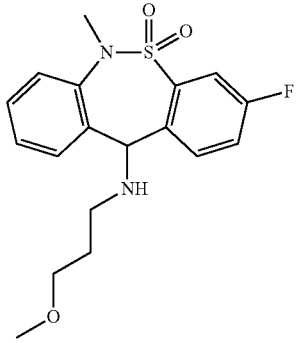 [SMILES: COCCCNC1c2ccccc2N(C)S(=O)(=O)c2cc(F)ccc21]

Method B. The product 40 was obtained as a viscous pale-yellow oil (33.8 mg, 93%). ¹H NMR (400 MHz, CDCl₃) δ 7.68 (dd, J=8.2, 2.7 Hz, 1H), 7.48 (dd, J=8.6, 5.2 Hz, 1H), 7.41-7.33 (m, 3H), 7.32-7.27 (m, 1H), 7.23-7.14 (m, 1H), 5.01 (s, 1H), 3.42 (td, J=6.2, 2.5 Hz, 2H), 3.38 (s, 3H), 3.29 (s, 3H), 2.63-2.49 (m, 2H), 2.25 (br s, 1H), 1.83-1.66 (m, 2H); ¹³C NMR (101 MHz, CDCl₃) (additional peaks due to C—F coupling) δ 163.0, 160.5, 140.9, 140.8, 139.1, 138.7, 134.6, 131.9, 130.2, 129.4, 128.3, 128.2, 119.3, 119.1, 116.0, 115.7, 71.3, 66.3, 58.8, 45.8, 38.8, 30.1; LR-MS calcd. for C₁₈H₂₂FN₂O₃S [M+H]⁺ 365.13, found 365.52.

Ethyl 7-((3-fluoro-6-methyl-5,5-dioxido-6,11-dihydrodibenzo[c,f][1,2]thiazepin-11-yl)amino)heptanoate (41)

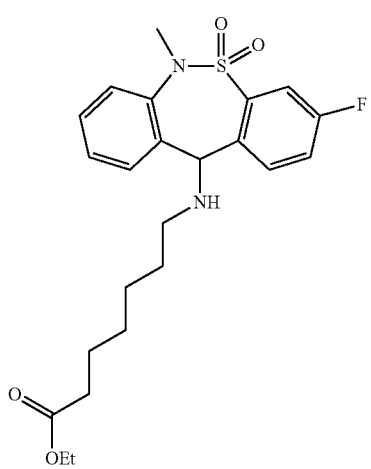 [SMILES: CCOC(=O)CCCCCCNC1c2ccccc2N(C)S(=O)(=O)c2cc(F)ccc21]

Method C. The product 41 was obtained as a viscous pale-yellow oil (39.0 mg, 87%). ¹H NMR (400 MHz, CDCl₃) δ 7.68 (dd, J=8.2, 2.7 Hz, 1H), 7.47 (dd, J=8.6, 5.2 Hz, 1H), 7.36 (qd, J=7.7, 4.0 Hz, 3H), 7.32-7.26 (m, 1H), 7.19 (ddd, J=8.5, 7.7, 2.7 Hz, 1H), 4.99 (s, 1H), 4.11 (q, J=7.1 Hz, 2H), 3.37 (s, 3H), 2.45 (t, J=7.1 Hz, 2H), 2.26 (t, J=7.5 Hz, 2H), 2.05 (br s, 1H), 1.64-1.53 (m, 2H), 1.52-1.42 (m, 2H), 1.35-1.26 (m, 4H), 1.24 (t, J=7.1 Hz, 3H); ¹³C NMR (101 MHz, CDCl₃) (additional peaks due to C—F coupling) δ 173.8, 163.0, 160.5, 140.9, 140.8, 139.0, 138.7, 134.5, 132.1, 132.0, 130.3, 129.5, 128.2, 128.2, 119.3, 119.1, 116.0, 115.7, 66.5, 60.3, 48.2, 38.9, 34.4, 30.0, 29.1, 27.1, 25.0, 14.4; LR-MS calcd. for C₂₃H₃₀FN₂O₄S [M+H]⁺ 449.19, found 449.81.

3-Chloro-11-((2-methoxyethyl)amino)-6-methyl-6,11-dihydrodibenzo[c,f][1,2]thiazepine 5,5-dioxide (42)

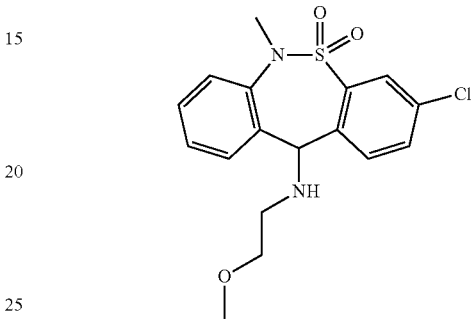

Method B. The product 42 was obtained as a viscous pale-yellow oil (184 mg, 100%). ¹H NMR (400 MHz, CDCl₃) δ 7.94 (d, J=2.1 Hz, 1H), 7.49-7.33 (m, 5H), 7.29 (td, J=7.4, 1.5 Hz, 1H), 5.07 (s, 1H), 3.53-3.44 (m, 2H), 3.43 (s, 3H), 3.32 (s, 3H), 2.73-2.59 (m, 2H), 2.43 (br s, 1H); ¹³C NMR (101 MHz, CDCl₃) δ 141.0, 139.5, 138.4, 137.1, 134.4, 132.2, 131.0, 129.6, 129.5, 128.4, 128.4, 128.3, 72.1, 65.6, 58.9, 47.6, 38.4; LR-MS calcd. for C₁₇H₂₀ClN₂O₃S [M+H]⁺ 367.09, found 367.50.

3-Bromo-10-((3-methoxypropyl)amino)-4-methyl-4,10-dihydrobenzo[f]thieno[3,2-c][1,2]thiazepine 5,5-dioxide (43)

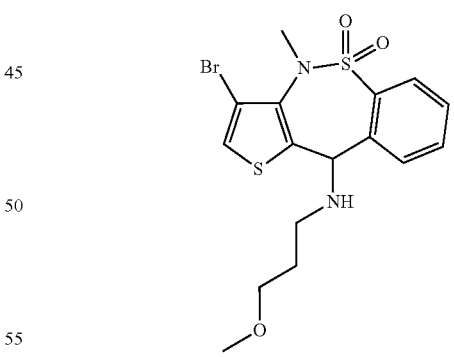

Method B. The product 43 was purified by repeated column chromatography (column 1: CH₂Cl₂:Et₂O-20:1, 3 column volumes→15:1, 2 column volumes/column 2: Hexanes:EtOAc, 1:1) and obtained as a viscous yellow oil (74.9 mg, 58%). ¹H NMR (500 MHz, CDCl₃) δ 8.04 (dd, J=7.7, 1.2 Hz, 1H), 7.69 (td, J=7.6, 1.3 Hz, 1H), 7.53 (td, J=7.6, 0.8 Hz, 1H), 7.48 (d, J=7.6 Hz, 1H), 7.23 (s, 1H), 5.35 (s, 1H), 3.54-3.45 (m, 2H), 3.34 (s, 3H), 2.83 (s, 3H), 2.81-2.74 (m, 1H), 2.74-2.67 (m, 1H), 1.88-1.71 (m, 2H); ¹³C NMR (126 MHz, CDCl₃) δ 135.5, 135.2, 135.1, 134.3, 134.0, 130.1, 128.9, 128.1, 122.5, 109.0, 71.2, 61.4, 58.8, 45.2, 39.5, 30.0; LR-MS calcd. for $C_{16}H_{20}BrN_2O_3S_2$ [M+H]$^+$ 433.01, found 434.02.

11-((3-Methoxypropyl)amino)-6-methyl-3-(methylthio)-6,11-dihydrodibenzo[c,f][1,2]thiazepine 5,5-dioxide (44)

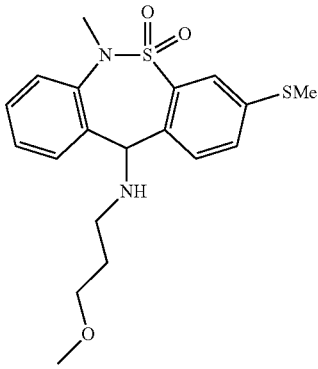 [SMILES: COCCCNC1c2ccccc2N(C)S(=O)(=O)c2cc(SC)ccc21]

Method B. The product 44 was purified by column chromatography (hexanes:EtOAc-1:1, 2 column volumes→EtOAc, 3 column volumes) and obtained as a viscous pale-yellow oil (31.1 mg, 79%). $^1$H NMR (400 MHz, CDCl$_3$) δ 7.78 (d, J=1.7 Hz, 1H), 7.43-7.31 (m, 5H), 7.31-7.25 (m, 1H), 4.97 (s, 1H), 3.45-3.38 (m, 2H), 3.35 (s, 3H), 3.29 (s, 3H), 2.57 (t, J=6.7 Hz, 2H), 2.51 (s, 3H), 2.29 (br s, 1H), 1.82-1.68 (m, 2H). $^{13}$C NMR (101 MHz, CDCl$_3$) (unusual broadening of some carbon peaks) δ 140.0, 139.5, 139.1, 138.9, 134.8, 130.4, 130.4, 129.9, 129.3, 128.1, 128.0, 125.3, 71.3, 66.6, 58.8, 45.7, 38.8, 30.1, 15.6; LR-MS calcd. for $C_{19}H_{25}N_2O_3S_2$ [M+H]$^+$ 393.13, found 392.74.

Ethyl 7-((6-methyl-3-(methylthio)-5,5-dioxido-6,11-dihydrodibenzeo[c,f][1,2]1,2]azepin-11-yl)amino)heptanotate (45)

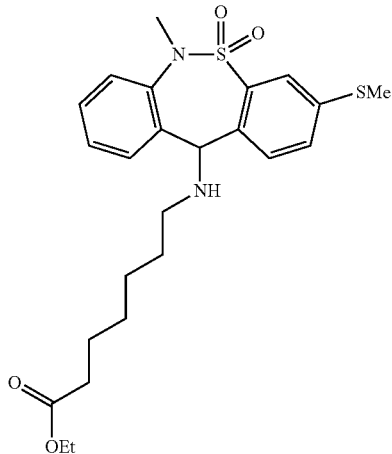 [SMILES: CCOC(=O)CCCCCCNC1c2ccccc2N(C)S(=O)(=O)c2cc(SC)ccc21]

Method C. The product 45 was obtained as a viscous pale-yellow oil (44.0 mg, 92%). $^1$H NMR (400 MHz, CDCl$_3$) δ 7.78 (d, J=1.3 Hz, 1H), 7.42-7.31 (m, 5H), 7.31-7.24 (m, 1H), 4.95 (s, 1H), 4.10 (q, J=7.1 Hz, 2H), 3.34 (s, 3H), 2.50 (s, 3H), 2.45 (t, J=7.1 Hz, 2H), 2.25 (t, J=7.5 Hz, 2H), 2.13 (br s, 1H), 1.64-1.53 (m, 2H), 1.52-1.40 (m, 2H), 1.33-1.24 (m, 4H), 1.23 (t, J=7.1 Hz, 3H); $^{13}$C NMR (101 MHz, CDCl$_3$) δ 173.8, 140.0, 139.5, 139.0, 138.9, 134.7, 130.5, 130.5, 129.8, 129.3, 128.0, 125.3, 66.8, 60.3, 48.1, 38.9, 34.4, 30.0, 29.1, 27.1, 25.0, 15.6, 14.4; LR-MS calcd. for $C_{24}H_{33}N_2O_4S_2$ [M+H]$^+$ 477.19, found 476.70.

3-chloro-6-methyl-11-(((tetrahydrofuran-3-yl)methyl amino)-6,11-dihydrodibenzo[c,f][1,2]thiazepine 5,5-dioxide (46)

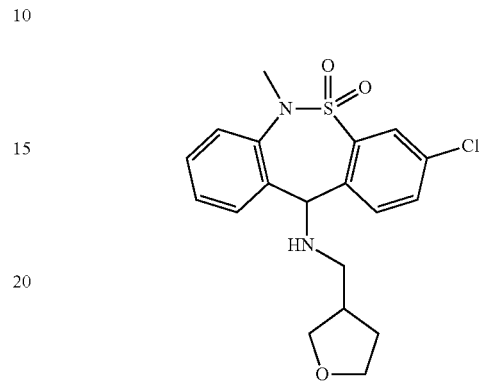

Method B. The product 46 was obtained as a colorless glass (92.8 mg, 95%). $^1$H NMR (400 MHz, CDCl$_3$) (additional splitting due to conformers) δ 7.97 (dd, J=4.3, 2.2 Hz, 1H), 7.51-7.27 (m, 6H), 4.98 (d, J=11.9 Hz, 1H), 3.86-3.76 (m, 2H), 3.74-3.65 (m, 1H), 3.54-3.42 (m, 1H), 3.31 (d, J=14.5 Hz, 3H), 2.55-2.27 (m, 3H), 2.30 (br s, 1H), 2.07-1.94 (m, 1H), 1.62-1.44 (m, 1H); $^{13}$C NMR (101 MHz, CDCl$_3$) (all peaks split due to conformers) δ 140.2, 140.0, 139.1, 138.9, 134.5, 132.5, 131.9, 131.6, 131.3, 130.6, 129.6, 128.8, 128.7, 128.12, 128.06, 128.0, 127.9, 72.1, 72.0, 67.92, 67.89, 67.4, 66.8, 51.72, 51.65, 39.8, 39.2, 38.9, 30.7, 30.6; LR-MS calcd. for $C_{19}H_{22}ClN_2O_3S$ [M+H]$^+$ 393.10, found 392.69.

3-chloro-6-methyl-11-((2-(1-methylpyrrolidin-2-yl)ethyl-6,11-dihydrodibenzo[c,1][1,2]thiazepine 5,5-dioxide (47)

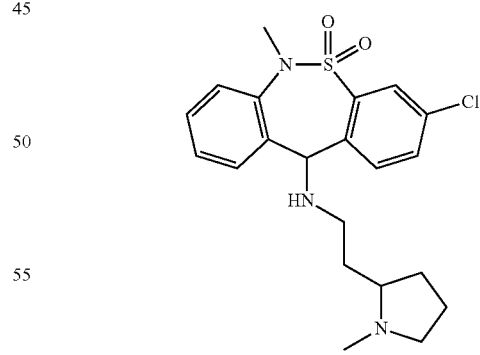

Method B. The product 47 was obtained as a viscous yellow oil (206 mg, 98%). $^1$H NMR (400 MHz, CDCl$_3$) (additional splitting due to conformers) δ 7.95 (s, 1H), 7.48-7.26 (m, 6H), 5.02 (d, J=4.7 Hz, 1H), 3.38 (d, J=9.9 Hz, 3H), 3.07-2.99 (m, 1H), 2.63-2.43 (m, 2H), 2.28 (d, J=8.8 Hz, 3H), 2,28 (br s, 1H), 2.16-2.02 (m, 2H), 1.89-1.76 (m, 2H), 1.76-1.59 (m, 2H), 1.56-1.33 (m, 2H); $^{13}$C NMR (101 MHz, CDCl$_3$) (all peaks split due to conformers) δ 140.5, 140.4, 139.2, 139.1, 138.6, 138.5, 137.3, 137.1, 134.4, 134.3, 132.27, 132.25, 131.0, 130.9, 129.9, 129.8, 129.44, 129.42, 128.6, 128.5, 128.3, 128.1, 128.0, 65.9, 65.8, 64.7, 64.6, 57.34, 57.32, 45.6, 45.5, 40.71, 40.67, 38.64, 38.56, 33.8, 33.7, 30.62, 30.60, 22.2, 22.1; LR-MS calcd. for $C_{21}H_{27}ClN_3O_2S$ [+H]$^+$ 420.15, found 419.71.

3-Iodo-11-((3-methoxypropyl)amino)-6-methyl-6, 11-dihydrodibenzo [c,f][1,2]thiazepine 5,5-dioxide (48)

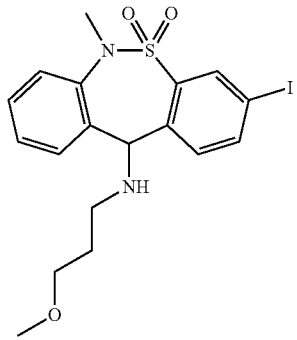 [SMILES: COCCCNC1c2ccccc2N(C)S(=O)(=O)c2cc(I)ccc21]

Method B. The product 48 was purified directly by column chromatography (hexanes:EtOAc-1:1, 2 column volumes→EtOAc, 2 column volumes) and obtained as a viscous pale-yellow oil (32.2 mg, 84%). $^1$H NMR (400 MHz, CDCl$_3$) δ 8.26 (d, J=1.8 Hz, 1H), 7.81 (dd, J=8.1, 1.8 Hz, 1H), 7.43-7.32 (m, 3H), 7.31-7.27 (m, 1H), 7.24 (d, J 8.2 Hz, 1H), 5.02 (s, 1H), 3.46-3.39 (m, 2H), 3.37 (s, 3H), 3.29 (s, 3H), 2.65-2.52 (m, 2H), 2.40 (br s, 1H), 1.77 (p, J=6.3 Hz, 2H); $^{13}$C NMR (101 MHz, CDCl$_3$) δ 141.3, 140.6, 138.7, 136.9, 131.4, 130.0, 129.5, 128.3, 128.0, 93.0, 71.3, 66.1, 58.8, 45.9, 38.6, 30.0; LR-MS calcd. for $C_{18}H_{22}IN_2O_3S$ [M+H]$^+$ 473.04, found 472.79.

Ethyl 7-((3-iodo-6-methyl-5,5-dioxido-6,11-dihydrodibenzo[c,f][1,2]thiazepin-11-yl)amino)heptanoate (49)

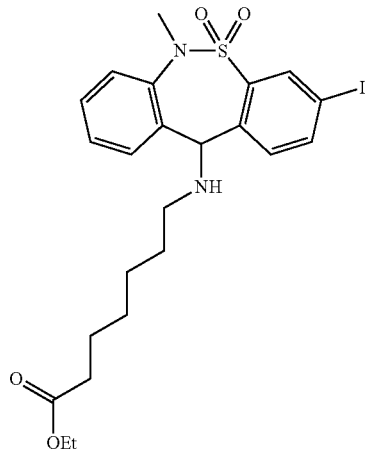 [SMILES: CCOC(=O)CCCCCCNC1c2ccccc2N(C)S(=O)(=O)c2cc(I)ccc21]

Method C. The product 49 was purified directly by column chromatography (CH$_2$Cl$_2$:Et$_2$O-20:1) and obtained as a viscous nearly-colorless oil (31.7 mg, 70%). $^1$H NMR (400 MHz, CDCl$_3$) δ 8.26 (d, J=1.8 Hz, 1H), 7.81 (dd, J=8.1, 1.8 Hz, 1H), 7.41-7.32 (m, 3H), 7.31-7.26 (m, 1H), 7.21 (d, J=8.2 Hz, 1H), 4.98 (s, 1H), 4.11 (q, J=7.1 Hz, 2H), 3.36 (s, 3H), 2.46 (t, J=7.1 Hz, 2H), 2.26 (t, J=7.5 Hz, 2H), 2.05 (br s, 1H), 1.65-1.53 (m, 2H), 1.53-1.42 (m, 2H), 1.35-1 .26 (m, 4H), 1.24 (t, J=7.1 Hz, 3H) ; $^{13}$C NMR (101 MHz, CDCl$_3$) δ 173.8, 141.3, 140.6, 138.7, 136.9, 131.5, 130.1, 129.5, 128.2, 128.1, 92.9, 66.3, 60.3, 48.2, 38.7, 34.4, 30.0, 29.1, 27.0, 25.0, 14.4; LR-MS calcd. for $C_{23}H_{30}IN_2O_4S$ [M+H]$^+$ 557.10, found 556.54.

7-Methoxy-(3-methoxypropyl)amino)-6-methyl-6, 11-dihydrodibenzo [c,f][1,2]thiazepine 5,5-dioxide (50)

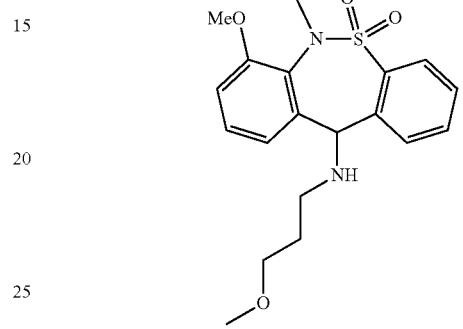

Method B. The product 50 was obtained as a viscous pale-yellow oil (36.6 mg, 97%). $^1$H NMR (500 MHz, CDCl$_3$) (observed as a-55:45 ratio of 2 conformers resulting in partial integrals) δ 7.96 (q, J=8.0 Hz, 1H), 7.59 (d, J=7.7 Hz, 0.45H), 7.52-7.33 (m, 2.55H), 7.29-7.21 (m, 1H), 7.06-6.91 (m, 1H), 6.91-6.80 (m, 1H), 5.35 (s, 0.45H), 4.67 (s, 0.55H), 3.93 (s, 1.65H), 3.89 (s, 1.35H) 3.55-3.43 (m, 2.55H), 3.39-3.31 (m, 2.45H), 3.25 (s, 3H), 2.77-2.46 (m, 2H), 2.05 (br s, 1H), 1.91-1.76 (m, 1H), 1.76-1.64 (m, 1H) ; $^{13}$C NMR (126 MHz, CDCl$_3$) (additional peaks due to conformers) δ 158.2, 157.0, 142.5, 141.8, 138.5, 137.8, 132.2, 131.8, 131.7, 129.7, 129.3, 129.0, 128.9, 128.2, 127,8, 126,3, 122.5, 112.6, 111.2, 71.4, 71,3, 70.9, 58.8, 58.7, 56.3, 46.1, 45.9, 37.9, 36.4, 30.1; LR-MS calcd. for $C_{19}H_{25}N_2O_4S$ [M+H]$^+$ 377.15, found 377.13.

Ethyl 7-((7-methoxy-6-methyl-5,5-dioxido-6,11-dihydrodibenzo[c,f][1,2] thiazepin-11-yl)amino) heptanoate (51)

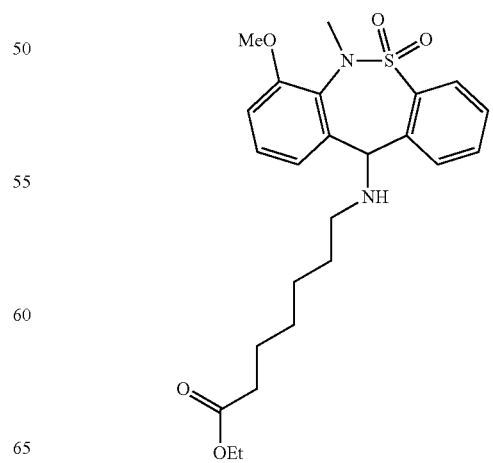

Method C. The product 51 was obtained as a viscous pale-yellow oil (44.6 mg, 97%). $^1$H NMR (500 MHz, CDCl$_3$) (observed as a ~55:45 ratio of 2 conformers resulting in partial integrals) δ 7.96 (dd, J=7.6, 1.6 Hz,1H), 7.58 (d, J=7.6 Hz, 0.45H), 7.52-7.33 (m, 2.55H), 7.29-7.21 (m, 1H), 7.06-6.81 (m, 2H), 5.34 (s, 0.45H), 4.67 (s, 0.55H), 4.10 (p, J=7.2 Hz, 2H), 3.93 (s, 1.65H), 3.89 (s, 1.35H), 3.48 (s, 1.65H), 3.22 (s, 1.35H), 2.65-2.33 (m, 2H), 2.31-2.20 (m, 2H), 1.87 (br s, 1H), 1.66-1.50 (m, 3H), 1.46-1.29 (m, 3H), 1.28-1.18 (m, 5H); $^{13}$C NMR (126 MHz, CDCl$_3$) (additional peaks due to conformers) δ 173.8, 158.2, 156.9, 142.5, 141.8, 138.4, 137.9, 132.3, 131.7, 129.6, 129.3, 129.1, 128.9, 128.2, 127.9, 126.3, 122.5, 112.6, 111.3, 70.8, 60.3, 56.3, 48.5, 48.2, 38.0, 36.5, 34.3, 30.0, 29.8, 29.1, 27.1, 25.0, 24.9, 14.4; LR-MS calcd. for C$_{24}$H$_{33}$N$_2$O$_5$S [M+H]$^+$ 461.21, found 460.98.

11-((7-(Aminooxy)-7-oxoheptyl)amino)-3-chloro-6-methyl-6,11-dihydrodibenzo[c,f][1,2]-thiazepine 5,5-dioxide (52)

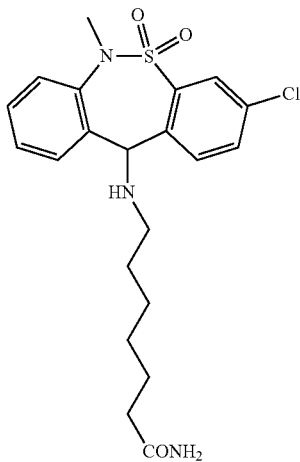 [SMILES: CN1c2ccccc2C(NCCCCCCC(N)=O)c2ccc(Cl)cc2S1(=O)=O]

Method A. the crude product was purified by column chromatography (hexanes:EtOAc-1:1->CH$_2$Cl$_2$+10% MeOH). The product 52 was obtained as a colorless oil (260 mg, 89%). $^1$H NMR (400 MHz, Acetone-d$_6$) δ 7.82 (d, J=2.2 Hz, 1H), 7.73 (d, J=8.4 Hz, 1H), 7.63 (dd, J=8.3, 2.2 Hz, 1H), 7.52 (dd, J=7.6, 1.3 Hz, 1H), 7.48 (dd, J=7.8, 1.0 Hz, 1H), 7.41 (td, J=7.6, 1.6 Hz, 1H), 7.34 (td, J=7.5, 1.4 Hz, 1H), 6.61 (s, 1H), 5.99 (s, 1H), 5.20 (s, 1H), 3.41 (s, 3H), 2.50 (t, J=7.0 Hz, 2H), 2.12 (t, J=7.4 Hz, 2H), 1.63-1.44 (m, 4H), 1.38-1.21 (m, 4H). $^{13}$C NMR (101 MHz, Acetone-d$_6$) δ 175.2, 142.3, 140.6, 139.7, 138.6, 134.2, 133.0, 132.8, 131.0, 130.0, 129.4, 128.8, 128.2, 66.4, 48.7, 39.2, 36.0, 30.6, 27.8, 26.2; LR-MS calcd. for C$_{21}$H$_{27}$ClN$_3$O$_3$S [M+H]$^+$ 436.15, found 435.70.

3-Bromo-11-((3-methoxypropyl)amino)-6-methyl-6,11-dihydrodibenzo[c,f][1,2]thiazepine 5,5-dioxide (53)

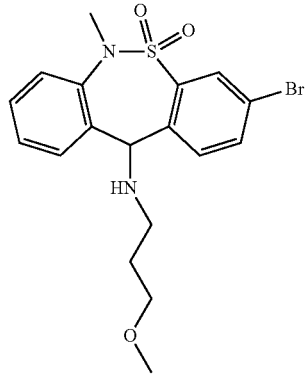 [SMILES: COCCCNC1c2ccccc2N(C)S(=O)(=O)c2cc(Br)ccc21]

Method A. The crude product was purified by column chromatography (hexanes:EtOAc-1:1). The product 53 was obtained as a colorless oil turning to a white solid (45 mg, 71%). $^1$H NMR (400 MHz, Acetone-d$_6$) δ 7.96 (d, J=2.1 Hz, 1H), 7.77 (dd, J=8.3, 2.1 Hz, 1H), 7.65 (d, J=8.3 Hz, 1H), 7.51 (dd, J=7.6, 1.5 Hz, 1H), 7.49 (dd, J=7.9, 1.2 Hz, IH), 7.41 (td, J=7.6, 1.6 Hz, 1H), 7.34 (td, J=7.4, 1.3 Hz, 1H), 5.18 (s, 1H), 3.42 (s, 3H), 3.39 (t, J=6.2 Hz, 2H), 3.22 (s, 3H), 2.58 (t, J=6.8 Hz, 2H), 2.54 (br s, 1H), 1.73 (p, J=6.6 Hz, 2H). $^{13}$C NMR (101 MHz, Acetone-d$_6$) δ 142.7, 140.8, 139.7, 139.1, 135.8, 133.1, 131.0, 130.8, 130.0, 129.4, 128.9, 121.9, 71.6, 66.4, 58.5, 46.2, 39.1, 30.8; LR-MS calcd. for C$_{18}$H$_{22}$BrN$_2$O$_3$S [M+H]$^+$ 425.05, found 425.06.

11-((3-Methoxypropyl)amino)-6-methyl-3-(methylsulfonyl)-6,11-dihydrodibenzo[c,f][1,2]thiazepine 5,5-dioxide (54)

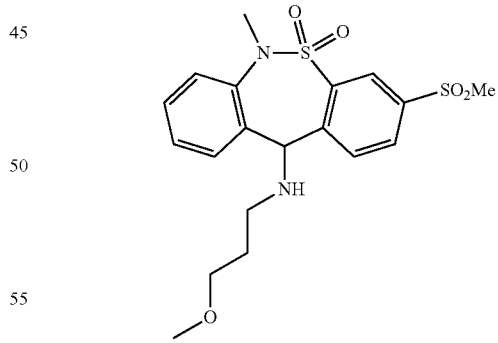

Method B. The product 54 was purified directly by column chromatography (CH$_2$Cl$_2$:Et$_2$O-6:4) and obtained as a viscous colorless oil (38.8 mg, 91%). $^1$H NMR (500 MHz, CDCl$_3$) δ 8.51 (d, J=1.9 Hz, 1H), 8.04 (dd, J=8.1, 1.9 Hz, 1H), 7.79 (d, J=8.2 Hz, 1H), 7.45-7.35 (m, 3H), 7.31 (td, J=7.4, 1.4 Hz, 1H), 5.24 (s, 1H), 3.45 (t, J=6.1 Hz, 2H), 3.43 (s, 3H), 3.31 (s, 3H), 3.06 (s, 3H), 2.71-2.58 (m, 2H), 2.27 (br s, 1H), 1.88-1.72 (m, 2H); $^{13}$C NMR (126 MHz, CDCl$_3$) δ 144.8, 140.8, 140.7, 139.2, 138.1, 130.8, 130.1, 129.7, 129.0, 128.6, 128.0, 127.9, 71.4, 64.9, 58.8, 46.2, 44.5, 38.2, 30.0; LR-MS calcd. for $C_{19}H_{25}N_2O_3S_2$ [M+H]$^+$ 425.12, found 425.72

11-((3-Methoxypropyl)amino)-6-methyl-3-(methylsulfinyl)-6,11-dihydrodibenzo[c,f][1,2]thiazepine 5,5-dioxide (55)

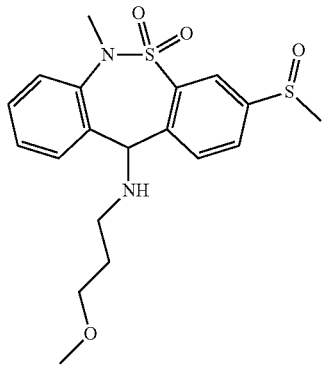 [SMILES: COCCCNC1c2ccccc2N(C)S(=O)(=O)c2cc(S(C)=O)ccc21]

Method B. The product 55 was purified directly by column chromatography (EtOAc:MeOH-20:1, 3 column volumes→EtOAc:MeOH-20:1+2% Et$_3$N, 3 column volumes) and obtained as a pale yellow-orange glass (35.5 mg, 87%, 1:1 mixture of diastereomers). $^1$H NMR (500 MHz, CDCl$_3$) (partial integrals due to mixture of diastereomers) δ 8.10 (d, J=1.8 Hz, 0.5H), 8.08 (d, J=1.8 Hz, 0.5H), 7.88 (ddd, J=9.7, 8.1, 1.9 Hz, 1H), 7.74 (d, J=8.0 Hz, 1H), 7.43-7.34 (m, 3H), 7.29 (tt, J=7.5, 1.7 Hz, 1H), 5.15 (s, 1H) 3.46-3.39 (m, 5H), 3.29 (s, 1.5H), 3.29 (s, 1.5H), 2.73 (s, 1.5H), 2.73 (s, 1.5H), 2.67-2.56 (m, 2H), 2.24 (br s, 1H), 1.84-1.72 (m, 2H) ; $^{13}$C NMR (126 MHz, CDCl$_3$) (additional peaks due to mixture of diastereomers) δ 146.6, 146.5, 141.7, 140.4, 140.3, 139.5, 139.2, 138.3, 138.2, 130.6, 130.5, 129.6, 129.5, 129.3, 129.5, 128.4, 128.1, 128.0, 127.10, 127.07, 124.0, 123.9, 71.34, 71.30, 65.6, 58.8, 46.1, 46.0, 44.0, 43.9, 38.4, 38.3, 30.0. LR-MS calcd, for $C_{19}H_{25}N_2O_4S_2$ [M+H]$^+$ 409.13, found 409.31.

11-((3-Methoxypropyl)amino)-6-methyl-3-phenyl-6,11-dihydrodibenzo[c,f][1,2]thiazepine 5,5-dioxide (56)

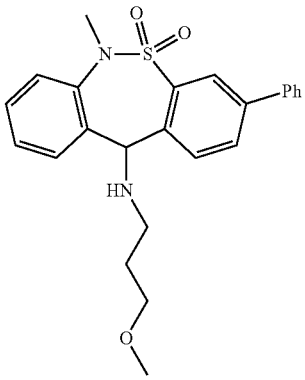 [SMILES: COCCCNC1c2ccccc2N(C)S(=O)(=O)c2cc(-c3ccccc3)ccc21]

Method A. The crude product was purified by column chromatography (hexanes:EtOAc-1:1). The product 56 was obtained as a colorless oil (75 mg, 89%). $^1$H NMR (400 MHz, Acetone-d$_6$) δ 8.11 (d, J=1.9 Hz, 1H), 7.88 (dd, J=8.1, 1.9 Hz, 1H), 7.77 (d, J=8.1 Hz, 1H), 7.73-7.67 (m, 2H), 7.57-7.46 (m, 4H), 7.45-7.41 (m, 1H), 7.39 (dd, J=7.7, 1.6 Hz, 1H), 7.34 (td, J=7.5, 1.4 Hz, 1H), 5.24 (s, H), 3.41 (m, 5H), 3.23 (s, 3H), 2.62 (t, J=6.8 Hz, 2H), 2.57 (br s, 1H), 1.75 (p, J=6.6 Hz, 2H); $^{13}$C NMR (101 MHz, Acetone-c$_6$) δ 141.7, 141.1, 140.9, 140.1, 139.7, 138.7, 131.6, 131.1, 130.9, 130.0, 129.8, 129.1, 129.1, 128.6, 127.7, 126.8, 71.6, 66.6, 58.5, 46.2, 38.9, 30.9; LR-MS calcd. for $C_{24}H_{27}N_2O_3S$ [M+H]$^+$ 423.17, found 423.22.

Preparation of Compounds 57 and 58

Compounds 57 and 58 were prepared from tianeptine sodium according to the following procedure. To a solution of tianeptine sodium salt (91.8 mg, 0.200 mmol) and triphenylphosphine (157 mg, 0.600 mmol) in anhydrous CH$_2$Cl$_2$ (3.9 mL) was added ethanolamine (12.1 μL, 0.200 mmol) and diisopropylethylamine (105 μL, 0.600 mmol) and the solution was 1.5 cooled to 0° C. Anhydrous carbon tetrachloride (96.5 μL, 1.00 mmol) was then added slowly over~75 min, and the reaction was allowed to warm to room temperature and stirred for 13 h. The reaction mixture was then purified directly by column chromatography (EtOAc, 6 column volumes→EtOAc+2% Et$_3$N, 3 column volumes → CH$_2$Cl$_2$:MeOH-10:1, 3 column volumes) to yield one fraction containing impure 58 and a second fraction containing 57 contaminated with a partial salt of EtN. The fraction containing 57 was dissolved in CH$_2$Cl$_2$ (10 mL) and washed with H$_2$O (5 mL) and 10% NH$_4$OH (5 mL). The organic layer was then dried over Na$_2$SO$_4$, concentrated, and dried thoroughly under high vacuum to yield the pure amide 57. The fraction containing 58 was purified on a second chromatography column (EtOAc, 8 column volumes→CH$_2$Cl$_2$: MeOH-10:1, 3 column volumes) to yield the pure oxazoline 58.

7-((3-Chloro-6-methyl-5,5-dioxido-6,11-dihydrodibenzo [c,f][1,2]thiazepin-11-yl)amino)-N-(2-hydroxyethyl) heptanamide (57)

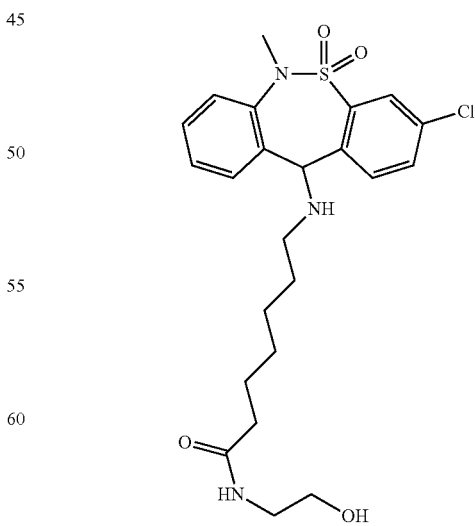

The product 57 was obtained as a viscous yellow oil (50.8 mg, 53%). $^1$H NMR (400 MHz, CDCl$_3$) δ 7.94 (d, J=2.1 Hz, 1H), 7.49-7.26 (m, 6H), 6.17 (br s, 1H), 4.97 (s, 1H), 3.67-3.58 (m, 2H), 3.37-3.30 (m, 2H), 3.33 (s, 3H), 2.52 (br s, 2H), 2.49-2.37 (m, 2H), 2.14 (t, J 7.5 Hz, 2H), 1.64-1.51 (m, 2H), 1.51-1.38 (m, 2H), 1.33-1.18 (m, 4H); $^{13}$C NMR (101 MHz, CDCl$_3$) δ 174.5, 140.2, 138.7, 138.4, 136.9, 134.4, 132.4, 131.6, 130.5, 129.5, 128.5, 128.2, 128.0, 66.5, 62.3, 48.0, 42.5, 38.9, 36.5, 29.8, 29.0, 26.9, 25.6; LR-MS calcd. for C$_{23}$H$_{31}$ClN$_3$O$_4$S [M+H]$^+$ 480.17, found 479.88.

3-Chloro-11-((6-(4,5-dihydrooxazol-2-yl)hexyl)amino)-6-methyl-6,11-dihydrodibenzo[c,f][1,2]thiazepine 5,5-dioxide (58)

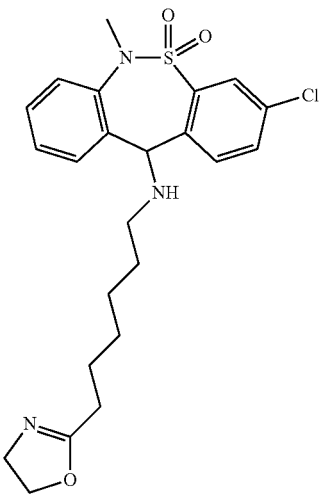 [SMILES: CN1c2ccccc2C(NCCCCCCC2=NCCO2)c2ccc(Cl)cc2S1(=O)=O]

The product 58 was obtained as a viscous pale-yellow oil (2.9 mg, 3.1%). $^1$H NMR (400 MHz, CDCl$_3$) δ 7.96 (d, J=2.0 Hz, 1H), 7.55-7.28 (m, 6H), 5.06 (br s, 1H), 4.21(t, J=9.4 Hz, 2H), 3.80 (t, J=9.4 Hz, 2H), 3.36 (s, 3H), 2.53-2.40 (m, 2H), 2.28-2.19 (m, 2H), 2.11 (br s, 1H), 1.60 (dt, J=14.6, 7.4 Hz, 2H 1.50 (br s, 2H), 1.31 (dt, J=7.3, 3.7 Hz, 4H); $^{13}$C NMR (101 MHz, CDCl$_3$) δ 168.7, 140.5, 138.8, 134.5, 132.4, 131.4, 130.3, 129.6, 128.6, 128.3, 128.1, 67.3, 66.3, 54.5, 48.2, 38.8, 30.0, 29.2, 28.0, 27.0, 26.0; LR-MS calcd. for C$_{23}$H$_{29}$ClN$_3$O$_3$S [M+H]$^+$ 462.16, found 462.10.

11-((3-Methoxypropyl)amino)-6-methyl-5,5-dioxido-6,11-dihydrodibenzo[c,f][1,2]thiazepin-3-yl acetate (59)

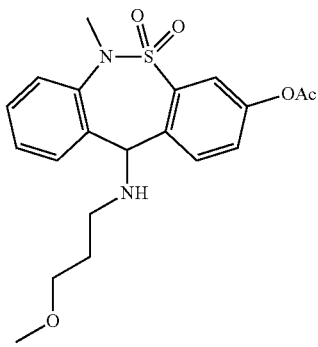 [SMILES: COCCCNC1c2ccccc2N(C)S(=O)(=O)c2cc(OC(C)=O)ccc21]

To a solution of alcohol 4m (65 mg, 0.223 mmol) in anhydrous CH$_2$Cl$_2$ (3.0 mL) was added 2M HCl in Et$_2$O (0.30 mL) and the resulting mixture was stirred for 4 h at room temperature and then concentrated in vacuo to provide the crude intermediate chloride as an orange solid (65 mg). This material was then aminated with 3-methoxypropylamine (0.10 mL) according to general Method A. The resulting crude product was dissolved in acetic acid (5 mL) and acetyl chloride (0.50 mL) was added at 5° C. The reaction was then allowed to warm to room temperature and stirred overnight. The mixture was then concentrated in vacuo and the residue was suspended/dissolved in H$_2$O and neutralized with saturated aqueous NaHCO$_3$. The aqueous mixture was then extracted with CH$_2$Cl$_2$ and the combined organics were dried over Na$_2$SO$_4$ and concentrated to provide the crude product. This material was purified by column chromatography (CH$_2$Cl$_2$+2% MeOH) to give pure product 59 as a yellowish oily solid (68 mg, 75% from alcohol 4m). $^1$1.1 NMR (400 MHz, Acetone-d$_6$) δ 7.71 (d, J=8.5 Hz, 1H), 7.62 (d, J=2.4 Hz, 1H), 7.51 (dd, J=7.6, 1.6 Hz, 1H), 7.48 (dd, J=7.8, 1.4 Hz, 1H), 7.43-7.30 (m, 3H), 5.19 (s, 1H), 3.43-3.36 (m, 2H), 3.41 (s, 3H), 3.22 (s, 3H), 2.82 (br s, 1H), 2.58 (t, J=6.8 Hz, 2H), 2.30 (s, 3H), 1.74 (p, J=6.5 Hz, 2H); $^{13}$C NMR (101 MHz, Acetone-d$_6$) δ 169.5, 151.2, 141.6, 141.0, 139.9, 137.1, 132.2, 130.8, 129.9, 129.3, 128.8, 126.3, 122.1, 71.6, 66.4, 58.5, 46.2, 38.9, 30.8, 20.9; LR-MS calcd. for C$_{20}$H$_{25}$N$_2$O$_5$S [M+H]$^+$ 405.15, found 405.00.

2-Chloro-11-((3-methoxypropyl)amino-6-methyl-6,11-dihydrodibenzo [c,f][1,2]thiazepine 5,5-dioxide (60)

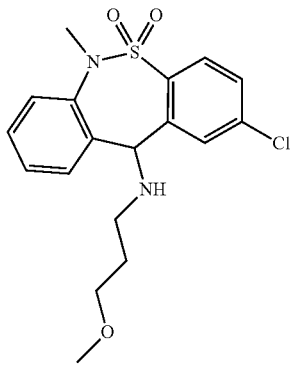 [SMILES: COCCCNC1c2ccccc2N(C)S(=O)(=O)c2ccc(Cl)cc21]

Method A. The product 60 was purified by column chromatography (hexanes:EtOAc-1:1) and obtained as a viscous colorless oil (72 mg, 95%). $^1$H NMR (400 MHz, Acetone-d$_6$) δ 7.88 (d, J=8.5 Hz, 1H), 7.76 (d, J=2.2 Hz, 1H), 7.56-7.47 (m, 3H), 7.41 (td, J=7.6, 1.7 Hz, 1H), 7.35 (td, J=7.4, 1.5 Hz, 1H), 5.28 (s, 1H), 3.42 (t, J=6.1 Hz, 2H), 3.41 (s, 3H), 3.24 (s, 3H), 2.81 (br s, 1H), 2.63 (t, J=6.8 Hz, 2H), 1.77 (dq, J=12.2, 6.2 Hz, 2H); $^{13}$C NMR (101 MHz, Acetone-d$_6$) δ 142.4, 141.0, 139.7, 139.4, 138.3, 130.7, 130.0, 129.9, 129.8, 129.1, 128.92, 128.86, 71.5, 65.2, 58.6, 46.2, 38.4, 30.8; LR-MS calcd. for CH$_{18}$H$_{22}$ClN$_2$OS [M+H]$^+$ 381.10, found 381.46.

Ethyl 7-((2-chloro-6-methyl-5,5-dioxido-6,11-dihydrodibenzo[c,f] [1,2]thiazepin-11-yl)amino)heptanoate (61)

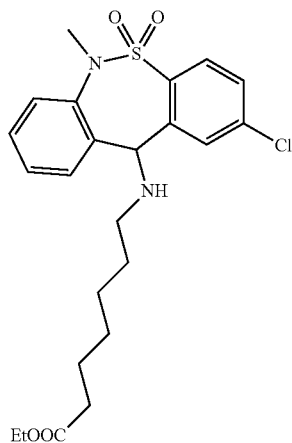 [SMILES: CCOC(=O)CCCCCCNC1c2ccccc2N(C)S(=O)(=O)c2ccc(Cl)cc21]

Method A. The product 61 was purified by column chromatography (hexanes:EtOAc-2:1) and obtained as a viscous colorless oil (120 mg, 81%). $^1$H NMR (400 MHz, Acetone-d$_6$) δ 7.88 (d, J=8.5 Hz, 1H), 7.76 (d, J=2.2 Hz, 1H), 7.57-7.51 (m, 2H), 7.49 (dd, J=7.8, 1.4 Hz, 1H), 7.40 (td, J=7.6, 1.7 Hz, 1H), 7.34 (td, J=7.4, 1.5 Hz, 1H), 5.28 (s, 1H), 4.06 (q, J=7.1 Hz, 2H), 3.40 (s, 3H), 2.80 (br s, 1H), 2.55 (t, J=7.0 Hz, 2H), 2.25 (t, J=7.4 Hz, 2H), 1.62-1.49 (m, 4H), 1.41-1.26 (m, 4H), 1.19 (t, J=7.1 Hz, 3H); $^{13}$C NMR (101 MHz, Acetone-d$_6$) δ 173.60, 142.40, 140.87, 139.76, 139.28, 138.29, 130.68, 130.22, 129.95, 129.89, 129.11, 128.90, 128.81, 65.37, 60.40, 48.67, 38.57, 34.56, 30.58, 27.68, 25.61, 14.58; LR-MS calcd. for $C_{23}H_{30}ClN_2O_4S$ [M+H]$^+$ 465.16, found 465.68.

7-Hydroxy-11-((3-methoxypropyl)amino)-6-methyl-6,11-dihydrodibenzo[c,f][1,2]thiazepine 5,5-dioxide (62)

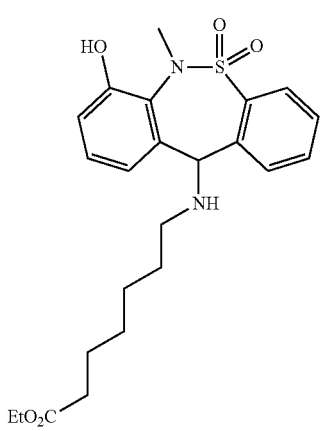 [SMILES: CCOC(=O)CCCCCCNC1c2ccccc2S(=O)(=O)N(C)c2c(O)cccc21]

Compound 62 was prepared according to the following procedure. To a solution of compound 51 (29.1 mg, 0.0631 mmol) in anhydrous CH$_2$Cl$_2$ (0.50 mL) at 0° C. was added aluminum chloride (50.5 mg, 0.379 mmol) followed by ethanethiol (84.4 µL, 1.14 mmol), and the resulting mixture was allowed to warm to room temperature and stirred for 1.5 h. The reaction was then quenched with water (5 mL) and extracted with CH$_2$Cl$_2$ (3×5 mL). The combined organics were washed with water (5 mL), dried over Na$_2$SO4, and concentrated to give a white solid. This material was purified by column chromatography (CH$_2$Cl$_2$: Et$_2$O-6:1, 2 column volumes→7:3, 2 column volumes) to provide the pure product 62 as a white solid (23.3 mg, 83%). $^1$H NMR (500 MHz, CDCl$_3$) (partial integrals due to conformers) δ 8.00-7.94 (m, 1H), 7.63-7.36 (m, 3H), 7.23-7.15 (m, 1H), 6.99 (d, J=8.0 Hz, 1H), 6.88 (dd, J=17.9, 7.7 Hz, 1H), 6.29 (br s, 1H), 5.24 (s, 0.5H), 4.74 (s, 0.5H), 4.11 (p, J=7.1 Hz, 2H), 3.56 (s, 1.5H), 3.17 (s, 1.5H), 2.67-2.57 (m, 0.5H), 2.51 (td, J=13.7, 6.8 Hz, 1H), 2.39 (dt, J=11.2, 7.3 Hz, 0.5H), 2.32-2.20 (m, 2H), 1.66-1.52 (m, 3H), 1.47-1.17 (m, 8H); $^{13}$C NMR (126 MHz, CDCl$_3$) (additional peaks due to conformers) δ 174.0, 173.90, 155.2, 153.8, 141.7, 140.9, 137.7, 132.8, 132.2, 131.8, 130.2, 129.7, 129.3, 128.7, 128.2, 125.0, 122.8, 117.4, 116.0, 71.2, 60.4, 48.7, 48.2, 39.7, 38.0, 34.4, 34.3, 30.0, 29.8, 29.12, 29.08, 27.10, 27.06, 25.0, 24.9, 14.4; LR-MS calcd. for $C_{23}H_{31}N_2O_5S$ [M+H]$^+$ 447.19, found 447.15.

3-(Isopropylthio)-11-((3-methoxypropyl)amino)-6-methyl-6,11-dihydrodibenzo[c,f][1,2]thiazepine 5,5-dioxide (63)

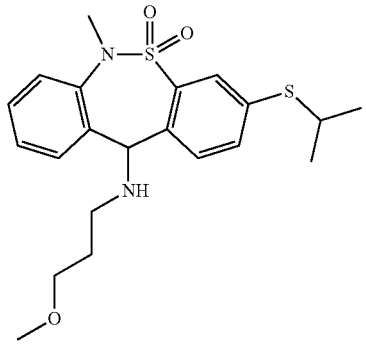 [SMILES: COCCCNC1c2ccccc2N(C)S(=O)(=O)c2cc(SC(C)C)ccc21]

Method B. The product 63 was purified by column chromatography (hexanes:EtOAc-1:1, 2 column volumes→EtOAc, 3 column volumes) and obtained as a viscous, pale-yellow oil (37.7 mg, 90%). $^1$H NMR (400 MHz, CDCl$_3$) δ 7.93 (d, J=1.9 Hz, 1H), 7.45 (dd, J=8.0, 1.9 Hz, 1H), 7.42-7.31 (m, 4H), 7.27 (dt, J=7.2, 2.2 Hz, 1H), 4.99 (s, 1H), 3.50-3.38 (m, 3H), 3.36 (s, 3H), 3.29 (s, 3H), 2.58 (t, J=6.7 Hz, 2H), 2.32 (s, 1H), 1.75 (tt, J=7.9, 4.1 Hz, 2H), 1.31 (d, J=6.7 Hz, 6H); $^{13}$C NMR (101 MHz, CDCl$_3$) δ 139.4, 139.0, 138.9, 137.4, 136.2, 134.2, 130.3, 130.2, 130.0, 129.3, 128.1, 128.0, 71.3, 66.5, 58.8, 45.7, 38.6, 38.0, 30.1, 23.12, 23 0; LR-MS calcd. for $C_{21}H_{29}N_2O_3S_2$ [M+H]$^+$ 421.16, found 421.50.

3-(Ethylthio)-11-((3-methoxypropyl)amino)-6-methyl-6,11-dihydrodibenzo[c,f][1,2]thiazepine 5,5-dioxide (64)

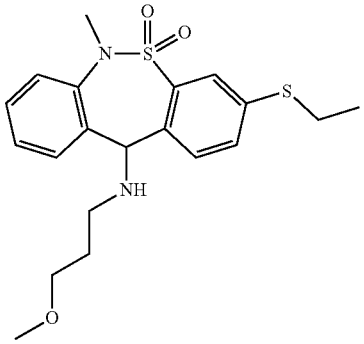 [SMILES: CCSc1ccc2c(c1)S(=O)(=O)N(C)c1ccccc1C2NCCCOC]

Method B. The product 64 was purified by column chromatography (hexanes:EtOAc-1:1, 2 column volumes→EtOAc, 3 column volumes) and obtained as a viscous, nearly colorless oil (36.6 mg, 90%). $^1$H NMR (500 MHz, CDCl$_3$) δ 7.84 (s, 1H), 7.42-7.31 (m, 5H), 7.30-7.25 (m, 1H), 4.97 (s, 1H), 3.45-3.37 (m, 2H), 3.35 (s, 3H), 3.29 (s, 3H), 2.98 (q, J=7.4 Hz, 2H), 2.62-2.52 (m, 2H), 2.32 (br s, 1H), 1.81-1.69 (m, 2H), 1.32 (t, J=7.4 Hz, 3H); $^{13}$C NMR (126 MHz, CDCl$_3$) δ 139.4, 138.9, 138.5, 135.2, 131.6, 130.4, 130.3, 129.3, 128.1, 128.1, 127.2, 71.3, 66.6, 58.8, 45.7, 38.7, 30.1, 27.2, 14.2; LR-MS calcd. for C$_{20}$H$_{27}$N$_2$O$_3$S$_2$ [M+H]$^+$ 407.15, found 407.14.

6-Ethyl-11-((3-methoxpropyl)amino)-6,11-dihydrodibenzo[c,f][1,2]thiazepine 5,5-dioxide (65)

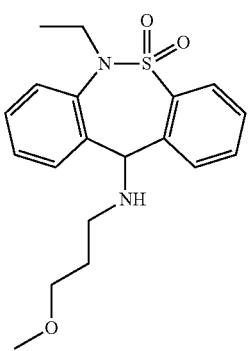 [SMILES: CCN1c2ccccc2C(NCCCOC)c2ccccc2S1(=O)=O]

Method B. The product 65 was purified by column chromatography (hexanes:EtOAc-1:1, 2 column volumes→EtOAc, 3 column volumes) and obtained as a viscous, colorless oil (30.6 mg, 85%). $^1$HNMR (500 MHz, CDCl$_3$) δ 7.98-7.94 (m, 1H), 7.52-7.45 (m, 2H), 7.43-7.38 (m, 3H), 7.31 (dtd, J=19.3, 7.4, 1.5 Hz, 2H), 5.16 (s, 1H), 3.96-3.77 (m, 2H), 3.50-3.39 (m, 2H), 3.31 (s, 3H), 2.68-2.56 (m, 2H), 2.32 (br s, 1H), 1.83-1.73 (m, 2H), 1.18 (t, J=7.2 Hz, 3H); $^{13}$C NMR (126 MHz, CDCl$_3$) δ 140.7, 139.9, 138.7, 136.9, 132.2, 129.3, 129.1, 129.0, 128.7, 128.4, 128.3, 71.3, 65.2, 58.8, 46.3, 45.8, 30.1, 14.9; LR-MS calcd. for C$_{19}$H$_{25}$N$_2$O$_3$S [M+H]$^+$ 361.16, found 361.06.

Ethyl 7-((6-ethyl-5,5-dioxido-6,11-dihydrodibenzo[c,f][1,2]thiazepin-11-yl)amino)heptanoate (66)

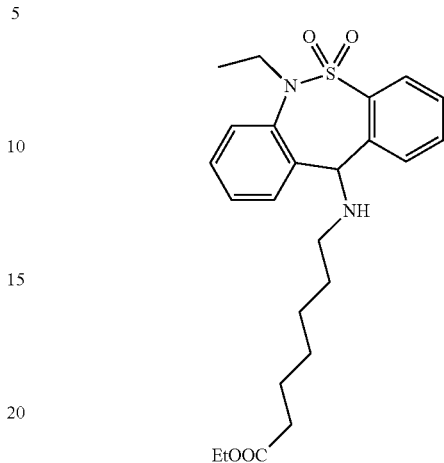

Method C. The product 66 was purified by column chromatography (CH$_2$Cl$_2$:Et$_2$O-20:1, 4 column volumes→10:1, 2 column volumes) and obtained as a viscous, colorless oil (33.8 mg, 76%). $^1$H NMR (500 MHz, CDCl$_3$) δ 7.96 (d, J=7.8 Hz, 1H), 7.50-7.46 (m, 2H), 7.43-7.38 (m, 3H), 7.35-7.27 (m, 2H), 5.13 (s, 1H), 4.11 (q, J=7.1 Hz, 2H), 3.95-3.77 (m, 2H), 2.55-2.43 (m, 2H), 2.26 (t, J=7.5 Hz, 2H), 2.09 (br s, 1H), 1.63-1.55 (m, 2H), 1.54-1.47 (m, 2H), 1.37-1.26 (m, 4H), 1.24 (t, J=7.1 Hz, 3H), 1.17 (t, J=7.2 Hz, 3H) ; $^{13}$C NMR (126 MHz, CDCl$_3$) δ 173.9, 139.9, 138.8, 136.9, 132.4, 129.5, 129.0, 129.0, 128.9, 128.5, 128.32, 128.26, 65.4, 60.3, 48.2, 46.4, 34.4, 30.0, 29.1, 27.1, 25.0, 14.8, 14.4; LR-MS calcd. for C$_{24}$H$_{33}$N$_2$O$_4$S [M+H]$^+$ 445.22, found 445.15.

3-Chloro-11-((3-methoxybutyl)amino)-6-methyl-6,11-dihydrodibenzo[c,f][1,2]thiazepine 5,5-dioxide (67)

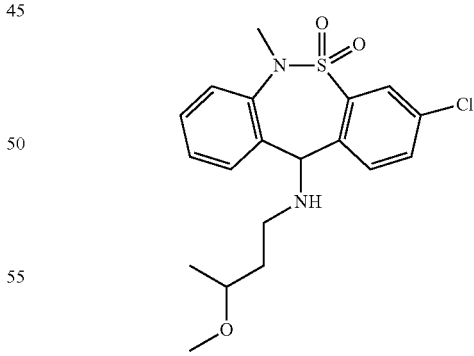

Method B. The product 67 was purified by column chromatography (hexanes:EtOAc-1:1, 2 column volumes→EtOAc, 2 column volumes) and obtained as a viscous, colorless oil (30.4 mg, 77%, 1:1 mixture of diastereomers). $^1$H NMR (400 MHz, CDCl$_3$) (partial integrals due to mixture of diastereomers) δ 7.95 (d, J=1.2 Hz, 1H), 7.49-7.32 (m, 5H), 7.32-7.27 (m, 1H), 5.04 (s, 0.5H), 5.02 (s, 0.5H), 3.43-3.34 (m, 1H), 3.38 (s, 1.5H), 3.37 (s, 1.5 H), 3.27 (s, 1.5H), 3.26 (s, 1.5H), 2.64-2.51 (m, 2H), 2.36 (br s, 1H), 1.75-1.57 (m, 2H), 1.10 (t, J=6.0 Hz, 3H); $^{13}$C NMR (101 MHz, CDCl$_3$) (additional peaks due to mixture of diastereomers) δ 140.5, 140.4, 138.6, 137.0, 134.3, 132.3, 131.2, 130.0, 129.5, 128.5, 128.3, 128.1, 75.7, 75.4, 66.2, 65.9, 56.1, 45.2, 44.9, 38.7, 36.8, 36.7, 19.11, 19.08; LR-MS calcd. for C$_{19}$H$_{24}$ClN$_2$O$_3$S [M+H]$^+$ 395.12, found 394.98.

3-Chloro-11-((3-methoxy-2-methylpropyl)amino)-6-methyl-6,11-dihydrodibenzo[c,f][1,2]thiazepine 5,5-dioxide (68)

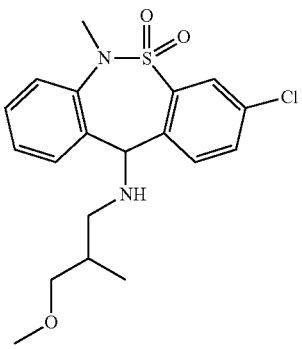 [SMILES: COCC(C)CNC1c2ccccc2N(C)S(=O)(=O)c2cc(Cl)ccc21]

Method B. The product 68 was purified by column chromatography (CH$_2$Cl$_2$: Et$_2$O-20:1, 2 column volumes→10:1, 2 column volumes) and obtained as a viscous, colorless oil (30.1 mg, 76%, 1:1 mixture of diastereomers). $^1$H NMR (400 MHz, CDCl$_3$) (partial integrals due to mixture of diastereomers) δ 7.97-7.93 (m, 1H), 7.51-7.32 (m, 5H), 7.29 (td, J=7.2, 1.5 Hz, 1H), 5.04 (s, 0.5H), 5.02 (s, 0.5H), 3.38 (s, 1.5H), 3.37 (s, 1.5H), 3.32-3.22 (m, 2H), 3.31 (s, 1.5H), 3.29 (s, 1.5H), 2.59-2.31 (m, 2H), 2.43 (br s, 1H), 2.03-1.90 (m, 1H), 0.89 (dd, J=6.9, 4.8 Hz, 3H); $^{13}$C NMR (101 HC 4, CDCl$_3$) (additional peaks due to mixture of diastereomers) δ 140.4, 140.3, 139.1, 138.59, 138.55, 137.2, 134.$^7$4, 134.26, 132.3, 131.1, 129.8, 129.43, 129.39, 128.49, 128.45, 128.3, 128.0, 77.32, 77.26, 66.1, 65.7, 59.0, 52.7, 52.5, 38.5, 34.0, 15.74, 15.67; LR-MS calcd. for C$_{19}$H$_{24}$ClN$_2$O$_3$S [M+H]$^+$ 395.12, found 394.98.

8-Chloro-11-((3-methoxypropyl)amino)-6-methyl-6,11-dihydrodibenzo [c,f][1,2]thiazepine 5,5-dioxide (69)

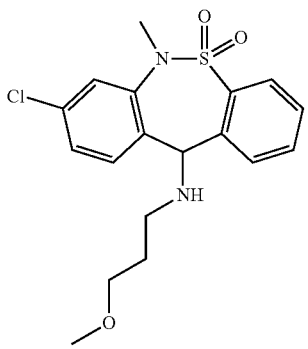 [SMILES: COCCCNC1c2ccc(Cl)cc2N(C)S(=O)(=O)c2ccccc21]

Method B. The product 69 was purified by column chromatography (hexanes:EtOAc-1:1, 2 column volumes→EtOAc, 3 column volumes) and obtained as a viscous, nearly colorless oil (33.8 mg, 89%). $^1$H NMR (500 MHz, CDCl$_3$) δ 7.98 (dd, J=7.8, 0.9 Hz, 1H), 7.54 (td, J=7.6, 1.2 Hz, 1R), 7.52-7.41 (m, 3H), 7.33 (d, J=2.1 Hz, 1H), 7.25 (dd, J=8.6, 2.3 Hz, 1H), 5.09 (s, 1H), 3.45-3.38 (m, 2H), 3.28 (s, 3H), 3.28 (s, 3H), 3.01 (br s, 1H), 2.61 (dt, J=13.2, 6.7 Hz, 1H), 2.53 (dt, J=11.4, 6.7 Hz, 1H), 1.83-1.71 (m, 2H) ; $^{1.3}$t NMR (126 MHz, CDCl$_3$) δ 140.5, 138.3, 137.3, 136.2, 134.5, 132.8, 132.1, 130.3, 128.68, 128.65, 128.0, 127.5, 71.2, 66.4, 58.8, 45.7, 38.6, 29.8; LR-MS calcd. for C$_{18}$H$_{22}$ClN$_2$O$_3$S [M+H]$^+$ 381.10, found 380.79.

Ethyl 7-((8chloro-6-methyl-5,5-dioxido-6,11-dihydrodibenzo[c,f][1,2] thiazepin-11-yl)amino)heptanoate (70)

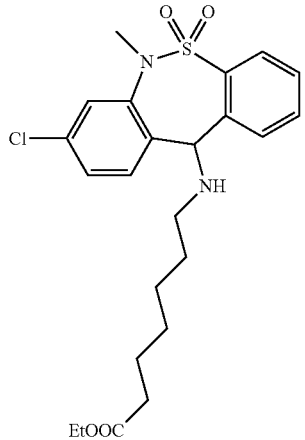 [SMILES: CCOC(=O)CCCCCCNC1c2ccc(Cl)cc2N(C)S(=O)(=O)c2ccccc21]

Method C. The product 70 was purified by column chromatography (CH$_2$Cl$_2$: Et$_2$O-20:1, 2 column volumes→10:1, 2 column volumes) and obtained as a viscous, nearly colorless oil (38.0 mg, 82%). $^1$H NMR (500 MHz, CDCl$_3$) δ 7.98 (dd, J=8.0, 1.1 Hz, 1H), 7.56-7.51 (m, 1H), 7.48-7.43 (m, 2H), 7.38 (d, J=8.4 Hz, 1H), 7.33 (d, J=2.1 Hz, H), 7.24 (dd, j-8.3, 2.1 Hz, 1H), 5.00 (s, 1H), 4.10 (q, J=7.1 Hz, 2H), 3.28 (s, 3H), 2.49-2.38 (m, 2H), 2.25 (t, J=7.5 Hz, 2H), 2.16 (br s, 1H), 1.58 (p, J=7.4 Hz, 2H), 1.53-1.40 (m, 2H), 1.32-1.25 (m, 4H), 1.23 (t, J=7.1 Hz, 3H); $^{13}$C NMR (126 MHz, CDCl$_3$) 173.9, 140.4, 138.3, 137.8, 136.7, 134.3, 132.7, 132.1, 130.2, 128.7, 128.5, 128.0, 127.6, 66.6, 60.3, 48.0, 38.7, 34.4, 29.9, 29.1, 27.0, 24.9, 14.4; LR-MS calcd. for C$_{23}$H$_{30}$ClN$_2$O$_4$S [M+H]$^+$ 465.16, found 464.58.

3-Bromo-11-((3-ethoxypropyl)amino)-6-methyl-6,11-dihydrodibenzo[c,f][1,2]thiazepine 5,5-dioxide (71)

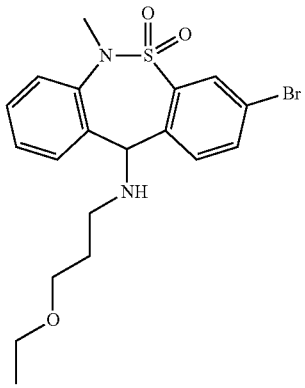 [SMILES: CCOCCCNC1c2ccccc2N(C)S(=O)(=O)c2cc(Br)ccc21]

Method B. The product 71 was purified by column chromatography (hexanes:EtOAc-1:1, 2 column volumes→EtOAc, 3 column volumes) and obtained as a viscous, colorless oil (37.5 mg, 85%). $^1$H NMR (500 MHz, CDCl$_3$) δ 8.09 (d, J=2.0 Hz, 1H), 7.61 (dd, J=8.3, 2.0 Hz, 1H), 7.43-7.33 (m, 4H), 7.29 (td, J=7.4, 1.4 Hz, 1H), 5.05 (s, 1H), 3.53-3.40 (m, 4H), 3.38 (s, 3H), 2.64-2.53 (m, 2H), 2.31 (br s, 1H), 1.83-1.70 (m, 2H), 1.15 (t, J=7.0 Hz, 3H); $^{13}$C NMR (126 MHz, CDCl$_3$) δ 140.6, 138.6, 135.3, 131.3, 129.8, 129.4, 128.3, 128.1, 122.0, 69.1, 66.4, 65.7, 46.0, 38.6, 30.0, 15.3; LR-MS calcd. for C$_{19}$H$_{24}$BrN$_2$O$_3$S [M+H]$^+$ 439.07, found 438.76.

7-Bromo-10-((3-methoxypropyl)amino)-4-methyl-4,10-dihydrobenzo[f]thieno[3,2-c][1,2]thiazepine 5,5-dioxide (72)

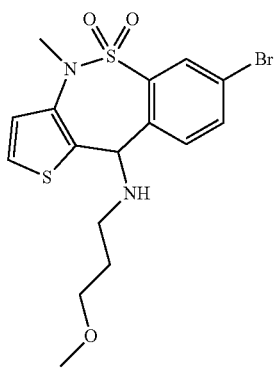 [SMILES: COCCCNC1c2ccc(Br)cc2S(=O)(=O)N(C)c2ccsc21]

Method B. The product 72 was purified by column chromatography (CH$_2$Cl$_2$: Et$_2$O-20:1, 3 column volumes→10:1, 3 column volumes→5:1, 4 column volumes) and obtained as a beige solid (22.1 mg, 51%). $^1$H NMR (400 MHz, CDCl$_3$) δ 8.11 (d, J=2.0 Hz, 1H), 7.77 (dd, J=8.2, 2.0 Hz, 1H), 7.39 (d, J=8.1 Hz, 1H), 7.21 (d, J=5.5 Hz, 1H), 6.82 (d, J=5.5 Hz, 1H), 5.39 (s, 1H), 3.54-3.43 (m, 2H), 3.34 (s, 3H), 3.05 (s, 3H), 2.77 (t, J=6.4 Hz, 2H), 1.88-1.76 (m, 2H); $^{13}$C NMR (101 MHz, CDCl$_3$) δ 137.3, 136.7, 131.1, 130.8, 124.5, 124.3, 121.9, 71.2, 60.8, 58.8, 45.4, 39.6, 29.9; LR-MS calcd. for C$_{16}$H$_{20}$BrN$_2$O$_3$S$_2$ [M+H]$^+$ 431.01, found 431.92.

7-Bromo-10-((3-ethoxypropyl)amino)-4-methyl-4,10-dihydrobenzo[f]thieno[3,2-c][1,2]thiazepine 5,5-dioxide (73)

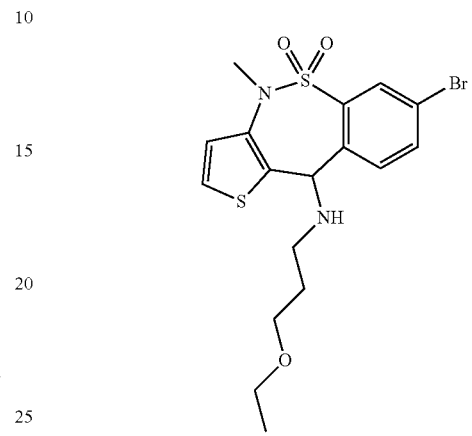

Method B. The product 73 was purified by column chromatography (CH$_2$Cl$_2$:Et$_2$O-20:1, 3 column volumes→10:1, 3 column volumes→5:1, 4 column volumes) and obtained as a beige solid (27.5 mg, 62%). $^1$H NMR (400 MHz, CDCl$_3$) δ 8.11 (d, J=2.1 Hz, 1H), 7.77 (dd, J=8.2, 2.1 Hz, 1H), 7.41 (d, J=8.1 Hz, 1H), 7.21 (d, J=5.5 Hz, 1H), 6.82 (d, J=5.5 Hz, 1H), 5.41 (s, 1H), 3.57-3.51 (m, 2H), 3.48 (q, J=7.0 Hz, 2H), 3.05 (s, 3H), 2.78 (t, J=6.4 Hz, 2H), 1.91-1.75 (m, 2H), 1.18 (t, J=7.0 Hz, 3H); $^{13}$C NMR (101 MHz, CDCl$_3$) δ 137.3, 136.7, 131.1, 130.8, 124.5, 124.3, 121.9, 69.0, 66.4, 60.6, 45.5, 39.6, 29.9, 15.4; LR-MS calcd. for C$_{17}$H$_{22}$BrN$_2$O$_3$S$_2$ [M+H]$^+$ 445.02, found 446.00.

Ethyl 7-((7-bromo-4-methyl-5,5-dioxido-4,10-dihydrobenzo[f]thieno[3,2-c][1,2]thiazepin-10-yl)amino)heptanoate (74)

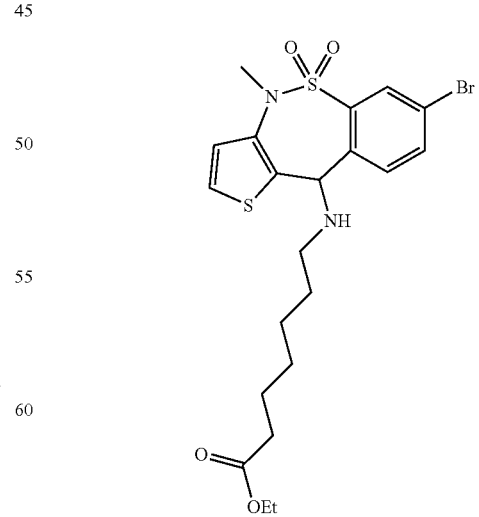

Method C. The product 74 was purified by column chromatography (CH$_2$Cl$_2$:Et$_2$O-20:1, 4 column volumes→10:1, 4 column volumes) and obtained as a dark-brown solid (52.5 mg, 51%). $^1$H NMR (400 MHz, CDCl$_3$) δ 8.11 (d, J=2.1 Hz, 1H), 7.76 (dd, J=8.2, 2.1 Hz, 1H), 7.30 (d, J=8.2 Hz, 1H), 7.19 (d, J=5.5 Hz, 1H), 6.81 (d, J=5.5 Hz, 1H), 5.31 (s, 1H), 4.11 (q, J=7.1 Hz, 2H), 3.03 (s, 3H), 2.62 (t, J=6.9 Hz, 2H), 2.27 (t, J=7.5 Hz, 2H), 1.66-1.55 (m, 2H), 1.55-1.45 (m, 2H), 1.40-1.27 (m, 4H), 1.24 (t, J=7.1 Hz, 3H) ; $^{13}$C NMR (101 MHz, CDCl$_3$) δ 173.9, 137.3, 136.5, 135.3, 135.0, 131.2, 130.8, 129.6, 124.5, 124.1, 121.7, 60.8, 60.3, 47.7, 39.6, 34.4, 29.9, 29.0, 26.9, 25.0, 14.4; LR-MS calcd. for C$_{21}$H$_{28}$BrN$_2$O$_4$S$_2$ [M+H]$^+$ 515.07, found 516.24.

3-(Benzyloxy)-11-((3-methoxypropyl)amino)-6-methyl-6,11-dihydrodibenzo[c,f][1,2]thiazepine 5,5-dioxide (75)

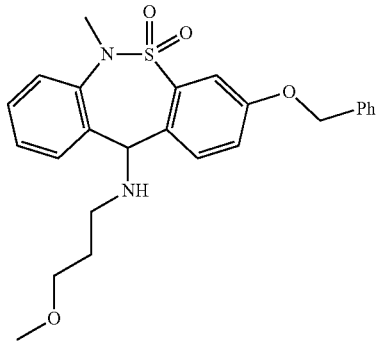 [SMILES: COCCCNC1c2ccccc2N(C)S(=O)(=O)c2cc(OCc3ccccc3)ccc21]

Method B. The product 75 was purified by column chromatography (hexanes:EtOAc-1:1, 3 column volumes→EtOAc, 4 column volumes) and obtained as a viscous, nearly colorless oil (31.9 mg, 70%). $^1$H NMR (500 MHz, CDCl$_3$) δ 7.59 (d, J=2.7 Hz, 1H), 7.44-7.31 (m, 9H), 7.30-7.26 (m, 1H), 7.08 (dd, J=8.5, 2.7 Hz, 1H), 5.09 (s, 2H), 4.93 (s, 1H), 3.45-3.37 (m, 2H), 3.35 (s, 3H), 3.29 (s, 3H), 2.56 (t, J=6.8 Hz, 2H), 2.28 (br s, 1H), 1.80-1.68 (m, 2H); $^{13}$C NMR (126 MHz, CDCl$_3$) δ 158.4, 139.9, 139.3, 139.0, 136.2, 131.8, 130.7, 130.6, 129.2, 128.8, 128.4, 128.1, 128.0, 127.8, 119.0, 114.0, 71.3, 70.6, 66.9, 58.8, 45.6, 38.9, 30.2; LR-MS calcd. for C$_{25}$H$_{29}$N$_2$O$_4$S [M+H]$^+$ 453.18, found 453.65.

11-((3-Ethoxypropyl)amino)-3-iodo-6-methyl-6,11-dihydrodibenzo [c,f][1,2]thiazepine 5,5-dioxide (76)

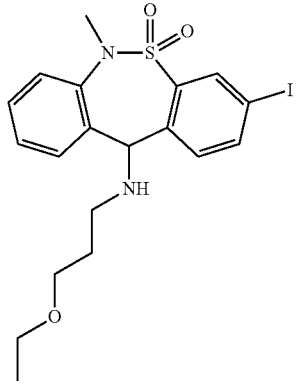 [SMILES: CCOCCCNC1c2ccccc2N(C)S(=O)(=O)c2cc(I)ccc21]

Method B. The product 76 was purified by column chromatography (hexanes:EtOAc-1:1, 2 column volumes→EtOAc, 3 column volumes) and obtained as a viscous, pale-yellow oil (43.0 mg, 88%). $^1$H NMR (500 MHz, CDCl$_3$) δ 8.26 (d, J=1.6 Hz, 1H), 7.80 (dd, J=8.1, 1.7 Hz, 1H), 7.40-7.37 (m, 2H), 7.35 (td, J=7.5, 1.4 Hz, 1H), 7.28 (td, J 7.7, 1.2 Hz, 1H), 7.24 (d, J=8.2 Hz, 1H), 5.02 (s, 1H), 3.52-3.40 (m, 4H), 3.38 (s, 3H), 2.59 (t, J=6.6 Hz, 2H), 2.27 (br s, 1H), 1.83-1.68 (m, 2H), 1.15 (t, J=7.0 Hz, 3H); $^{13}$C NMR (126 MHz, CDCl$_3$) δ 141.2, 140.6, 139.3, 138.5, 138.4, 136.9, 131.1, 129.6, 129.4, 128.3, 128.1, 92.8, 69.1, 66.4, 65.7, 45.9, 38.6, 30.1, 15.3; LR-MS calcd. for C$_{19}$H$_{24}$IN$_2$O$_3$S [M+H]$^+$ 487.05, found 487.69.

7-Chloro-10-((3-methoxypropyl)amino)-4-methyl-4,10-dihydrobenzo[f]thieno[3,2-c][1,2]thiazepine 5,5-dioxide (77)

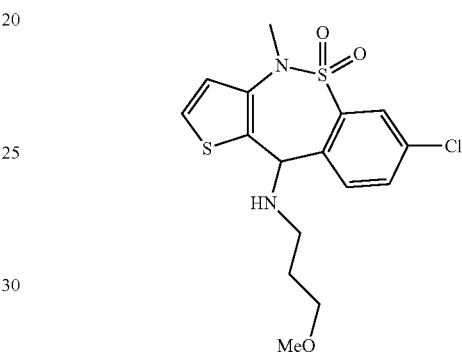

Method B. The product 77 was purified by column chromatography (20:1 CH$_2$Cl$_2$:Et$_2$→10:1 CH$_2$Cl$_2$:Et$_2$O→5:1 CH$_2$Cl$_2$:Et$_2$O) and obtained as a dark-green solid (24.7 mg, 54%). $^1$H NMR (400 MHz, CDCl$_3$) δ 7.97 (d, J=2.3 Hz, 1H), 7.61 (dd, J=8.2, 2.3 Hz, 1H), 7.42 (dd, J=8.2, 0.7 Hz, 1H), 7.19 (d, J=5.4 Hz, 1H), 6.82 (d, J=5.5 Hz, 1H), 5.37 (s, 1H), 3.50 (td, J=6.3, 2.0 Hz, 2H), 3.35 (s, 3H), 3.04 (s, 3H), 2.75 (d, J=6.5 Hz, 2H), 1.80 (q, J=6.0 Hz, 2H); $^{13}$C NMR (101 MHz, CDCl$_3$) δ 137.1, 134.7, 134.0, 133.6, 130.3, 130.1, 128.4, 124.5, 124.0, 110.1, 71.2, 60.8, 58.8, 45.3, 39.6, 30.2; LR-MS cald. for C$_{16}$H$_{20}$ClN$_2$O$_3$S$_2$ [M+H]$^+$ 387.06, found 387.24.

7-Chloro-10-((-ethoxypropyl)amino)-4-methyl-4,10-dihydrobenzo[f]thieno[3,2-c][1,2]thiazepine 5,5-dioxide (78)

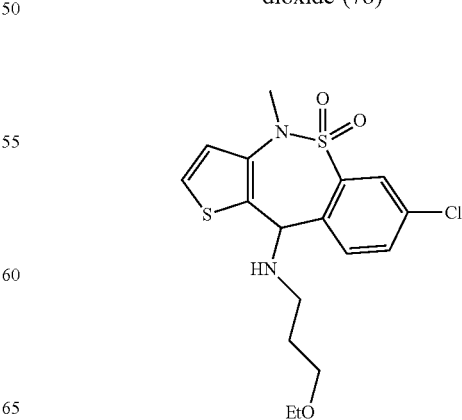

Method B. The product 78 was purified by column chromatography (20:1 CH$_2$Cl$_2$:Et$_2$O→10:1 CH$_2$Cl$_2$:Et$_2$O→5:1 CH$_2$Cl$_2$:Et$_2$O) and obtained as a dark-green solid (28.3 mg, 61%). $^1$H NMR (400 MHz, CDCl$_3$) S (d, J=2.3 Hz, 1H), 7.61 (dd, J=8.2, 2.3 Hz, 1H), 7.48-7.42 (m, 1H), 7.19 (d, J=5.5 Hz, 1H), 6.82 (d, J=5.5 Hz, 1H), 5.39 (s, 1H), 3.59-3.46 (m, 4H), 3.04 (s, 3H), 2.79-2.72 (m, 2H), 1.81 (q, J=6.3 Hz, 2H), 1.20 (t, J=7.0 Hz, 3H); $^{13}$C NMR (101 MHz, CDCl$_3$) δ 137.4, 135.4, 135.1, 134.3, 133.9, 130.6, 130.5, 128.7, 124.8, 124.3, 69.3, 66.7, 60.9, 45.7, 39.9, 30.6, 15.7; LR-MS cald. for C$_{17}$H$_{22}$ClN$_2$O$_3$S$_2$ [M+H]$^+$ 401.08, found 401.23.

Ethyl 7-((7-chloro-4-methyl-5,5-dioxido-4,10-dihydrobenzo[f]thieno[3,2-c][1,2]thiazepin-10-yl)amino)heptanoate (79)

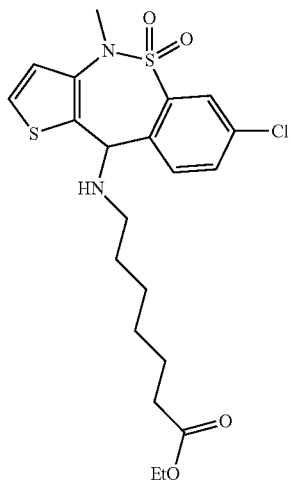 [SMILES: CCOC(=O)CCCCCCNC1c2ccc(Cl)cc2S(=O)(=O)N(C)c2ccsc21]

Method C. The product 79 was purified by column chromatography (20:1 CH$_2$Cl$_2$:Et$_2$O→10:1 CH$_2$Cl$_2$:Et$_2$O→5:1 CH$_2$Cl$_2$:Et$_2$O) and obtained as a dark reddish-brown solid (3.5 mg, 6%). $^1$H NMR (400 MHz, CDCl$_3$) δ 7.98 (d, J=2.2 Hz, 1H), 7.61 (dd, J=8.2, 2.3 Hz, 1H), 7.37 (d, J=8.2 Hz, 1H), 7.20 (d, J=5.5 Hz, 1H), 6.82 (d, J=5.5 Hz, 1H), 5.33 (s, 1H), 4.12 (q, J=7.1 Hz, 2H), 3.04 (s, 3H), 2.63 (t, J=6.9 Hz, 2H), 2.28 (t, J=7.5 Hz, 2H), 1.67-1.58 (m, 2H), 1.53 (t, J=6.8 Hz, 3H), 1.35 J=10.0, 5.9 Hz, 4H), 1.25 (t, J=7.1 Hz, 3H) ; $^{13}$C NMR (126 MHz, CDCl$_3$) δ 180.3, 137.2, 135.3, 133.6, 133.5, 128.5, 124.5, 124.4, 124.1, 60.9, 60.3, 47.8, 39.6, 34.5, 30.0, 29.1, 27.0, 23.1; LR-MS cald. for C$_{21}$H$_{28}$ClN$_2$O$_4$S$_2$ [M+H]$^+$ 471.12, found 471.42.

7-((6-Methyl-5,5-dioxido-6,11-dihydrodibenzo[c,f][1,2]thiazepin-11-yl)amino)heptanoic acid hydrochloride salt (80)

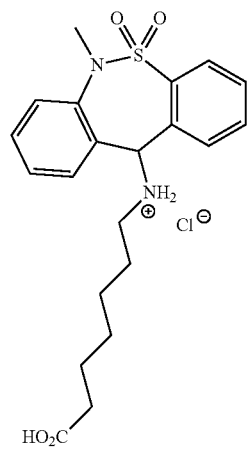 [SMILES: CN1c2ccccc2C([NH2+]CCCCCCC(=O)O)c2ccccc2S1(=O)=O ; [Cl-]]

Compound 9 (32.0 mg, 0.0743 mmol) was heated in aqueous HCl (0.5 M, 2.0 mL) at 70° C. for 2 h. The reaction mixture was then concentrated and dried thoroughly in vacuo to provide the pure HCl salt of the acid 80 as a colorless glass (32.6 mg, quantitative yield). $^1$H NMR (400 MHz, Methanol-d$_4$) δ 8.15-8.10 (m, 1H), 7.94-7.89 (m, 1H), 7.89-7.81 (m, 2H), 7.75 (d, J=7.8 Hz, 1H), 7.67-7.61 (m, 1H), 7.56 (dd, J=8.1, 1.1 Hz, 1H), 7.48 (td, J=7.6, 1.3 Hz, 1H), 5.96 (s, 1H), 3.19 (s, 3H), 3.01-2.92 (m, 1H), 2.83-2.73 (m, 1H), 2.33-2.21 (m, 2H), 1.75-1.61 (m, 2H), 1.61-1.50 (m, 2H), 1.36-1.24 (m, 4H).

Ethyl 7-((3-bromo-6-methyl-5,5-dioxido-6,11-dihydrodibenzo [c,f] [1,2]thiazepin-11-yl)amino)heptanoate (81)

Method C. The product 81 was purified by column chromatography (CH$_2$Cl$_2$:Et$_2$O-20:1, 4 column volumes→7:3, 2 column volumes) and obtained as a viscous, colorless oil (42.0 mg, 821m. $^1$H NMR (500 MHz, CDCl$_3$) δ 8.09 (d, J=2.1 Hz, 1H), 7.61 (dd, J=8.2, 2.1 Hz, 1H), 7.40-7.33 (m, 4H), 7.31-7.27 (m, 1H), 4.98 (3, 1H), 4.11 (q, J=7.1 Hz, 2H), 3.37 (s, 3H), 2.45 (t, J=7.1 Hz, 2H), 2.26 (t, J=7.5 Hz, 2H), 2.03 (br s, 1H), 1.63-1.54 (m, 2H), 1.52-1.43 (m, 2H), 1.34-1.26 (m, 4H), 1.24 (t, J=7.1 Hz, 3H) ; $^{13}$C NMR (126 MHz, CDCl$_3$) δ 173.8, 140.6, 138.9, 138.6, 137.6, 135.3, 131.4, 131.3, 130.1, 129.4, 128.2, 128.1, 122.0, 66.3, 60.3, 48.2, 38.8, 34.4, 30.0, 29.1, 27.0, 25.0, 14.4; LR-MS cald. for C$_{23}$H$_{30}$BrN$_2$O$_4$S [M+H]$^+$ 509.11, found 509.92.

7-((3-Bromo-6-methyl-5,5-dioxido-6,11-dihydrodibenzo[c,f][1,2]thiazepin-11-yl)amino)heptanoic acid hydrochloride salt (82)

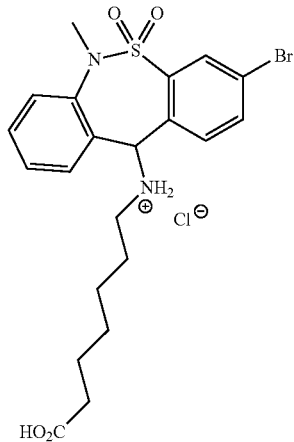 [SMILES: CN1c2ccccc2C([NH2+]CCCCCCC(=O)O)c2ccc(Br)cc2S1(=O)=O ; [Cl-]]

Compound 81 (20.0 mg, 0.0393 mmol) was heated in aqueous HCl (0.5 M, 1.5 mL) at 70° C. for 3 h. The reaction mixture was then concentrated and dried thoroughly in vacuo to provide the pure HCl salt of the acid 82 as a glassy, white foam (19.9 mg, 98%). $^1$H NMR (500 MHz, Methanol-d$_4$) δ 8.22 (d, J=2.1 Hz, 1H), 8.02 (dd, J 8.2, 2.1 Hz, 1H), 7.86-7.81 (m, 1H), 7.74 (d, J=7.8 Hz, 1H), 7.66-7.62 (m, 1H), 7.57 (dd, J=8.1, 1.1 Hz, 1H), 7.49 (td, J=7.7, 1.3 Hz, 1H), 5.95 (s, 1H), 3.24 (s, 3H), 2.96 (ddd, J=12.1, 10.4, 5.5 Hz, 1H), 2.82 (ddd, J=12.2, 10.3, 5.9 Hz, 1H), 2.27 (t, J=7.3 Hz, 2H), 1.74-1.61 (m, 2H), 1.61-1.53 (m, 2H), 1.37-1.28 (m, 4H); $^{13}$C NMR (126 MHz, Methanol-d$_4$) δ 177.4, 142.5, 141.8, 138.3, 137.0, 134.7, 133.4, 132.2, 129.1, 128.7, 128.6, 127.4, 126.5, 67.6, 48.3, 39.7, 34.6, 29.5, 27.1, 26.8, 25.6; LR-MS cald. for C$_{21}$H$_{26}$BrN$_2$O$_4$S [M+H]$^+$ 481.08, found 481.05.

3-Chloro-11-((3-hydroxypropyl)amino)-6-methyl-6, 11-dihydrodibenzo[c,f][1,2]iazepine 5,5-dioxide (83)

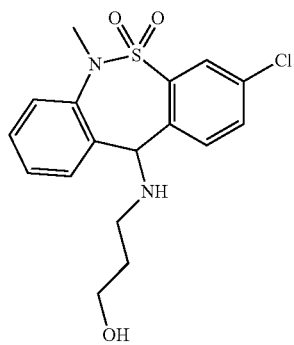 [SMILES: CN1c2ccccc2C(NCCCO)c2ccc(Cl)cc2S1(=O)=O]

Method B. The product 83 was purified by column chromatography (CH$_2$Cl$_2$:Et$_2$O-1:1, 3 column volumes→CH$_2$Cl$_2$:Et$_2$O-1:1+5% MeOH, 3 column volumes) and obtained as a cloudy, colorless glass (27.1 mg, 74%). $^1$H NMR (500 MHz, CDCl$_3$) δ 7.98 (d, J=2.2 Hz, 1H), 7.50 (dd, J=8.2, 2.2 Hz, 1H), 7.45-7.40 (m, 2H), 7.38-7.31 (m, 2H), 7.31-7.27 (m, 1H), 5.01 (s, 1H), 3.82-3.74 (m, 2H), 3.25 (br s, 2H), 3.25 (s, 3H), 2.68-2.60 (m, 2H), 1.75-1.63 (m, 2H); $^{13}$C NMR (126 MHz, CDCl$_3$) δ 139.9, 139.2, 136.2, 135.6, 134.6, 132.5, 132.4, 131.5, 129.6, 128.8, 128.1, 127.6, 67.1, 63.7, 47.4, 39.1, 31.2; LR-MS cald. for C$_{17}$H$_{20}$ClN$_2$O$_3$S [M+H]$^+$ 367.09, found 367.09.

7-((3-Iodo-6-methyl-5,5-dioxido-6,11-dihydrodibenzo [c,f][1,2]thiazepin-11-yl)amino)heptanoic acid hydrochloride salt (84)

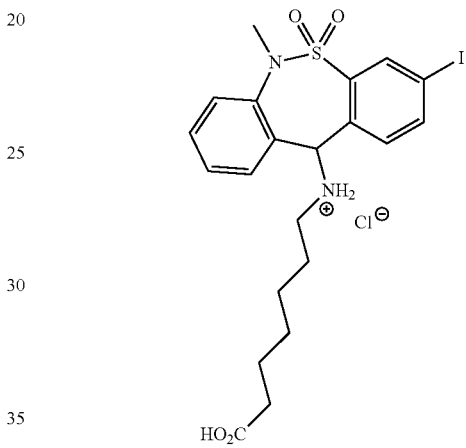

Compound 49 (25 mg, 0.045 mmol) was heated in aqueous HCl (0.5 M, 1.5 mL) at 70° C. for 3 h. The reaction mixture was then concentrated and dried thoroughly in vacuo to provide the pure HCl salt of the acid 84 as a viscous, yellowish oil (25 mg, quantitative yield). $^1$H NMR (400 MHz, Methanol-d$_4$) δ 8.38 (d, J=1.5 Hz, 1H), 8.22 (dd, J=7.5, 1.9 Hz, 1H), 7.78-7.72 (m, 1H), 7.65 (dd, J=15.3, 7.7 Hz, 2H), 7.57 (dd, J=8.1, 1.2 Hz, 1H), 7.48 (t, J=7.3 Hz, 1H), 5.95 (s, 1H), 1.22 (s, 3H), 3,01-2,92 (m, IH), 2.86-2.78 (m, IH), 2.26 (t, J 7.2 Hz, 2H), 1.74-1.62 (m, 2H), 1.61-1.53 (m, 2H), 1.33 (m, 4H) ; $^{13}$C NMR (101 MHz, Methanol-d$_4$) δ 177.3, 144.5, 142.6, 141.4, 137.9, 136.9, 136.9, 133.5, 129.1, 128.7, 128.5, 126.3, 97.9, 67.9, 48.6, 39.8, 34.6, 29.4, 27.1, 26.7, 25.6; LR-MS calcd. for C$_{21}$H$_{26}$IN$_2$O$_4$S [M+H]$^+$ 529.07, found 529.08.

EXAMPLE 1

Mu-Opioid Receptor Activity

Transfection. Human or mouse MOR cDNA was transfected alongside Gα$_{oB}$ with RLuc8 inserted at position 91 (Gα$_{oB}$-RLuc8), Gβ$_1$ (β$_1$), and Gγ$_2$ fused to the full-length mVenus at its N terminus (mVenus-γ2) into HEK-293T cells (5×10$^6$ cells/plate) in 10-cm dishes using PEI (Polysciences Inc.; Warrington, Pa.) in a 1:1 ratio diluted in Opti-MEM (Life Technologies Corp.; Grand Island, N.Y.) to assay for G protein activation as described previously (Rives, M.-L. et al. *J. Biol. Chem.* 2012, 287, 27050-4; Negri, A.; Rives, M.-L.; Caspers, M. J. et al. *J. Chem. Inf. Model.* 2013, 53, 521-526). Cells were maintained in the Dulbecco's Modified Eagle Medium (high glucose #11965; Life Technologies) supplemented with 10% FBS (Premium Select, Atlanta Biologicals; Atlanta, Ga.) and 100 U/mL penicillin and 100 μg/mL streptomycin (#15140, Life Technologies). After 24 hours the media was changed, and the experiment was performed 24 hours later (48 hours after transfection).

BRET. Transfected cells were dissociated and resuspended in phosphate-buffered saline (PBS). Approximately 200,000 cells/well were added to a black-framed, white well 96-well plate (#60050; Perkin Elmer; Waltham, Mass.). The microplate was centrifuged and the cells were resuspended in PBS. Then 5 μM of the luciferase substrate coelenterazine H was added to each well for 5 minutes. Following coelenterazine H addition, ligands were added and the BRET signal was measured at 5 minutes on a PHERAstar FS plate reader. Quantification of the BRET signal required calculating the ratio of the light emitted by the energy acceptor, mVenus (510-540 nm), over the light emitted by the energy donor, RLuc8 (485 nm). This drug-induced BRET signal was normalized using the $E_{max}$ of DAMGO as the 100% maximal response for G protein activation. Dose response curves were fit using three-parameter logistics equation in GraphPad Prism 6.

The following compounds listed in Table 1 activated human and/or mouse MOR. Accordingly, the compounds listed in Table 1 are agonists of MOR.

TABLE 1

| Compound | Structure | $EC_{50}$ Human MOR | $EC_{50}$ Mouse MOR |
|---|---|---|---|
| DAMGO | 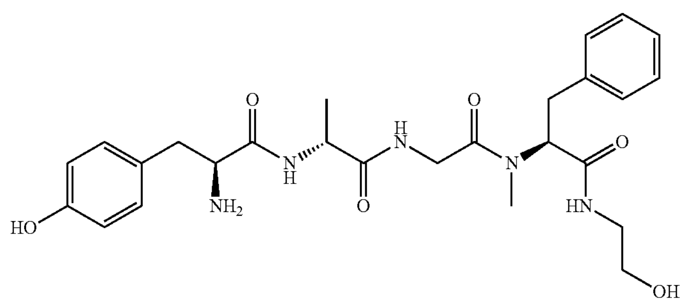 [SMILES: C[C@@H](NC(=O)[C@@H](N)Cc1ccc(O)cc1)C(=O)NCC(=O)N(C)[C@@H](Cc1ccccc1)C(=O)NCCO] | 2.07 ± 1.21 nM | 6.98 ± 2.10 nM |
| 6 | 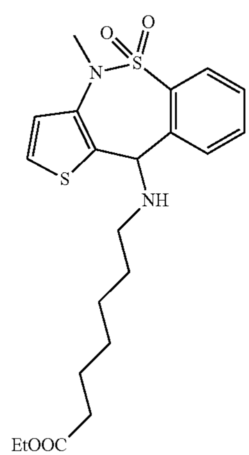 [SMILES: CCOC(=O)CCCCCCNC1c2ccccc2S(=O)(=O)N(C)c2ccsc21] | <10 μM | — |
| 7 | 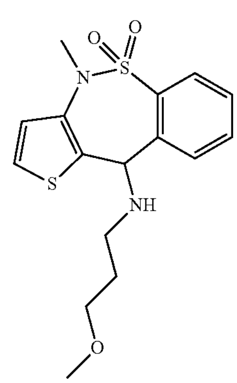 [SMILES: COCCCNC1c2ccccc2S(=O)(=O)N(C)c2ccsc21] | <10 μM | — |

TABLE 1-continued
| Compound | Structure | EC$_{50}$ Human MOR | EC$_{50}$ Mouse MOR |
|---|---|---|---|
| 8 | 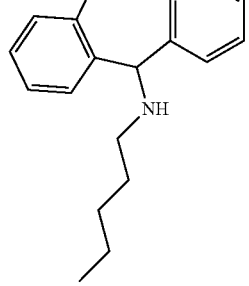 | <10 μM | <10 μM |
| 9 | 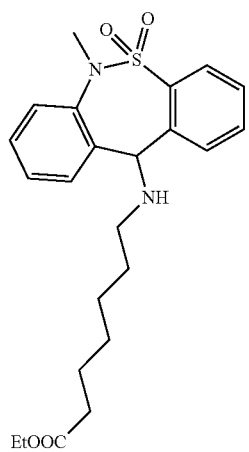 [SMILES: CCOC(=O)CCCCCCNC1c2ccccc2N(C)S(=O)(=O)c2ccccc21] | <10 μM | <10 μM |
| 10 | 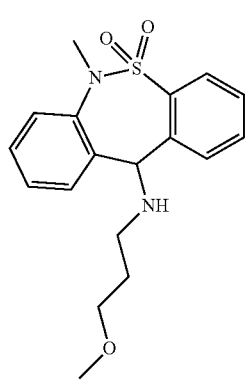 [SMILES: COCCCNC1c2ccccc2N(C)S(=O)(=O)c2ccccc21] | <10 μM | — |
| 11 | 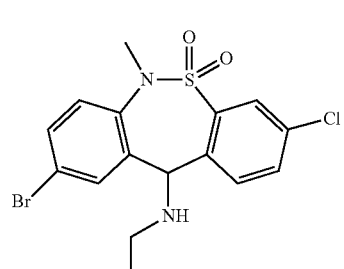 | <10 μM | — |

TABLE 1-continued

| Compound | Structure | EC$_{50}$ Human MOR | EC$_{50}$ Mouse MOR |
|---|---|---|---|
| 13 | 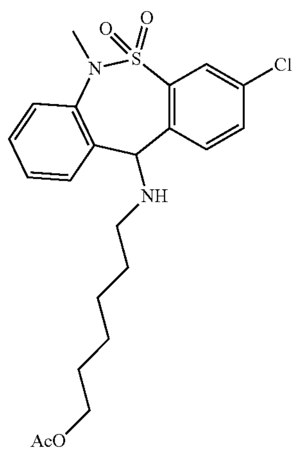 [SMILES: CC(=O)OCCCCCCNC1c2ccccc2N(C)S(=O)(=O)c2cc(Cl)ccc21] | <10 μM | — |
| 14 | 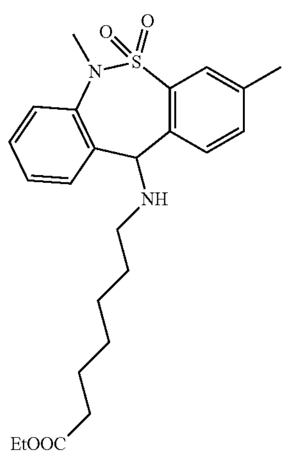 [SMILES: CCOC(=O)CCCCCCNC1c2ccccc2N(C)S(=O)(=O)c2cc(C)ccc21] | <10 μM | — |
| 15 | 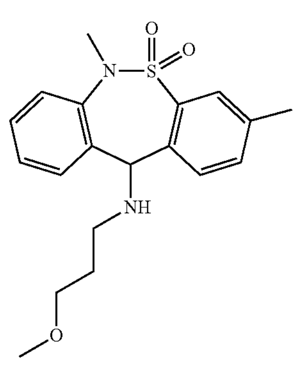 [SMILES: COCCCNC1c2ccccc2N(C)S(=O)(=O)c2cc(C)ccc21] | <10 μM | — |

TABLE 1-continued

| Compound | Structure | EC$_{50}$ Human MOR | EC$_{50}$ Mouse MOR |
|---|---|---|---|
| 16 | 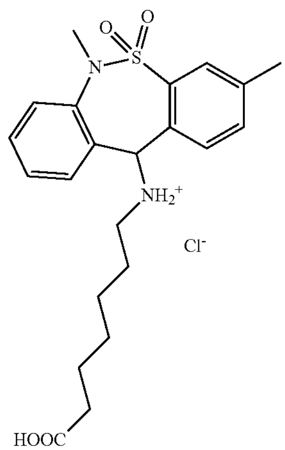 [SMILES: Cc1ccc2c(c1)S(=O)(=O)N(C)c1ccccc1C2[NH2+]CCCCCCC(=O)O ; [Cl-]] | <10 μM | — |
| 17 | 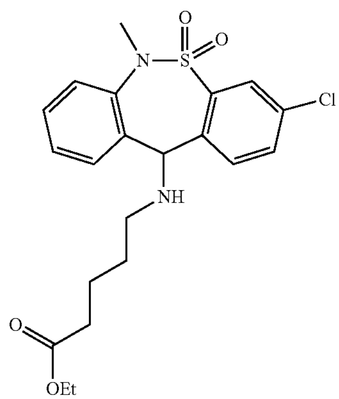 | <10 μM | <10 μM |
| 18 | 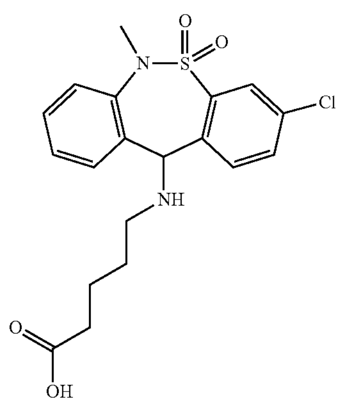 | <10 μM | <10 μM |
| 19 | 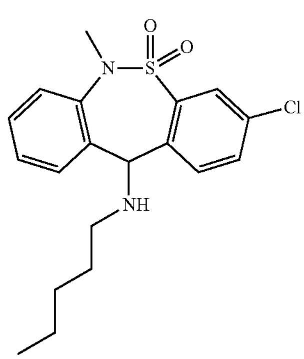 [SMILES: CCCCCNC1c2ccccc2N(C)S(=O)(=O)c2cc(Cl)ccc21] | <10 μM | <10 μM |

TABLE 1-continued

| Compound | Structure | EC$_{50}$ Human MOR | EC$_{50}$ Mouse MOR |
| --- | --- | --- | --- |
| 20 | 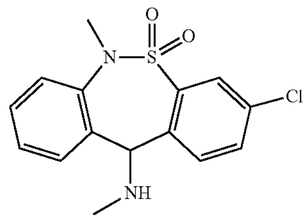 [SMILES: CNC1c2ccccc2N(C)S(=O)(=O)c2cc(Cl)ccc21] | <10 μM | <10 μM |
| 21 | 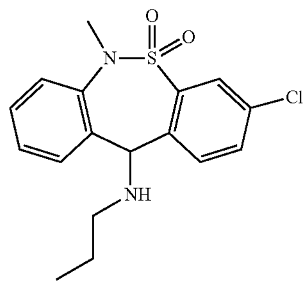 [SMILES: CCCNC1c2ccccc2N(C)S(=O)(=O)c2cc(Cl)ccc21] | <10 μM | <10 μM |
| 22 | 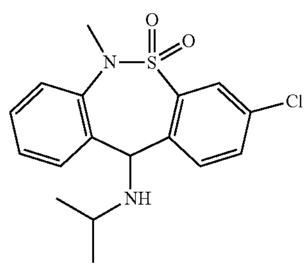 [SMILES: CC(C)NC1c2ccccc2N(C)S(=O)(=O)c2cc(Cl)ccc21] | <10 μM | <10 μM |
| 23 | 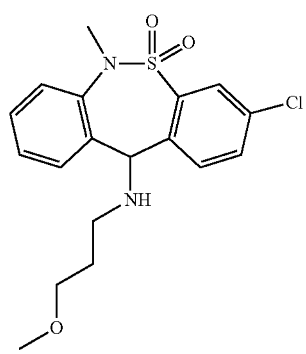 [SMILES: COCCCNC1c2ccccc2N(C)S(=O)(=O)c2cc(Cl)ccc21] | 264.5 ± 85.3 nM | 1.20 ± 0.03 μM |
| 24 | 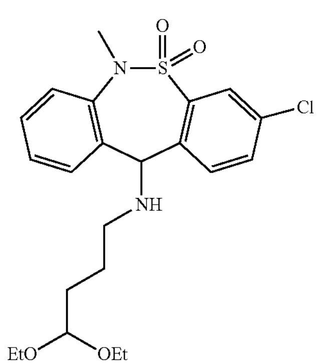 [SMILES: CCOC(CCCNC1c2ccccc2N(C)S(=O)(=O)c2cc(Cl)ccc21)OCC] | <10 μM | — |

TABLE 1-continued

| Compound | Structure | EC$_{50}$ Human MOR | EC$_{50}$ Mouse MOR |
|---|---|---|---|
| 25 | 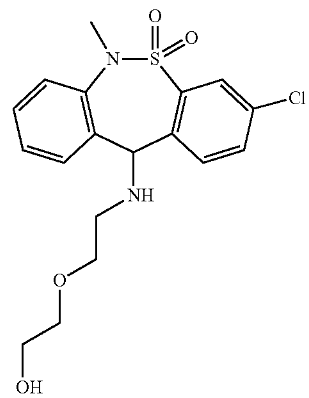 | 8.592 ± 0.5 μM | — |
| 26 | 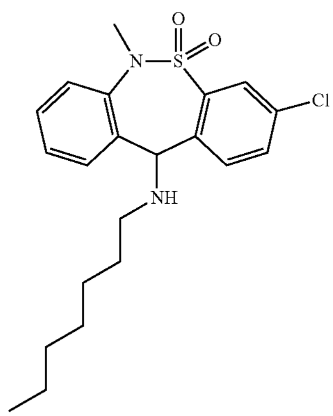 [SMILES: CCCCCCCNC1c2ccccc2N(C)S(=O)(=O)c2cc(Cl)ccc21] | <10 μM | — |
| 27 | 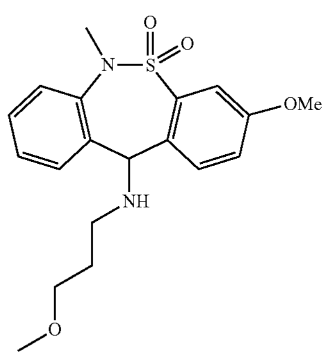 [SMILES: COCCCNC1c2ccccc2N(C)S(=O)(=O)c2cc(OC)ccc21] | <10 μM | — |
| 28 | 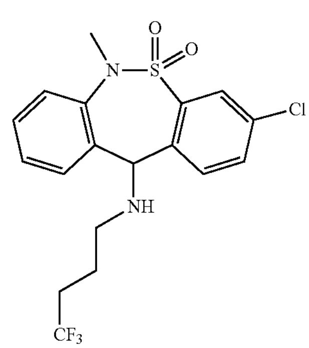 [SMILES: CN1c2ccccc2C(NCCCC(F)(F)F)c2ccc(Cl)cc2S1(=O)=O] | <10 μM | — |

TABLE 1-continued

| Compound | Structure | EC$_{50}$ Human MOR | EC$_{50}$ Mouse MOR |
|---|---|---|---|
| 29 | 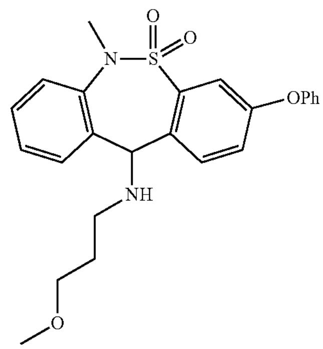 [SMILES: COCCCNC1c2ccccc2N(C)S(=O)(=O)c2cc(Oc3ccccc3)ccc21] | <10 μM | — |
| 31 | 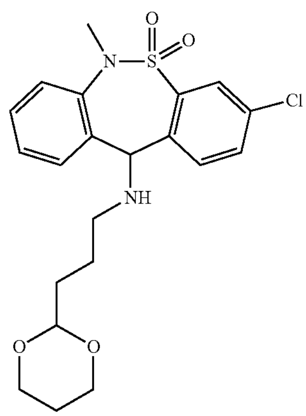 [SMILES: CN1c2ccccc2C(NCCCC2OCCCO2)c2ccc(Cl)cc2S1(=O)=O] | <10 μM | — |
| 32 | 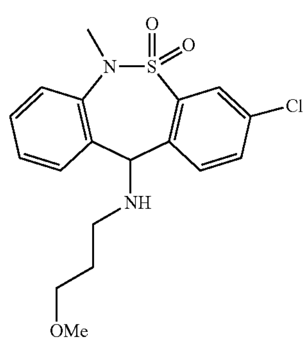 [SMILES: COCCCNC1c2ccccc2N(C)S(=O)(=O)c2cc(Cl)ccc21] | 563.1 ± 247 nM | — |
| 33 | 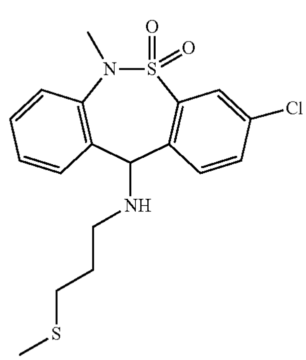 | <10 μM | — |

TABLE 1-continued

| Compound | Structure | EC$_{50}$ Human MOR | EC$_{50}$ Mouse MOR |
|---|---|---|---|
| 34 | 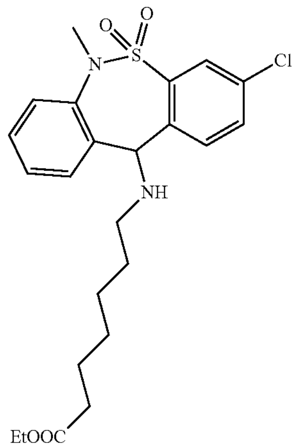 [SMILES: CCOC(=O)CCCCCCNC1c2ccccc2N(C)S(=O)(=O)c2cc(Cl)ccc21] | 657 ± 366 nM | — |
| 35 | 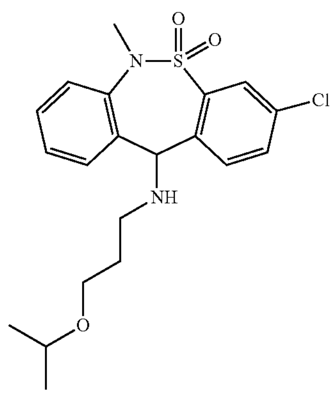 [SMILES: CC(C)OCCCNC1c2ccccc2N(C)S(=O)(=O)c2cc(Cl)ccc21] | <10 μM | — |
| 36 | 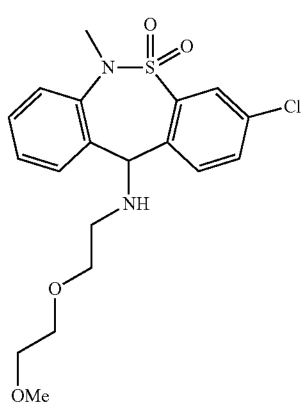 [SMILES: COCCOCCNC1c2ccccc2N(C)S(=O)(=O)c2cc(Cl)ccc21] | <10 μM | — |

TABLE 1-continued

| Compound | Structure | EC$_{50}$ Human MOR | EC$_{50}$ Mouse MOR |
|---|---|---|---|
| 37 | 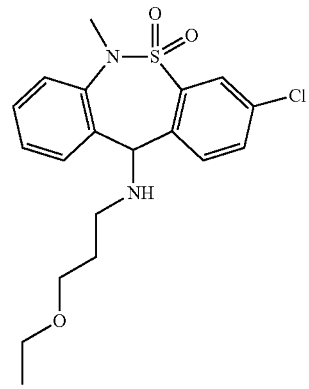 [SMILES: CCOCCCNC1c2ccccc2N(C)S(=O)(=O)c2cc(Cl)ccc21] | 893 ± 147 nM | — |
| 39 | 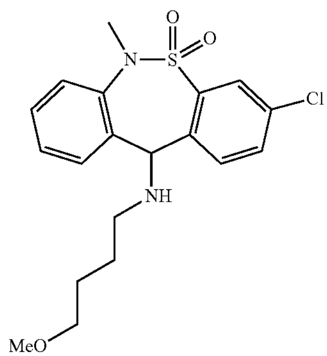 [SMILES: COCCCCNC1c2ccccc2N(C)S(=O)(=O)c2cc(Cl)ccc21] | <10 μM | — |
| 40 | 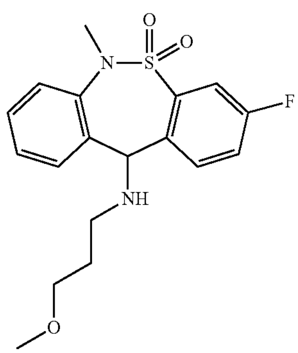 [SMILES: COCCCNC1c2ccccc2N(C)S(=O)(=O)c2cc(F)ccc21] | 5.53 ± 0.25 μM | — |
| 41 | 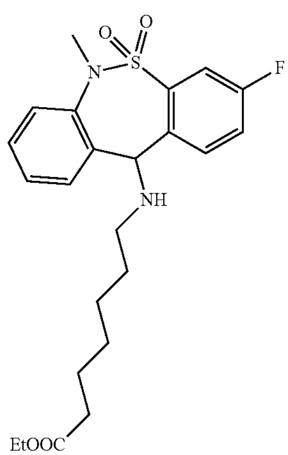 [SMILES: CCOC(=O)CCCCCCNC1c2ccccc2N(C)S(=O)(=O)c2cc(F)ccc21] | 2.04 ± 0.334 μM | — |

TABLE 1-continued

| Compound | Structure | EC$_{50}$ Human MOR | EC$_{50}$ Mouse MOR |
|---|---|---|---|
| 42 | 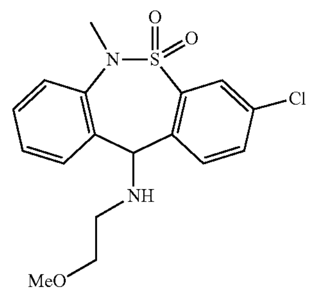 [SMILES: COCCNC1c2ccccc2N(C)S(=O)(=O)c2cc(Cl)ccc21] | <10 μM | — |
| 43 | 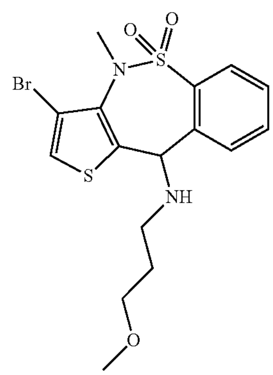 [SMILES: COCCCNC1c2ccccc2S(=O)(=O)N(C)c2c(Br)csc21] | <20 μM | — |
| 44 | 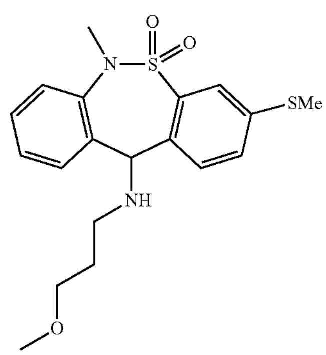 [SMILES: COCCCNC1c2ccccc2N(C)S(=O)(=O)c2cc(SC)ccc21] | <10 μM | <10 μM |
| 45 | 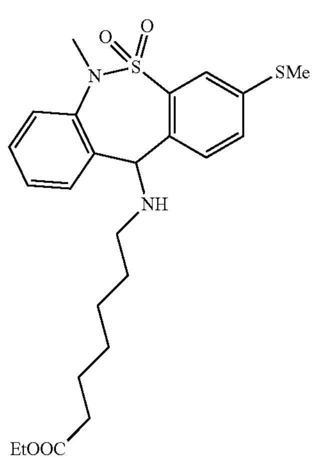 [SMILES: CCOC(=O)CCCCCCNC1c2ccccc2N(C)S(=O)(=O)c2cc(SC)ccc21] | <10 μM | <10 μM |

TABLE 1-continued

| Compound | Structure | EC$_{50}$ Human MOR | EC$_{50}$ Mouse MOR |
|---|---|---|---|
| 46 | 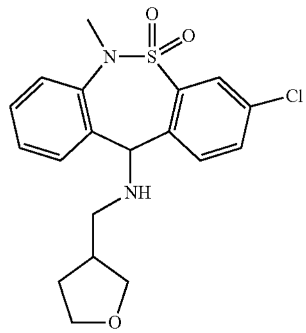 [SMILES: CN1c2ccccc2C(NCC2CCOC2)c2ccc(Cl)cc2S1(=O)=O] | <10 µM | — |
| 47 | 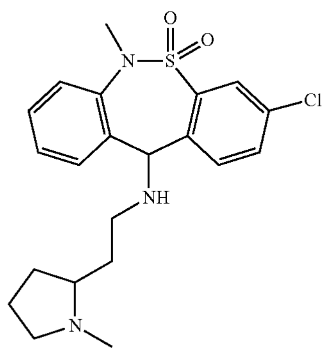 [SMILES: CN1CCCC1CCNC1c2ccccc2N(C)S(=O)(=O)c2cc(Cl)ccc21] | <20 µM | — |
| 48 | 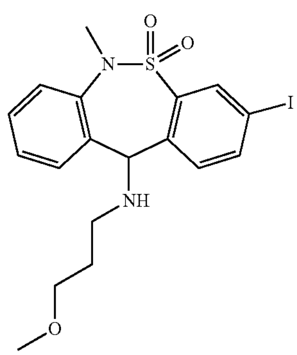 [SMILES: COCCCNC1c2ccccc2N(C)S(=O)(=O)c2cc(I)ccc21] | 15.2 ± 6.9 nM | |
| 49 | 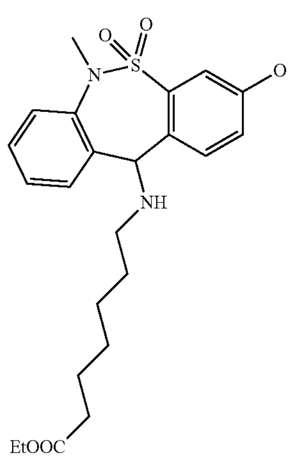 [SMILES: CCOC(=O)CCCCCCNC1c2ccccc2N(C)S(=O)(=O)c2cc(O)ccc21] | 137 ± 17 nM | — |

TABLE 1-continued
| Compound | Structure | EC$_{50}$ Human MOR | EC$_{50}$ Mouse MOR |
|---|---|---|---|
| 50 | 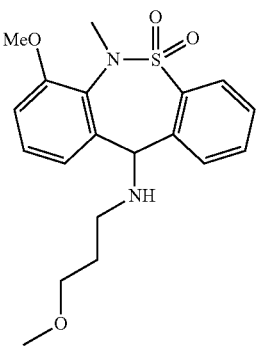 [SMILES: COCCCNC1c2ccccc2S(=O)(=O)N(C)c2c(OC)cccc21] | <20 μM | — |
| 51 | 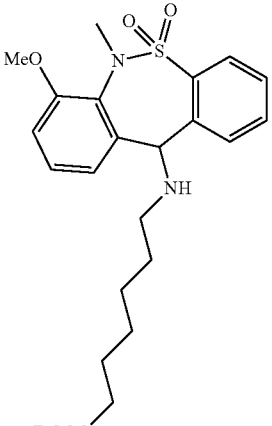 | <10 μM | — |
| 52 | 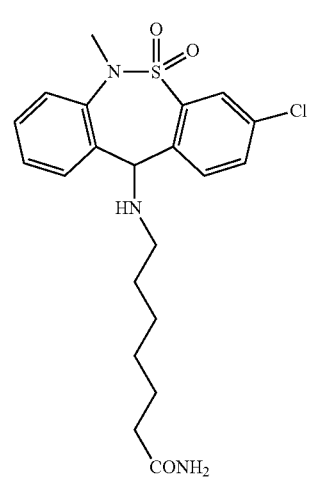 [SMILES: CN1c2ccccc2C(NCCCCCCC(N)=O)c2ccc(Cl)cc2S1(=O)=O] | <10 μM | — |

TABLE 1-continued

| Compound | Structure | EC$_{50}$ Human MOR | EC$_{50}$ Mouse MOR |
|---|---|---|---|
| 53 | 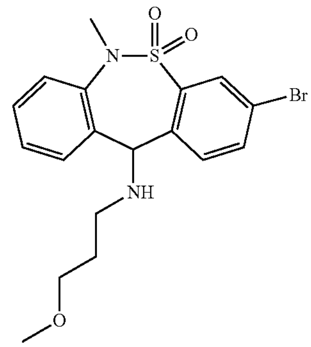 [SMILES: COCCCNC1c2ccccc2N(C)S(=O)(=O)c2cc(Br)ccc21] | 74.1 ± 17.9 nM | — |
| 55 | 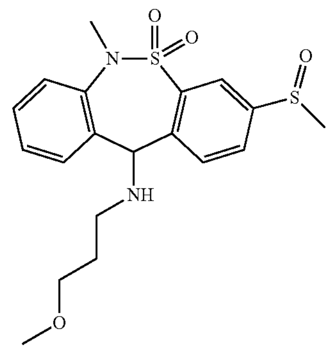 [SMILES: COCCCNC1c2ccccc2N(C)S(=O)(=O)c2cc(S(C)=O)ccc21] | <20 µM | — |
| 56 | 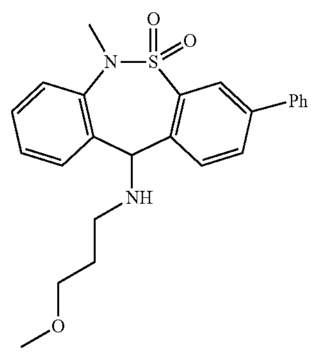 [SMILES: COCCCNC1c2ccccc2N(C)S(=O)(=O)c2cc(-c3ccccc3)ccc21] | <10 µM | — |
| 57 | 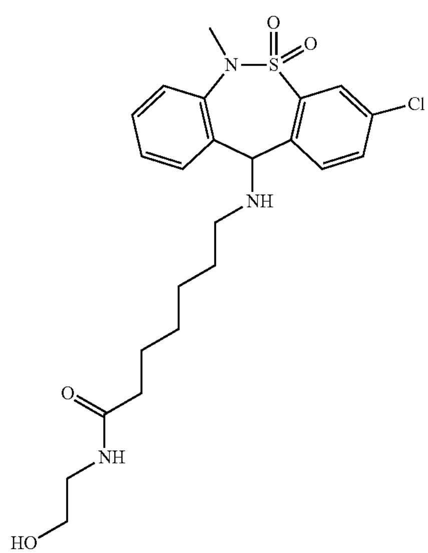 [SMILES: CN1c2ccccc2C(NCCCCCCC(=O)NCCO)c2ccc(Cl)cc2S1(=O)=O] | <10 µM | — |

TABLE 1-continued
| Compound | Structure | EC$_{50}$ Human MOR | EC$_{50}$ Mouse MOR |
|---|---|---|---|
| 58 | 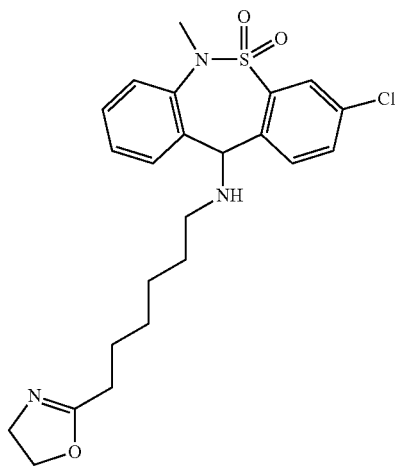 [SMILES: CN1c2ccccc2C(NCCCCCCC2=NCCO2)c2ccc(Cl)cc2S1(=O)=O] | <10 μM | — |
| 59 | 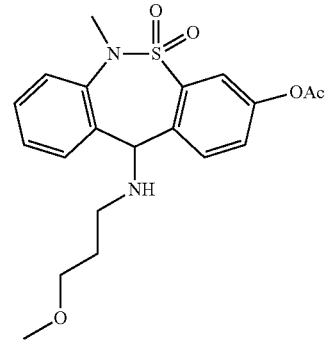 [SMILES: COCCCNC1c2ccccc2N(C)S(=O)(=O)c2cc(OC(C)=O)ccc21] | <10 μM | — |
| 60 | 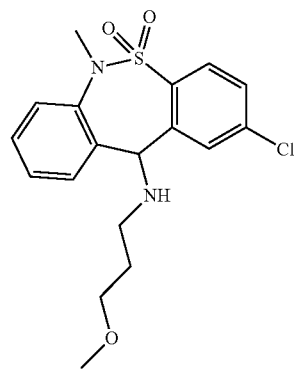 [SMILES: COCCCNC1c2ccccc2N(C)S(=O)(=O)c2ccc(Cl)cc21] | <20 μM | — |

| Compound | Structure | EC$_{50}$ Human MOR | EC$_{50}$ Mouse MOR |
|---|---|---|---|
| 61 | 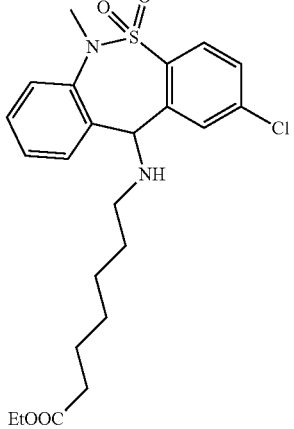 | <10 μM | — |
| 62 | 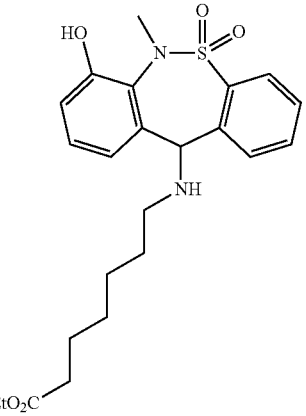 | >20 μM | — |
| 63 | 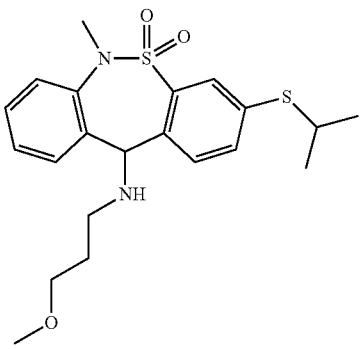 [SMILES: COCCCNC1c2ccccc2N(C)S(=O)(=O)c2cc(SC(C)C)ccc21] | <10 μM | — |
| 64 | 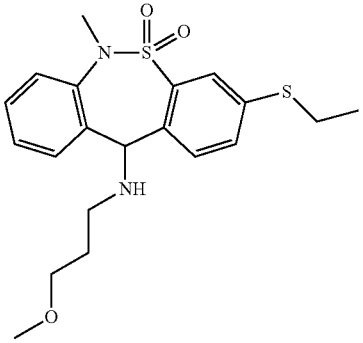 [SMILES: CCSc1ccc2c(c1)S(=O)(=O)N(C)c1ccccc1C2NCCCOC] | <10 μM | — |

TABLE 1-continued
| Compound | Structure | EC$_{50}$ Human MOR | EC$_{50}$ Mouse MOR |
|---|---|---|---|
| 65 | 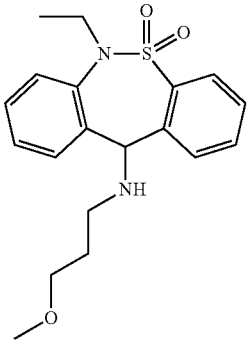 [SMILES: CCN1c2ccccc2C(NCCCOC)c2ccccc2S1(=O)=O] | >20 μM | — |
| 66 | 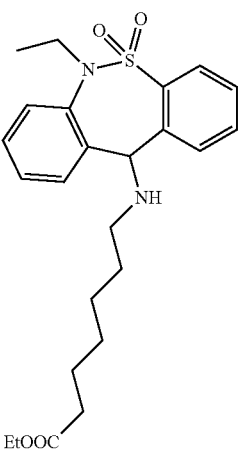 [SMILES: CCOC(=O)CCCCCCNC1c2ccccc2N(CC)S(=O)(=O)c2ccccc21] | <10 μM | — |
| 67 | 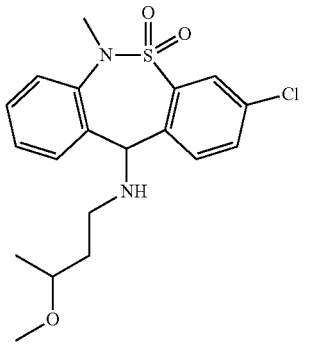 [SMILES: COC(C)CCNC1c2ccccc2N(C)S(=O)(=O)c2cc(Cl)ccc21] | <10 μM | — |
| 68 | 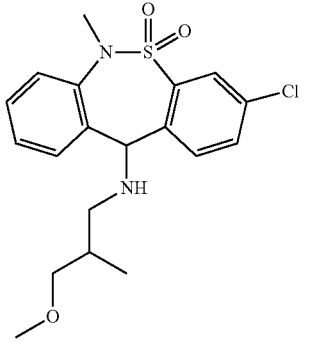 [SMILES: COCC(C)CNC1c2ccccc2N(C)S(=O)(=O)c2cc(Cl)ccc21] | <10 μM | — |

TABLE 1-continued
| Compound | Structure | EC$_{50}$ Human MOR | EC$_{50}$ Mouse MOR |
|---|---|---|---|
| 69 | 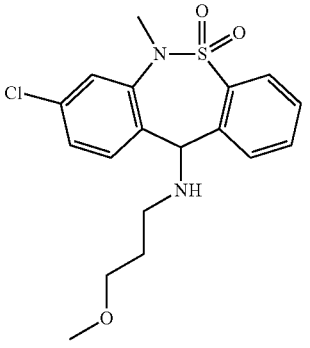 [SMILES: COCCCNC1c2ccc(Cl)cc2N(C)S(=O)(=O)c2ccccc21] | <20 µM | — |
| 70 | 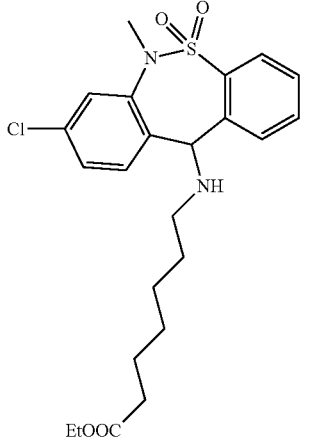 [SMILES: CCOC(=O)CCCCCCNC1c2ccc(Cl)cc2N(C)S(=O)(=O)c2ccccc21] | <10 µM | — |
| 71 | 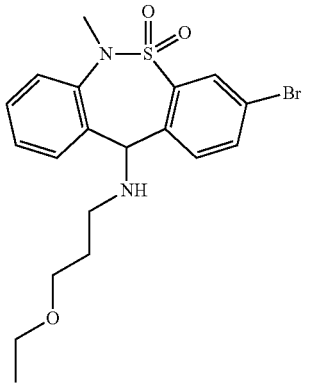 [SMILES: CCOCCCNC1c2ccccc2N(C)S(=O)(=O)c2cc(Br)ccc21] | 222 ± 78 nM | — |
| 72 | 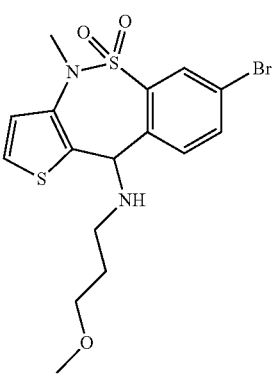 [SMILES: COCCCNC1c2ccc(Br)cc2S(=O)(=O)N(C)c2ccsc21] | <10 µM | — |

TABLE 1-continued
| Compound | Structure | EC$_{50}$ Human MOR | EC$_{50}$ Mouse MOR |
|---|---|---|---|
| 73 | 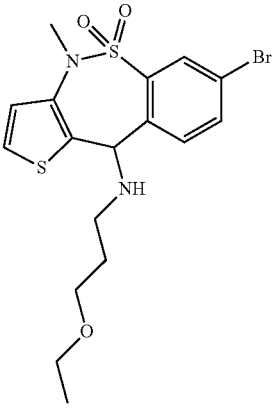 [SMILES: CCOCCCNC1c2ccc(Br)cc2S(=O)(=O)N(C)c2ccsc21] | <10 μM | — |
| 74 | 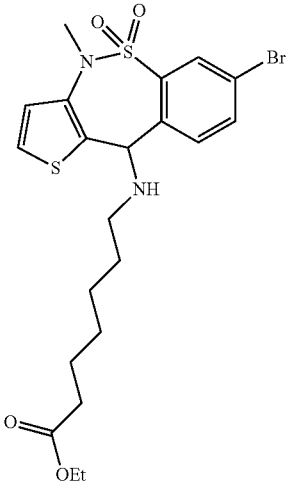 [SMILES: CCOC(=O)CCCCCCNC1c2ccc(Br)cc2S(=O)(=O)N(C)c2ccsc21] | <10 μM | — |
| 75 | 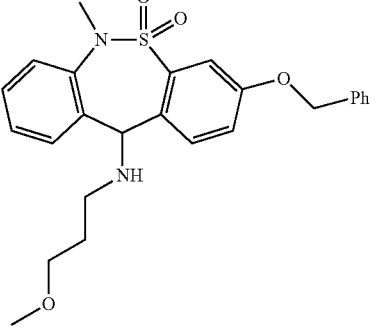 | >20 μM | — |

TABLE 1-continued

| Compound | Structure | EC$_{50}$ Human MOR | EC$_{50}$ Mouse MOR |
|---|---|---|---|
| 76 | 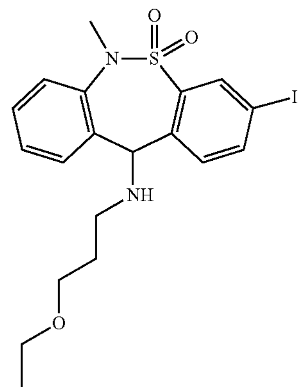 [SMILES: CCOCCCNC1c2ccccc2N(C)S(=O)(=O)c2cc(I)ccc21] | 145 nM | — |
| 77 | 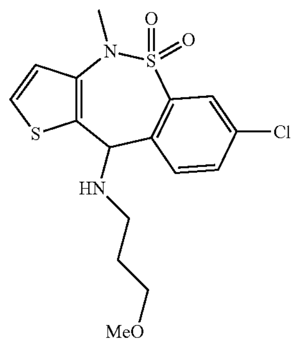 [SMILES: COCCCNC1c2ccc(Cl)cc2S(=O)(=O)N(C)c2ccsc21] | <10 μM | — |
| 78 | 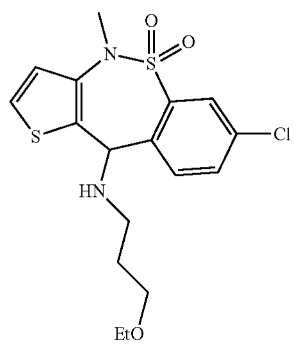 [SMILES: CCOCCCNC1c2ccc(Cl)cc2S(=O)(=O)N(C)c2ccsc21] | <10 μM | — |
| 79 | 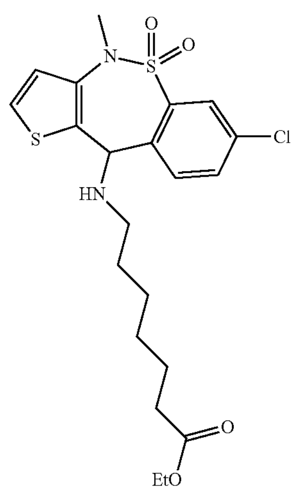 [SMILES: CCOC(=O)CCCCCCNC1c2ccc(Cl)cc2S(=O)(=O)N(C)c2ccsc21] | <10 μM | — |

TABLE 1-continued

| Compound | Structure | EC$_{50}$ Human MOR | EC$_{50}$ Mouse MOR |
|---|---|---|---|
| 80 | 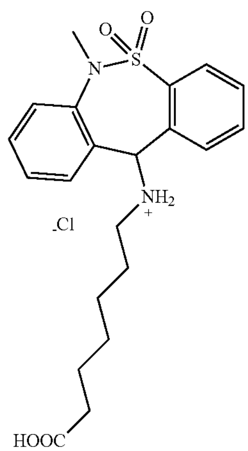 [SMILES: CN1c2ccccc2C(NCCCCCCC(=O)O)c2ccccc2S1(=O)=O] | <10 μM | <10 μM |
| 81 | 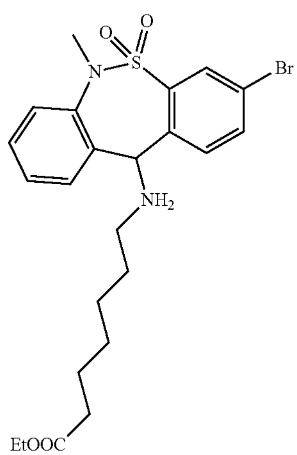 [SMILES: CCOC(=O)CCCCCCNC1c2ccccc2N(C)S(=O)(=O)c2cc(Br)ccc21] | 573 nM | — |
| 82 | 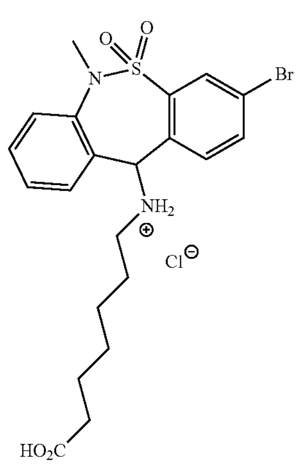 [SMILES: CN1c2ccccc2C([NH2+]CCCCCCC(=O)O)c2ccc(Br)cc2S1(=O)=O ; [Cl-]] | 122 nM | — |

TABLE 1-continued

| Compound | Structure | EC$_{50}$ Human MOR | EC$_{50}$ Mouse MOR |
|---|---|---|---|
| 83 | [structure: methyl-N-S(O)$_2$ dibenzothiazepine with Cl, bearing CH(NH$_2$)-CH$_2$CH$_2$CH$_2$-OH side chain] | 1.81 μM | — |
| 84 | [structure: methyl-N-S(O)$_2$ dibenzothiazepine with I, bearing CH(NH$_2$)-(CH$_2$)$_n$-CO$_2$H side chain with Cl$^−$ counterion] | 40.0 nM | — |
| tianeptine | [structure: methyl-N-S(O)$_2$ dibenzothiazepine with Cl, bearing CH(NH)-(CH$_2$)$_n$-CO$_2^−$ Na$^+$ side chain] | 194 ± 70 nM | 641 ± 120 nM |

Data represents mean ± SEM of various independent trials (n > 2);
"—" indicates not tested.

EXAMPLE 2

Potency of Analogs Relative to Tianeptine

Potency of compounds showing improvement over tianeptine. Specifically, the data show that R$_2$ether side chains are significantly more potent than analogous alcohol side chains (which were inactive or very low potency). Further, the data show the strong trend for increasing potency as the size of the halogen substituent is increased from fluoro through iodo, a trend that holds across several example subgenera. Accordingly, the compounds dislosed herein have increasing potency based on the following trend: R$_5$=I>R$_5$=Br>R$_5$=Cl>R$_5$=F. Compounds with activity similar to tianeptine have improved pharmacokinetic profiles.

TABLE 2

| Compound | Structure | EC$_{50}$ Human MOR | EC$_{50}$ Mouse MOR |
|---|---|---|---|
| DAMGO | 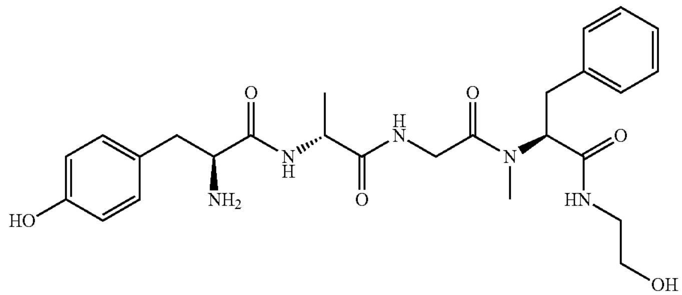 [SMILES: C[C@@H](NC(=O)[C@@H](N)Cc1ccc(O)cc1)C(=O)NCC(=O)N(C)[C@@H](Cc1ccccc1)C(=O)NCCO] | 2.07 ± 1.21 nM | 6.98 ± 2.10 nM |
| 23 | 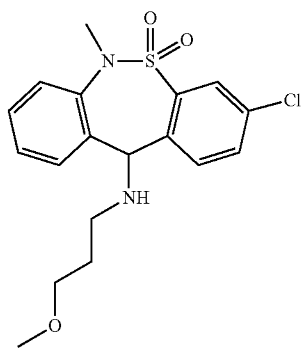 [SMILES: COCCCNC1c2ccccc2N(C)S(=O)(=O)c2cc(Cl)ccc21] | 264.5 ± 85.3 nM | 1.20 ± 0.03 µM |
| 83 | 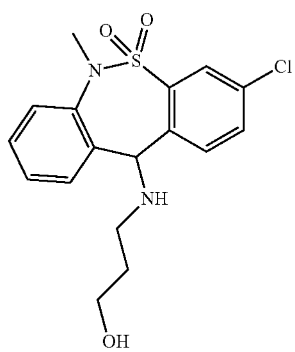 [SMILES: CN1c2ccccc2C(NCCCO)c2ccc(Cl)cc2S1(=O)=O] | 1.81 µM | — |
| 32 | 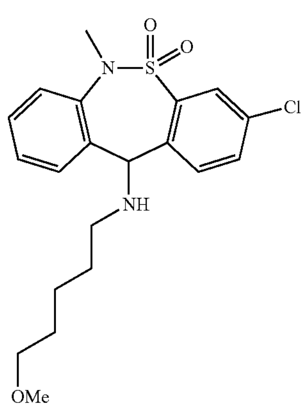 [SMILES: COCCCCCNC1c2ccccc2N(C)S(=O)(=O)c2cc(Cl)ccc21] | 563.1 ± 247 nM | — |

TABLE 2-continued

| Compound | Structure | EC$_{50}$ Human MOR | EC$_{50}$ Mouse MOR |
| --- | --- | --- | --- |
| 30 | *structure* | X | — |
| 25 | *structure* | 8.592 ± 0.5 µM | — |
| 40 | *structure* | 5.53 ± 0.25 µM | — |
| 23 | *structure* | 264.5 ± 85.3 nM | 1.20 ± 0.03 µM |

TABLE 2-continued

| Compound | Structure | EC$_{50}$ Human MOR | EC$_{50}$ Mouse MOR |
|---|---|---|---|
| 53 | 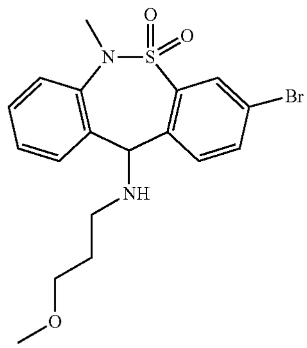 [SMILES: COCCCNC1c2ccccc2N(C)S(=O)(=O)c2cc(Br)ccc21] | 74.1 ± 17.9 nM | — |
| 48 | 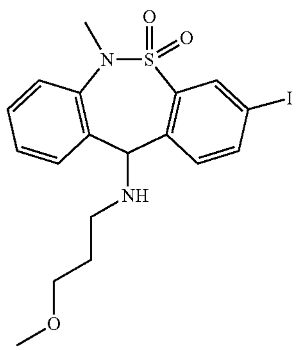 [SMILES: COCCCNC1c2ccccc2N(C)S(=O)(=O)c2cc(I)ccc21] | 15.2 ± 6.9 nM | |
| 37 | 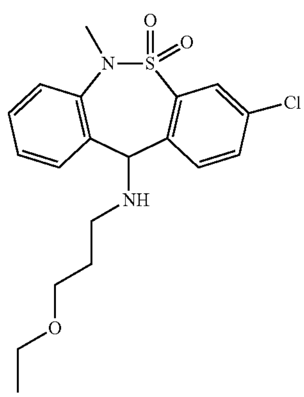 [SMILES: CCOCCCNC1c2ccccc2N(C)S(=O)(=O)c2cc(Cl)ccc21] | 893 ± 147 nM | — |
| 71 | 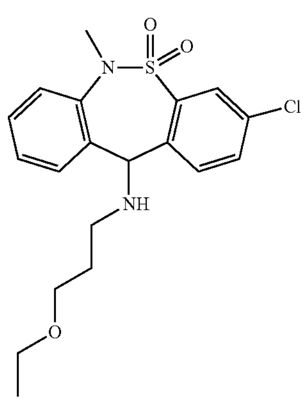 [SMILES: CCOCCCNC1c2ccccc2N(C)S(=O)(=O)c2cc(Cl)ccc21] | 222 ± 78 nM | — |

TABLE 2-continued
| Compound | Structure | EC$_{50}$ Human MOR | EC$_{50}$ Mouse MOR |
|---|---|---|---|
| 76 | 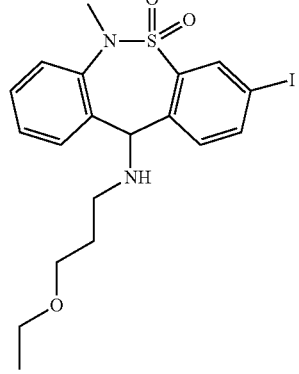 | 145 nM | — |
| 41 | 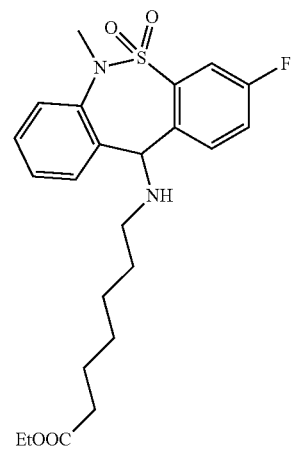 [SMILES: CCOC(=O)CCCCCCNC1c2ccccc2N(C)S(=O)(=O)c2cc(F)ccc21] | 2.04 ± 0.334 μM | — |
| 34 | 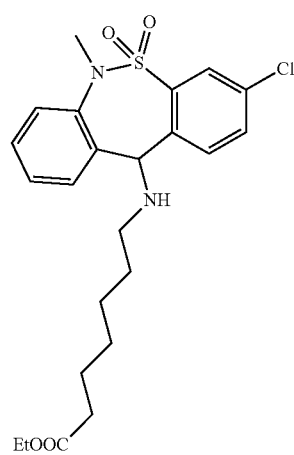 [SMILES: CCOC(=O)CCCCCCNC1c2ccccc2N(C)S(=O)(=O)c2cc(Cl)ccc21] | 657 ± 366 nM | — |

TABLE 2-continued
| Compound | Structure | EC$_{50}$ Human MOR | EC$_{50}$ Mouse MOR |
|---|---|---|---|
| 81 | 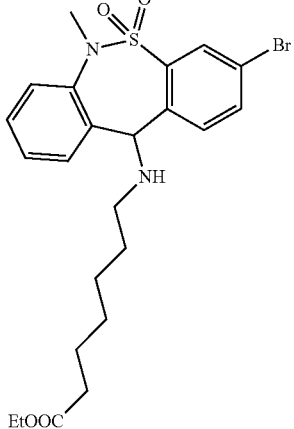 | 573 nM | — |
| 49 | 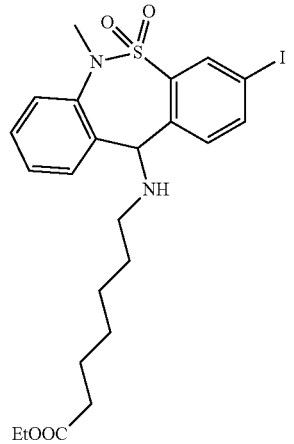 [SMILES: CCOC(=O)CCCCCCNC1c2ccccc2N(C)S(=O)(=O)c2cc(I)ccc21] | 137 ± 17 nM | — |
| tianeptine | 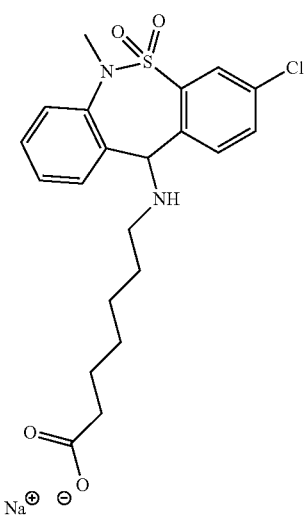 [SMILES: CN1c2ccccc2C(NCCCCCCC(=O)[O-])c2ccc(Cl)cc2S1(=O)=O ; [Na+]] | 194 ± 70 nM | 641 ± 120 nM |

TABLE 2-continued

| Compound | Structure | EC$_{50}$ Human MOR | EC$_{50}$ Mouse MOR |
|---|---|---|---|
| 82 | [structure: 6-methyl-6,11-dihydrodibenzo[1,2]thiazepine 5,5-dioxide with Br substituent, NH$_2^+$ Cl$^-$ side chain terminating in HO$_2$C] | 122 nM | — |
| 84 | [structure: 6-methyl-6,11-dihydrodibenzo[1,2]thiazepine 5,5-dioxide with I substituent, NH$_2^+$ Cl$^-$ side chain terminating in EtOOC] | 40.0 nM | — |

Data represent mean ± SEM of various independent trials.
"X" indicates not active (EC$_{50}$ > 50 µM);
"—" indicates not tested.

EXAMPLE 3

MOR Agonism of Additional 6-methyl-6,11-dihydrodibenzo[1,2]thiazepine 5,5-dioxide Compounds An additional aspect of the invention provides analogs of the compounds of Table 1 that are MOR agonists. Additional 6-methyl-6,11-dihydrodibenzo[1,2]thiazepine 5,5-dioxide compounds, which are analogs of those described in Table 1, are tested in in vitro human and mouse MOR assays. These analogs agonize MOR activity. Additional compounds disclosed herein which are analogs of those described in Table 1 or 2, are tested in in vitro human and mouse MOR assays. These analogs agonize MOR activity.

An additional aspect of the invention provides analogs of the compounds of Table 2 that are MOR agonists. Additional 6-methyl-6,11-dihydrodibenzo[1,2]thiazepine 5,5-dioxide compounds, which are analogs of those describe in Table 2, are tested in in vitro human and mouse MOR assays. These analogs agonize NOR activity. Compounds which are analogs of those described in Table 2 are tested in in vitro human and mouse MOR assays. These analogs agonize MOR activity.

EXAMPLE 4

Administration of MOR Agonists

An amount of any one of compounds 6-11, 13-29, 31-53 or 55-84 is administered to a subject afflicted with depression or major depression. The amount of the compound is effective to treat the subject afflicted with depression or major depression.

An amount of any one of compounds 6-11, 13-29, 31-53 or 55-84 is administered to a subject afflicted with pain. The amount of the compound is effective to treat the subject afflicted with pain.

An amount of any one of compounds 6-11, 13-29, 31-53 or 55-84 is administered to a subject afflicted with anxiety. The amount of the compound is effective to treat the subject afflicted with anxiety.

An amount of any one of the compounds dislosed herein, which are analogs of those describe din Table 1 or 2, is administered to a subject afflicted with depression or major depression. The amount of the compound is effective to treat the subject afflicted with depression or major depression.

An amount of any one of the compounds dislosed herein, which are analogs of those describe din Table 1 or 2, is administered to a subject afflicted with pain. The amount of the compound is effective to treat the subject afflicted with pain.

An amount of any one of the compounds dislosed herein, which are analogs of those describe din Table 1 or 2, is administered to a subject afflicted with anxiety. The amount of the compound is effective to treat the subject afflicted with anxiety.

An amount of any one of compounds 59-84 is administered to a subject afflicted with pain. The amount of the compound is effective to treat the subject afflicted with depression or major depression.

An amount of any one of compounds 59-84 is administered to a subject afflicted with pain. The amount of the compound is effective to treat the subject afflicted with pain.

An amount of any one of compounds 59-84 is administered to a subject afflicted with anxiety. The amount of the compound is effective to treat the subject afflicted with anxiety.

EXAMPLE 5

Metabolism and Pharmacokinetics

The pharmacokinetics and brain distribution of tianeptine and 23 were determined as follows in male C57BL/6 mice following a single intraperitoneal dose administration. For each compound, a group of twenty four male mice were administered with a solution formulation of the drug in normal saline intraperitoneally at a dose of 10 mg/kg. Blood samples (approximately 60 µL) were collected under light isoflurane anesthesia from the retro orbital plexus at 0.08, 0.25, 0.5, 1, 2, 4, 8 and 24 hr. Plasma samples were separated by centrifugation of whole blood and stored below −70° C. until bioanalysis. Immediately after collection of blood, brain samples were collected from each mouse at 0.08, 0.25, 0.5, 1, 2, 4, 8 and 24 hr. Brain samples were homogenized using ice-cold phosphate buffer saline (pH 7.4) and homogenates were stored below −70° C. until analysis. Total homogenate volume was three times the tissue weight. All samples were processed for analysis by protein precipitation using acetonitrile (ACN) and analyzed with fit-for-purpose LC/MS/MS method (LLOQ-1.01 ng/mL in plasma and brain). Pharmacokinetic parameters were calculated using the non-compartmental analysis tool of Phoenix WinNonlin® (Version 6.3).

Tianeptine is known to be metabolized primarily by β-oxidation of the carboxylic acid side chain, in a manner similar to fatty acids (Grislain, L et al 1990) Other carboxylic analogs known in the prior art are expected to be metabolized in a similar manner. Therefore, replacement of the carboxylic acid side chain with functionality that cannot be easily metabolized via β-oxidation results in compounds with slower metabolism, longer duration of action, and improved therapeutic profile. The compounds disclosed herein with modified side chains (e.g. ethers, esters, or alkyl groups) prevent β-oxidation. For example, the ether compound 23 has a much longer half-life and higher systemic exposure (AUC) than tianeptine, and is therefore expected to have an improved therapeutic profile (Tables 3 and 4).

Other compounds disclosed herein including compounds having an ether, polyether or ester at the $R_2$ group have an analogous half-life and systemic exposure to 23. Other compounds disclosed have pharmacokinetic profiles similar to compound 23. Further, these compounds have improved pharmacokinetics relative to tianeptine.

TABLE 3

Pharmacokinetic parameters of tianeptine in plasma and brain following a single intraperitoneal administration in male C57BL/6 mice.

| Route | Matrix | Dose (mg/kg) | $T_{max}$ (hr) | $C_{max}$ (ng/mL) | $AUC_{last}$ (hr*ng/mL) | $T_{1/2}$ (hr) | CL (mL/min/kg) | $MRT_{last}$ (hr) |
|---|---|---|---|---|---|---|---|---|
| i.p. | Plasma | 10 | 0.08 | 4879.11 | 1110.23 | 0.12 | 149.65 | 0.19 |
|  | Brain* |  | 0.08 | 356.77 | 104.41 | 0.14 | 1580.88 | 0.23 |

*brain conc. and AUC expressed as ng/g and hr*ng/g respectively

TABLE 4

Pharmacokinetic parameters of 23 in plasma and brain following a single intraperitoneal administration in male C57BL/6 mice.

| Route | Matrix | Dose (mg/kg) | $T_{max}$ (hr) | $C_{max}$ (ng/mL) | $AUC_{last}$ (hr*ng/mL) | $T_{1/2}$ (hr) | CL (mL/min/kg) | $MRT_{last}$ (hr) |
|---|---|---|---|---|---|---|---|---|
| i.p. | Plasma | 10 | 0.25 | 1535.74 | 3058.80 | 3.93 | 44.27 | 2.29 |
|  | Brain* |  | 0.08 | 377.63 | 335.03 | 5.12 | 260.44 | 1.27 |

*brain conc. and AUC expressed as ng/g and hr*ng/g respectively

EXAMPLE 6

Esters as Prodrugs

Carboxylic esters are well known as prodrugs for the corresponding carboxylic acids obtained by hydrolysis (Beaumont, et al. 2003). Such ester prodrugs show improved oral bioavailability, better brain penetration, or longer duration of action compared to their carboxylic acid counterparts. Accordingly, compounds of this application having an ester side chain, although biologically active on their own, also act as prodrugs for the corresponding carboxylic acids. Further, one skilled in the art will be able to apply the methods and knowledge of this application to prepare additional prodrugs. For example, the type of ester (e.g. methyl, ethyl, propyl, isopropyl, phenyl) or the length of the side chain may be varied to adjust the activity and pharmacokinetic properties of the prodrugs and their corresponding carboxylic acid hydrolysis products. Examples of additional prodrugs and their preparation are shown in Scheme 1.
Compounds 6, 9, 14, 17, 34, 41, 45, 49, 51, 61, 62, 66, 70, 74, 79, and 81 act as produrgs to deliver the corresponding acid.
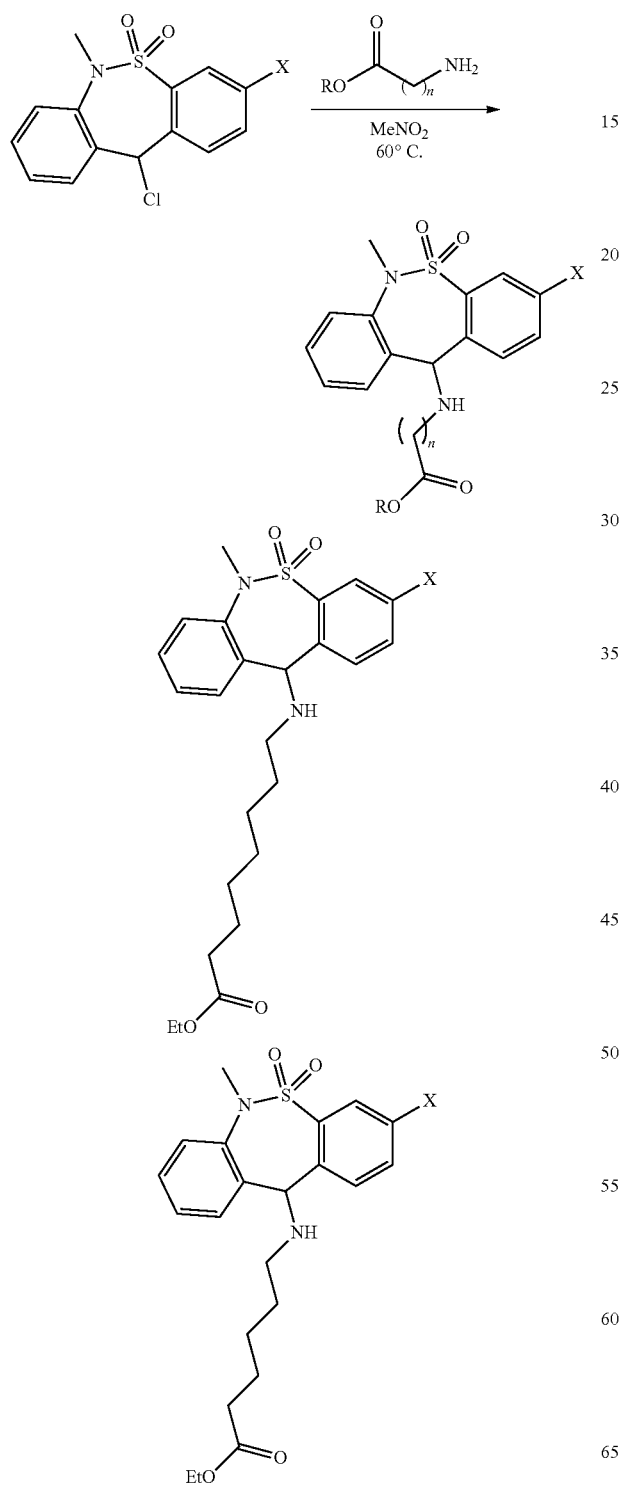
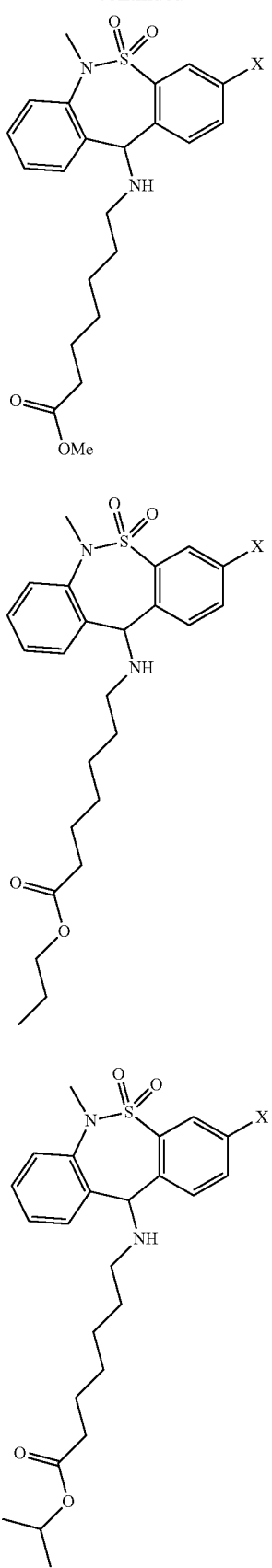

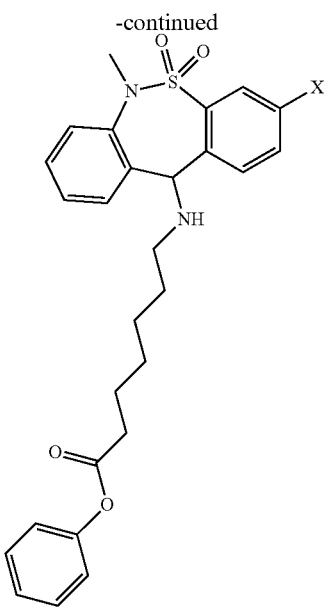

X = F, Cl, Br, I, Me, SMe, OMe, OPh R = Me, Et, Pr, iPr, Ph n = 2-10

EXAMPLE 7

Combinations with NMDA Receptor Antagonists

Antagonists of the N-methyl-D-aspartate receptor (NMDAR) are known to potentiate the beneficial effects of opioid receptor agonists in the treatment of pain and to prevent development of tolerance to those effects (Trujillo, K. A. et al. 1994; Mao, J. et al. 1996). NMDAR antagonists are also known to be effective in the treatment of depression (Murrough, J. W. et al. 2013). Therefore, pharmaceutical compositions of tianeptine or the novel compounds disclosed herein, combined with NMDAR antagonists, may be useful in the treatment of pain or mood disorders. Alternatively, the opioid modulator and NMDAR antagonist may be dosed separately, as a novel method for treating pain or mood disorders.

Non-Limiting Examples of NMDA Receptor Antagonists:

Dextromorphinans—dextromethorphan, dextrorphan, dextrallorphan

Adamantanes—memantine, amantadine, rimantadine, nitromemantine (YQW-36); Aylcyclohexylamines: ketamine (and its analogs, e.g. tiletamine), phencyclidine (and its analogs, e.g. tenocyclidine, eticyclidine, rolicyclidine), methoxetamine (and its analogs), gacyclidine (GK-11); Miscellaneous: neramexane, lanicemine (AZD6765), diphenidine, dizocilpine (MK-801), 8a-phenyldecahydroguinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A), AP-7

EXAMPLE 8

Combinations with NMDA Receptor Partial Agonists

Weak partial agonists of NMDAR are also known (Moskal, J. R. et al. 2005), and may be expected to produce beneficial or synergistic effects similar to an antagonist when intrinsic glutamate signaling activity is high or overactivated. Therefore, pharmaceutical compositions of tianeptine or the novel compounds disclosed herein, combined with NMDAR partial agonists, may be useful in the treatment of pain or mood disorders. Alternatively, the opioid modulator and NMDAR partial agonist may be dosed separately, as a novel method for treating pain or mood disorders.

Non-Limiting Examples of NMDA Receptor Partial Agonists:

NRX-1074, rapastinel (GLYX-13)

EXAMPLE 9

Combinations with Neurokinin 1 Receptor Antagonists

Antagonists of the neurokin 1 receptor (NK-1) are known to modulate the effects of opioid agonists, specifically in reward and self-administration protocols. More specifically, NK-1 antagonists attenuate opioid reward and self-administration in animal models (Robinson, J. E. et al. 2012). NK-1 antagonists are also known to be effective in the treatment of depression (Kramer, M. S. et al. 2004). Therefore, pharmaceutical compositions of tianeptine or the novel compounds disclosed herein, combined with NK-1 antagonists, may be useful in the treatment of pain or mood disorders with increased efficacy and less potential for abuse. Alternatively, the opioid modulator and NK-1 antagonist may be dosed separately, as a novel method for treating pain or mood disorders.

Non-Limiting Examples of Neurokinin 1 Receptor Antagonists: aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ=11974, RP 67580, NKP608, VPD-737, GR 205171, LY686017, AV608, SR140333B, SSR240600C, FK 888, GR 82334

EXAMPLE 10

Combinations with Neurokinin 2 Receptor Antagonists

Antagonists of the neurokin 2 receptor (NK-2) are known to show antidepressant effects and to synergize with tricyclic antidepressants (Overstreet, D.H. et al. 2010). Therefore, pharmaceutical compositions of tianeptine or the novel compounds disclosed herein, combined with NK-2 antagonists, may be useful in the treatment of mood disorders with increased efficacy. Alternatively, the opioid modulator and NK-2 antagonist may be dosed separately, as a novel method for treating mood disorders.

Non-Limiting Examples of Neurokinin 2 Receptor Antagonists: saredutant, ibodutant, nepadutant, GR-159897, MEN-10376

EXAMPLE 11

Combinations with Neurokinin 3 Receptor Antagonists

Antagonists of the neurokin 3 receptor (NK-3) are known to show antidepressant effects (Salome, et al. 2006). Further, the actions of NK-3 modulators show a dependency on the opioid receptor system (Panocka, I. et al. 2001). Therefore, pharmaceutical compositions of tianeptine or the novel compounds disclosed herein, combined with NK-3 antagonists, may be useful in the treatment of mood disorders with increased efficacy. Alternatively, the opioid modulator and NK-3 antagonist may be dosed separately, as a novel method for treating mood disorders.

Non-Limiting Examples of Neurokinin 3 Receptor Antagonists: osanetant, talnetant, SB-222200, SB-218795

Discussion

The compounds disclosed herein activate MOR or dually activate MOR and DOR. Therefore, they are useful as analgesics. Furthermore, this activity leads to modulation of the glutamatergic system and triggers antidepressant effects. Accordingly, the compounds disclosed herein are also useful as antidepressants.

An additional aspect of the invention provides synthetic methods and chemical intermediates that may be used to encompass chemical space about the 6 methyl-6,11-dihydrodibenzo[1,2]thiazepine 5,5-dioxide or 4-methyl-4,10-dihydrobenzo[f]thieno[3,2-c][1,2]thiazepine 5,5-dioxide core structure.

REFERENCES

Barbier, E.; Vendruscolo, L. F.; Schlosburg, J. E.; Edwards, S.; Juergens, N.; Park, P. E.; Misra, K. K.; Cheng, K.; Rice, K. C.; Schank, J.; Schulteis, G.; Koob, G. F.; Heilig, M. *Neuropsychopharmacology* 2013, 38, 976-984.
Beaumont, K.; Webster, R.; Gardner, I.; Dack, K. *Curr. Drug Metab.* 2003, 4, 461-485.
Berrocoso, E.; Sáanchez-Bláazquez, P.; Garzón, J.; Mico, J. A. *Curr. Pharm. Des.* 2009, 15, 1612-1622.
Besson, A.; Privat, A. M.; Eschalier, A.; Fialip, J. *Psychopharmacology* 1996, 123, 71-78.
Bodkin, J. A.; Zornberg, G. L.; Lukas, S. E.; Cole, J. O. *J. Clin. Psychopharmacol.* 1995, 15, 49-57.
Buchwald, S. L.; Huang, X.; Zim, D. Ligands for metals and improved metal-catalyzed processes based thereon. US2004/171833 A1, 2004.
Corbett, A. D.; Henderson, G.; McKnight, A. T.; Paterson, S. J.; Brit. *J. Pharmacol.* 2006, 147, S153-S162.
Dreher, S. D.; Lim, S.-E.; Sandrock, D. L.; Molander, G. A. *J. Org. Chem.* 2009, 74, 3626-3631.
Durand, P.; Richard, P.; Renaut, P. *J. Org. Chem.* 1998, 63, 9723-9727.
Gilleron, P.; Wlodarczyk, N.; Houssin, R.; Farce, A.; Laconde, G.; Goossens, J.-F.; Lemoine, A.; Pommery, N.; Hénichart, J.-P.; Millet, R. Bioorg. *Med. Chem. Lett.* 2007, 17, 5465-5471.
Grislain, L.; Gele, P.; Bertrand, M.; Luijten, W.; Bromet, N.; Salvadori, C.; Kamoun, A. *Drug Metab. Dispos.* 1990, 18, 804-808.
Invernizzi, R.; Pozzi, L.; Garattini, S.; Samanin, R. *Neuropharmacology* 1992, 31, 221-227.
Jutkiewicz, E. M. *Mol. Interv.* 2006, 6, 162-169.
Kramer, M. S.; Winokur, A.; Kelsey, J.; Preskorn, S. H.; Rothschild, A. J.; Snavely, D.; Ghosh, K.; Ball, W. A.; Reines, S. A.; Munjack, D.; Apter, J. T.; Cunningham, L.; Kling, M.; Bari, M.; Getson-, A.; Lee, Y. *Neuropsychopharmacology* 2004, 29, 385-392.
Mao, J.; Price, D. D.; Caruso, F. S.; Mayer, D. J. *Pain* 1996, 67, 361-368.
McNeill, E.; Barder, T. E.; Buchwald, S. L. *Org. Lett.* 2007, 99, 3785-3788.
Moskal, J. R.; Kuo, A. G.; Weiss, C.; Wood, P. L.; Hanson, A. O.; Kelso, S.; Harris, R. B.; Disterhoft, J. F. *Neuropharmacology* 2005, 49, 1077-1087.
Murrough, J. W.; Iosifescu, D. V.; Chang, L. C.; Al Jurlj, Green, C. E.; Perez, A. M.; Iqbal, S.; Pillemer, S.; Foulkes, A.; Shah, A.; Charney, D. S.; Mathew, S. J. *Am. J. Psychiatry* 2013, 170, 1134-1142.
Overstreet, D. H.; Naimoli, V. M.; Griebel, G. *Pharmacol. Biochem. Behav.* 2010, 96, 206-210.
Robinson, J. E.; Fish, E. W.; Krouse, M. C.; Thorsell, A.; Heilig, M.; Malanga, C. J. *Psychopharmacology* 2012, 220, 215-224.
Pan, J.; Wang, X.; Zhang, Y.; Buchwald, S. L. *Org. Lett.* 2011, 13, 4974-4976.
Panocka, I.; Massi, M.; Lapo, I.; Swiderski, T.; Kowalczyk, M.; Sadowski, B. *Peptides* 2001, 22, 1037-1042.
Paul, I.A.; Skolnick, P. *Ann. N. Y. Acad. Sci.* 2003, 1003, 250-272.
Salomé, N.; Stemmelin, J.; Cohen, C.; Griebel, G. *Pharmacol. Biochem. Behav.* 2006, 83, 533-539.
Svoboda, K. R.; Adams, C. E.; Lup ca, C. R.; J. Neurosci. 1999, 19, 85-95.
Trujillo, K. A.; Akil, H. *Brain Res.* 1994, 633, 178-188.
Uy, R.; Yang, L.; Zhou, H.; Price, S. C.; You, W. *Macromolecules* 2011, 44, 9146-9154.
Williams, J. T.; Ingram, S. L.; Henderson, G.; Chavkin, C.; von Zastrow, M.; Schultz, S.; Koch, T.; Evans, C. J.; MacDonald, J. C. *Pharmacol. Rev.* 2013, 65, 223-254.
Xie, C. W., Lew s D. V. J. *Neurophysi* 1997, 78: 759-766.
Zarat, C. A. Jr; Singh, J. B,; Carlson, P. J.; Brutsche, N. E.; Ameli, R.; Luckenbaugh, D. A.; Charney, D. S.; Manji, H. K. *Arch. Gen. Psychiatry* 2006, 63, 856-864.

What is claimed is:
1. The compound having the structure:

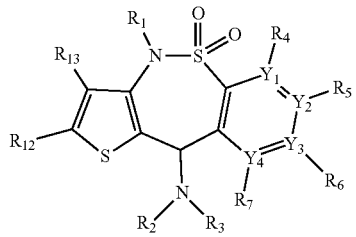

wherein
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-OCH$_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

R$_{12}$ and R$_{13}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C, wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present, or a pharmaceutically acceptable salt thereof.

2. The compound of claim 1 having the structure:

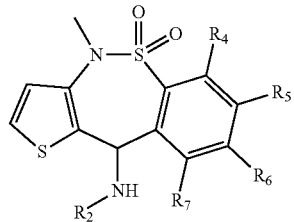

wherein

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, (alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_5$ is —Cl, —Br, —F, or —I;

R$_4$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl), or a pharmaceutically acceptable salt thereof.

3. The compound of claim 1 having the structure:

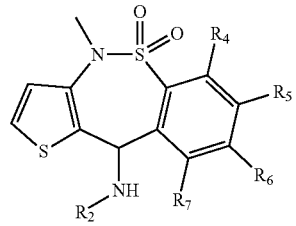

wherein

R$_2$ is -(alkyl), -(alkyl)-CO$_2$H, -(alkyl)-CO$_2$-(alkyl), -(alkyl)-O-(alkyl) or -(alkyl)-O-(alkyl)-O-(alkyl);

R$_5$ is —Cl, —Br, —F, or —I;

R$_4$, R$_6$ and R$_7$ are each independently —H, —Cl, —Br, —F, —I, —CN, —CF$_3$, —OCF$_3$, -(alkyl), -(alkenyl), -(alkynyl), (aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl) or —SO$_2$-(heteroaryl), or a pharmaceutically acceptable salt thereof.

4. A compound having the structure:

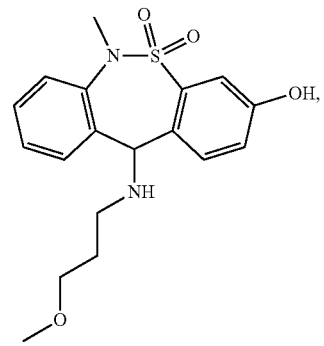

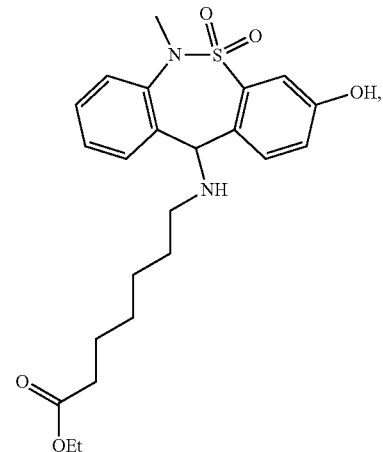

289
-continued
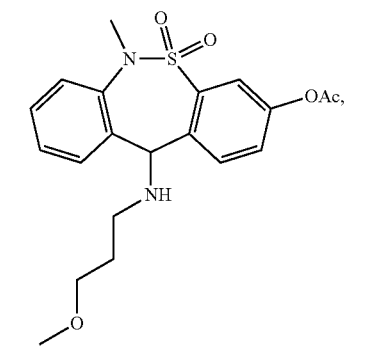
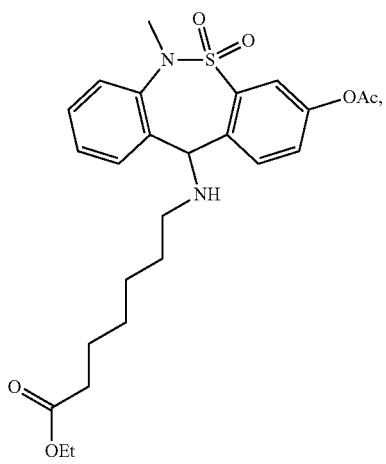
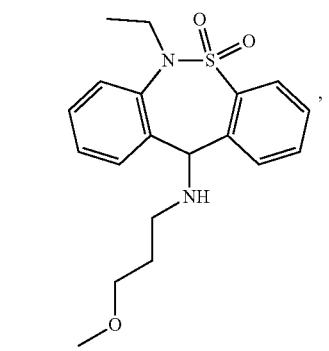
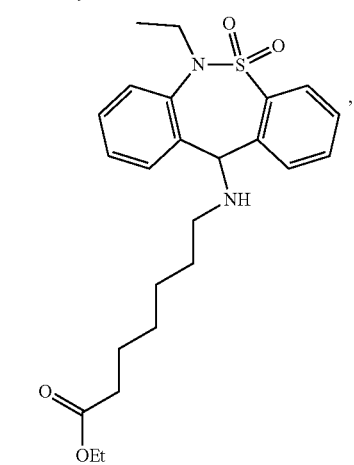
290
-continued
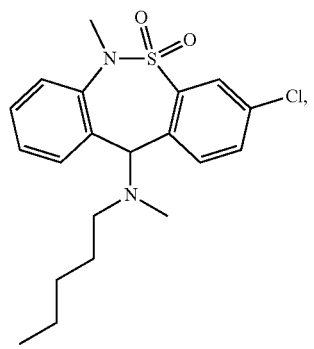
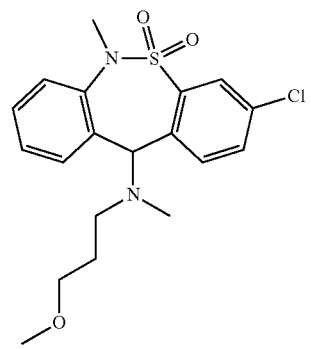
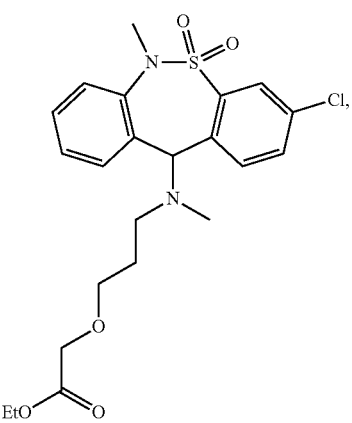

291
-continued
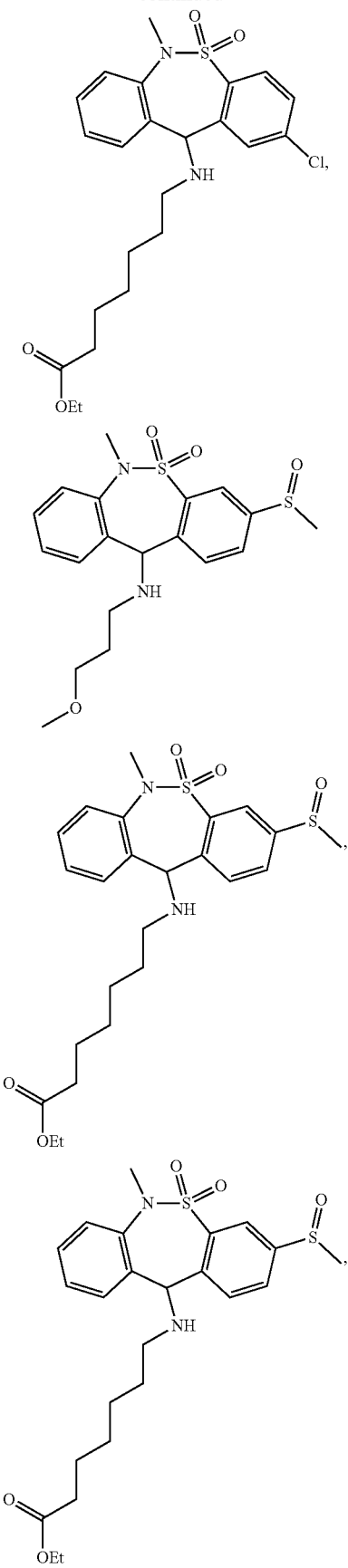
292
-continued
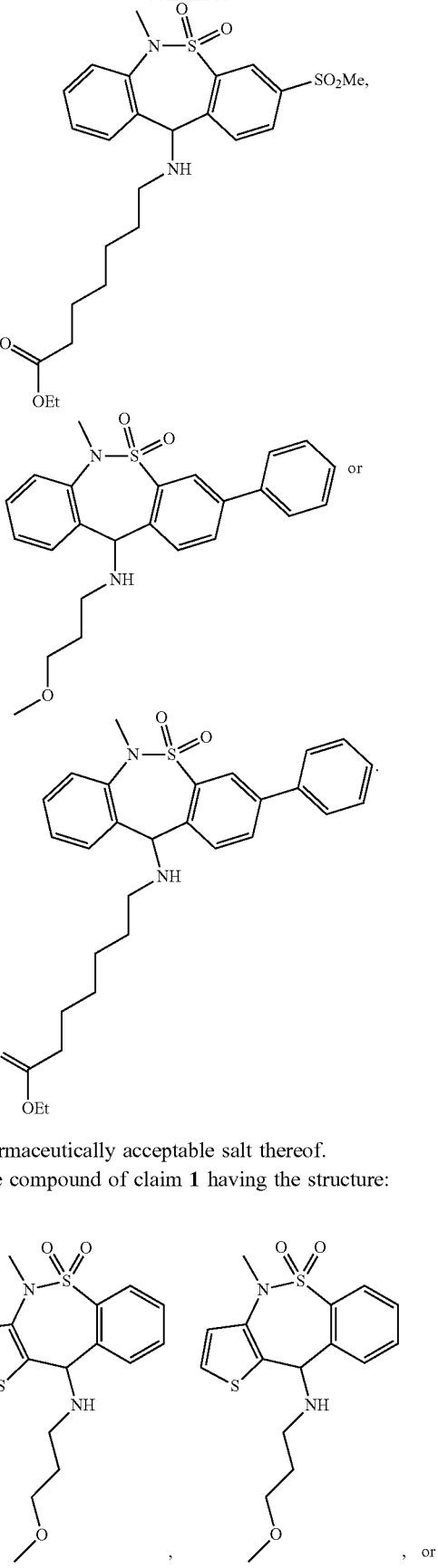
or a pharmaceutically acceptable salt thereof.
5. The compound of claim 1 having the structure:

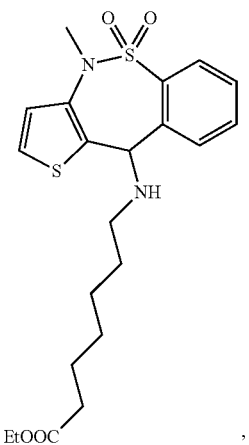
or a pharmaceutically acceptable salt thereof.
6. The compound of claim 1 having the structure:
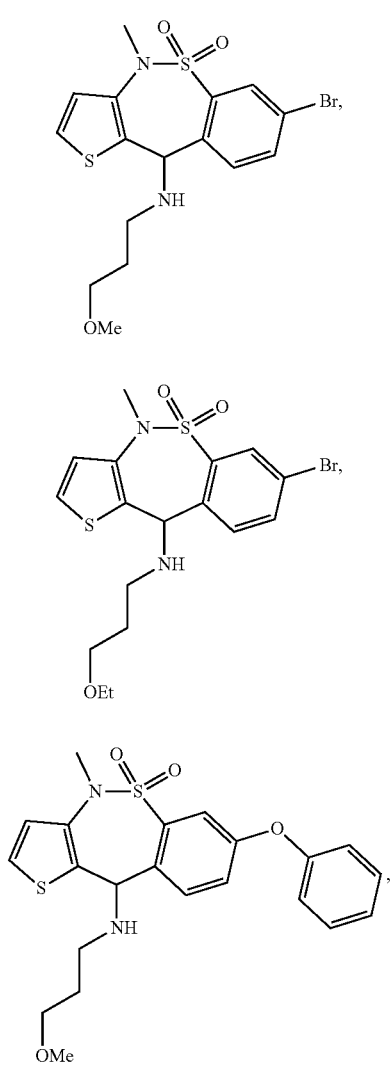
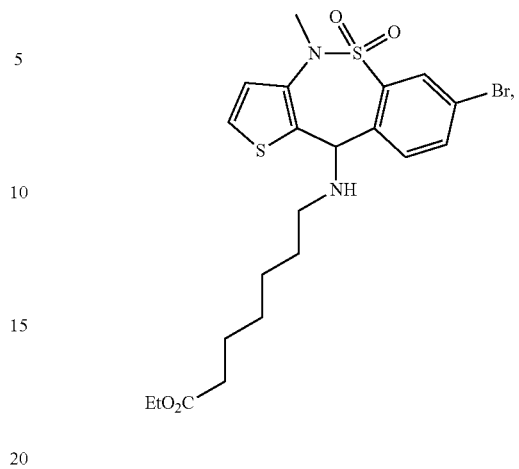
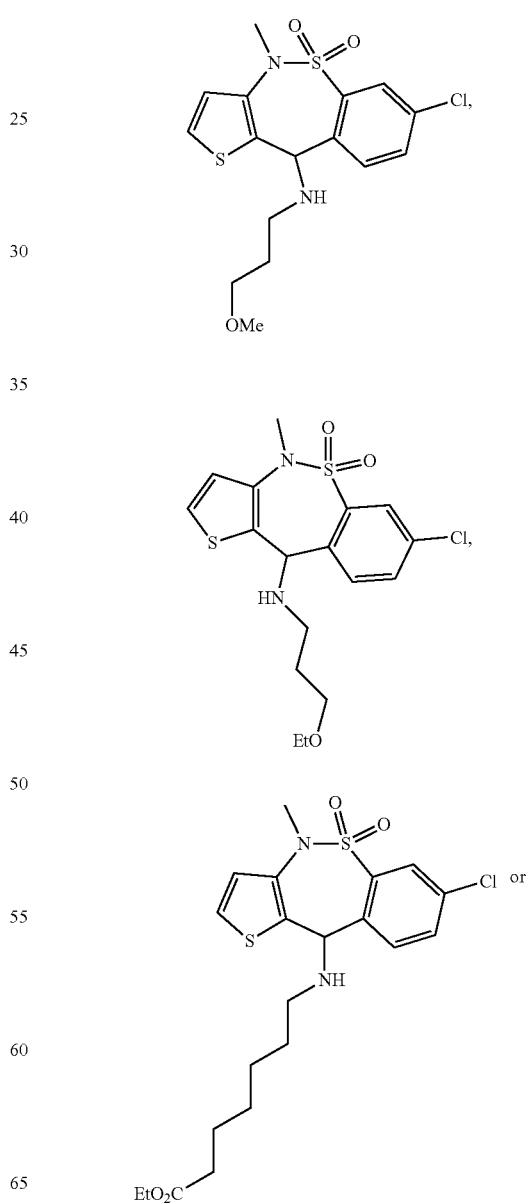

-continued

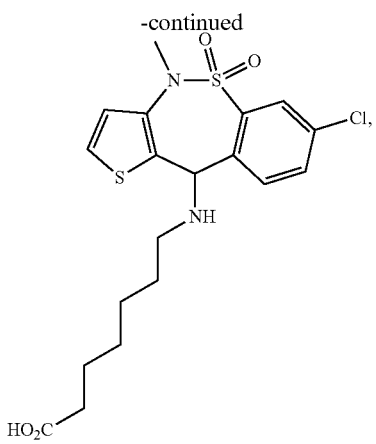

or a pharmaceutically acceptable salt thereof.

7. A pharmaceutical composition comprising the compound of claim 1 and a pharmaceutically acceptable carrier.

8. A compound having the structure:

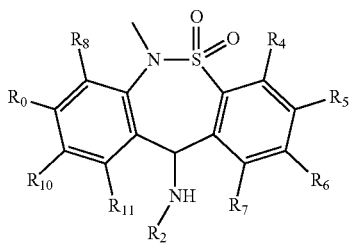

wherein
$R_2$ is -(alkyl), -(alkenyl), -(alkynyl), -(alkyl)-OH, -(alkyl)-$CO_2$-(alkyl), -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole),
wherein each alkyl, alkenyl, alkynyl or hydroxyalkyl is unsubstituted, and each alkyl of -(alkyl)-$CO_2$-(alkyl) is unbranched;
$R_5$ is —Br, or —I;
$R_4$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl) or —$SO_2$-(heteroaryl); and
$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl),
—S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl),
or a pharmaceutically acceptable salt or ester thereof.

9. A compound having the structure:

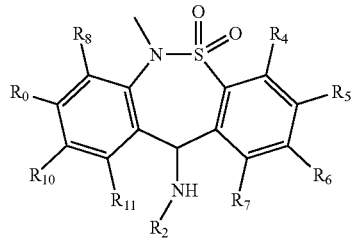

wherein
$R_2$ is -(alkyl), -(alkyl)-O-(alkyl) or -(alkyl)-O-(alkyl)-O-(alkyl),
wherein each alkyl is unsubstituted;
$R_5$ is —Cl, —Br, —F, or —I;
$R_4$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl) or —$SO_2$-(heteroaryl),
$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl),
wherein when $R_4$, $R_6$, and $R_7$ are each —H, and $R_5$ is Cl, then $R_2$ is other than —$(CH_2)_6CH_3$,
or a pharmaceutically acceptable salt or ester thereof.

10. A compound having the structure:

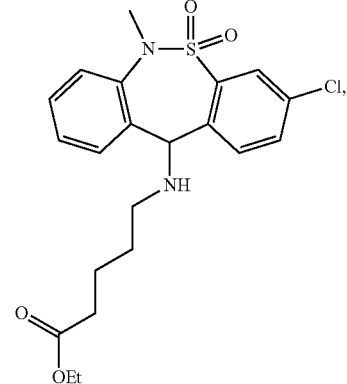

297
-continued
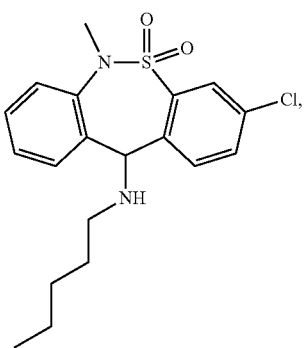
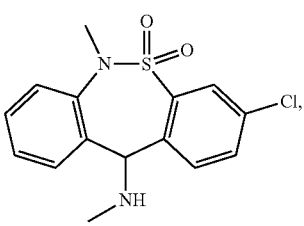
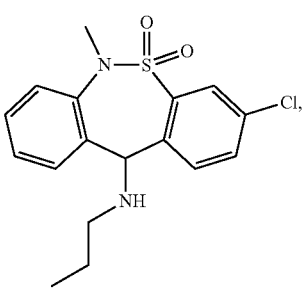
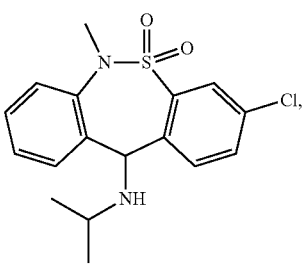
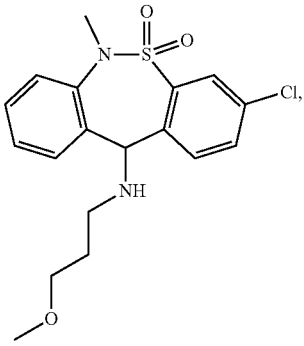
298
-continued
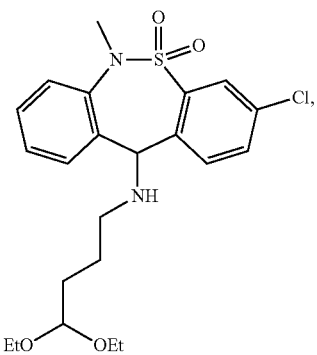
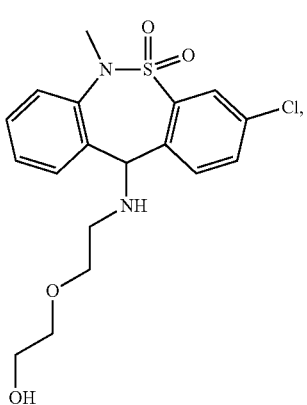
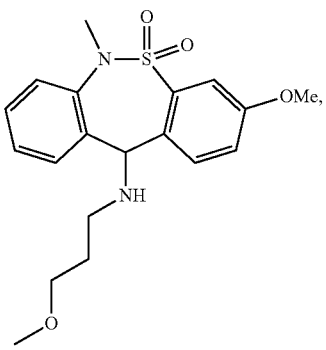
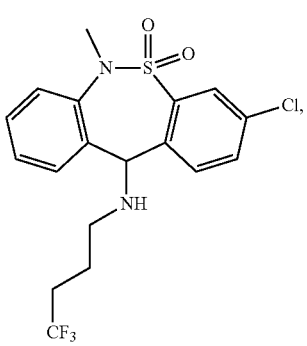

299
-continued
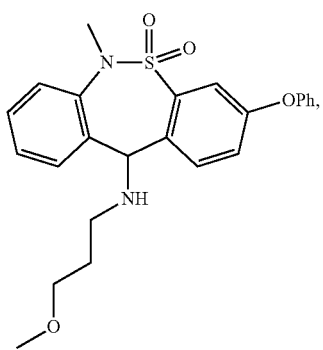
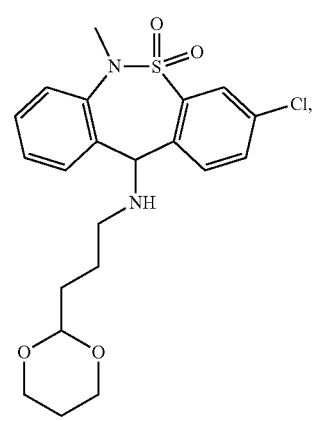
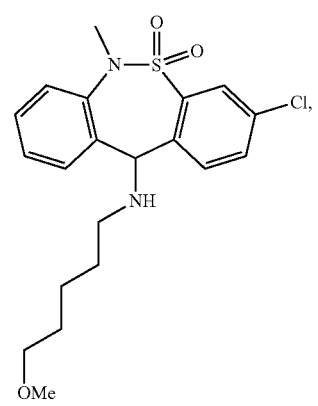
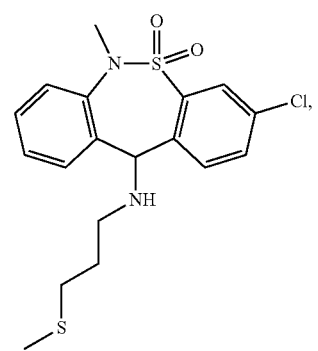
300
-continued
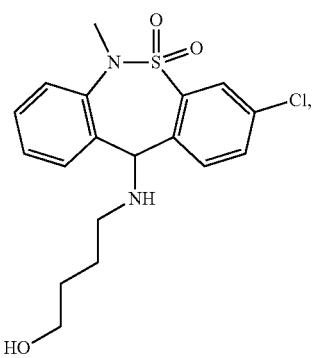
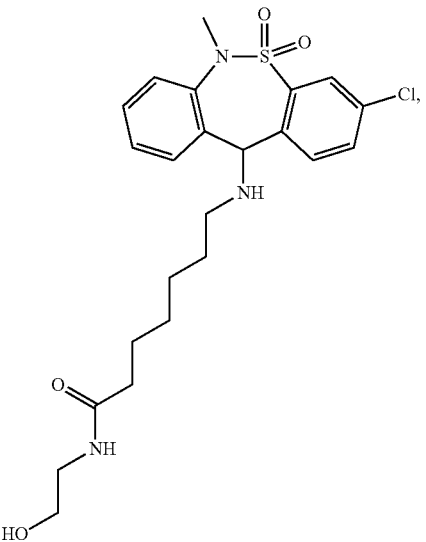
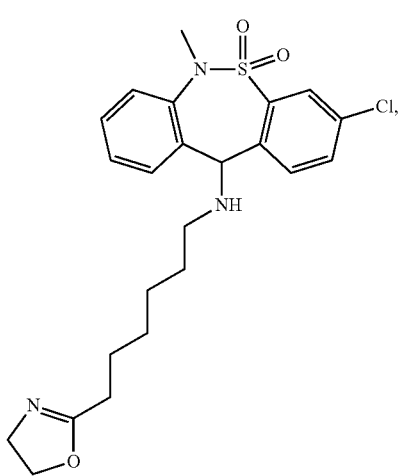

301
-continued
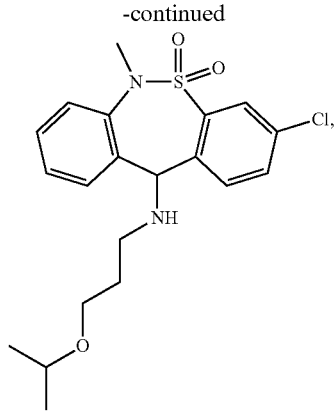
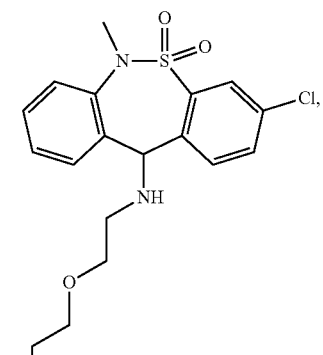
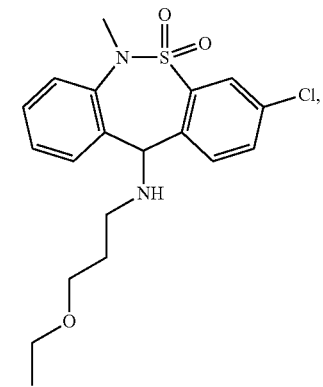
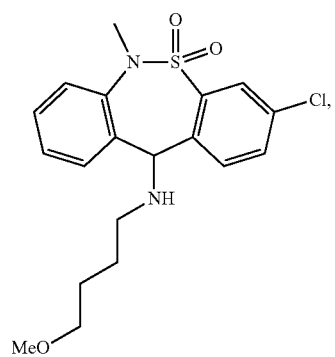
302
-continued
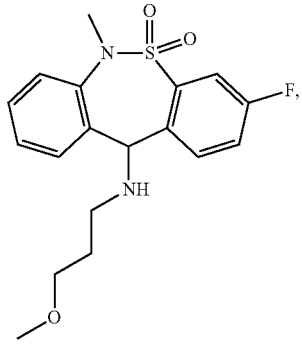
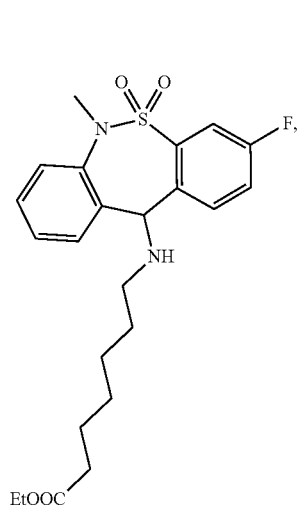
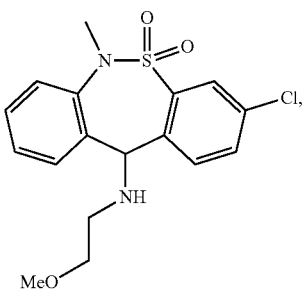
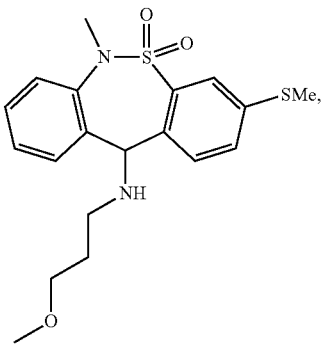

303
-continued
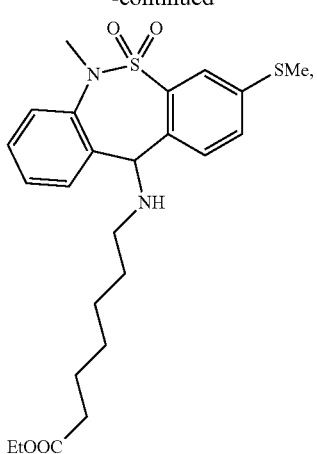
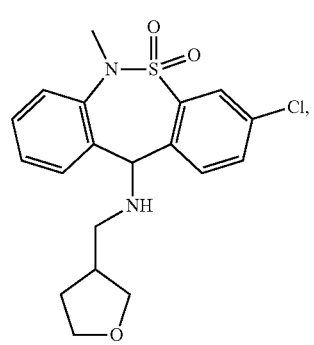
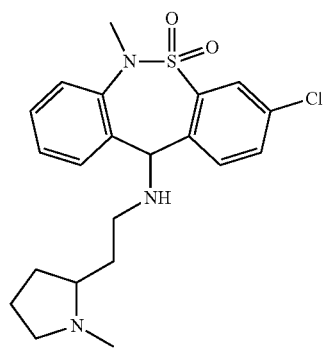
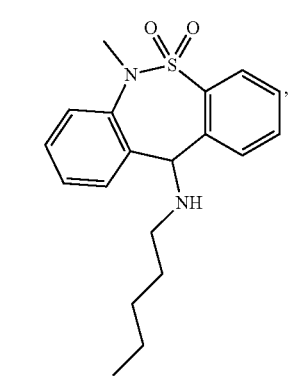
304
-continued
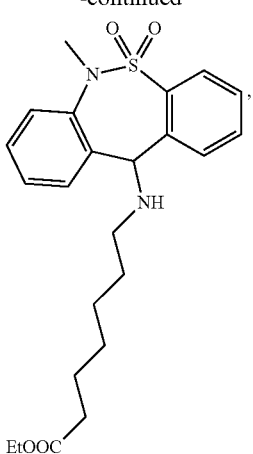
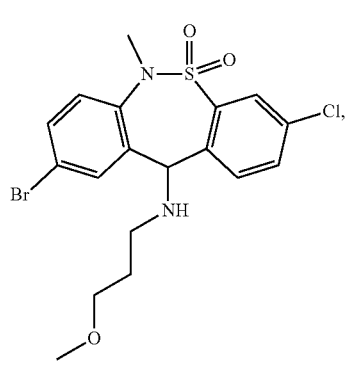
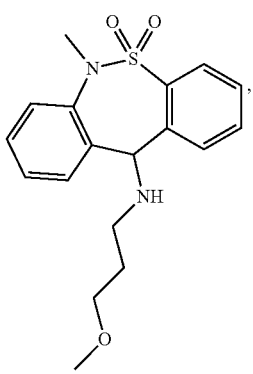
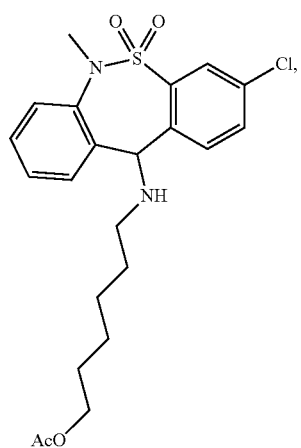

305
-continued
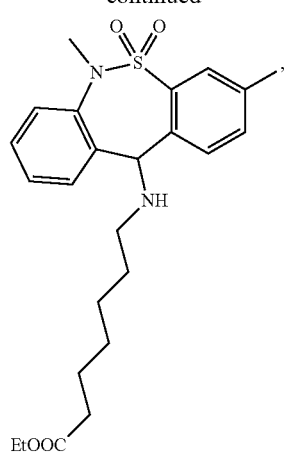
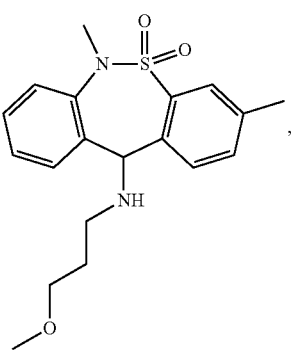
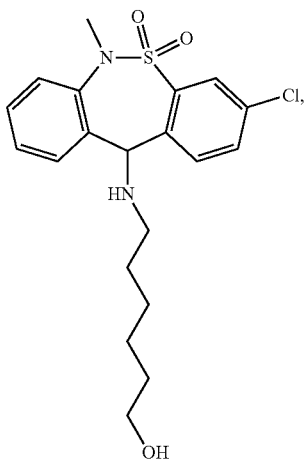
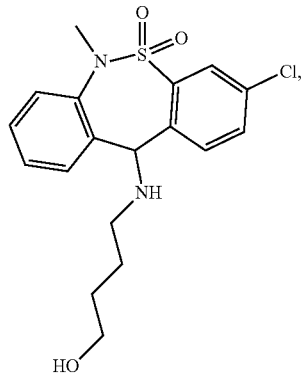
306
-continued
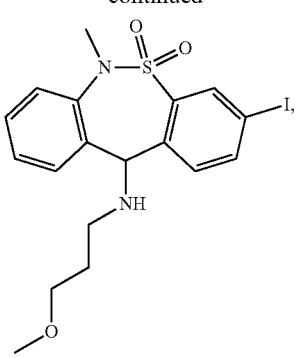
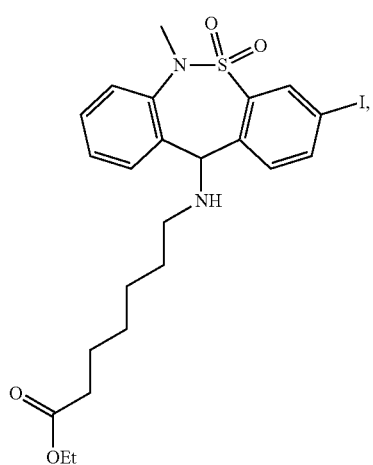
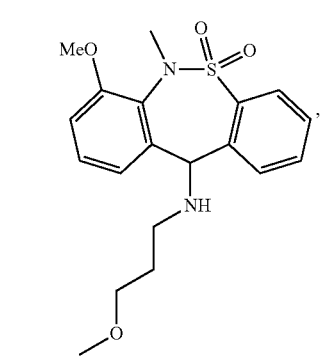
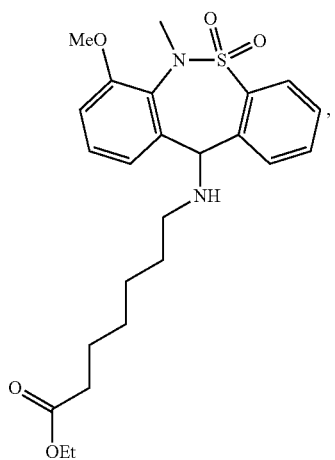

or a pharmaceutically acceptable salt thereof.

11. A compound having the structure:

309
-continued
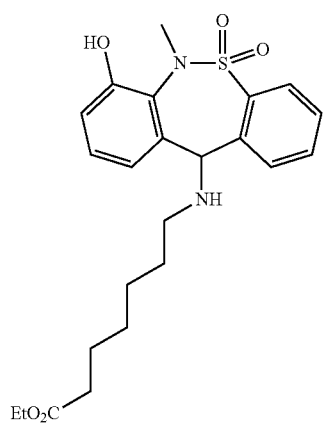
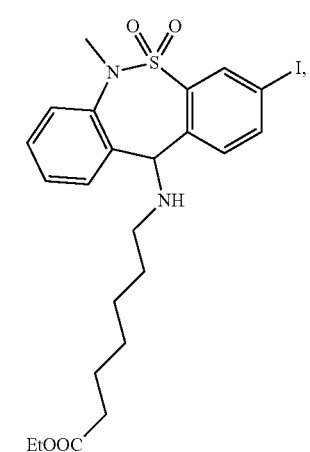
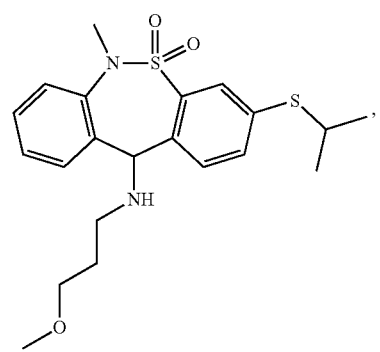
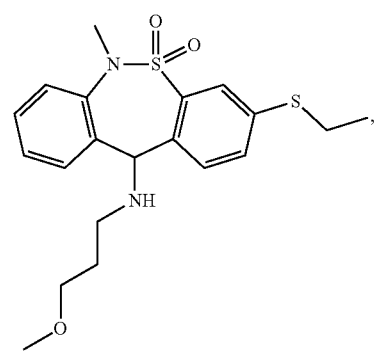
310
-continued
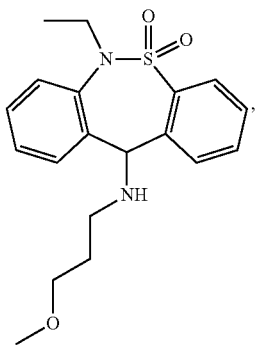
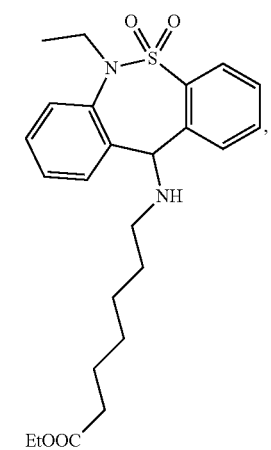
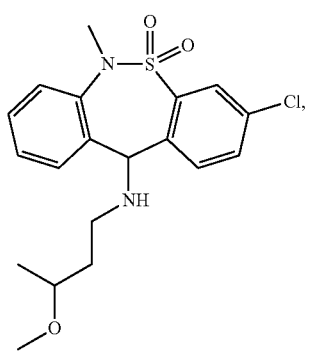
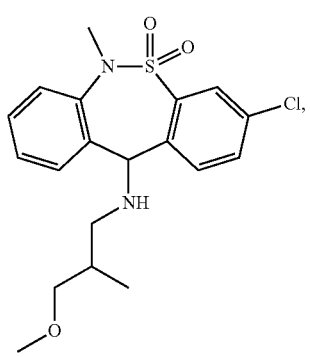

-continued

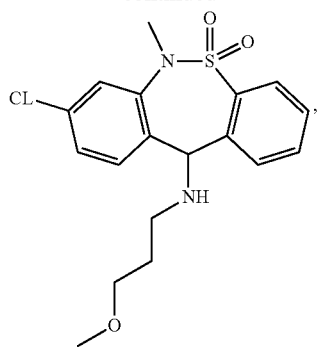

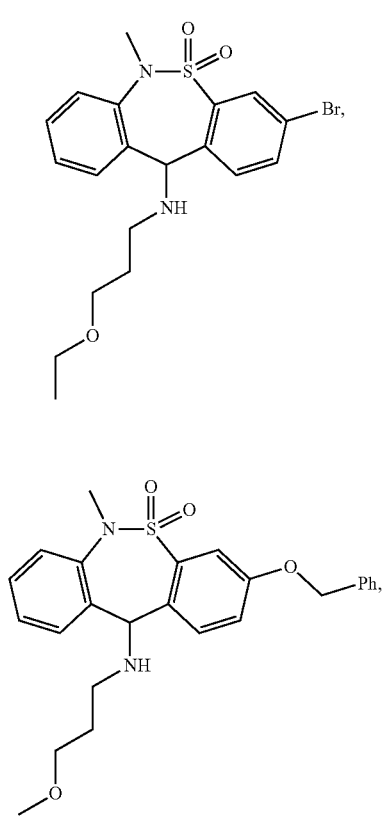

-continued

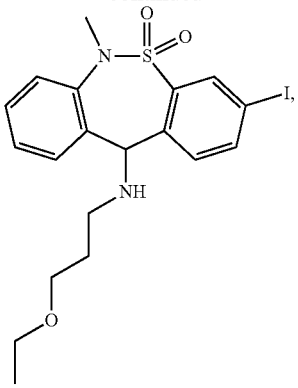

or a pharmaceutically acceptable salt thereof.

12. A pharmaceutical composition comprising the compound of claim 4 and a pharmaceutically acceptable carrier.

13. A pharmaceutical composition comprising the compound of claim 8 and a pharmaceutically acceptable carrier.

14. A pharmaceutical composition comprising the compound of claim 9 and a pharmaceutically acceptable carrier.

15. A pharmaceutical composition comprising the compound of claim 10 and a pharmaceutically acceptable carrier.

16. A pharmaceutical composition comprising the compound of claim 11 and a pharmaceutically acceptable carrier.

17. A compound having the structure:

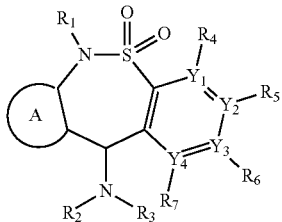

wherein
A is an aryl or heteroaryl, with or without substitution;
R₁ is —H or -(alkyl);
R₂ is -(alkyl)-CO₂H or -(alkyl)-C(O)—NH₂;
R₃ is —H or -(alkyl);
R₅ is I;
R₄, R₆ and R₇ are each absent or present, and when present, are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); and
Y₁, Y₂, Y₃ and Y₄ are each independently N or C,
wherein when Y₁ is N, then R₄ is absent, and when Y₁ is C, then R₄ is present; when Y₂ is N, then R₅ is absent, and when Y₂ is C, then R₅ is present; when Y₃ is N, then R₆ is absent, and when Y₃ is C, then R₆ is present; when Y₄ is N, then R₇ is absent, and when Y₄ is C, then R₇ is present,
or a pharmaceutically acceptable salt thereof.

18. The compound of claim 17 having the structure:

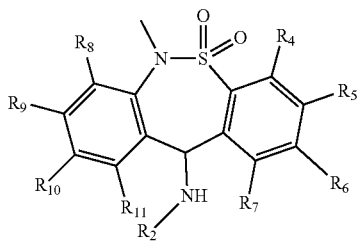

wherein
R₂ is -(alkyl)-CO₂H or -(alkyl)-C(O)—NH₂;
R₅ is —I;
R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl) or —SO₂-(heteroaryl); and
R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl),
or a pharmaceutically acceptable salt thereof.

19. The compound of claim 18,
wherein
R₂ is -(alkyl)-CO₂H or -(alkyl)-C(O)—NH₂,
wherein each alkyl is unsubstituted and unbranched,
or a pharmaceutically acceptable salt thereof.

20. The compound of claim 17 having the structure:

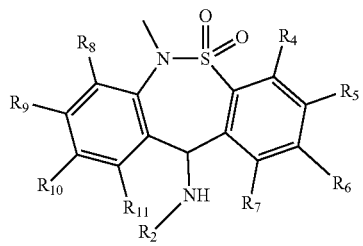

wherein
R₂ is -(alkyl)-CO₂H;
R₅ is —I;
R₄, R₆, R₇, R₈, R₉, R₁₀ and R₁₁ are each —H,
or a pharmaceutically acceptable salt thereof.

21. The compound of claim 20,
wherein
R₂ is -(alkyl)-CO₂H,
wherein the alkyl is unsubstituted and unbranched,
or a pharmaceutically acceptable salt thereof.

22. The compound of claim 20,
wherein
R₂ is —(C₁-C₁₂ alkyl)-CO₂H,
or a pharmaceutically acceptable salt thereof.

23. The compound of claim 22,
wherein
R₂ is —(C₁-C₁₂ alkyl)-CO₂H,
wherein the alkyl is unsubstituted and unbranched,
or a pharmaceutically acceptable salt thereof.

24. The compound of claim 17 having the structure:

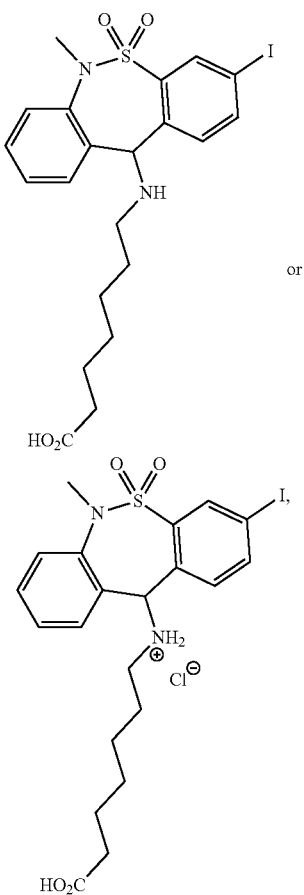

or a pharmaceutically acceptable salt thereof.

25. A pharmaceutical composition comprising the compound of claim 17 and a pharmaceutically acceptable carrier.

26. A pharmaceutical composition comprising the compound of claim 24 and a pharmaceutically acceptable carrier.

27. A method of treating a subject afflicted with pain, a depressive disorder or a mood disorder comprising administering an effective amount of the compound of claim 1 to the subject so as to thereby treat the subject.

28. A method of activating a mu-opioid receptor or delta-opioid receptor comprising contacting the mu-opioid receptor or delta-opioid receptor with an effective amount of the compound of claim 1 so as to thereby activate the mu-opioid receptor or delta-opioid receptor.

29. A method of treating a subject afflicted with pain, a depressive disorder or a mood disorder comprising administering an effective amount of the compound of claim 4 to the subject so as to thereby treat the subject.

30. A method of activating a mu-opioid receptor or delta-opioid receptor comprising contacting the mu-opioid receptor or delta-opioid receptor with an effective amount of the compound of claim 4 so as to thereby activate the mu-opioid receptor or delta-opioid receptor.

31. A method of treating a subject afflicted with pain, a depressive disorder or a mood disorder comprising administering an effective amount of the compound of claim 17 to the subject so as to thereby treat the subject.

32. A method of activating a mu-opioid receptor or delta-opioid receptor comprising contacting the mu-opioid receptor or delta-opioid receptor with an effective amount of the compound of claim 17 so as to thereby activate the mu-opioid receptor or delta-opioid receptor.

33. A method of treating a subject afflicted with pain, a depressive disorder or a mood disorder comprising administering an effective amount of the compound of claim 8 to the subject so as to thereby treat the subject.

34. A method of treating a subject afflicted with pain, a depressive disorder or a mood disorder comprising administering an effective amount of the compound of claim 9 to the subject so as to thereby treat the subject.

35. A method of treating a subject afflicted with pain, a depressive disorder or a mood disorder comprising administering an effective amount of the compound of claim 10 to the subject so as to thereby treat the subject.

36. A method of treating a subject afflicted with pain, a depressive disorder or a mood disorder comprising administering an effective amount of the compound of claim 11 to the subject so as to thereby treat the subject.

37. A method of treating a subject afflicted with pain, a depressive disorder or a mood disorder comprising administering an effective amount of the compound of claim 24 to the subject so as to thereby treat the subject.

* * * * *